(12) United States Patent
Flynn et al.

(10) Patent No.: US 11,530,206 B2
(45) Date of Patent: Dec. 20, 2022

(54) PHENYLAMINOPYRIMIDINE AMIDE AUTOPHAGY INHIBITORS AND METHODS OF USE THEREOF

(71) Applicant: Deciphera Pharmaceuticals, LLC, Waltham, MA (US)

(72) Inventors: Daniel L. Flynn, Waltham, MA (US); Yu Mi Ahn, Waltham, MA (US); Timothy Caldwell, Waltham, MA (US); Lakshminarayana Vogeti, Waltham, MA (US)

(73) Assignee: Deciphera Pharmaceuticals, LLC, Waltham, MA (US)

( * ) Notice: Subject to any disclaimer, the term of this patent is extended or adjusted under 35 U.S.C. 154(b) by 0 days.

(21) Appl. No.: 16/870,384

(22) Filed: May 8, 2020

(65) Prior Publication Data

US 2020/0354352 A1 Nov. 12, 2020

Related U.S. Application Data

(60) Provisional application No. 62/911,728, filed on Oct. 7, 2019, provisional application No. 62/911,730, filed on Oct. 7, 2019, provisional application No. 62/846,251, filed on May 10, 2019, provisional application No. 62/846,258, filed on May 10, 2019.

(51) Int. Cl.

| | |
|---|---|
| *C07D 401/12* | (2006.01) |
| *C07D 401/14* | (2006.01) |
| *C07D 403/12* | (2006.01) |
| *C07D 403/14* | (2006.01) |
| *C07D 413/14* | (2006.01) |
| *C07D 417/04* | (2006.01) |
| *C07D 487/04* | (2006.01) |
| *C07D 487/08* | (2006.01) |
| *A61K 31/506* | (2006.01) |
| *A61K 31/444* | (2006.01) |
| *A61P 35/00* | (2006.01) |
| *A61K 31/519* | (2006.01) |
| *A61K 45/06* | (2006.01) |

(52) U.S. Cl.
CPC ......... *C07D 413/14* (2013.01); *C07D 401/14* (2013.01); *C07D 487/04* (2013.01); *C07D 487/08* (2013.01); *A61K 31/519* (2013.01); *A61K 45/06* (2013.01)

(58) Field of Classification Search
CPC .. C07D 401/12; C07D 401/14; C07D 403/12; C07D 403/14; C07D 413/14; C07D 417/04; C07D 487/04; C07D 487/08; A61K 31/506; A61K 31/444; A61P 35/00
See application file for complete search history.

(56) References Cited

U.S. PATENT DOCUMENTS

| | | |
|---|---|---|
| 6,262,088 B1 | 7/2001 | Phillips |
| 6,492,376 B2 | 12/2002 | Phillips |
| 6,495,574 B2 | 12/2002 | Phillips |
| 6,495,684 B2 | 12/2002 | Phillips |
| 6,552,030 B2 | 4/2003 | Phillips |
| 6,559,147 B2 | 5/2003 | Phillips |
| 6,686,367 B2 | 2/2004 | Phillips |
| 6,773,599 B1 | 8/2004 | Lowe et al. |
| 6,906,067 B2 | 6/2005 | Moriarty et al. |
| 7,087,614 B2 | 8/2006 | Guo et al. |
| 7,122,542 B2 | 10/2006 | Singh et al. |
| 7,144,911 B2 | 12/2006 | Flynn et al. |
| 7,166,599 B2 | 1/2007 | Bornemann et al. |
| 7,173,028 B2 | 2/2007 | Dahmann et al. |
| 7,202,257 B2 | 4/2007 | Flynn et al. |
| 7,253,174 B2 | 8/2007 | Ahmed et al. |
| 7,276,510 B2 | 10/2007 | Kukla et al. |
| 7,279,576 B2 | 10/2007 | Flynn et al. |
| 7,342,037 B2 | 3/2008 | Flynn et al. |
| 7,364,656 B1 | 4/2008 | Lowe et al. |
| 7,442,705 B2 | 10/2008 | Guillemont et al. |
| 7,449,465 B2 | 11/2008 | Freyne et al. |
| 7,452,879 B2 | 11/2008 | Singh et al. |
| 7,479,495 B2 | 1/2009 | Moriarty et al. |
| 7,504,410 B2 | 3/2009 | Bryant et al. |
| 7,531,566 B2 | 5/2009 | Flynn et al. |
| 7,560,466 B2 | 7/2009 | Singh et al. |
| 7,582,648 B2 | 9/2009 | Singh et al. |
| 7,601,836 B2 | 10/2009 | Pitts et al. |
| 7,666,895 B2 | 2/2010 | Flynn et al. |
| 7,709,480 B2 | 5/2010 | Dahmann et al. |
| 7,737,283 B2 | 6/2010 | Flynn et al. |
| 7,790,756 B2 | 9/2010 | Flynn et al. |
| 7,858,633 B2 | 12/2010 | Li et al. |
| 7,868,013 B2 | 1/2011 | Li et al. |
| 7,884,111 B2 | 2/2011 | Argade et al. |
| 7,897,762 B2 | 3/2011 | Flynn et al. |

(Continued)

FOREIGN PATENT DOCUMENTS

| | | |
|---|---|---|
| CN | 103242341 A | 8/2013 |
| JP | 4072615 B2 | 4/2008 |

(Continued)

OTHER PUBLICATIONS

International Search Report and Written Opinion for International Application No. PCT/US2020/032087 dated Jul. 2, 2020.

(Continued)

*Primary Examiner* — Bruck Kifle

(74) *Attorney, Agent, or Firm* — Goodwin Procter LLP

(57) ABSTRACT

Described herein are compounds that are inhibitors of autophagy and their use in the treatment of disorders such as cancers.

37 Claims, No Drawings

Specification includes a Sequence Listing.

(56) References Cited

U.S. PATENT DOCUMENTS

| | | | |
|---|---|---|---|
| 8,044,040 B2 | 10/2011 | Ahmed et al. |
| 8,143,293 B2 | 3/2012 | Flynn et al. |
| 8,163,756 B2 | 4/2012 | Flynn et al. |
| 8,178,671 B2 | 5/2012 | Singh et al. |
| 8,188,113 B2 | 5/2012 | Flynn et al. |
| 8,193,206 B2 | 6/2012 | Yen et al. |
| 8,278,331 B2 | 10/2012 | Flynn et al. |
| 8,338,439 B2 | 12/2012 | Singh et al. |
| 8,354,407 B2 | 1/2013 | Djung et al. |
| 8,399,433 B2 | 3/2013 | Appari et al. |
| 8,410,093 B2 | 4/2013 | Li et al. |
| 8,420,630 B2 | 4/2013 | Dahmann et al. |
| 8,450,335 B2 | 5/2013 | Singh et al. |
| 8,461,179 B1 | 6/2013 | Flynn et al. |
| 8,486,951 B2 | 7/2013 | Flynn et al. |
| 8,552,002 B2 | 10/2013 | Ding et al. |
| 8,569,319 B2 | 10/2013 | Flynn et al. |
| 8,586,565 B2 | 11/2013 | Flynn et al. |
| 8,609,679 B2 | 12/2013 | Singh et al. |
| 8,637,672 B2 | 1/2014 | Flynn et al. |
| 8,710,222 B2 | 4/2014 | Singh et al. |
| 8,741,911 B2 | 6/2014 | Allgeier et al. |
| 8,748,627 B2 | 6/2014 | Gu et al. |
| 8,791,130 B2 | 7/2014 | Baker-Glenn et al. |
| 8,809,341 B2 | 8/2014 | Argade et al. |
| 8,907,095 B2 | 12/2014 | Xia et al. |
| 8,921,565 B2 | 12/2014 | Flynn et al. |
| 8,940,756 B2 | 1/2015 | Flynn et al. |
| 9,012,635 B2 | 4/2015 | Flynn et al. |
| 9,096,624 B2 | 8/2015 | Crew et al. |
| 9,133,183 B2 | 9/2015 | Flynn et al. |
| 9,139,566 B2 | 9/2015 | Marik et al. |
| 9,145,402 B2 | 9/2015 | Baker-Glenn et al. |
| 9,181,223 B2 | 11/2015 | Kaufman et al. |
| 9,187,474 B2 | 11/2015 | Flynn et al. |
| 9,193,719 B2 | 11/2015 | Flynn et al. |
| 9,212,181 B2 | 12/2015 | Singh et al. |
| 9,296,737 B2 | 3/2016 | Singh et al. |
| 9,309,224 B2 | 4/2016 | Flynn et al. |
| 9,334,267 B2 | 5/2016 | Flynn et al. |
| 9,382,228 B2 | 7/2016 | Flynn et al. |
| 9,387,202 B2 | 7/2016 | Flynn et al. |
| 9,409,921 B2 | 8/2016 | Singh et al. |
| 9,457,019 B2 | 10/2016 | Flynn et al. |
| 9,598,432 B2 | 3/2017 | Argade et al. |
| 9,725,419 B2 | 8/2017 | Li et al. |
| 9,751,893 B2 | 9/2017 | Singh et al. |
| 9,783,504 B2 | 10/2017 | Gray et al. |
| 9,840,517 B2 | 12/2017 | Liu et al. |
| 9,987,276 B2 | 6/2018 | Singh et al. |
| 10,010,548 B2 | 7/2018 | Singh et al. |
| 10,259,826 B2 | 4/2019 | Singh et al. |
| 10,273,242 B2 | 4/2019 | Liu et al. |
| 10,316,002 B2 | 6/2019 | Gray et al. |
| 10,329,270 B2 | 6/2019 | Qiu et al. |
| 10,336,734 B2 | 7/2019 | Mahajan et al. |
| 2009/0036434 A1 | 2/2009 | Jones et al. |
| 2009/0312321 A1 | 12/2009 | Ren et al. |
| 2010/0298557 A1 | 11/2010 | Yagi et al. |
| 2012/0122840 A1 | 5/2012 | Kumar et al. |
| 2014/0073634 A1 | 3/2014 | Jones et al. |
| 2015/0045370 A1 | 2/2015 | Cohen et al. |
| 2015/0174132 A1 | 6/2015 | Foley et al. |
| 2018/0290984 A1 | 10/2018 | Schonbrunn et al. |
| 2019/0091217 A1 | 3/2019 | Flynn et al. |
| 2019/0117650 A1 | 4/2019 | Singh et al. |
| 2019/0192512 A1 | 6/2019 | Singh et al. |
| 2020/0129489 A1 | 4/2020 | Flynn et al. |
| 2020/0253973 A1 | 8/2020 | Flynn et al. |
| 2020/0253981 A1 | 8/2020 | Fisher et al. |
| 2020/0352920 A1 | 11/2020 | Flynn et al. |
| 2020/0354346 A1 | 11/2020 | Flynn et al. |
| 2020/0354352 A1 | 11/2020 | Flynn et al. |
| 2021/0015801 A1 | 1/2021 | Flynn et al. |
| 2021/0128556 A1 | 5/2021 | Flynn et al. |

FOREIGN PATENT DOCUMENTS

| | | |
|---|---|---|
| WO | WO-2003/30909 A1 | 4/2003 |
| WO | WO-2003/032997 A1 | 4/2003 |
| WO | WO-2006/128129 | 11/2006 |
| WO | WO-2009/122180 A1 | 10/2009 |
| WO | WO-2011/082285 A1 | 7/2011 |
| WO | WO-2013/136070 A1 | 9/2013 |
| WO | WO-2015/039613 A1 | 3/2015 |
| WO | WO-2015/057963 A1 | 4/2015 |
| WO | WO-2016/033100 A1 | 3/2016 |
| WO | WO-2017/156493 A1 | 9/2017 |
| WO | WO-2018/160774 A1 | 9/2018 |
| WO | WO-2019/199864 A1 | 10/2019 |

OTHER PUBLICATIONS

McIver et al., "Synthesis and Structure-Activity Relationships of a Novel Series of Pyrimidines as Potent Inhibitors of TBK1/IKK Kinases," Biorganic & Medicinal Chemistry Letters, 2012, 22: 7169-7173.

International Search Report and Written Opinion for International Application No. PCT/US2020/032090 dated Jun. 29, 2020.

International Search Report and Written Opinion for International Application No. PCT/US2020/037906 dated Aug. 7, 2020.

Lazarus et al., "Discovery and Structure of a New Inhibitor Scaffold of the Autophagy Initiating Kinase ULK1," Bioorg Med Chem., 2015, 23(17): 5483-5488.

PHENYLAMINOPYRIMIDINE AMIDE AUTOPHAGY INHIBITORS AND METHODS OF USE THEREOF

CROSS-REFERENCE TO RELATED APPLICATIONS

This application claims priority to U.S. Ser. No. 62/846,251 filed May 10, 2019, U.S. Ser. No. 62/846,258 filed May 10, 2019, U.S. Ser. No. 62/911,728 filed Oct. 7, 2019, and U.S. Ser. No. 62/911,730 filed Oct. 7, 2019, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 5, 2020, is named DCP-079WO-_SL.txt and is 27,196 bytes in size.

BACKGROUND

Autophagy (literally meaning "self eating") is a process that enables cells to recycle cellular organelles, proteins, stored lipids, glucagon, and other materials for the purpose of generating nutrients under periods of stress. These cellular contents are recycled by engulfment in vesicles called autophagosomes. Autophagosomes subsequently merge with lysosomes that degrade the autophagosomal contents for recycling of nutrients to the cell. Tumor cells are prone to activate autophagy, as these cells have a high metabolic demand, experience cellular stress, and frequently are in hypoxic environments with limited blood flow and nutrient supply. Moreover, chemotherapy and targeted therapies have been shown to induce autophagy as a treatment resistance mechanism, and combination of autophagy inhibition (by genetic loss of function mutations in autophagy genes or by pharmacologic means) with chemotherapeutic regimens has been shown to suppress tumor growth and trigger tumor cell apoptosis to a greater extent than single agent chemotherapy.

Mutant Ras proteins drive approximately 30 percent of all human cancers—including 95 percent of pancreatic cancers and 45 percent of colorectal cancers, and treatment of these mutant Ras cancers is currently an area of high unmet medical need. Mutant Ras cancers are highly proliferative and depend on basal levels of autophagy for survival, suggesting that inhibition of autophagy in these "autophagy addicted" cancers is a viable therapeutic approach.

Currently, the most widely used autophagy inhibitors are chloroquine and hydroxychloroquine, which are well-known anti-malarial agents. These anti-malarials have been thought to block autophagy by being sequestered in the lysosomal compartment, raising the pH of these lysomes and thereby inactivating proteases that degrade and recycle nutrients. These anti-malarial agents have multiple mechanisms of action beyond inhibiting lysosomes and are known to induce retinopathies in patients. Hence there is a need for more targeted agents which selectively block autophagy and do not exhibit the toxicities of these anti-malarial agents. ULK1 kinase is the initiating protein of autophagy and is a serine/threonine kinase. The ULK1 kinase complex is activated in response to cellular stress including nutrient deprivation and energy depletion. Nutrient deprivation activates ULK kinase activity through inhibition of mTORC1, and energy depletion activates ULK kinase activity through activation by AMP-activated protein kinase AMPK. Importantly, kinase dead mutants of ULK kinase block initiation of canonical autophagy, suggesting that small molecule inhibitors of ULK kinase activity would be able to block autophagy.

Further mechanistic studies have shown that genetic deletion of ULK1 inhibits autophagy in cancer cells, relieving FOX3A turn-over and upregulation of the pro-apoptotic protein PUMA. In addition to classical activation of canonical autophagy, ULK1 kinase activity has been shown to be required for Bcl-2-L-13 mediated mitophagy (autophagy of damaged mitochondria). ULK1 and ULK2 kinases have also been demonstrated to rewire cancer cell glucose metabolism. ULK inhibitors may also find utility in blocking these noncanonical protumoral activities of ULK.

Autophagy is also upregulated in host cells and tissues in cancer. Autophagy in pancreatic tissue stellate cells was demonstrated to support tumor growth. Pancreatic stellate cells were shown to support pancreatic cancer tumor metabolism through autophagic alanine secretion. Inhibition of host tissue autophagy was demonstrated to lead to a depletion in circulating arginine (a required amino acid for tumor metabolism and growth) through liver-mediated increases in arginase secretion. Activation of ULK1 kinase was also shown to inactivate the STING pathway in immune cells through inhibitory phosphorylation of STING, mediating a negative feedback mechanism for limiting an innate immune cell response mediated by interferons. Thus, not only is autophagy activated in tumor cells (cancer cell autonomous), but also in other cells in the tumor microenvironment or host tissues (cancer call nonautonomous) to support tumor survival and growth.

Mutant Ras cancers are addicted to autophagy. In pancreatic cancer, mutant Ras signals predominantly through the MAPKAP pathway. Mutant Ras activates RAF kinases, which in turn activate MEK kinases, which finally activate ERK kinases: mutant Ras RAF MEK ERK. Despite mutant Ras signaling through the MAPKAP pathway, inhibitors of this pathway have provided no or little clinical benefit in clinical trials when used as single agents. It has been recently reported that inhibition of the MAPKAP pathway induces autophagy as a compensatory survival mechanism. When MEK inhibitors were combined with the autophagy inhibitor hydroxychloroquine, there was synergistic activity leading to regression of a number of mutant Ras or mutant BRAF cancers. Similarly, when ERK inhibitors were combined with the autophagy inhibitor hydroxychloroquine or chloroquine, there was synergistic activity leading to inhibition of mutant Ras pancreatic cancers. It has been demonstrated that genetic depletion of RAF kinases (CRAF and BRAF) led to synergistic anti-tumor activity in mutant Ras cancer cell lines when autophagy was also genetically depleted. In composite, recent publications highlight that dual inhibition of the MAPKAP pathway and the autophagy pathway in mutant Ras cancers is a promising treatment regimen for patients with mutant Ras cancers. It has also been demonstrated that other targeted therapies and chemotherapeutic agents activate tumor autophagy as a resistance mechanism; hence there is rationale for combining such targeted therapeutics or chemotherapeutic agents with inhibitors of autophagy.

Mutations in the gene encoding LRRK2 kinase are causative of Parkinson's disease. LRRK2 point mutations are found in both familial (inherited) as well as sporadic Parkinson's disease patients. The most common mutation of LRRK2 in Parkinson's disease is LRRK2 G2019S. These mutations in LRRK2 are gain-of-function mutations that cause overactivation of LRRK2 signaling. Ongoing autophagy is a process that is used by brain neuronal cells to maintain health and homeostasis. Autophagy is a process by which cells identify, localize, and destroy aged organelles and structural elements within cells, and particularly in the case of proteins known to aggregate in neurons, autophagy eliminates such toxic protein aggregates to maintain neuronal health. LRRK2 activity suppresses autophagy, and the LRRK2 G2019S gain-of-function mutant even more so suppresses autophagy and has been linked to aggressive forms of Parkinson's disease.

Increased LRRK2 kinase activity has also been linked to immunoinflammatory diseases including colitis and Crohn's disease and inflammatory bowel disease. In the gastrointestinal tract, LRRK2 is present in antigen-presenting cells including dendritic cells. LRRK2 activity has been shown to be important in Dectin-1 mediated innate immune responses, including an activation of the NFkB pathway and increased TNF-alpha production in dendritic cells of patients with Crohn's disease.

Inhibitors of LRRK2 are sought for the treatment of neurodegenerative diseases including Parkinson's disease, and also are sought for the treatment of gastrointestinal diseases including Crohn's disease, ulcerative colitis, and inflammatory bowel disease.

There is a need for new targeted therapies which inhibit autophagy and can be used in combination with MAPKAP pathway inhibitors, chemotherapeutic agents, and/or other targeted therapeutics.

SUMMARY

Described herein are compounds that are inhibitors of autophagy, pharmaceutical compositions, and their use as agents in the treatment of disorders such as cancer, processes for their preparation, and pharmaceutical compositions containing them as an active ingredient. Such pharmaceutical compositions may comprise the compound as the sole active agent or in combination with other active agents in the presence of a pharmaceutically acceptable excipient. In an embodiment, the described compounds are inhibitors of ULK kinase activity, including ULK1 and ULK2 activity.

For example, compounds provided herein may be described as represented by Formula (I)

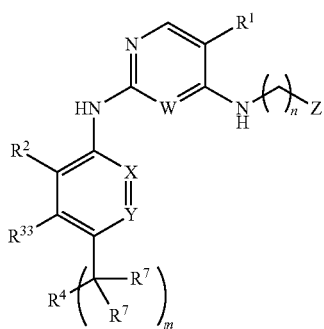

Formula I or a pharmaceutically acceptable salt, enantiomer, stereoisomer, or tautomer thereof, wherein: W is CH or N; X is CH or N; Y is $C(R^3)$ or N; $R^1$ is selected from the group consisting of halogen, cyano, $C_1$-$C_5$alkyl, and $C_3$-$C_5$cycloalkyl, wherein each $C_1$-$C_5$alkyl and $C_3$-$C_5$cycloalkyl may be optionally substituted by one, two or three independent occurrences of fluorine; $R^2$ is selected from the group consisting of H, halogen, cyano, $C_1$-$C_5$alkyl, $C_3$-$C_6$cycloalkyl, $C_2$-$C_5$alkenyl, $C_2$-$C_5$alkynyl, $C_1$-$C_5$alkoxy, and $C_1$-$C_5$alkoxy-$C_2$-$C_5$alkyl, wherein each $C_1$-$C_5$alkyl, $C_3$-$C_6$cycloalkyl, $C_2$-$C_5$alkenyl, $C_2$-$C_5$alkynyl, and $C_1$-$C_5$alkoxy may be optionally substituted by one, two, or three independent occurrences of fluorine or cyano; each occurrence of $R^3$ and $R^{33}$ is independently selected from the group consisting of H, halogen, $C_1$-$C_6$alkyl, and $C_1$-$C_6$alkoxy, wherein each $C_1$-$C_6$alkyl and $C_1$-$C_6$alkoxy may be optionally substituted by one or more independent occurrences of fluorine; $R^4$ is selected from the group consisting of B, D, $NR^6R^9$, $NR^6$—$C(R^{10})_2)_p$—$NR^9R^9$, $C(O)$—$NR^6R^9$; $C(O)$—B; $C(O)$-D, and CN; B is selected from an N-linked heterocyclyl having at least one nitrogen and optionally having an additional ring nitrogen or oxygen and heteroaryl, wherein B may be optionally substituted on one or more available carbons by $R^7$ and may be optionally substituted on an available nitrogen by $R^9$; D is selected from a C-linked heterocyclyl having at least one nitrogen and optionally having an additional ring nitrogen or oxygen and heteroaryl, wherein D may be optionally substituted on one or more available carbons by $R^7$ and may be optionally substituted on an available nitrogen by $R^9$; each occurrence of $R^5$ is independently selected from the group consisting of H, $C_1$-$C_6$alkyl, $C_3$-$C_6$cycloalkyl, and heterocyclyl, wherein each $C_1$-$C_6$alkyl and $C_3$-$C_6$cycloalkyl may be optionally substituted by one or more independent occurrences of fluorine; each occurrence of $R^7$ is independently selected from the group consisting of H, $C_1$-$C_6$alkyl, $C_3$-$C_6$cycloalkyl, cyano, and) $(C(R^{10})_2)_h$—$NR^9R^9$ wherein each $C_1$-$C_6$alkyl and $C_3$-$C_6$cycloalkyl may be optionally substituted by one or more independent occurrences of fluorine, or two $R^7$ are joined together with the atom to which they are attached to form oxo; each occurrence of $R^6$ and $R^9$ is independently selected from the group consisting of H, $C_1$-$C_6$alkyl, $C_3$-$C_6$cycloalkyl, $C_1$-$C_5$alkoxy-$C_2$-$C_5$alkyl, $C(=O)R^5$, $SO_2R^5$, and D, wherein each $C_1$-$C_6$alkyl and $C_3$-$C_6$cycloalkyl may be optionally substituted by one or more independent occurrences of fluorine; each occurrence of $R^{10}$ is independently selected from the group consisting of H, $C_1$-$C_3$alkyl, and $C_3$-$C_5$cycloalkyl, wherein each $C_1$-$C_3$alkyl and $C_3$-$C_5$cycloalkyl may be optionally substituted by one or more independent occurrences of fluorine, or two $R^{10}$ are joined together with the carbon to which they are attached to form a $C_3$-$C_5$cycloalkyl; Z is selected from the group consisting of a 4 membered lactam ring bound through the nitrogen atom or a 6-10 membered lactam ring bound through the nitrogen atom, wherein a lactam ring atom may optionally be oxygen or $NR^6$ when the lactam ring is a 6-10 membered ring and an available carbon atom on 4 membered lactam ring or a 6-10 membered lactam is optionally substituted by $R^{36}$; each occurrence of $R^{36}$ is independently selected from $C_1$-$C_6$alkyl and $C_3$-$C_6$cycloalkyl, wherein each $C_1$-$C_6$alkyl and $C_3$-$C_6$cycloalkyl may be optionally substituted by one or more independent occurrences of fluorine, or two $R^{36}$ are joined together with the carbon to which they are attached to form a $C_3$-$C_6$cycloalkyl; h is 1, 2, or 3; m is 0, 1, 2, or 3; n is 2, 3, or 4; and p is 2 or 3; provided that both X and Y are not N.

DETAILED DESCRIPTION

The features and other details of the disclosure will now be more particularly described. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

The term "alkyl" as used herein refers to a saturated straight or branched hydrocarbon. Exemplary alkyl groups include, but are not limited to, straight or branched hydrocarbons of 1-6, 1-5, 1-4, 1-3, or 1-2 carbon atoms, referred to herein as $C_1$-$C_6$alkyl, $C_1$-$C_5$alkyl, $C_1$-$C_4$alkyl, $C_1$-$C_3$alkyl, and $C_1$-$C_2$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_2$-$C_6$alkenyl, and $C_3$-$C_4$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_1$-$C_6$alkoxy, and $C_2$-$C_6$alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_1$-$C_6$alkoxy-$C_1$-$C_6$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_2$-$C_6$alkynyl, and $C_3$-$C_6$alkynyl, respectively. Exemplary alkynyl groups include, but are not limited to, ethynyl, propynyl, butynyl, pentynyl, hexynyl, methylpropynyl, etc.

The term "cyano" as used herein refers to the radical —CN.

The terms "cycloalkyl" or a "carbocyclic group" as used herein refers to a saturated or partially unsaturated hydrocarbon group of, for example, 3-6, or 4-6 carbons, referred to herein as $C_3$-$C_6$cycloalkyl or $C_4$-$C_6$cycloalkyl, respectively. Exemplary cycloalkyl groups include, but are not limited to, cyclohexyl, cyclopentyl, cyclopentenyl, cyclobutyl or cyclopropyl.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_3$-$C_6$cycloalkoxy groups. Exemplary cycloalkoxy groups include, but are not limited to, cyclopropoxy, cyclobutoxy, cyclopentoxy, cyclohexyloxy, etc.

The terms "halo" or "halogen" as used herein refer to F, Cl, Br, or I.

The term "heteroaryl" as used herein refers to a monocyclic aromatic 5 or 6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to saturated or partially unsaturated, 4-10 membered ring structures, including monocyclic, bridged or fused rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

As used herein, the term "lactam" refers to cyclic amides of amino carboxylic acids, having a 1-azacycloalkan-2-one structure, or analogues having unsaturation or heteroatoms replacing one or more carbon atoms of the ring. An "alpha-lactam," refers to a lactam comprised of a 3-membered ring. A "beta-lactam," refers to a lactam comprised of a 4-membered ring. A "gamma-lactam," refers to a lactam comprised of a 5-membered ring. A "delta-lactam," refers to a lactam comprised of a 6-membered ring. An "epsilon-lactam," refers to a lactam comprised of a 7-membered ring.

The term "oxo" as used herein refers to the radical =O.

A "combination therapy" is a treatment that includes the administration of two or more therapeutic agents, e.g., a compound of Formula I and a MAPKAP pathway inhibitor, to a patient in need thereof.

"Disease," "disorder," and "condition" are used interchangeably herein.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

A "MAPKAP pathway inhibitor" is an inhibitor of the MAP kinase signaling pathway. Inhibitors of this pathway include Ras inhibitors (e.g. AMG-510, MRTX 849), RAF inhibitors (e.g. dabrafenib, vemurafenib, LY3009120), MEK inhibitors (e.g. trametinib, binimetinib, selumetinib, cobimetinib), and ERK inhibitors (e.g. ulixertinib, SCH772984, LY3214996). The terms "MAPKAP pathway inhibitor" and "MAPKAP kinase inhibitor are used interchangeably herein.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The presently described compounds encompasses various stereoisomers of these compounds and mixtures thereof. Mixtures of enantiomers or diastereomers may be designated "(±)" in nomenclature, but the skilled artisan will recognize that a structure may denote a chiral center implicitly.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds described herein are administered in therapeutically effective amounts to treat a disorder.

"Treating" includes any effect, e.g., lessening, reducing, modulating, or eliminating, that results in the improvement of the condition, disease, disorder and the like.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more H atom replaced with deuterium.

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

Compounds

Described herein is a compound represented by Formula I:

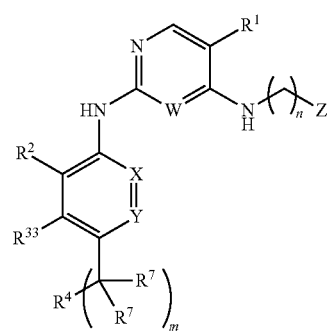

Formula I or a pharmaceutically acceptable salt, enantiomer, stereoisomer, or tautomer thereof, wherein: W is CH or N; X is CH or N; Y is C($R^3$) or N; $R^1$ is selected from the group consisting of halogen, cyano, $C_1$-$C_5$alkyl, and $C_3$-$C_5$cycloalkyl, wherein each $C_1$-$C_5$alkyl and $C_3$-$C_5$cycloalkyl may be optionally substituted by one, two or three independent occurrences of fluorine; $R^2$ is selected from the group consisting of H, halogen, cyano, $C_1$-$C_5$alkyl, $C_3$-$C_6$cycloalkyl, $C_2$-$C_5$alkenyl, $C_2$-$C_5$alkynyl, $C_1$-$C_5$alkoxy, and $C_1$-$C_5$alkoxy-$C_2$-$C_5$alkyl, wherein each $C_1$-$C_5$alkyl, $C_3$-$C_6$cycloalkyl, $C_2$-$C_5$alkenyl, $C_2$-$C_5$alkynyl, and $C_1$-$C_5$alkoxy may be optionally substituted by one, two, or three independent occurrences of fluorine or cyano; each occurrence of $R^3$ and $R^{33}$ is independently selected from the group consisting of H, halogen, $C_1$-$C_6$alkyl, and $C_1$-$C_6$alkoxy, wherein each $C_1$-$C_6$alkyl and $C_1$-$C_6$alkoxy may be optionally substituted by one or more independent occurrences of fluorine; $R^4$ is selected from the group consisting of B, D, $NR^6R^9$, $NR^6$—$(C(R^{10})_2)_p$—$NR^9R^9$, $C(O)$—$NR^6R^9$; $C(O)$—B; $C(O)$-D, and CN; B is selected from an N-linked heterocyclyl having at least one nitrogen and optionally having an additional ring nitrogen or oxygen and heteroaryl, wherein B may be optionally substituted on one or more available carbons by $R^7$ and may be optionally substituted on an available nitrogen by $R^9$; D is selected from a C-linked heterocyclyl having at least one nitrogen and optionally having an additional ring nitrogen or oxygen and heteroaryl, wherein D may be optionally substituted on one or more available carbons by $R^7$ and may be optionally substituted on an available nitrogen by $R^9$; each occurrence of $R^5$ is independently selected from the group consisting of H, $C_1$-$C_6$alkyl, $C_3$-$C_6$cycloalkyl, and heterocyclyl, wherein each $C_1$-$C_6$alkyl and $C_3$-$C_6$cycloalkyl may be optionally substituted by one or more independent occurrences of fluorine; each occurrence of $R^7$ is independently selected from the group consisting of H, $C_1$-$C_6$alkyl, $C_3$-$C_6$cycloalkyl, cyano, and) $(C(R^{10})_2)_h$—$NR^9R^9$, wherein each $C_1$-$C_6$alkyl and $C_3$-$C_6$cycloalkyl may be optionally substituted by one or more independent occurrences of fluorine, or two $R^7$ are joined together with the atom to which they are attached to form oxo; each occurrence of $R^6$ and $R^9$ is independently selected from the group consisting of H, $C_1$-$C_6$alkyl, $C_3$-$C_6$cycloalkyl, $C_1$-$C_5$alkoxy-$C_2$-$C_5$alkyl, $C(=O)R^5$, $SO_2R^5$, and D, wherein each $C_1$-$C_6$alkyl and $C_3$-$C_6$cycloalkyl may be optionally substituted by one or more independent occurrences of fluorine; each occurrence of $R^{10}$ is independently selected from the group consisting of H, $C_1$-$C_3$alkyl, and $C_3$-$C_5$cycloalkyl, wherein each $C_1$-$C_3$alkyl and $C_3$-$C_5$cycloalkyl may be optionally substituted by one or more independent occurrences of fluorine, or two $R^{10}$ are joined together with the carbon to which they are attached to form a $C_3$-$C_5$cycloalkyl; Z is selected from the group consisting of a 4 membered lactam ring bound through the nitrogen atom or a 6-10 membered lactam ring bound through the nitrogen atom, wherein a lactam ring atom may optionally be oxygen or $NR^6$ when the lactam ring is a 6-10 membered ring and an available carbon atom on 4 membered lactam ring or a 6-10 membered lactam is optionally substituted by $R^{36}$; each occurrence of $R^{36}$ is independently selected from $C_1$-$C_6$alkyl and $C_3$-$C_6$cycloalkyl, wherein each $C_1$-$C_6$alkyl and $C_3$-$C_6$cycloalkyl may be optionally substituted by one or more independent occurrences of fluorine, or two $R^{36}$ are joined together with the carbon to which they are attached to form a $C_3$-$C_6$cycloalkyl; h is 1, 2, or 3; m is 0, 1, 2, or 3; n is 2, 3, or 4; and p is 2 or 3; provided that both X and Y are not N.

In some embodiments, W is N. In some embodiments, X is CH and Y is N. In some embodiments, X is CH and Y is $C(R^3)$.

In some embodiments, Z is selected from:

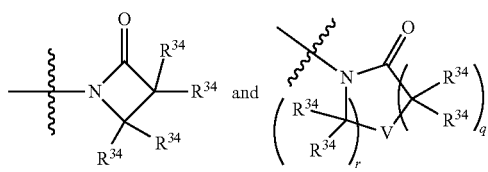

wherein V is selected from the group consisting of oxygen, $CH_2$, and $NR^6$; each occurrence of $R^{34}$ is independently selected from H and $R^{36}$, wherein each occurrence of $R^{36}$ is independently selected from $C_1$-$C_6$alkyl and $C_3$-$C_6$cycloalkyl, or two $R^{36}$ are joined together with the carbon to which they are attached to form a $C_3$-$C_6$cycloalkyl; q is 0, 1, 2, or 3; and r is 2 or 4, provided that, if q is 0, then r is not 2.

In some embodiments, Z is selected from:

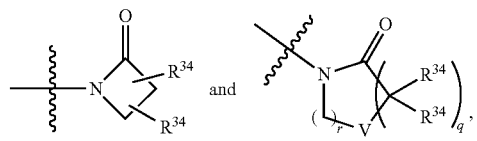

wherein V is selected from the group consisting of oxygen, $C(R^{34})_2$, and $NR^6$; each occurrence of $R^{34}$ is independently selected from H and $R^{36}$, wherein each occurrence of $R^{36}$ is independently selected from $C_1$-$C_6$alkyl and $C_3$-$C_6$cycloalkyl, or two $R^{36}$ are joined together with the carbon to which they are attached to form a $C_3$-$C_6$cycloalkyl; q is 0, 1, 2, or 3; and r is 2 or 3, provided that, if q is 0, then r is not 2.

In some embodiments, Z is selected from the group consisting of:

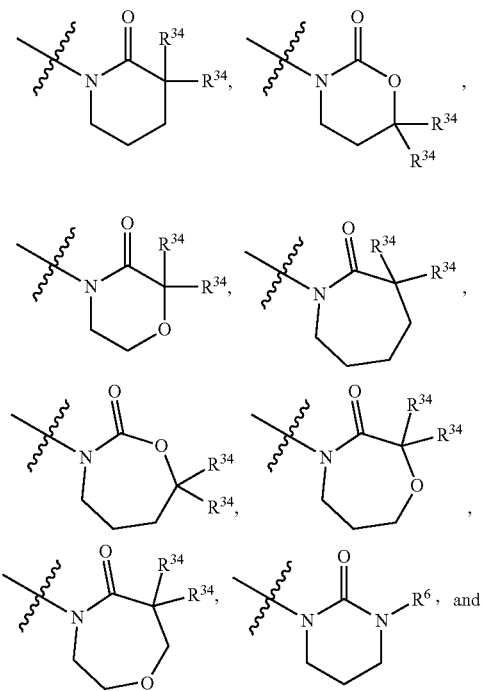

In some embodiments, Z is selected from:
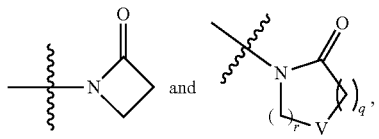
wherein V is selected from the group consisting of oxygen, CH$_2$, and NR$^6$; q is 0, 1, 2, or 3; and r is 2 or 3, provided that, if q is 0, then r is not 2.
In some embodiments, Z is selected from the group consisting of:
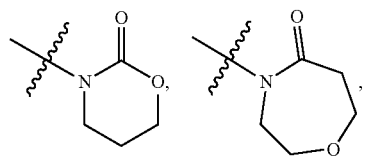
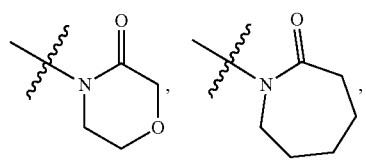
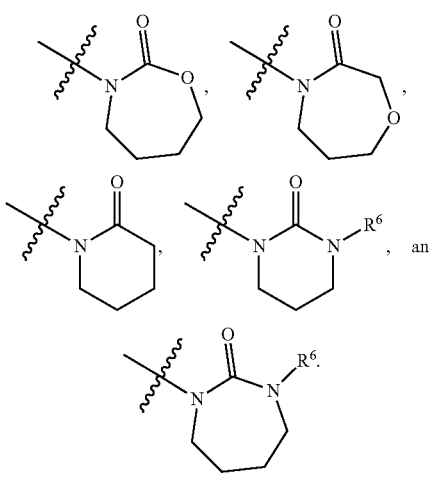
In some embodiments, R$^4$ is B.
In some embodiments, R$^4$ is selected from the group consisting of:
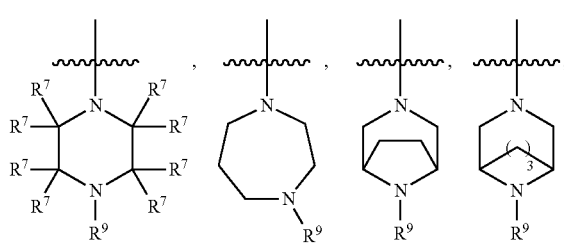
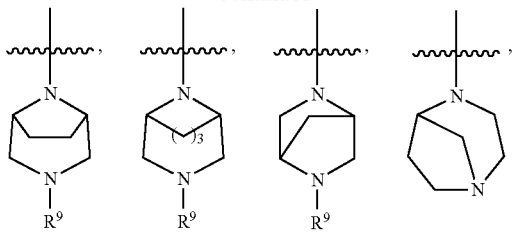
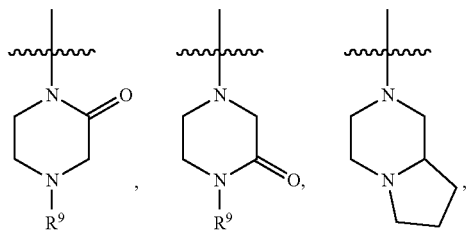
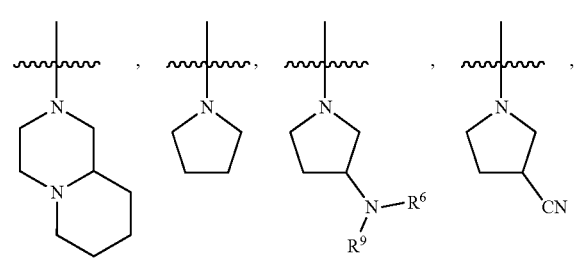
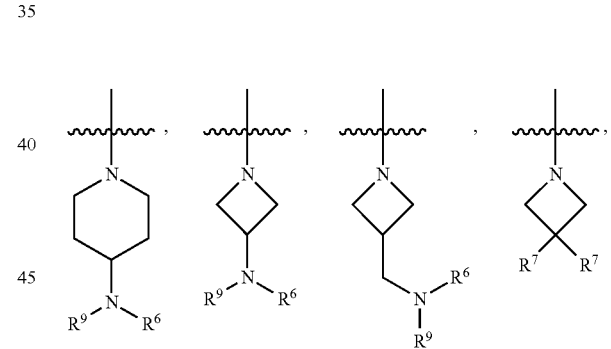
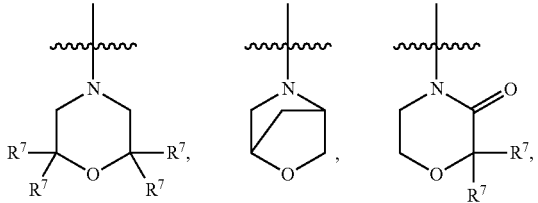
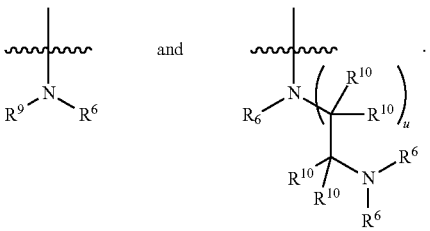
wherein u is 1 or 2.

In some embodiments, $R^4$ is selected from the group consisting of:

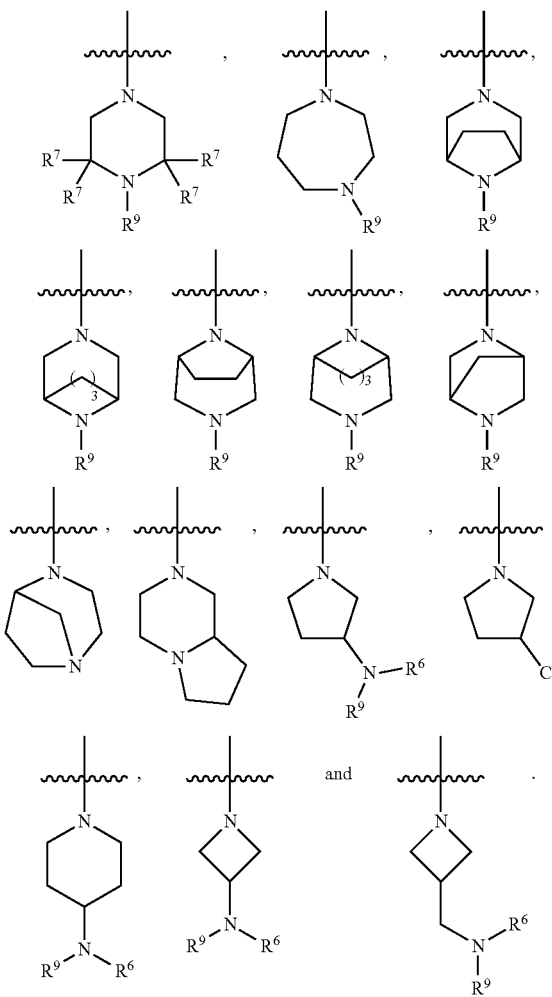

In some embodiments, $R^4$ is selected from the group consisting of:

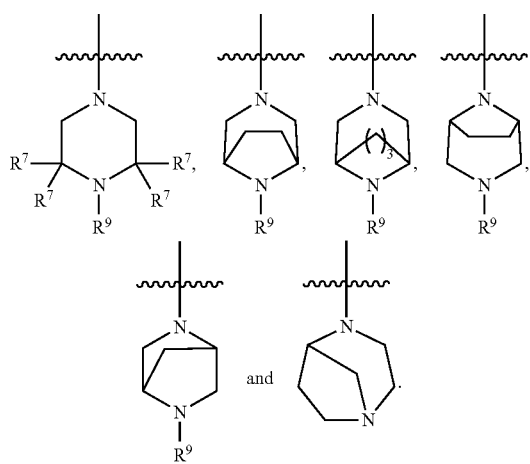

In some embodiments, $R^4$ is selected from the group consisting of:

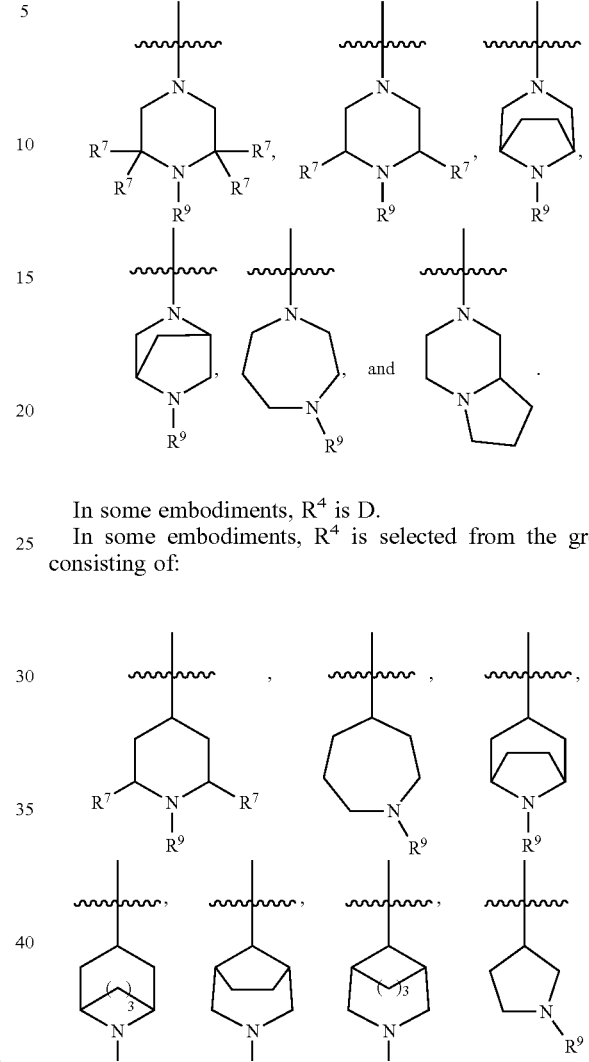

In some embodiments, $R^4$ is D.

In some embodiments, m is 0. In some embodiments, m is 1. In some embodiments, m is 2. In some embodiments, m is 3.

In some embodiments, $R^1$ is selected from the group consisting of halogen, $C_1$-$C_5$alkyl, and $C_3$-$C_5$cycloalkyl, wherein $C_1$-$C_5$alkyl may be optionally substituted with one, two, or three occurrences of fluorine. In some embodiments, $R^1$ is $CF_3$. In some embodiments, $R^1$ is $CF_2H$. In some embodiments, $R^1$ is halogen. In some embodiments, $R^1$ is bromo. In some embodiments, $R^1$ is cyclopropyl.

In some embodiments, $R^2$ is selected from the group consisting of H, $C_3$-$C_5$cycloalkyl, $C_1$-$C_5$alkyl, halogen, CN, $C_2$-$C_5$alkenyl, and $C_2$-$C_5$alknyl, wherein $C_1$-$C_5$alkyl may be optionally substituted with one, two, or three independent occurrences of fluorine. In some embodiments, $R^2$ is selected from the group consisting of $C_{1-2}$alkyl and $C_{3-4}$cycloalkyl. In some embodiments, $R^2$ is selected from the group consisting of chloro and bromo.

In some embodiments, $R^2$ is selected from the group consisting of $C_1$-$C_5$alkyl, H, and $C_3$-$C_4$cycloalkyl. In some embodiments, $R^2$ is selected from the group consisting of $C_1$-$C_2$alkyl and $C_3$-$C_4$cycloalkyl. In some embodiments, $R^2$ is selected from the group consisting of chloro and bromo.

In some embodiments, n is 3.

In some embodiments, the compound is represented by Formula II:

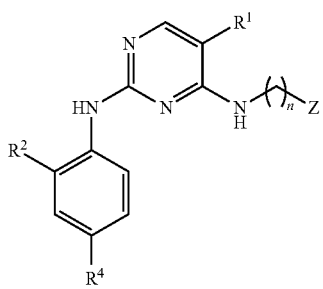

Formula II or a pharmaceutically acceptable salt thereof, wherein: n is 2, 3, or 4; $R^1$ is selected from the group consisting of halogen, cyano, $C_1$-$C_5$alkyl, and $C_3$-$C_5$cycloalkyl, wherein each $C_1$-$C_5$alkyl and $C_3$-$C_5$cycloalkyl may be optionally substituted by one, two or three independent occurrences of fluorine; $R^2$ is selected from the group consisting of halogen, $C_1$-$C_2$alkyl and $C_3$-$C_4$cycloalkyl; $R^4$ is selected from the group consisting of:

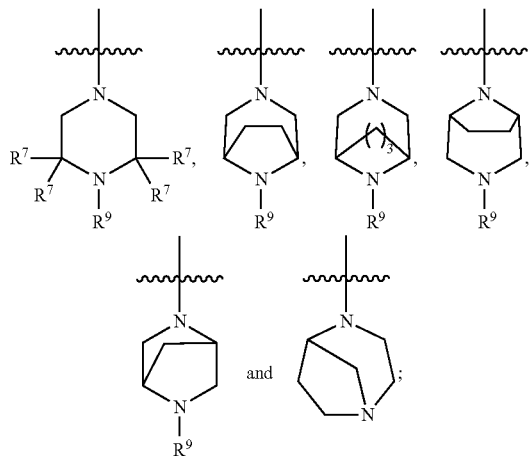

each occurrence of $R^6$ and $R^9$ is independently selected from the group consisting of H, $C_1$-$C_6$alkyl, $C_3$-$C_6$cycloalkyl, $C(=O)R^5$, $SO_2R^5$, and D, wherein each $C_1$-$C_6$alkyl and $C_3$-$C_6$cycloalkyl may be optionally substituted by one or more independent occurrences of fluorine; each occurrence of $R^5$ is independently selected from the group consisting of H, $C_1$-$C_6$alkyl, $C_3$-$C_6$cycloalkyl, and heterocyclyl, wherein each $C_1$-$C_6$alkyl and $C_3$-$C_6$cycloalkyl may be optionally substituted by one or more independent occurrences of fluorine; each occurrence of $R^7$ is independently selected from the group consisting of H, $C_1$-$C_6$ alkyl, and $C_3$-$C_6$cycloalkyl, wherein each $C_1$-$C_6$alkyl and $C_3$-$C_6$cycloalkyl may be optionally substituted by one or more independent occurrences of fluorine, or two $R^7$ are joined together with the atom to which they are attached to form oxo; D is selected from a C-linked heterocyclyl having at least one nitrogen and optionally having an additional ring nitrogen or oxygen and heteroaryl, wherein D may be optionally substituted on one or more available carbons by $R^7$ and may be optionally substituted on an available nitrogen by $R^9$; Z is selected from the group consisting of:

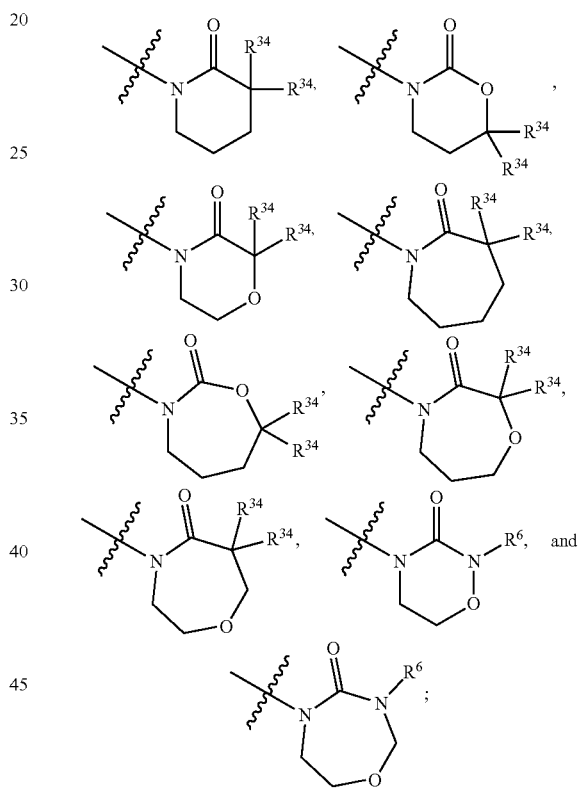

and each occurrence of $R^{34}$ is independently selected from H and $R^{36}$, wherein each occurrence of $R^{36}$ is independently selected from $C_1$-$C_6$alkyl and $C_3$-$C_6$cycloalkyl, wherein each $C_1$-$C_6$alkyl and $C_3$-$C_6$cycloalkyl may be optionally substituted by one or more independent occurrences of fluorine, or two $R^{36}$ are joined together with the carbon to which they are attached to form a $C_3$-$C_6$cycloalkyl.

In some embodiments, $R^1$ is selected from the group consisting of halogen, $C_1$-$C_5$alkyl, and $C_3$-$C_5$cycloalkyl, wherein $C_1$-$C_5$alkyl may be optionally substituted with one, two, or three occurrences of fluorine, and $C_3$-$C_5$cycloalkyl. In some embodiments, $R^1$ is $CF_3$. In some embodiments, $R^1$ is $CF_2H$. In some embodiments, $R^1$ is halogen. In some embodiments, $R^1$ is bromo. In some embodiments, $R^1$ is cyclopropyl.

In some embodiments, $R^2$ is selected from the group consisting of H, $C_3$-$C_4$cycloalkyl, $C_1$-$C_5$alkyl, and halogen.

In some embodiments, $R^2$ is selected from the group consisting of $C_1$-$C_2$alkyl, $C_3$-$C_4$cycloalkyl, bromo, and chloro.

In some embodiments, $R^4$ is selected from the group consisting of:

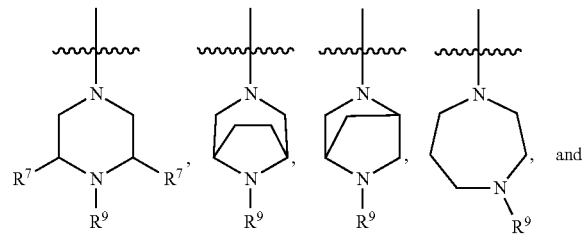

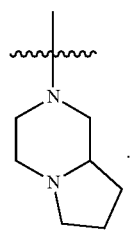

In some embodiments, $R^4$ is selected from the group consisting of:

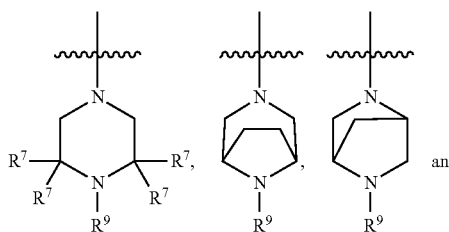

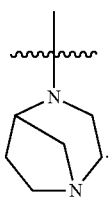

In some embodiments, each $R^6$ and $R^9$ is independently selected from the group consisting of H, $C_1$-$C_6$alkyl, and $C_3$-$C_6$cycloalkyl, wherein each of $C_1$-$C_6$alkyl and $C_3$-$C_6$cycloalkyl is optionally substituted by one or more independent occurrences of fluorine.

In some embodiments, $R^7$ is H.

In some embodiments, each occurrence of $R^{34}$ is independently selected from the group consisting of H and $C_1$-$C_5$alkyl, wherein $C_1$-$C_5$alkyl may be optionally substituted by one, two, or three independent occurrences of fluorine. In some embodiments, two $R^{34}$ are joined together with the carbon to which they are attached to form $C_3$-$C_6$cycloalkyl.

In some embodiments, Z is selected from the group consisting of:

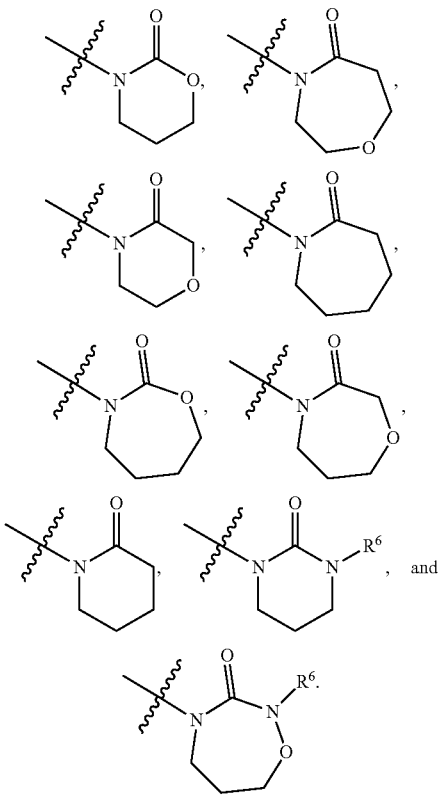

In some embodiments, Z is selected from the group consisting of:

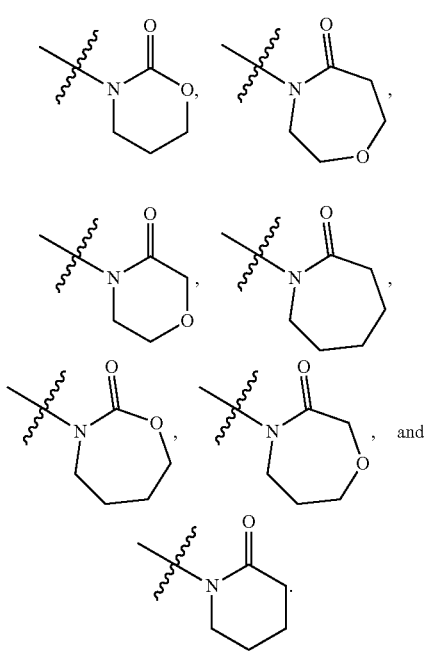

In some embodiments, n is 3.

In an embodiment, the compound is represented by a formula selected from the group consisting of:
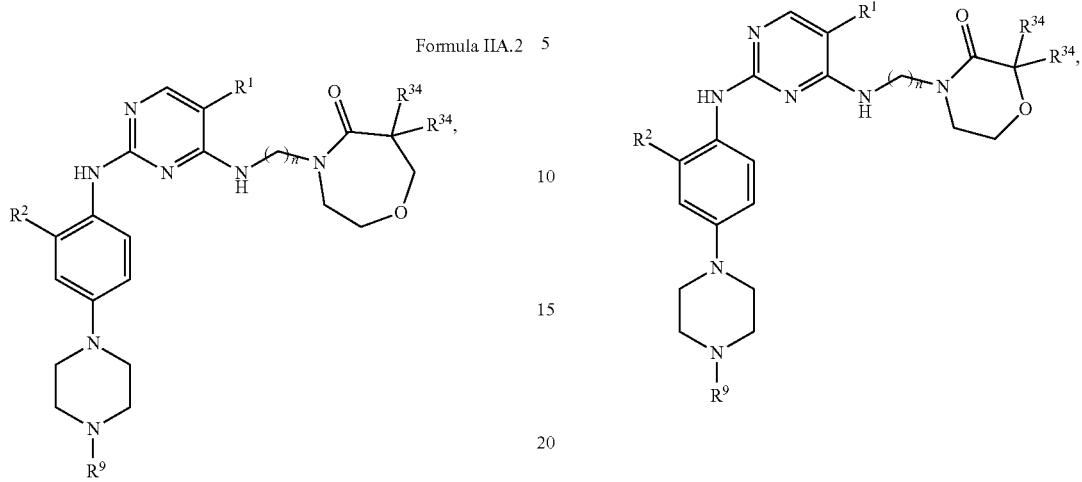
Formula IIA.2
Formula IIA.3
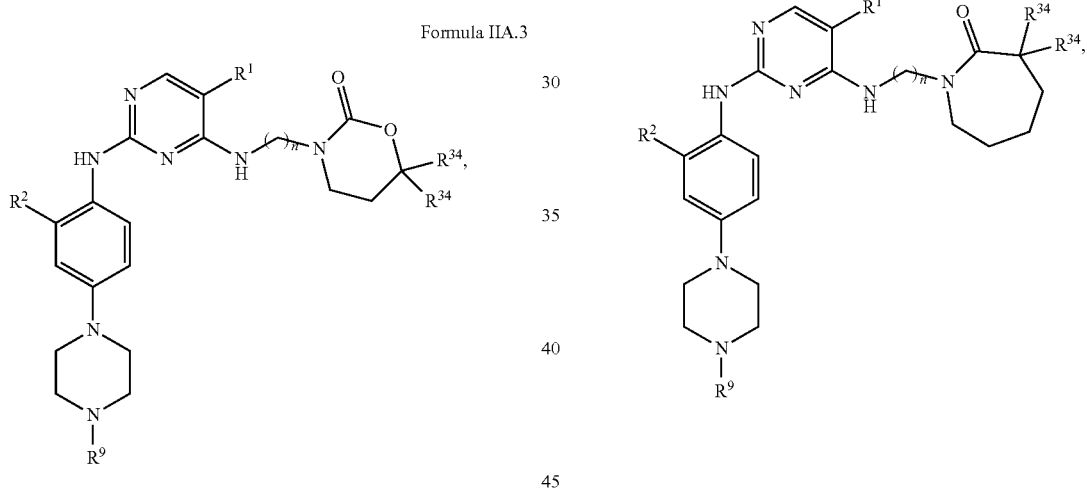
Formula IIA.4
Formula IIA.5
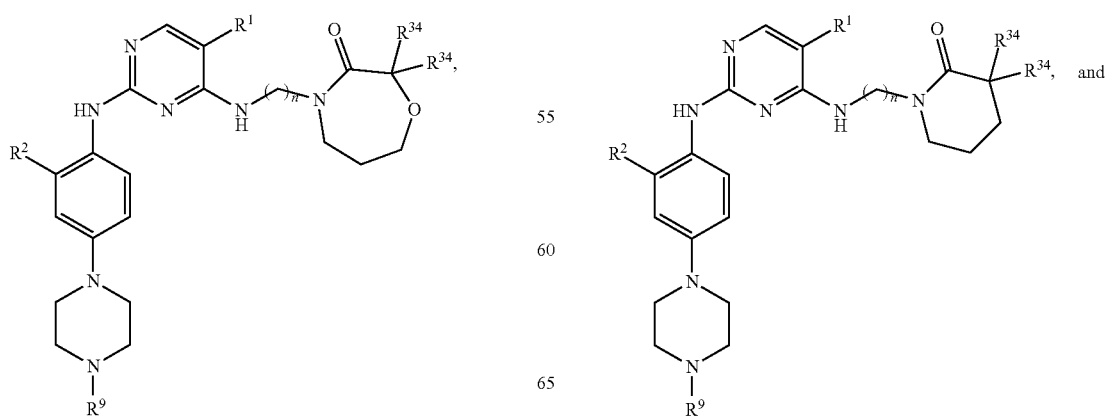
Formula IIA.6
Formula IIA.7

-continued

Formula IIA.8

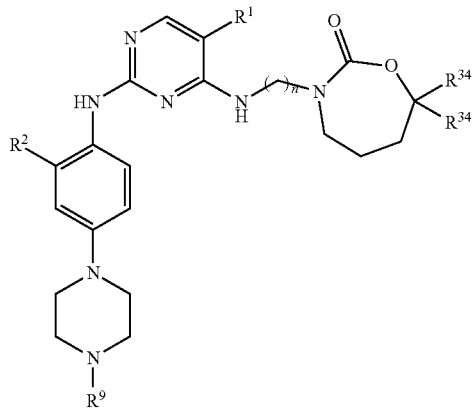

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^9$ is independently selected from the group consisting of H, $C_1$-$C_3$alkyl, and $C_3$-$C_5$cycloalkyl; each occurrence of $R^{34}$ is selected from the group consisting of H, $C_1$-$C_2$alkyl, and $C_3$-$C_5$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each occurrence of $R^{34}$ is independently selected from the group consisting of H and $C_1$-$C_2$alkyl; and n is 3. In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each $R^{34}$ is H; and n is 3.

In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each occurrence of $R^{34}$ is independently selected from the group consisting of H and $C_1$-$C_2$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^9$ is independently selected from H and $C_1$-$C_3$alkyl; each $R^{34}$ is H; and n is 3.

In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each occurrence of $R^{34}$ is independently selected from the group consisting of H and $C_1$-$C_2$alkyl; and n is 3 In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each $R^{34}$ is H; and n is 3.

In some embodiments, the compound is represented by a formula selected from the group consisting of:

Formula IIA.9

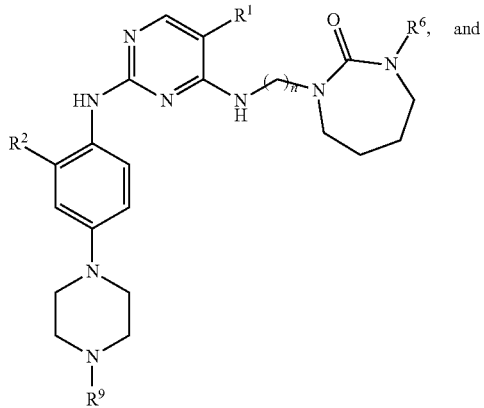

Formula IIA.10

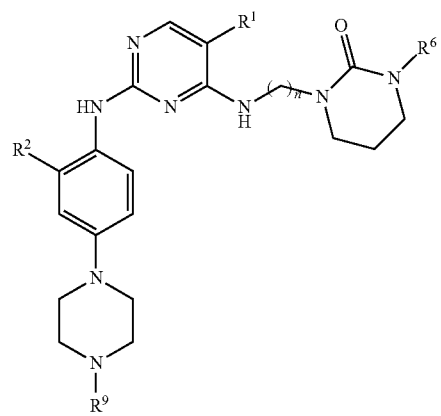

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^6$ is independently selected from $C_1$-$C_3$alkyl and $C_3$-$C_4$cycloalkyl; each occurrence of $R^9$ is independently selected from the group consisting of H, $C_1$-$C_3$alkyl, and $C_3$-$C_5$cycloalkyl; and n is 3.

In some embodiments, each occurrence of $R^1$ is bromo; each occurrence of $R^2$ is independently selected from the group consisting of $C_1$-$C_2$alkyl, $C_3$-$C_4$cycloalkyl, bromo, and chloro; each occurrence of $R^6$ is selected from $C_1$-$C_3$alkyl and $C_3$-$C_4$cycloalkyl; each occurrence of $R^9$ is selected from H and $C_1$-$C_3$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; each occurrence of $R^9$ is independently selected from H and $C_1$-$C_3$alkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; each occurrence of $R^9$ is independently selected from H and $C_1$-$C_3$alkyl; and n is 3.

In an embodiment, the compound is represented by a formula selected from the group consisting of:
Formula IIA.11
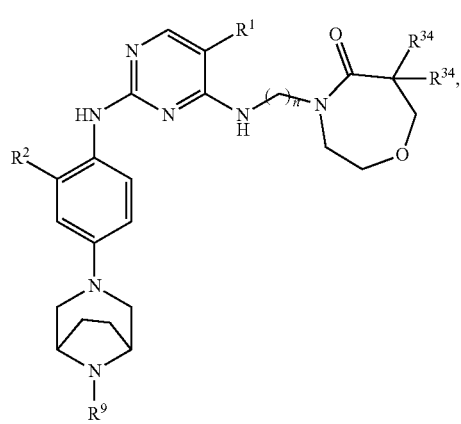
Formula IIA.12
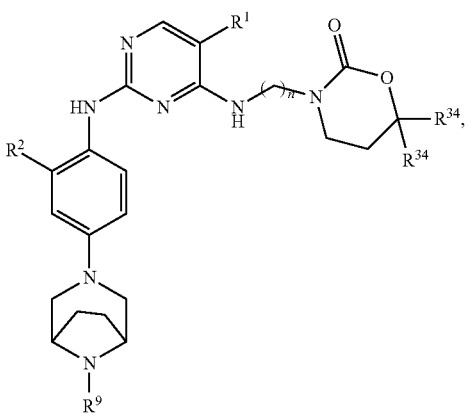
Formula IIA.13
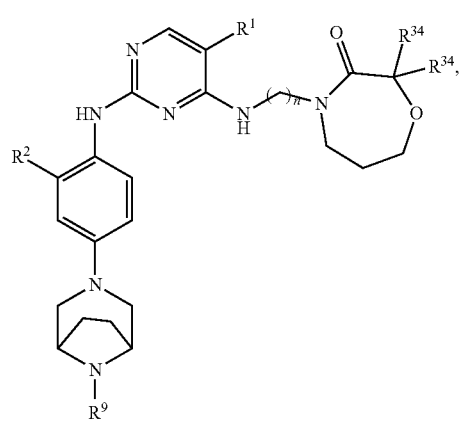
Formula IIA.14
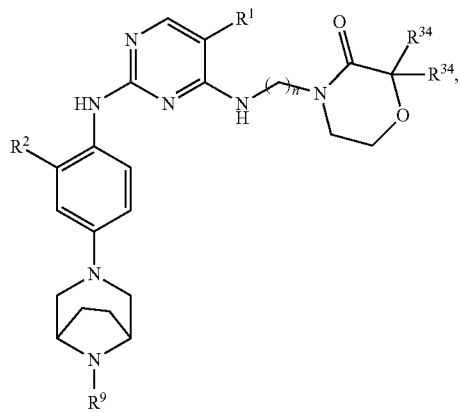
Formula IIA.15
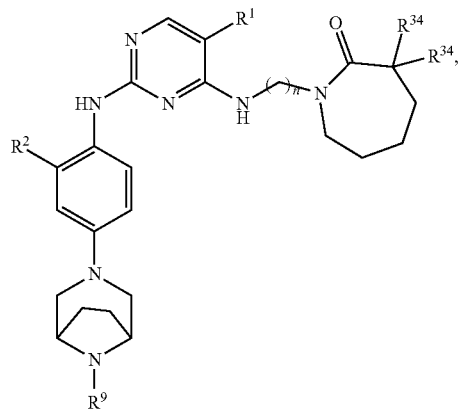
Formula IIA.16
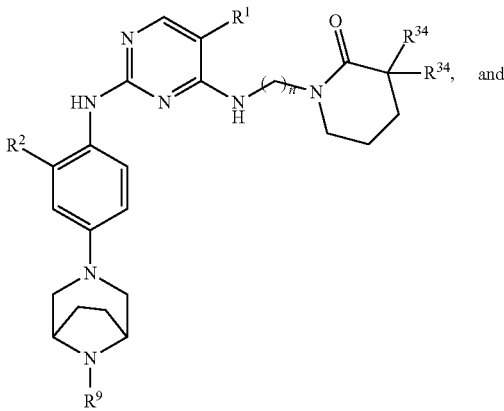
and Formula IIA.17

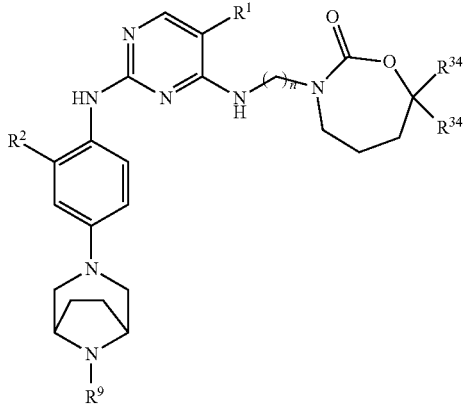

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^9$ is independently selected from the group consisting of H, $C_1$-$C_3$alkyl, and $C_3$-$C_5$cycloalkyl; each occurrence of $R^{34}$ is selected from the group consisting of H, $C_1$-$C_2$alkyl, and $C_3$-$C_5$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each occurrence of $R^{34}$ is independently selected from the group consisting of H and $C_1$-$C_2$alkyl; and n is 3. In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each $R^{34}$ is H; and n is 3.

In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^9$ is independently selected from H and $C_1$-$C_3$alkyl; each occurrence of $R^{34}$ is independently selected from the group consisting of H and $C_1$-$C_2$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^9$ is independently selected from H and $C_1$-$C_3$alkyl; each $R^{34}$ is H; and n is 3.

In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each occurrence of $R^{34}$ is independently selected from the group consisting of H and $C_1$-$C_2$alkyl; and n is 3 In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each $R^{34}$ is H; and n is 3.

In some embodiments, the compound is represented by a formula selected from the group consisting of:

Formula IIA.18

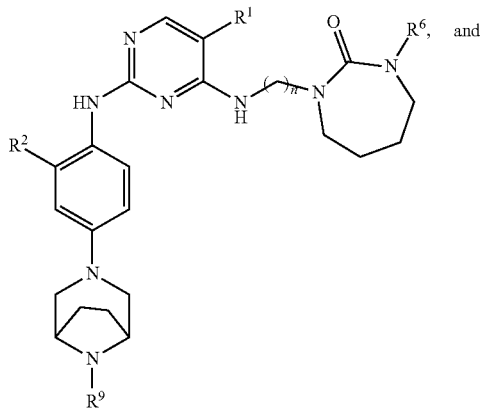

and

Formula IIA.19

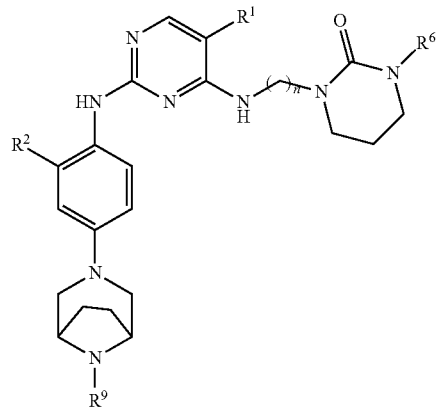

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^6$ is independently selected from $C_1$-$C_3$alkyl and $C_3$-$C_4$cycloalkyl; each occurrence of $R^9$ is independently selected from the group consisting of H, $C_1$-$C_3$alkyl, and $C_3$-$C_5$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^6$ is selected from $C_1$-$C_3$alkyl and $C_3$-$C_4$cycloalkyl; each occurrence of $R^9$ is selected from H and $C_1$-$C_3$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^6$ is independently selected from the group consisting of $C_1$-$C_3$alkyl and $C_3$-$C_4$cycloalkyl; each occurrence of $R^9$ is independently selected from H and $C_1$-$C_3$alkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^6$ is independently selected from the group consisting of $C_1$-$C_3$alkyl and $C_3$-$C_4$cycloalkyl; each occurrence of $R^9$ is independently selected from H and $C_1$-$C_3$alkyl; and n is 3.

In some embodiments, the compound is represented by a formula selected from the group consisting of:
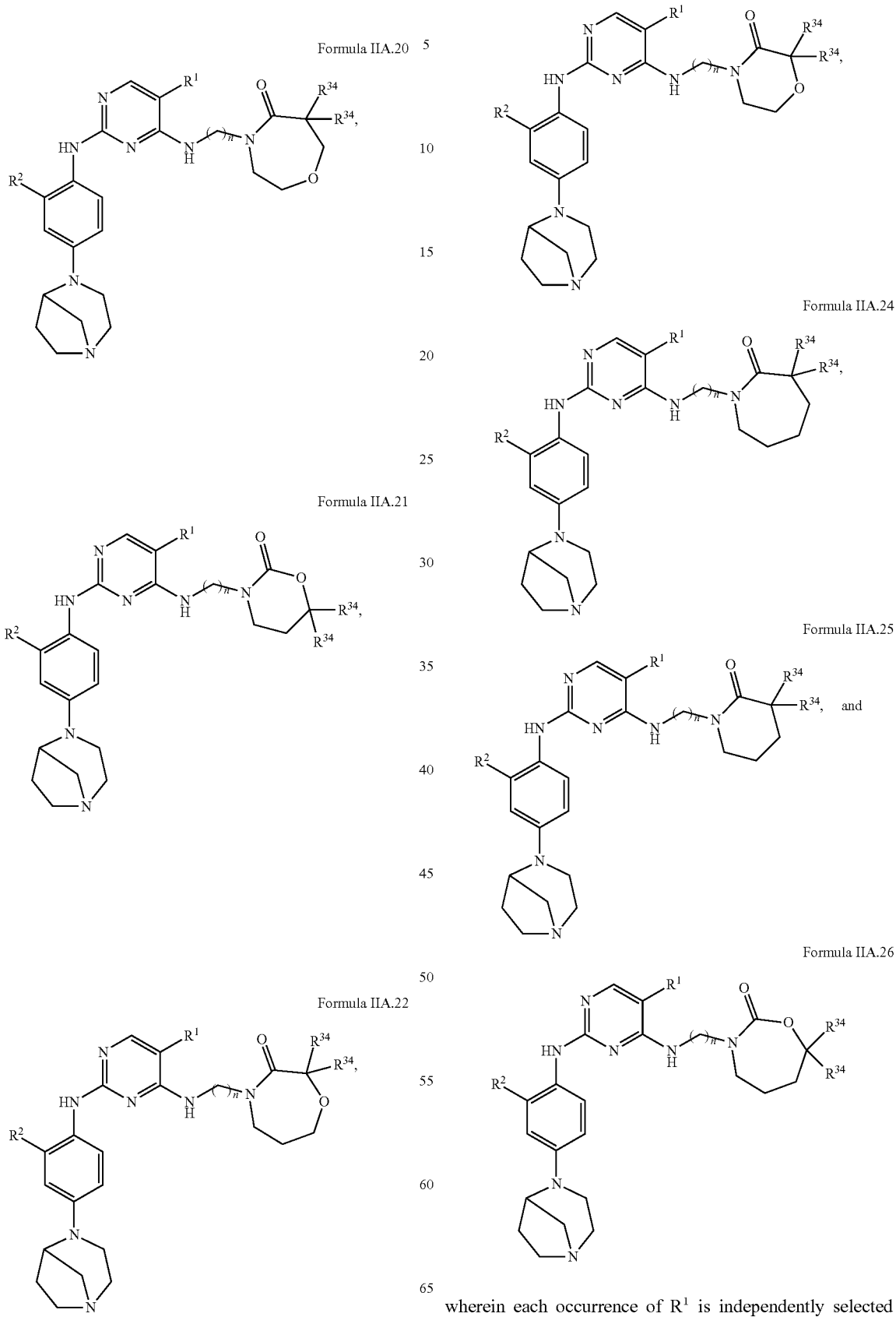
wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^{34}$ is selected from the group consisting of H, $C_1$-$C_2$alkyl, and $C_3$-$C_5$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^{34}$ is independently selected from the group consisting of H and $C_1$-$C_2$alkyl; and n is 3. In some embodiments, each occurrence of $R^1$ is bromo; each occurrence of $R^2$ is independently selected from $C_1$-$C_2$alkyl, $C_3$-$C_4$cycloalkyl, bromo, and chloro; each $R^{34}$ is H; and n is 3.

In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^{34}$ is independently selected from the group consisting of H and $C_1$-$C_2$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each $R^{34}$ is H; and n is 3.

In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^{34}$ is independently selected from the group consisting of H and $C_1$-$C_2$alkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each $R^{34}$ is H; and n is 3.

In some embodiments, the compound is represented by a formula selected from the group consisting of:

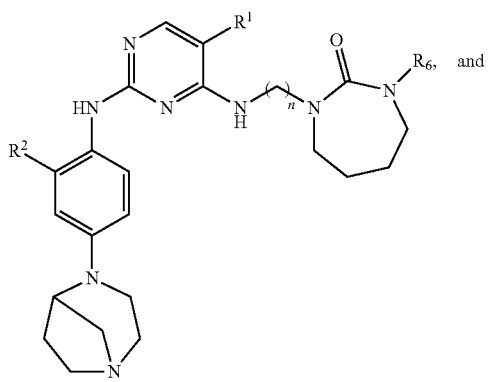

Formula IIA.27

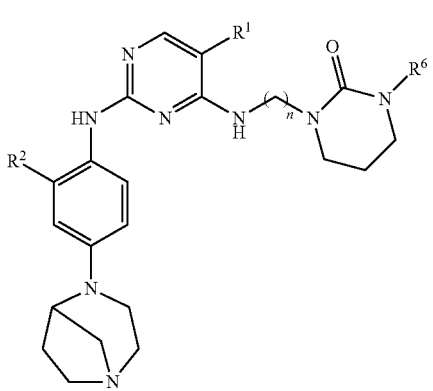

Formula IIA.28 wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^6$ is independently selected from $C_1$-$C_3$alkyl and $C_3$-$C_4$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^6$ is selected from $C_1$-$C_3$alkyl and $C_3$-$C_4$cycloalkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; and n is 3.

In some embodiments, the compound is represented by a formula selected from the group consisting of:

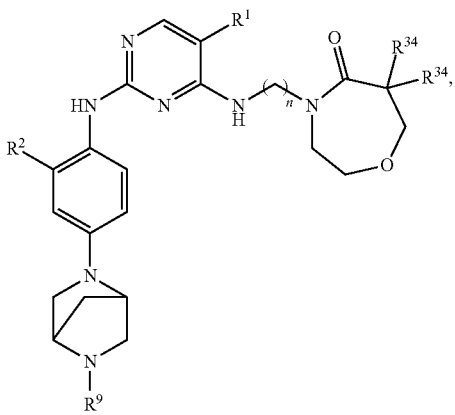

Formula IIA.29

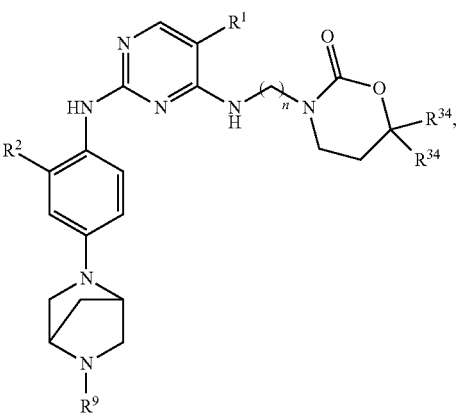

Formula IIA.30

-continued

Formula IIA.31

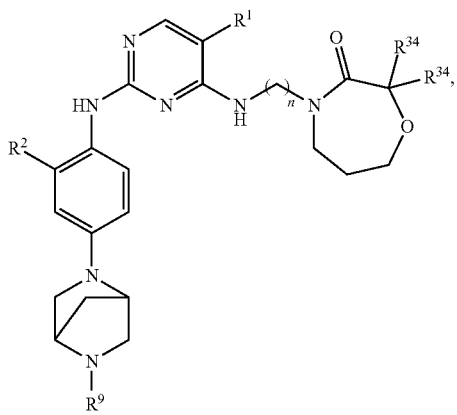

Formula IIA.32

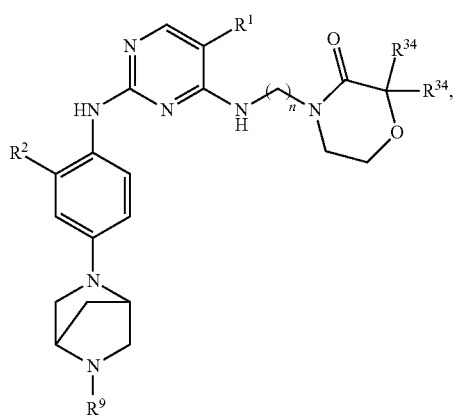

Formula IIA.33

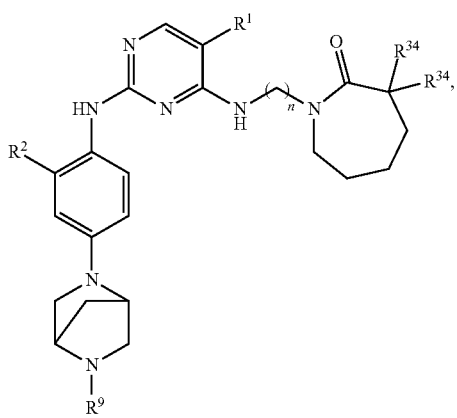

-continued

Formula IIA.34

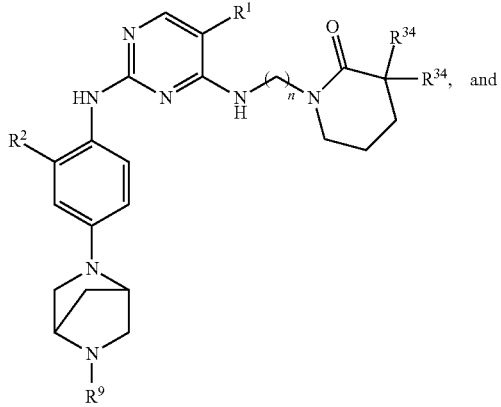

and

Formula IIA.35

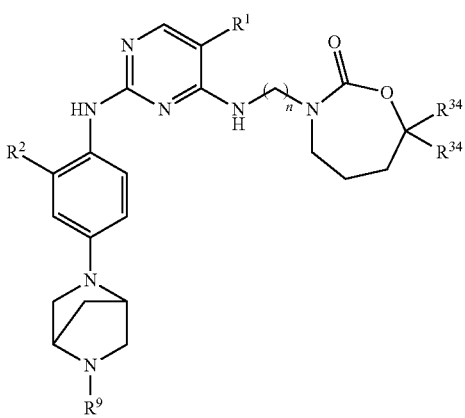

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^9$ is independently selected from the group consisting of H, $C_1$-$C_3$alkyl, and $C_3$-$C_5$cycloalkyl; each occurrence of $R^{34}$ is selected from the group consisting of H, $C_1$-$C_2$alkyl, and $C_3$-$C_5$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each occurrence of $R^{34}$ is independently selected from the group consisting of H and $C_1$-$C_2$alkyl; and n is 3. In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each $R^{34}$ is H; and n is 3.

In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^9$ is independently selected from H and $C_1$-$C_3$alkyl; each occurrence of $R^{34}$ is independently selected from the group consisting of H and $C_1$-$C_2$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^9$ is independently selected from H and $C_1$-$C_3$alkyl; each $R^{34}$ is H; and n is 3.

In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each occurrence of $R^{34}$ is independently selected from the group consisting of H and $C_1$-$C_2$alkyl; and n is 3 In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each $R^{34}$ is H; and n is 3.

In some embodiments, the compound is represented by a formula selected from:

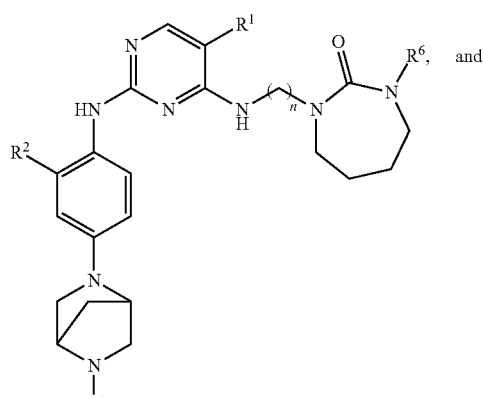

Formula IIA.36

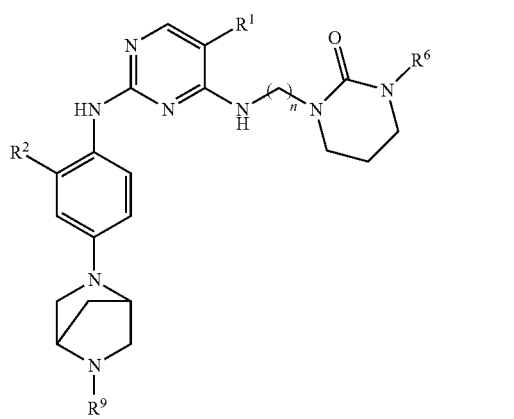

Formula IIA.37 wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^6$ is independently selected from $C_1$-$C_3$alkyl and $C_3$-$C_4$cycloalkyl; each occurrence of $R^9$ is independently selected from the group consisting of H, $C_1$-$C_3$alkyl, and $C_3$-$C_5$cycloalkyl; and n is 3.

In some embodiments, each occurrence of $R^1$ is bromo; each occurrence of $R^2$ is independently selected from the group consisting of $C_1$-$C_2$alkyl, $C_3$-$C_4$cycloalkyl, bromo, and chloro; each occurrence of $R^6$ is selected from $C_1$-$C_3$alkyl and $C_3$-$C_4$cycloalkyl; each occurrence of $R^9$ is selected from H and $C_1$-$C_3$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; each occurrence of $R^9$ is independently selected from H and $C_1$-$C_3$alkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; each occurrence of $R^9$ is independently selected from H and $C_1$-$C_3$alkyl; and n is 3.

In some embodiments, the compound is represented by a formula selected from the group consisting of:

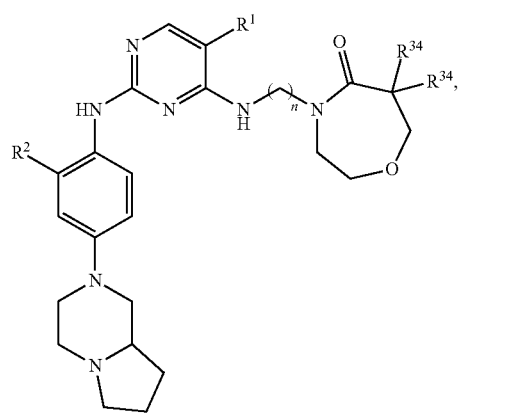

Formula IIA.38

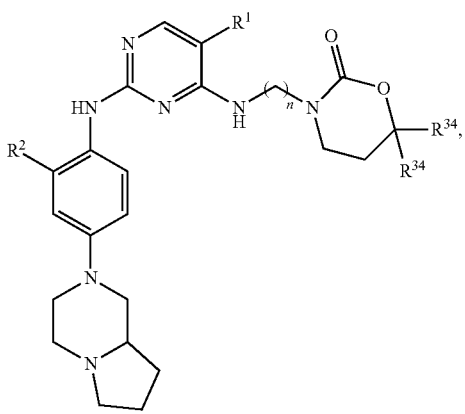

Formula IIA.39

Formula IIA.40

Formula IIA.41
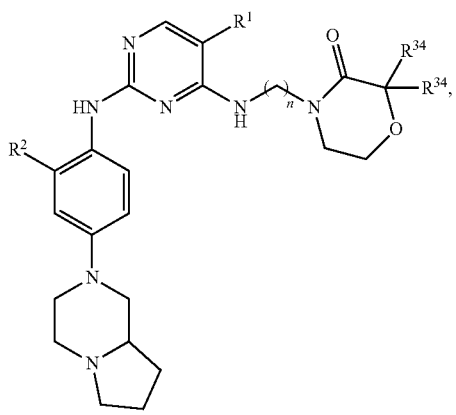

Formula IIA.42
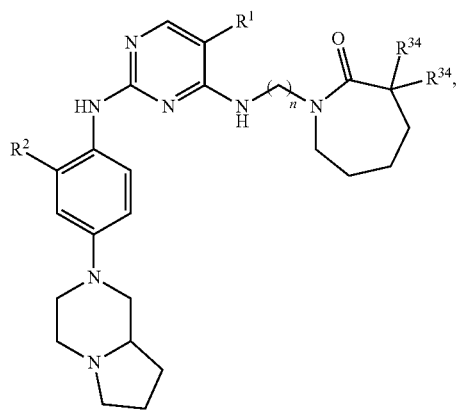

Formula IIA.43
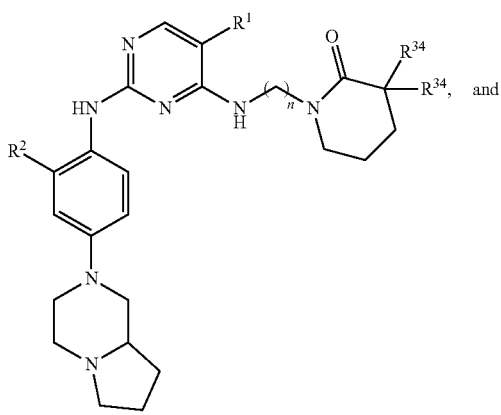

Formula IIA.44
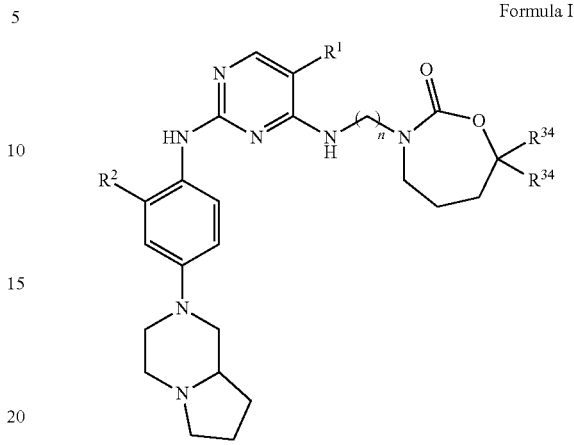

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^{34}$ is selected from the group consisting of H, $C_1$-$C_2$alkyl, and $C_3$-$C_5$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^{34}$ is independently selected from the group consisting of H and $C_1$-$C_2$alkyl; and n is 3. In some embodiments, each occurrence of $R^1$ is bromo; each occurrence of $R^2$ is independently selected from $C_1$-$C_2$alkyl, $C_3$-$C_4$cycloalkyl, bromo, and chloro; each $R^{34}$ is H; and n is 3.

In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^{34}$ is independently selected from the group consisting of H and $C_1$-$C_2$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each $R^{34}$ is H; and n is 3.

In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^{34}$ is independently selected from the group consisting of H and $C_1$-$C_2$alkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each $R^{34}$ is H; and n is 3.

In some embodiments, the compound is represented by a formula selected from the group consisting of:

Formula IIA.45

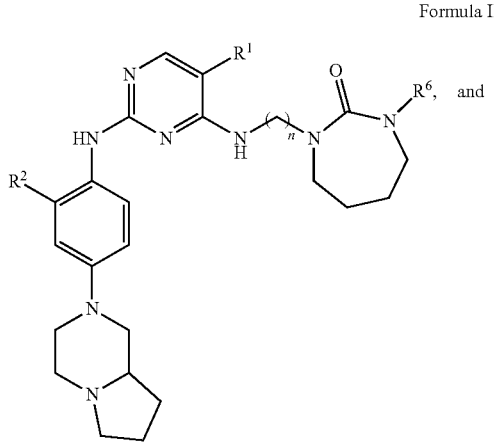

and

Formula IIA.46

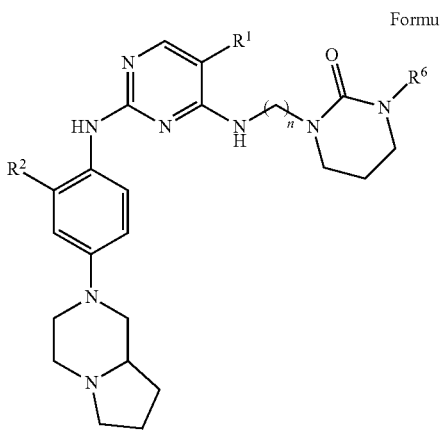

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^6$ is independently selected from $C_1$-$C_3$alkyl and $C_3$-$C_4$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^6$ is selected from $C_1$-$C_3$alkyl and $C_3$-$C_4$cycloalkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; and n is 3.

In some embodiments, the compound is represented by:

Formula IIA.2-A

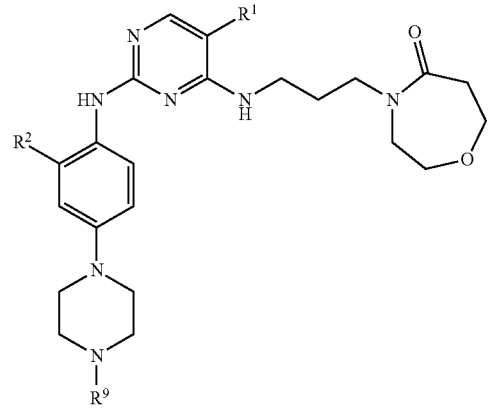

wherein $R^1$ is selected from the group consisting of bromo, chloro, $CF_3$, $CF_2H$, and cyclopropyl; $R^2$ is selected from the group consisting of $C_1$-$C_2$alkyl, $C_3$-$C_4$cycloalkyl, and halogen; and $R^9$ is selected from the group consisting of $C_1$-$C_3$alkyl, H, and $C_3$-$C_5$cycloalkyl. In some embodiments, $R^1$ is $CF_3$; $R^2$ is selected from the group consisting of $C_1$-$C_2$alkyl, $C_3$-$C_4$cycloalkyl, bromo, and chloro; and $R^9$ is selected from $C_1$-$C_3$alkyl and H. In some embodiments, $R^1$ is bromo; $R^2$ is selected from the group consisting of $C_1$-$C_2$alkyl, $C_3$-$C_4$cycloalkyl, bromo, and chloro; and $R^9$ is selected from $C_1$-$C_3$alkyl and H. In some embodiments, $R^1$ is $CF_2H$; $R^2$ is selected from the group consisting of $C_1$-$C_2$alkyl, $C_3$-$C_4$cycloalkyl, bromo, and chloro; and $R^9$ is selected from $C_1$-$C_3$alkyl and H.

In some embodiments, the compound is represented by:

Formula IIA.7-A

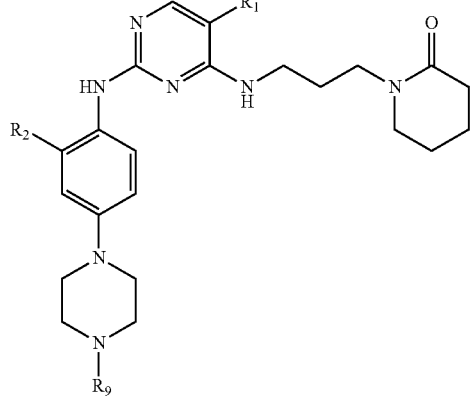

wherein $R^1$ is selected from the group consisting of bromo, chloro, $CF_3$, $CF_2H$, and cyclopropyl; $R^2$ is selected from the group consisting of $C_1$-$C_2$alkyl, $C_3$-$C_4$cycloalkyl, and halogen; and $R^9$ is selected from the group consisting of $C_1$-$C_3$alkyl, H, and $C_3$-$C_5$cycloalkyl. In some embodiments, $R^1$ is $CF_3$; $R^2$ is selected from the group consisting of $C_1$-$C_2$alkyl, $C_3$-$C_4$cycloalkyl, bromo, and chloro; and $R^9$ is selected from $C_1$-$C_3$alkyl and H. In some embodiments, $R^1$ is bromo; $R^2$ is selected from the group consisting of $C_1$-$C_2$alkyl, $C_3$-$C_4$cycloalkyl, bromo, and chloro; and $R^9$ is selected from $C_1$-$C_3$alkyl and H. In some embodiments, $R^1$ is $CF_2H$; $R^2$ is selected from the group consisting of $C_1$-$C_2$alkyl, $C_3$-$C_4$cycloalkyl, bromo, and chloro; and $R^9$ is selected from $C_1$-$C_3$alkyl and H.

In some embodiments, the compound is represented by:

Formula IIA.8-A

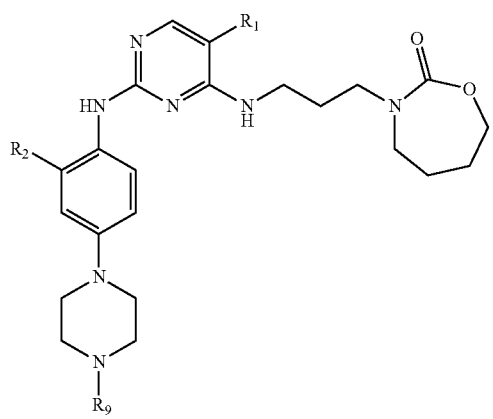

wherein $R^1$ is selected from the group consisting of bromo, chloro, $CF_3$, $CF_2H$, and cyclopropyl; $R^2$ is selected from the group consisting of $C_1$-$C_2$alkyl, $C_3$-$C_4$cycloalkyl, and halogen; and $R^9$ is selected from the group consisting of $C_1$-$C_3$alkyl, H, and $C_3$-$C_5$cycloalkyl. In some embodiments, $R^1$ is $CF_3$; $R^2$ is selected from the group consisting of $C_1$-$C_2$alkyl, $C_3$-$C_4$cycloalkyl, bromo, and chloro; and $R^9$ is selected from $C_1$-$C_3$alkyl and H. In some embodiments, $R^1$ is bromo; $R^2$ is selected from the group consisting of $C_1$-$C_2$alkyl, $C_3$-$C_4$cycloalkyl, bromo, and chloro; and $R^9$ is selected from $C_1$-$C_3$alkyl and H. In some embodiments, $R^1$ is $CF_2H$; $R^2$ is selected from the group consisting of $C_1$-$C_2$alkyl, $C_3$-$C_4$cycloalkyl, bromo, and chloro; and $R^9$ is selected from $C_1$-$C_3$alkyl and H.

In some embodiments, the compound is represented by:

Formula IIA.11-A

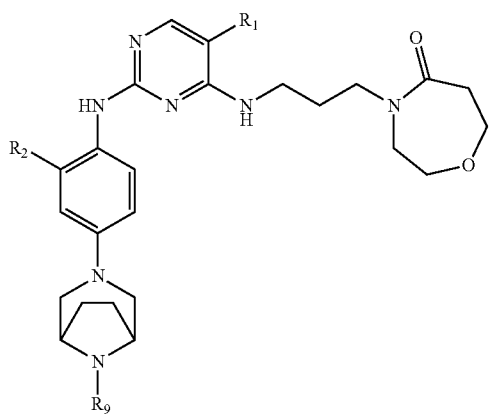

wherein $R^1$ is selected from the group consisting of bromo, chloro, $CF_3$, $CF_2H$, and cyclopropyl; $R^2$ is selected from the group consisting of $C_1$-$C_2$alkyl, $C_3$-$C_4$cycloalkyl, and halogen; and $R^9$ is selected from the group consisting of $C_1$-$C_3$alkyl, H, and $C_3$-$C_5$cycloalkyl. In some embodiments, $R^1$ is $CF_3$; $R^2$ is selected from the group consisting of $C_1$-$C_2$alkyl, $C_3$-$C_4$cycloalkyl, bromo, and chloro; and $R^9$ is selected from $C_1$-$C_3$alkyl and H. In some embodiments, $R^1$ is bromo; $R^2$ is selected from the group consisting of $C_1$-$C_2$alkyl, $C_3$-$C_4$cycloalkyl, bromo, and chloro; and $R^9$ is selected from $C_1$-$C_3$alkyl and H. In some embodiments, $R^1$ is $CF_2H$; $R^2$ is selected from the group consisting of $C_1$-$C_2$alkyl, $C_3$-$C_4$cycloalkyl, bromo, and chloro; and $R^9$ is selected from $C_1$-$C_3$alkyl and H.

In some embodiments, the compound is represented by:

Formula IIA.14-A

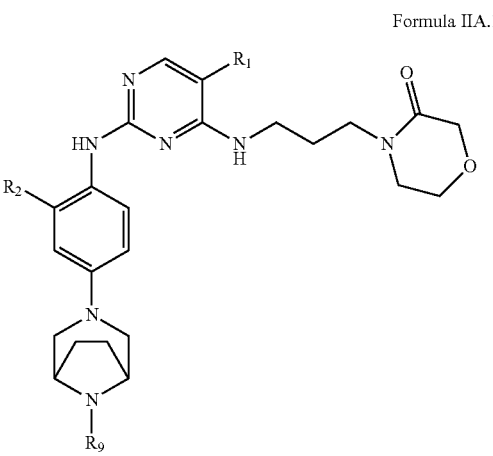

wherein $R^1$ is selected from the group consisting of bromo, chloro, $CF_3$, $CF_2H$, and cyclopropyl; $R^2$ is selected from the group consisting of $C_1$-$C_2$alkyl, $C_3$-$C_4$cycloalkyl, and halogen; and $R^9$ is selected from the group consisting of $C_1$-$C_3$alkyl, H, and $C_3$-$C_5$cycloalkyl. In some embodiments, $R^1$ is $CF_3$; $R^2$ is selected from the group consisting of $C_1$-$C_2$alkyl, $C_3$-$C_4$cycloalkyl, bromo, and chloro; and $R^9$ is selected from $C_1$-$C_3$alkyl and H. In some embodiments, $R^1$ is bromo; $R^2$ is selected from the group consisting of $C_1$-$C_2$alkyl, $C_3$-$C_4$cycloalkyl, bromo, and chloro; and $R^9$ is selected from $C_1$-$C_3$alkyl and H. In some embodiments, $R^1$ is $CF_2H$; $R^2$ is selected from the group consisting of $C_1$-$C_2$alkyl, $C_3$-$C_4$cycloalkyl, bromo, and chloro; and $R^9$ is selected from $C_1$-$C_3$alkyl and H.

In some embodiments, the compound is represented by:

Formula IIA.38-A

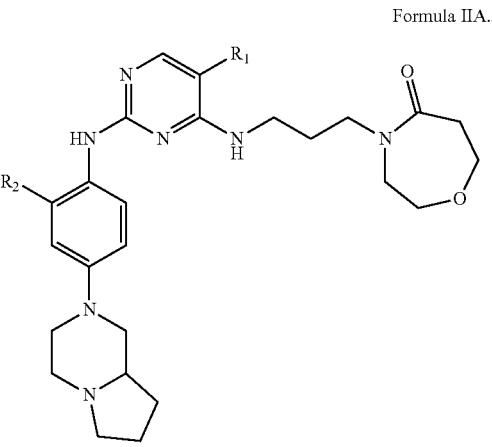

wherein $R^1$ is selected from the group consisting of bromo, chloro, $CF_3$, $CF_2H$, and cyclopropyl; and $R^2$ is selected from the group consisting of $C_1$-$C_2$alkyl, $C_3$-$C_4$cycloalkyl, and halogen. In some embodiments, $R^1$ is $CF_3$; and $R^2$ is selected from the group consisting of $C_1$-$C_2$alkyl, $C_3$-$C_4$cycloalkyl, bromo, and chloro. In some embodiments, $R^1$ is bromo; and $R^2$ is selected from the group consisting of $C_1$-$C_2$alkyl, $C_3$-$C_4$cycloalkyl, bromo, and chloro. In some embodiments, $R^1$ is $CF_2H$; and $R^2$ is selected from the group consisting of $C_1$-$C_2$alkyl, $C_3$-$C_4$cycloalkyl, bromo, and chloro.

In some embodiments, the compound is represented by:

Formula IIA.44-A

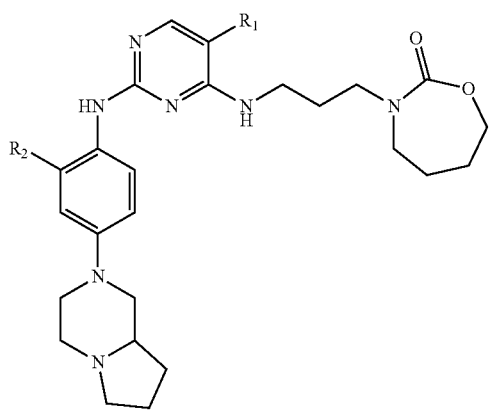

wherein $R^1$ is selected from the group consisting of bromo, chloro, $CF_3$, $CF_2H$, and cyclopropyl; and $R^2$ is selected from the group consisting of $C_1$-$C_2$alkyl, $C_3$-$C_4$cycloalkyl, and halogen. In some embodiments, $R^1$ is $CF_3$; and $R^2$ is selected from the group consisting of $C_1$-$C_2$alkyl, $C_3$-$C_4$cycloalkyl, bromo, and chloro. In some embodiments, $R^1$ is bromo; and $R^2$ is selected from the group consisting of $C_1$-$C_2$alkyl, $C_3$-$C_4$cycloalkyl, bromo, and chloro. In some embodiments, $R^1$ is $CF_2H$; and $R^2$ is selected from the group consisting of $C_1$-$C_2$alkyl, $C_3$-$C_4$cycloalkyl, bromo, and chloro.

In some embodiments, the compound is represented by:

Formula III

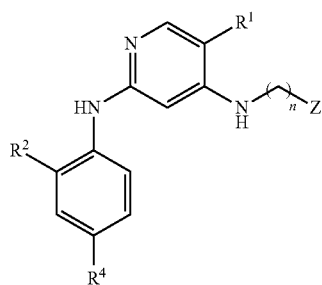

or a pharmaceutically acceptable salt thereof, wherein: n is 2, 3, or 4; $R^1$ is selected from the group consisting of halogen, cyano, $C_1$-$C_5$alkyl, and $C_3$-$C_5$cycloalkyl, wherein each $C_1$-$C_5$alkyl and $C_3$-$C_5$cycloalkyl may be optionally substituted by one, two or three independent occurrences of fluorine; $R^1$ is selected from the group consisting of $C_1$-$C_2$alkyl, $C_3$-$C_4$cycloalkyl, and halogen; $R^4$ is selected from the group consisting of:

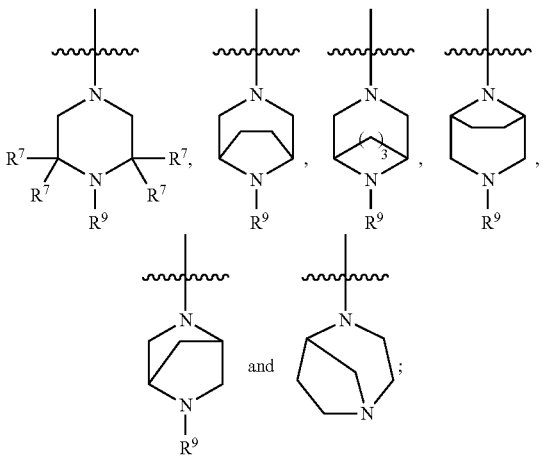

each occurrence of $R^6$ and $R^9$ is independently selected from the group consisting of H, $C_1$-$C_6$alkyl, $C_3$-$C_6$cycloalkyl, C(=O)$R^5$, $SO_2R^5$, and D, wherein each $C_1$-$C_6$alkyl and $C_3$-$C_6$cycloalkyl may be optionally substituted by one or more independent occurrences of fluorine; each occurrence of $R^5$ is independently selected from the group consisting of H, $C_1$-$C_6$alkyl, $C_3$-$C_6$cycloalkyl, and heterocyclyl, wherein each $C_1$-$C_6$alkyl and $C_3$-$C_6$cycloalkyl may be optionally substituted by one or more independent occurrences of fluorine; each occurrence of $R^7$ is independently selected from the group consisting of H, $C_1$-$C_6$ alkyl, and $C_3$-$C_6$cycloalkyl, wherein each $C_1$-$C_6$alkyl and $C_3$-$C_6$cycloalkyl may be optionally substituted by one or more independent occurrences of fluorine, or two $R^7$ are joined together with the atom to which they are attached to form oxo; D is selected from a C-linked heterocyclyl having at least one ring nitrogen and optionally having an additional ring nitrogen or oxygen and heteroaryl, wherein D may be optionally substituted on one or more available carbons by $R^7$ and may be optionally substituted on an available nitrogen by $R^9$; Z is selected from the group consisting of:

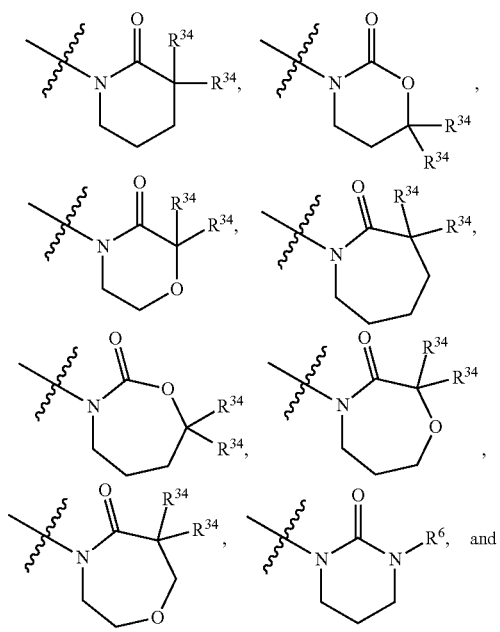

-continued

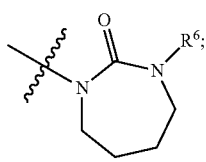

and each occurrence of $R^{34}$ is independently selected from H and $R^{36}$, wherein each occurrence of $R^{36}$ is independently selected from $C_1$-$C_6$alkyl and $C_3$-$C_6$cycloalkyl, wherein each $C_1$-$C_5$alkyl and $C_3$-$C_6$cycloalkyl may be optionally substituted by one or more independent occurrences of fluorine, or two $R^{36}$ are joined together with the carbon to which they are attached to form a $C_3$-$C_6$cycloalkyl.

In some embodiments, $R^1$ is selected from the group consisting of halogen, $C_1$-$C_5$alkyl, and $C_3$-$C_5$cycloalkyl, wherein $C_1$-$C_5$alkyl may be optionally substituted with one, two, or three occurrences of fluorine, and $C_3$-$C_5$cycloalkyl. In some embodiments, $R^1$ is $CF_3$. In some embodiments, $R^1$ is $CF_2H$. In some embodiments, $R^1$ is halogen. In some embodiments, $R^1$ is bromo. In some embodiments, $R^1$ is cyclopropyl.

In some embodiments, $R^2$ is selected from the group consisting of H, $C_3$-$C_4$cycloalkyl, $C_1$-$C_5$alkyl, and halogen. In some embodiments, $R^2$ is selected from the group consisting of $C_1$-$C_2$alkyl, $C_3$-$C_4$cycloalkyl, bromo, anc chloro.

In some embodiments, $R^4$ is selected from the group consisting of:

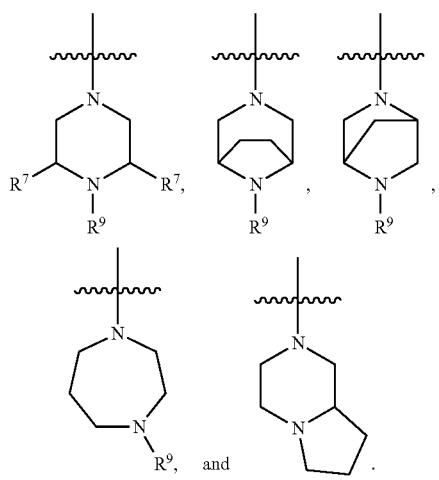

In some embodiments, $R^4$ is selected from the group consisting of:

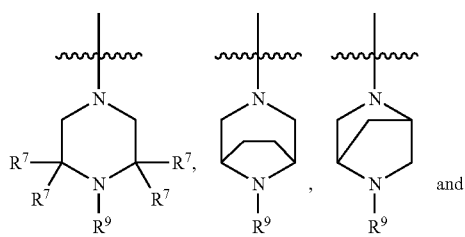

-continued

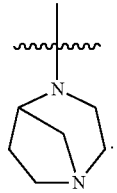

In some embodiments, each $R^6$ and $R^9$ is independently selected from the group consisting of H, $C_1$-$C_6$alkyl, and $C_3$-$C_6$cycloalkyl, wherein each of $C_1$-$C_6$alkyl and $C_3$-$C_6$cycloalkyl is optionally substituted by one or more independent occurrences of fluorine.

In some embodiments, $R^7$ is H.

In some embodiments, $R^{34}$ is selected from the group consisting of H and $C_1$-$C_5$alkyl, wherein $C_1$-$C_5$alkyl may be optionally substituted by one, two, or three independent occurrences of fluorine. In some embodiments, two $R^{34}$ are joined together with the carbon to which they are attached to form $C_3$-$C_6$cycloalkyl;

In some embodiments, Z is selected from the group consisting of:

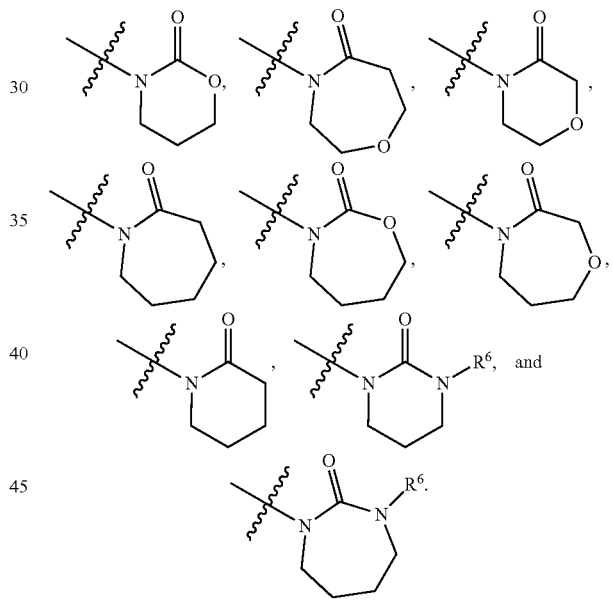

In some embodiments, Z is selected from the group consisting of:

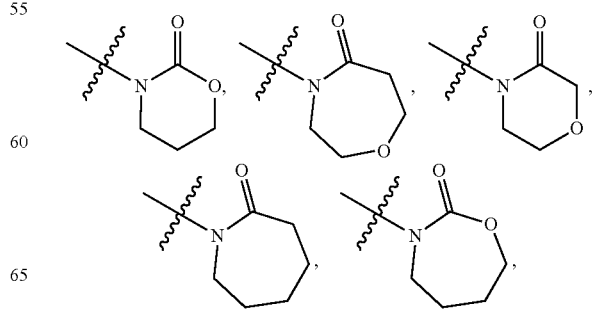

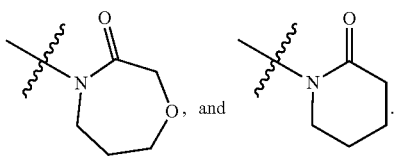
In some embodiments, n is 3.
In some embodiments, the compound is represented by a formula selected from the group consisting of:
Formula IIIA.2
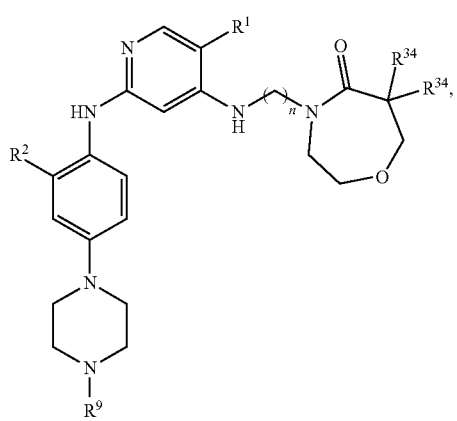
Formula IIIA.3
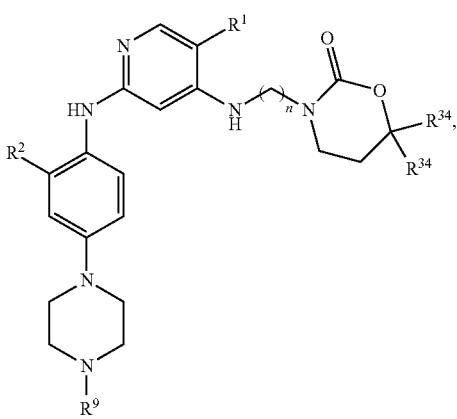
Formula IIIA.4
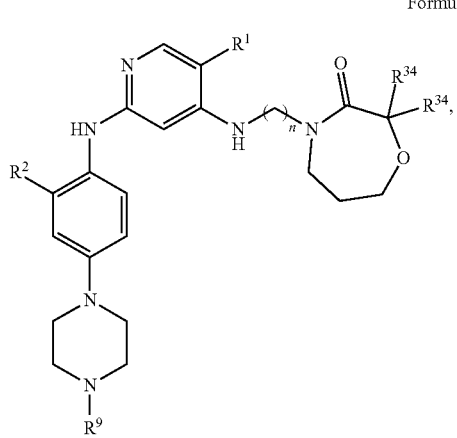
Formula IIIA.5
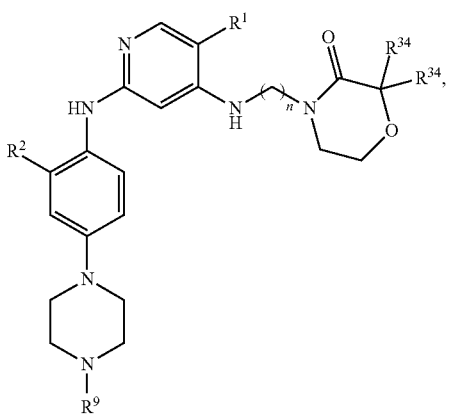
Formula IIIA.6
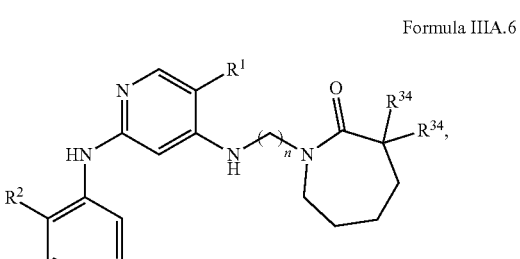
Formula IIIA.7
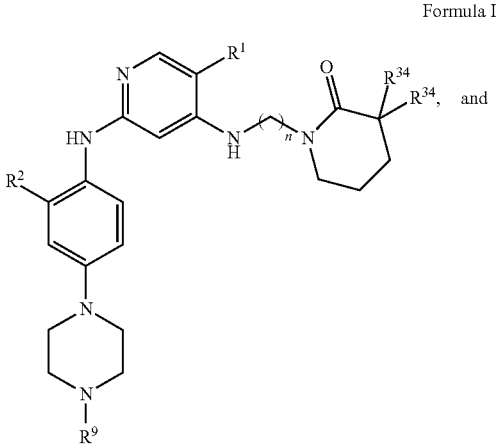
and Formula IIIA.8

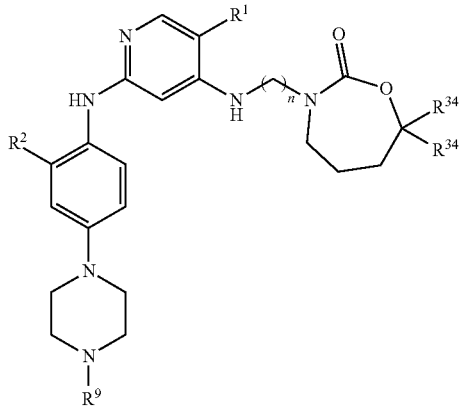

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^9$ is independently selected from the group consisting of H, $C_1$-$C_3$alkyl, and $C_3$-$C_5$cycloalkyl; each occurrence of $R^{34}$ is selected from the group consisting of H, $C_1$-$C_2$alkyl, and $C_3$-$C_5$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each occurrence of $R^{34}$ is independently selected from the group consisting of H and $C_1$-$C_2$alkyl; and n is 3. In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each $R^{34}$ is H; and n is 3.

In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^9$ is independently selected from H and $C_1$-$C_3$alkyl; each occurrence of $R^{34}$ is independently selected from the group consisting of H and $C_1$-$C_2$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^9$ is independently selected from H and $C_1$-$C_3$alkyl; each $R^{34}$ is H; and n is 3.

In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each occurrence of $R^{34}$ is independently selected from the group consisting of H and $C_1$-$C_2$alkyl; and n is 3 In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^9$ is independently selected from H and $C_1$-$C_3$alkyl; each $R^{34}$ is H; and n is 3.

In some embodiments, the compound is represented by a formula selected from the group consisting of:

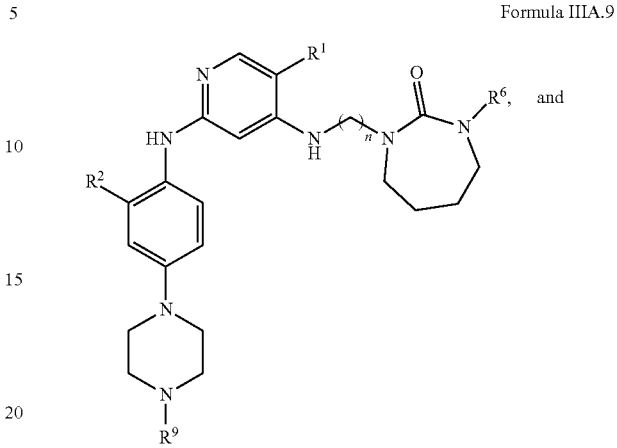

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^6$ is independently selected from $C_1$-$C_3$alkyl and $C_3$-$C_4$cycloalkyl; each occurrence of $R^9$ is independently selected from the group consisting of H, $C_1$-$C_3$alkyl, and $C_3$-$C_5$cycloalkyl; and n is 3.

In some embodiments, each occurrence of $R^1$ is bromo; each occurrence of $R^2$ is independently selected from the group consisting of $C_1$-$C_2$alkyl, $C_3$-$C_4$cycloalkyl, bromo, and chloro; each occurrence of $R^6$ is selected from $C_1$-$C_3$alkyl and $C_3$-$C_4$cycloalkyl; each occurrence of $R^9$ is selected from H and $C_1$-$C_3$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; each occurrence of $R^9$ is independently selected from H and $C_1$-$C_3$alkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; each occurrence of $R^9$ is independently selected from H and $C_1$-$C_3$alkyl; and n is 3.

In some embodiments, the compound is represented by a formula selected from the group consisting of:
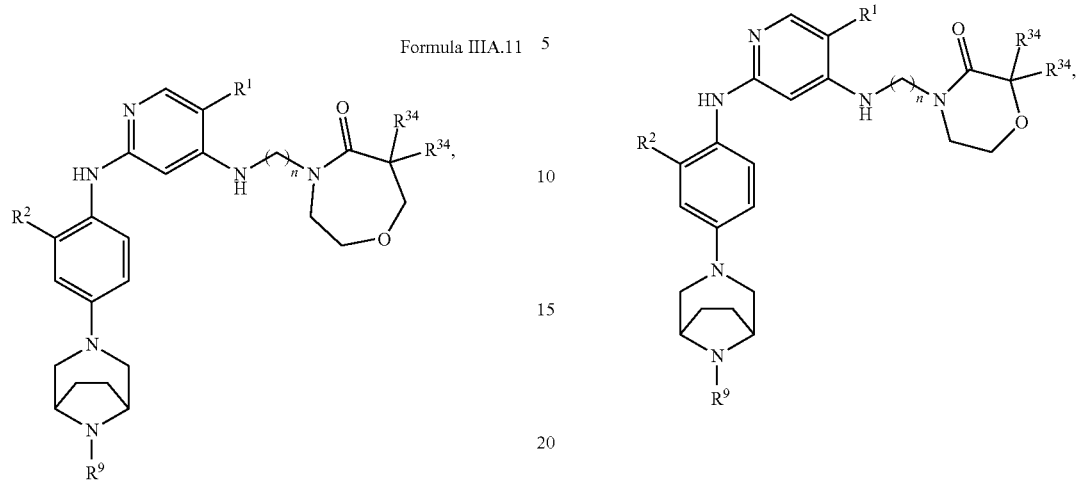
Formula IIIA.11
Formula IIIA.14
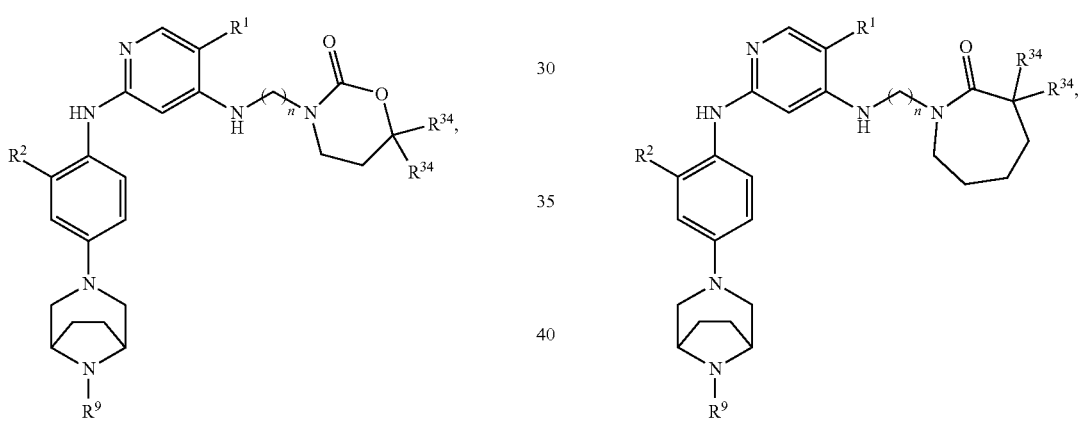
Formula IIIA.12
Formula IIIA.15
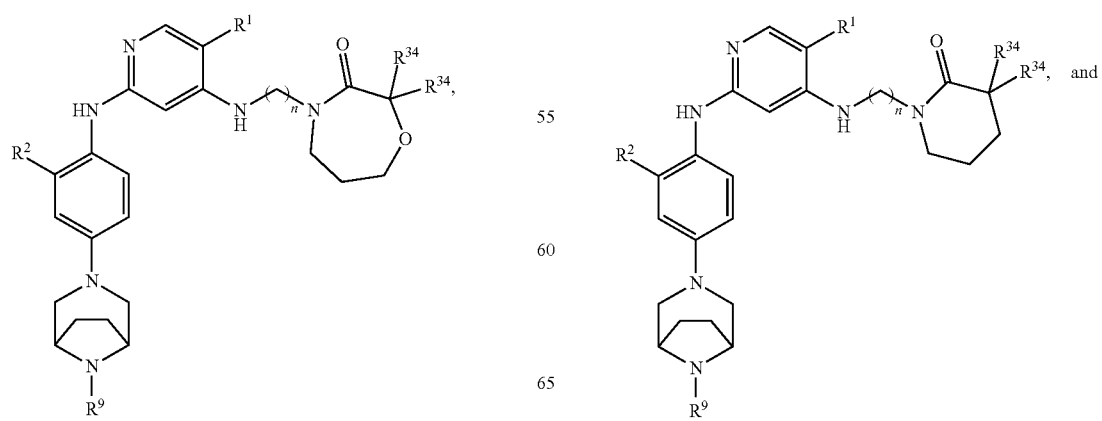
Formula IIIA.13
Formula IIIA.16, and -continued Formula IIIA.17

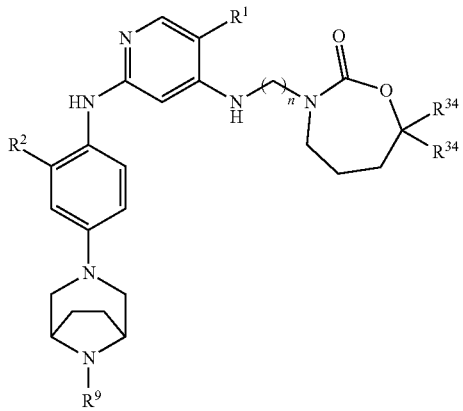

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^9$ is independently selected from the group consisting of H, $C_1$-$C_3$alkyl, and $C_3$-$C_5$cycloalkyl; each occurrence of $R^{34}$ is selected from the group consisting of H, $C_1$-$C_2$alkyl, and $C_3$-$C_5$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each occurrence of $R^{34}$ is independently selected from the group consisting of H and $C_1$-$C_2$alkyl; and n is 3. In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each $R^{34}$ is H; and n is 3.

In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^9$ is independently selected from H and $C_1$-$C_3$alkyl; each occurrence of $R^{34}$ is independently selected from the group consisting of H and $C_1$-$C_2$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^9$ is independently selected from H and $C_1$-$C_3$alkyl; each $R^{34}$ is H; and n is 3.

In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each occurrence of $R^{34}$ is independently selected from the group consisting of H and $C_1$-$C_2$alkyl; and n is 3 In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each $R^{34}$ is H; and n is 3.

In some embodiments, the compound is represented by a formula selected from the group consisting of:

Formula IIIA.18

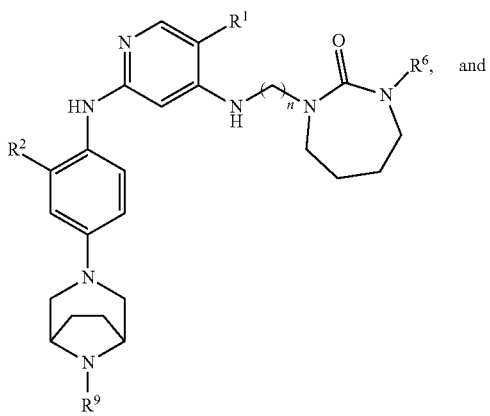

Formula IIIA.19

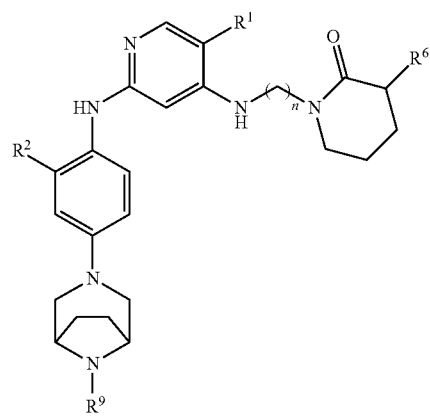

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^6$ is independently selected from $C_1$-$C_3$alkyl and $C_3$-$C_4$cycloalkyl; each occurrence of $R^9$ is independently selected from the group consisting of H, $C_1$-$C_3$alkyl, and $C_3$-$C_5$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^6$ is selected from $C_1$-$C_3$alkyl and $C_3$-$C_4$cycloalkyl; each occurrence of $R^9$ is selected from H and $C_1$-$C_3$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^6$ is independently selected from the group consisting of $C_1$-$C_3$alkyl and $C_3$-$C_4$cycloalkyl; each occurrence of $R^9$ is independently selected from H and $C_1$-$C_3$alkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^6$ is independently selected from the group consisting of $C_1$-$C_3$alkyl and $C_3$-$C_4$cycloalkyl; each occurrence of $R^9$ is independently selected from H and $C_1$-$C_3$alkyl; and n is 3.

In some embodiments, the compound is represented by a formula selected from the group consisting of:
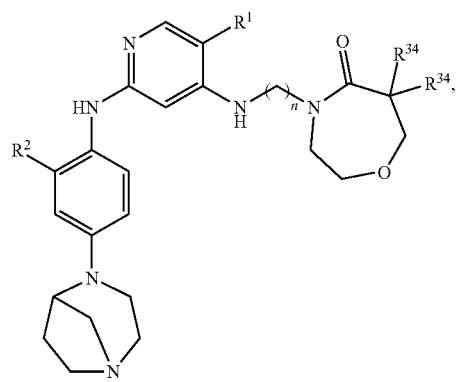
Formula IIIA.20
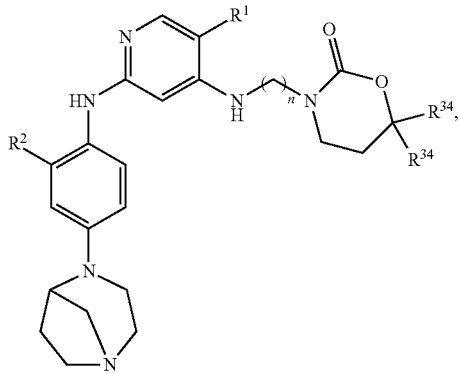
Formula IIIA.21
Formula IIIA.22
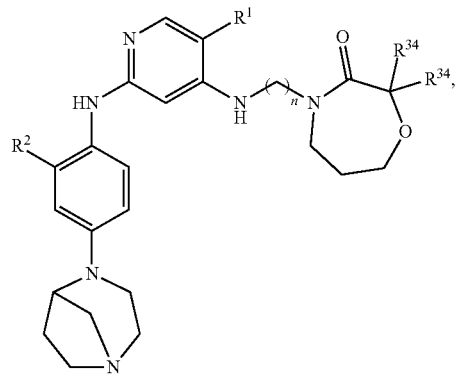
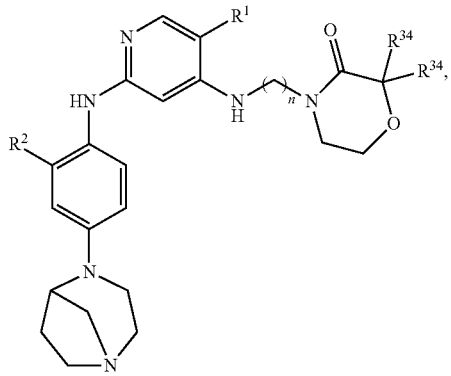
Formula IIIA.23
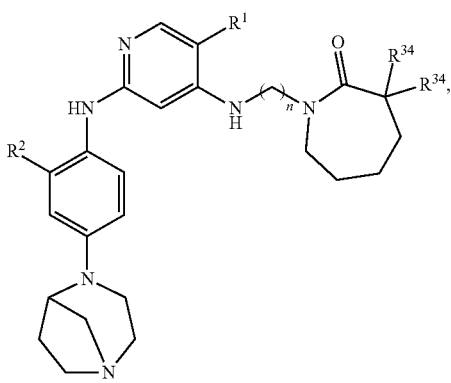
Formula IIIA.24
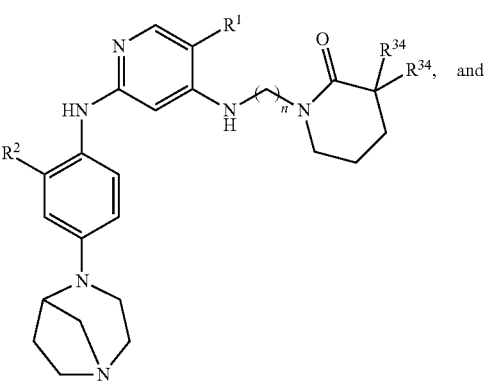
Formula IIIA.25
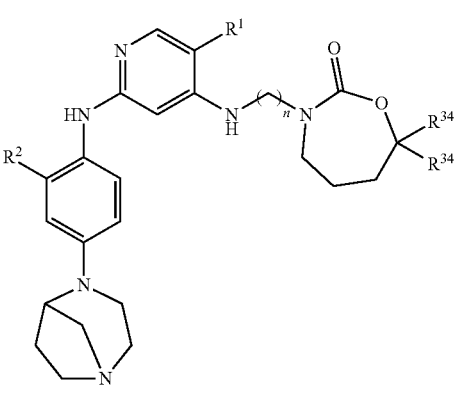
Formula IIIA.26
wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^{34}$ is selected from the group consisting of H, $C_1$-$C_2$alkyl, and $C_3$-$C_5$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^{34}$ is independently selected from the group consisting of H and $C_1$-$C_2$alkyl; and n is 3. In some embodiments, each occurrence of $R^1$ is bromo; each occurrence of $R^2$ is independently selected from $C_1$-$C_2$alkyl, $C_3$-$C_4$cycloalkyl, bromo, and chloro; each $R^{34}$ is H; and n is 3.

In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^{34}$ is independently selected from the group consisting of H and $C_1$-$C_2$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each $R^{34}$ is H; and n is 3.

In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^{34}$ is independently selected from the group consisting of H and $C_1$-$C_2$alkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each $R^{34}$ is H; and n is 3.

In some embodiments, the compound is represented by a formula selected from the group consisting of:

Formula IIIA.27

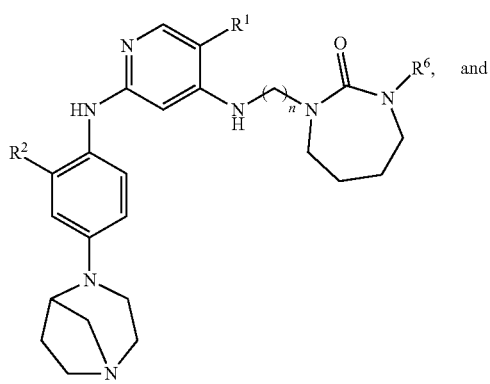

and

Formula IIIA.28

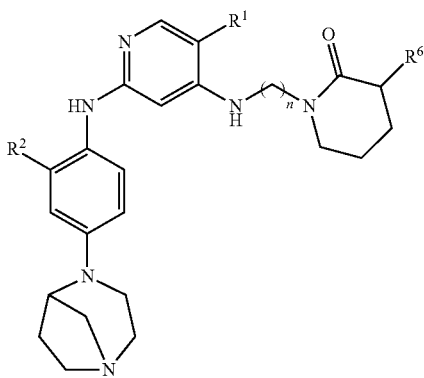

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^6$ is independently selected from $C_1$-$C_3$alkyl and $C_3$-$C_4$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^6$ is selected from $C_1$-$C_3$alkyl and $C_3$-$C_4$cycloalkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; and n is 3.

In some embodiments, the compound is represented by a formula selected from the group consisting of:

Formula IIIA.29

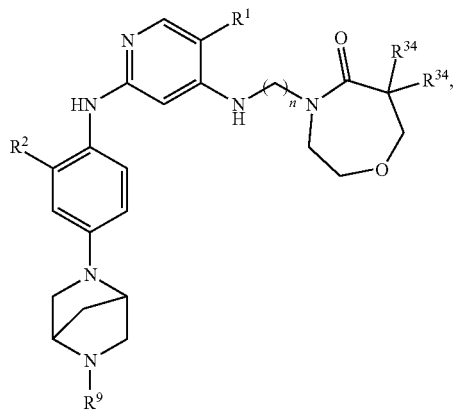

Formula IIIA.30

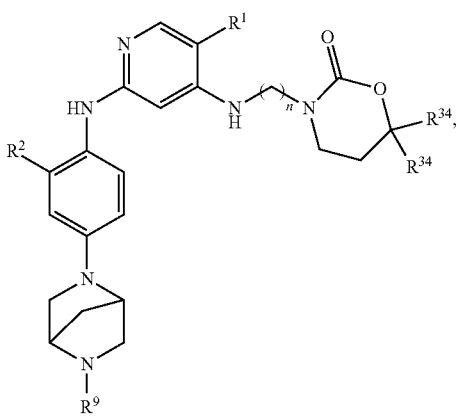

Formula IIIA.31

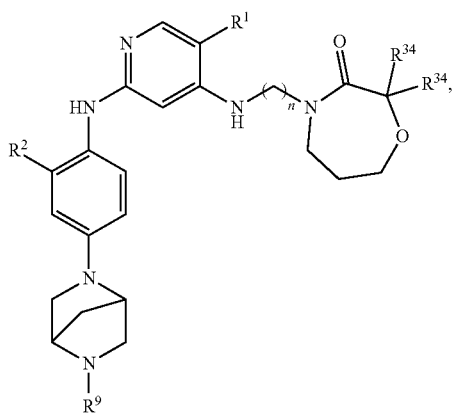

Formula IIIA.32

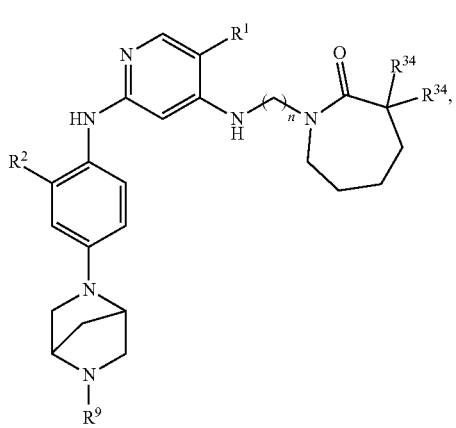

Formula IIIA.33

Formula IIIA.34

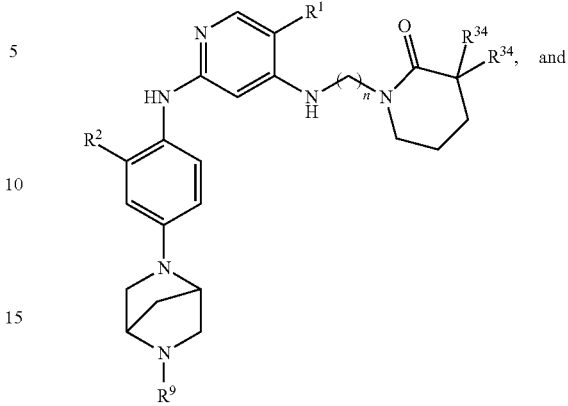

and

Formula IIIA.35

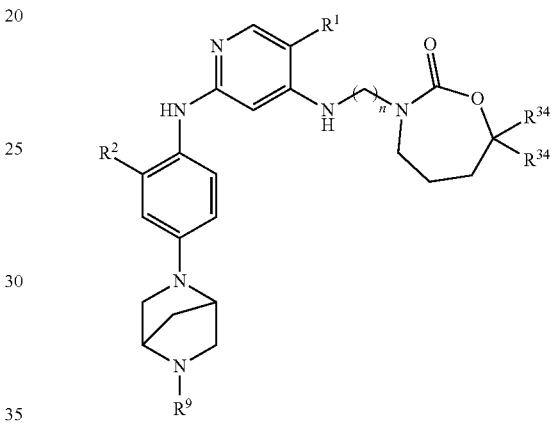

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^9$ is independently selected from the group consisting of H, $C_1$-$C_3$alkyl, and $C_3$-$C_5$cycloalkyl; each occurrence of $R^{34}$ is selected from the group consisting of H, $C_1$-$C_2$alkyl, and $C_3$-$C_5$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each occurrence of $R^{34}$ is independently selected from the group consisting of H and $C_1$-$C_2$alkyl; and n is 3. In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each $R^{34}$ is H; and n is 3.

In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^9$ is independently selected from H and $C_1$-$C_3$alkyl; each occurrence of $R^{34}$ is independently selected from the group consisting of H and $C_1$-$C_2$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^9$ is independently selected from H and $C_1$-$C_3$alkyl; each $R^{34}$ is H; and n is 3.

In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each occurrence of $R^{34}$ is independently selected from the group consisting of H and $C_1$-$C_2$alkyl; and n is 3 In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^9$ is selected from H and $C_1$-$C_3$alkyl; each $R^{34}$ is H; and n is 3.

In some embodiments, the compound is represented by a formula selected from:

Formula IIIA.36

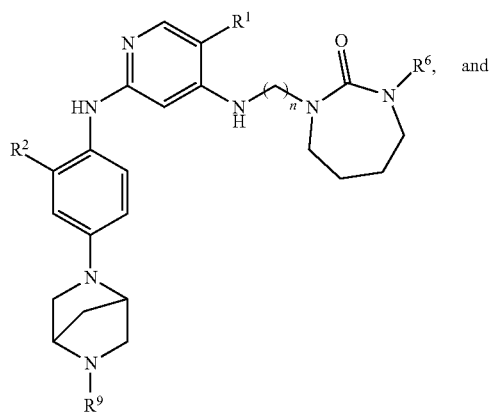

Formula IIIA.37

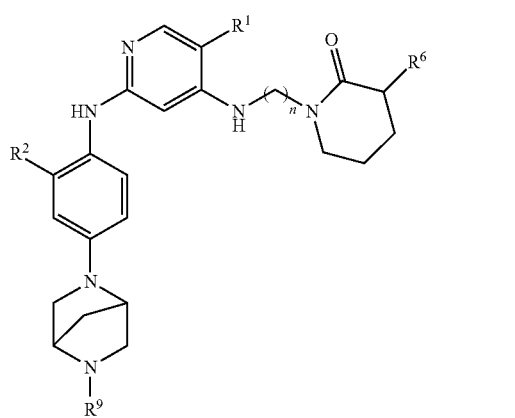

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^6$ is independently selected from $C_1$-$C_3$alkyl and $C_3$-$C_4$cycloalkyl; each occurrence of $R^9$ is independently selected from the group consisting of H, $C_1$-$C_3$alkyl, and $C_3$-$C_5$cycloalkyl; and n is 3.

In some embodiments, each occurrence of $R^1$ is bromo; each occurrence of $R^2$ is independently selected from the group consisting of $C_1$-$C_2$alkyl, $C_3$-$C_4$cycloalkyl, bromo, and chloro; each occurrence of $R^6$ is selected from $C_1$-$C_3$alkyl and $C_3$-$C_4$cycloalkyl; each occurrence of $R^9$ is selected from H and $C_1$-$C_3$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; each occurrence of $R^9$ is independently selected from H and $C_1$-$C_3$alkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; each occurrence of $R^9$ is independently selected from H and $C_1$-$C_3$alkyl; and n is 3.

In some embodiments, the compound is represented by a formula selected from the group consisting of:

Formula IIIA.38

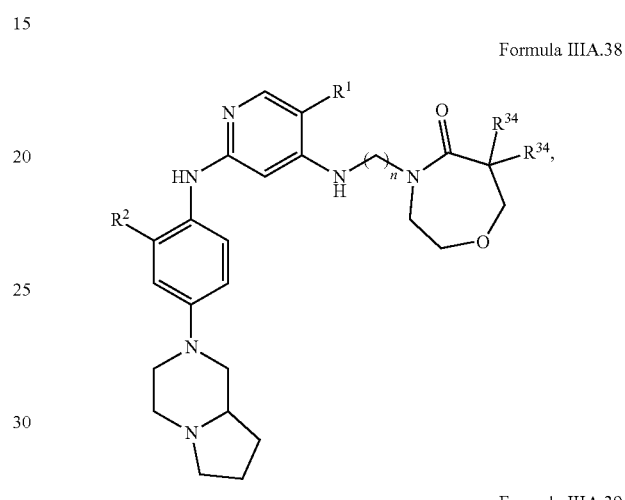

Formula IIIA.39

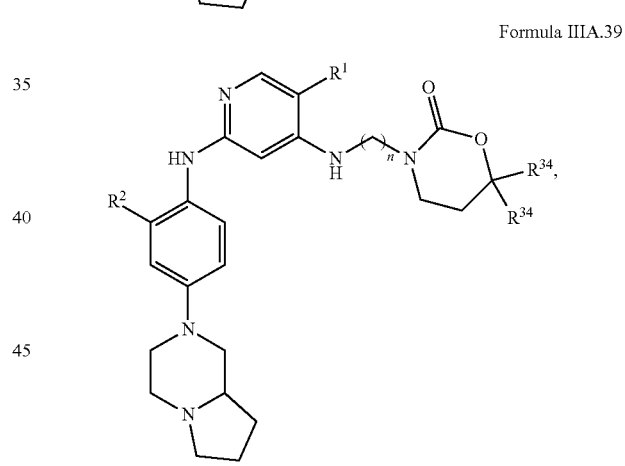

Formula IIIA.40

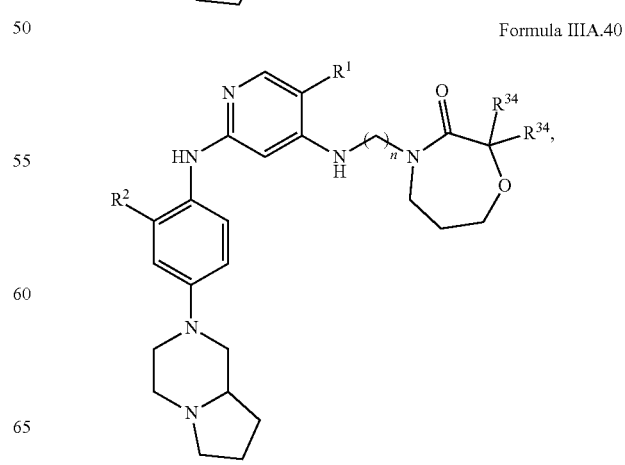

Formula IIIA.41

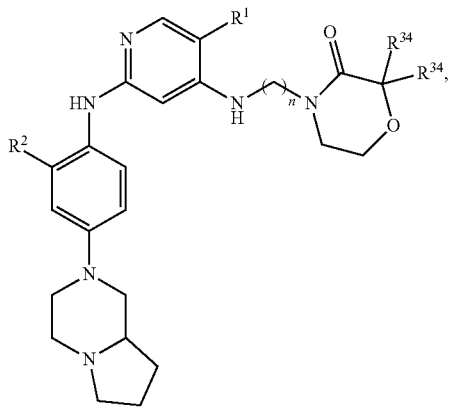

Formula IIIA.42

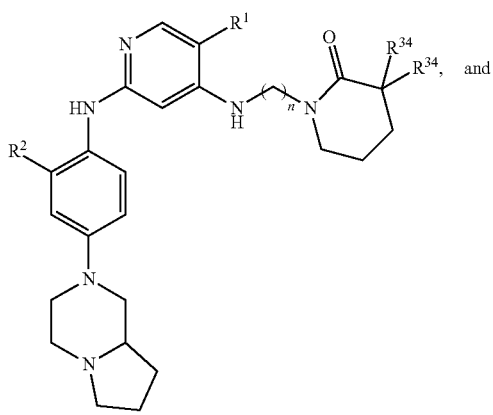

Formula IIIA.43

Formula IIIA.44

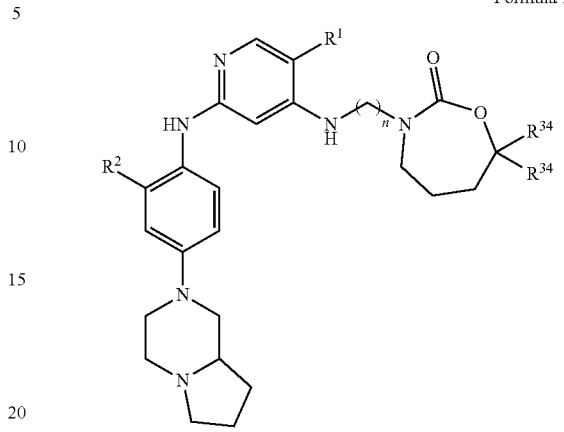

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^{34}$ is selected from the group consisting of H, $C_1$-$C_2$alkyl, and $C_3$-$C_5$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^{34}$ is independently selected from the group consisting of H and $C_1$-$C_2$alkyl; and n is 3. In some embodiments, each occurrence of $R^1$ is bromo; each occurrence of $R^2$ is independently selected from $C_1$-$C_2$alkyl, $C_3$-$C_4$cycloalkyl, bromo, and chloro; each $R^{34}$ is H; and n is 3.

In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^{34}$ is independently selected from the group consisting of H and $C_1$-$C_2$alkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each $R^{34}$ is H; and n is 3.

In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^{34}$ is independently selected from the group consisting of H and $C_1$-$C_2$alkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each $R^{34}$ is H; and n is 3.

In some embodiments, the compound is represented by a formula selected from the group consisting of:

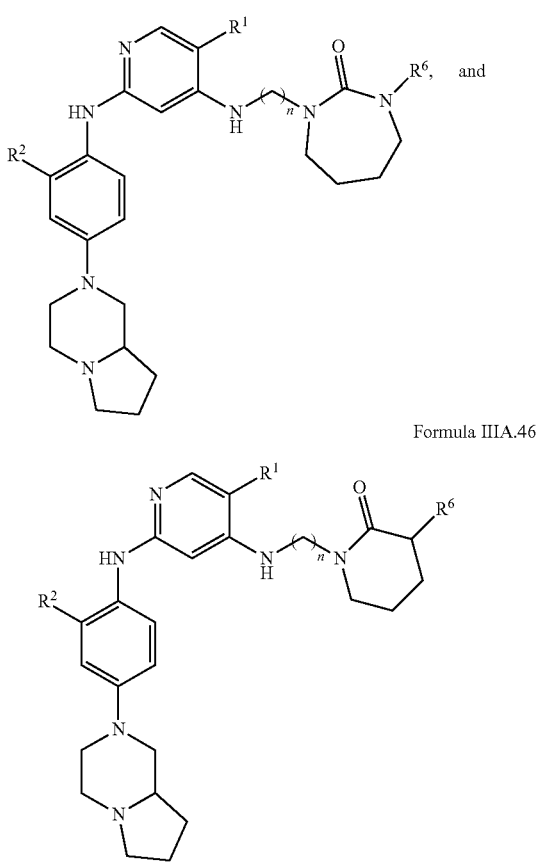

Formula IIIA.45

Formula IIIA.46 wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$alkyl, $C_3$-$C_4$cycloalkyl, and halogen; each occurrence of $R^6$ is independently selected from $C_1$-$C_3$alkyl and $C_3$-$C_4$cycloalkyl; and n is 3.

In some embodiments, each occurrence of $R^1$ is bromo; each occurrence of $R^2$ is independently selected from $C_1$-$C_2$alkyl, $C_3$-$C_4$cycloalkyl, bromo, and chloro; each occurrence of $R^6$ is selected from $C_1$-$C_3$alkyl and $C_3$-$C_4$cycloalkyl; and n is 3. In some embodiments, each occurrence of $R^1$ is $CF_3$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; and n is 3. In some embodiments, each occurrence of $R^1$ is $CF_2H$; each occurrence of $R^2$ is independently selected from $C_1$-$C_2$alkyl, $C_3$-$C_4$cycloalkyl, bromo, and chloro; each occurrence of $R^6$ is independently selected from $C_1$-$C_3$alkyl and $C_3$-$C_4$cycloalkyl; and n is 3.

In an embodiment, described herein is a compound selected from the group consisting of: 1-(3-((5-bromo-2-((2-cyclopropyl-4-(4-methylpiperazin-1-yl)phenyl)amino)pyrimidin-4-yl)amino)propyl)piperidin-2-one, 1-(3-((2-((4-(4-ethylpiperazin-1-yl)-2-methylphenyl)amino)-5-(trifluoromethyl)pyrimidin-4-yl)amino)propyl)piperidin-2-one, 1-(3-((5-chloro-2-((2-cyclopropyl-4-(4-methylpiperazin-1-yl)phenyl)amino)pyrimidin-4-yl)amino)propyl)piperidin-2-one, 1-(3-((2-((2-cyclopropyl-4-(4-methyl-1,4-diazepan-1-yl)phenyl)amino)-5-(trifluoromethyl)pyrimidin-4-yl)amino)propyl)piperidin-2-one, 1-(3-((5-chloro-2-((2-methyl-4-(1-methylpiperidin-4-yl)phenyl)amino)pyrimidin-4-yl)amino)propyl)piperidin-2-one, (R)-1-(3-ethyl-4-((4-((3-(2-oxopiperidin-1-yl)propyl)amino)-5-(trifluoromethyl)pyrimidin-2-yl)amino)phenyl)pyrrolidine-3-carbonitrile, 1-(3-((2-((4-(4-cyclopropylpiperazin-1-yl)-2-methylphenyl)amino)-5-(trifluoromethyl)pyrimidin-4-yl)amino)propyl)piperidin-2-one, 1-(3-((5-bromo-2-((2-isopropyl-4-(4-methylpiperazin-1-yl)phenyl)amino)pyrimidin-4-yl)amino)propyl)piperidin-2-one, 1-(3-((2-((2-ethyl-4-(4-ethylpiperazin-1-yl)phenyl)amino)-5-(trifluoromethyl)pyrimidin-4-yl)amino)propyl)piperidin-2-one, 1-(3-((2-((2-cyclopropyl-4-(4-methylpiperazin-1-yl)phenyl)amino)-5-(trifluoromethyl)pyrimidin-4-yl)amino)propyl)piperidin-2-one, 4-(3-cyclopropyl-4-((4-((3-(2-oxopiperidin-1-yl)propyl)amino)-5-(trifluoromethyl)pyrimidin-2-yl)amino)phenyl)-1-methylpiperazin-2-one, 1-(3-((5-bromo-2-((4-(4-ethylpiperazin-1-yl)-2-isopropylphenyl)amino)pyrimidin-4-yl)amino)propyl)piperidin-2-one, 1-(3-((2-((2-ethyl-4-(4-methylpiperazin-1-yl)phenyl)amino)-5-(trifluoromethyl)pyrimidin-4-yl)amino)propyl)piperidin-2-one, 1-(3-((2-((2-methyl-4-(1-methylpiperidin-4-yl)phenyl)amino)-5-(trifluoromethyl)pyrimidin-4-yl)amino)propyl)piperidin-2-one, 1-(3-((5-chloro-2-((4-(4-ethylpiperazin-1-yl)-2-isopropylphenyl)amino)pyrimidin-4-yl)amino)propyl)piperidin-2-one, 1-(3-((2-((2-cyclopropyl-4-(piperazin-1-yl)phenyl)amino)-5-(trifluoromethyl)pyrimidin-4-yl)amino)propyl)piperidin-2-one, 1-(3-((2-((2-cyclopropyl-5-fluoro-4-(4-methylpiperazin-1-yl)phenyl)amino)-5-(trifluoromethyl)pyrimidin-4-yl)amino)propyl)piperidin-2-one, 1-(3-((2-((2-methyl-4-(piperazin-1-yl)phenyl)amino)-5-(trifluoromethyl)pyrimidin-4-yl)amino)propyl)piperidin-2-one, 1-(3-((2-((2-methyl-4-(4-methylpiperazin-1-yl)phenyl)amino)-5-(trifluoromethyl)pyrimidin-4-yl)amino)propyl)piperidin-2-one, 1-(3-((2-((4-(4-(2-fluoroethyl)piperazin-1-yl)-2-methylphenyl)amino)-5-(trifluoromethyl)pyrimidin-4-yl)amino)propyl)piperidin-2-one, 1-(3-((5-chloro-2-((2-methyl-4-(piperidin-4-yl)phenyl)amino)pyrimidin-4-yl)amino)propyl)piperidin-2-one, 1-(3-((2-((4-(4-acetylpiperazin-1-yl)-2-cyclopropylphenyl)amino)-5-(trifluoromethyl)pyrimidin-4-yl)amino)propyl)piperidin-2-one, 1-(3-((5-chloro-2-((2-ethyl-4-(4-methylpiperazin-1-yl)phenyl)amino)pyrimidin-4-yl)amino)propyl)piperidin-2-one, (S)-1-(3-ethyl-4-((4-((3-(2-oxopiperidin-1-yl)propyl)amino)-5-(trifluoromethyl)pyrimidin-2-yl)amino)phenyl)pyrrolidine-3-carbonitrile, 1-(3-((5-bromo-2-((2-ethyl-4-(4-methylpiperazin-1-yl)phenyl)amino)pyrimidin-4-yl)amino)propyl)piperidin-2-one, 1-(3-((2-((4-(4-isopropylpiperazin-1-yl)-2-methylphenyl)amino)-5-(trifluoromethyl)pyrimidin-4-yl)amino)propyl)piperidin-2-one, 1-(3-((2-((2-isopropyl-4-(4-methylpiperazin-1-yl)phenyl)amino)-5-(trifluoromethyl)pyrimidin-4-yl)amino)propyl)piperidin-2-one, 1-(3-((2-((4-(4-cyclobutylpiperazin-1-yl)-2-methylphenyl)amino)-5-(trifluoromethyl)pyrimidin-4-yl)amino)propyl)piperidin-2-one, 1-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)piperidin-2-one, 1-(3-((2-((2-cyclopropyl-4-(4-ethylpiperazin-1-yl)phenyl)amino)-5-(trifluoromethyl)pyrimidin-4-yl)amino)propyl)piperidin-2-one, 1-(3-((2-((2-methyl-4-(piperidin-4-yl)phenyl)amino)-5-(trifluoromethyl)pyrimidin-4-yl)amino)propyl)piperidin-2-one, 1-(3-((2-((4-(1,4-diazepan-1-yl)phenyl)amino)-5-(trifluoromethyl)

pyrimidin-4-yl)amino)propyl)piperidin-2-one, 1-(3-((2-((2-ethyl-4-(4-methyl-1,4-diazepan-1-yl)phenyl)amino)-5-(trifluoromethyl)pyrimidin-4-yl)amino)propyl)piperidin-2-one, 1-(3-((2-((4-(4-ethylpiperazin-1-yl)-2-isopropylphenyl)amino)-5-(trifluoromethyl)pyrimidin-4-yl)amino)propyl)piperidin-2-one, 1-(3-((2-((4-(4-ethyl-1,4-diazepan-1-yl)phenyl)amino)-5-(trifluoromethyl)pyrimidin-4-yl)amino)propyl)piperidin-2-one, 1-(3-((2-((4-methyl-6-morpholinopyridin-3-yl)amino)-5-(trifluoromethyl)pyrimidin-4-yl)amino)propyl)piperidin-2-one, 3-(3-((2-((2-ethyl-4-(4-methylpiperazin-1-yl)phenyl)amino)-5-(trifluoromethyl)pyrimidin-4-yl)amino)propyl)-1,3-oxazinan-2-one, 3-(3-((2-((2-cyclopropyl-4-(4-methylpiperazin-1-yl)phenyl)amino)-5-(trifluoromethyl)pyrimidin-4-yl)amino)propyl)-1,3-oxazinan-2-one, 3-(3-((5-chloro-2-((2-ethyl-4-(4-methylpiperazin-1-yl)phenyl)amino)pyrimidin-4-yl)amino)propyl)-1,3-oxazinan-2-one, 3-(3-((5-bromo-2-((2-ethyl-4-(4-methylpiperazin-1-yl)phenyl)amino)pyrimidin-4-yl)amino)propyl)-1,3-oxazinan-2-one, 3-(3-((5-cyclopropyl-2-((2-ethyl-4-(4-methylpiperazin-1-yl)phenyl)amino)pyrimidin-4-yl)amino)propyl)-1,3-oxazinan-2-one, 3-(3-((2-((2-ethyl-4-(piperazin-1-yl)phenyl)amino)-5-(trifluoromethyl)pyrimidin-4-yl)amino)propyl)-1,3-oxazinan-2-one, 3-(3-((2-((2-cyclopropyl-4-(piperazin-1-yl)phenyl)amino)-5-(trifluoromethyl)pyrimidin-4-yl)amino)propyl)-1,3-oxazinan-2-one, 3-(3-((5-bromo-2-((2-cyclopropyl-4-(4-methylpiperazin-1-yl)phenyl)amino)pyrimidin-4-yl)amino)propyl)-1,3-oxazinan-2-one, 3-(3-((2-((2-methyl-4-(piperazin-1-yl)phenyl)amino)-5-(trifluoromethyl)pyrimidin-4-yl)amino)propyl)-1,3-oxazinan-2-one, 3-(3-((2-((2-ethyl-4-((1R,5 S)-8-methyl-3,8-diazabicyclo[3.2.1]octan-3-yl)phenyl)amino)-5-(trifluoromethyl)pyrimidin-4-yl)amino)propyl)-1,3-oxazinan-2-one, rac-(R)-3-(3-((2-((2-ethyl-4-(hexahydropyrrolo[1,2-a]pyrazin-2(1H)-yl)phenyl)amino)-5-(trifluoromethyl)pyrimidin-4-yl)amino)propyl)-1,3-oxazinan-2-one, rac-(R)-3-(3-((2-((2-cyclopropyl-4-(hexahydropyrrolo[1,2-a]pyrazin-2(1H)-yl)phenyl)amino)-5-(trifluoromethyl)pyrimidin-4-yl)amino)propyl)-1,3-oxazinan-2-one, 3-(3-((2-((2-ethyl-4-(4-methyl-2-oxopiperazin-1-yl)phenyl)amino)-5-(trifluoromethyl)pyrimidin-4-yl)amino)propyl)-1,3-oxazinan-2-one, 3-(3-((2-((2-methyl-4-(4-methylpiperazin-1-yl)phenyl)amino)-5-(trifluoromethyl)pyrimidin-4-yl)amino)propyl)-1,3-oxazinan-2-one, 4-(3-((2-((2-cyclopropyl-4-(4-methylpiperazin-1-yl)phenyl)amino)-5-(trifluoromethyl)pyrimidin-4-yl)amino)propyl)morpholin-3-one, 1-(3-((2-((2-cyclopropyl-4-(4-methylpiperazin-1-yl)phenyl)amino)-5-(trifluoromethyl)pyrimidin-4-yl)amino)propyl)azepan-2-one, 4-(3-((2-((2-ethyl-4-morpholinophenyl)amino)-5-(trifluoromethyl)pyrimidin-4-yl)amino)propyl)-1,4-oxazepan-3-one, 4-(3-((2-((2-cyclopropyl-4-morpholinophenyl)amino)-5-(trifluoromethyl)pyrimidin-4-yl)amino)propyl)-1,4-oxazepan-3-one, 4-(3-((2-((2-cyclopropyl-4-(4-methylpiperazin-1-yl)phenyl)amino)-5-(trifluoromethyl)pyrimidin-4-yl)amino)propyl)-1,4-oxazepan-3-one, 4-(3-((2-((2-ethyl-4-(4-methylpiperazin-1-yl)phenyl)amino)-5-(trifluoromethyl)pyrimidin-4-yl)amino)propyl)-1,4-oxazepan-3-one, 4-(3-((5-chloro-2-((2-cyclopropyl-4-(4-methylpiperazin-1-yl)phenyl)amino)pyrimidin-4-yl)amino)propyl)-1,4-oxazepan-3-one, 4-(3-((5-chloro-2-((2-ethyl-4-morpholinophenyl)amino)pyrimidin-4-yl)amino)propyl)-1,4-oxazepan-3-one, 4-(3-((5-chloro-2-((2-ethyl-4-(4-methylpiperazin-1-yl)phenyl)amino)pyrimidin-4-yl)amino)propyl)-1,4-oxazepan-3-one, 4-(3-((5-chloro-2-((2-cyclopropyl-4-morpholinophenyl)amino)pyrimidin-4-yl)amino)propyl)-1,4-oxazepan-3-one, 4-(3-((2-((4-(4-ethylpiperazin-1-yl)-2-isopropylphenyl)amino)-5-(trifluoromethyl)pyrimidin-4-yl)amino)propyl)-1,4-oxazepan-3-one, 4-(3-((5-cyclopropyl-2-((2-ethyl-4-(4-methylpiperazin-1-yl)phenyl)amino)pyrimidin-4-yl)amino)propyl)-1,4-oxazepan-3-one, 4-(3-((2-((2-cyclopropyl-4-(piperazin-1-yl)phenyl)amino)-5-(trifluoromethyl)pyrimidin-4-yl)amino)propyl)-1,4-oxazepan-3-one, 4-(3-((2-((2-ethyl-4-(4-methyl-1,4-diazepan-1-yl)phenyl)amino)-5-(trifluoromethyl)pyrimidin-4-yl)amino)propyl)-1,4-oxazepan-3-one, 4-(3-((2-((2-ethyl-5-fluoro-4-(4-methylpiperazin-1-yl)phenyl)amino)-5-(trifluoromethyl)pyrimidin-4-yl)amino)propyl)-1,4-oxazepan-3-one, 4-(3-((5-bromo-2-((2-cyclopropyl-4-(4-methylpiperazin-1-yl)phenyl)amino)pyrimidin-4-yl)amino)propyl)-1,4-oxazepan-3-one, 4-(3-((5-bromo-2-((2-ethyl-4-(4-methylpiperazin-1-yl)phenyl)amino)pyrimidin-4-yl)amino)propyl)-1,4-oxazepan-3-one, 4-(3-((5-bromo-2-((2-isopropyl-4-(4-methylpiperazin-1-yl)phenyl)amino)pyrimidin-4-yl)amino)propyl)-1,4-oxazepan-3-one, 4-(3-((2-((2-methyl-4-(4-methylpiperazin-1-yl)phenyl)amino)-5-(trifluoromethyl)pyrimidin-4-yl)amino)propyl)-1,4-oxazepan-5-one, 4-(3-((2-((2-ethyl-4-(4-methylpiperazin-1-yl)phenyl)amino)-5-(trifluoromethyl)pyrimidin-4-yl)amino)propyl)-1,4-oxazepan-5-one, 4-(3-((2-((2-cyclopropyl-4-(4-methylpiperazin-1-yl)phenyl)amino)-5-(trifluoromethyl)pyrimidin-4-yl)amino)propyl)-1,4-oxazepan-5-one, 4-(3-((2-((2-cyclopropyl-4-morpholinophenyl)amino)-5-(trifluoromethyl)pyrimidin-4-yl)amino)propyl)-1,4-oxazepan-5-one, 4-(3-((2-((2-ethyl-4-morpholinophenyl)amino)-5-(trifluoromethyl)pyrimidin-4-yl)amino)propyl)-1,4-oxazepan-5-one, 4-(3-((2-((4-(4-ethylpiperazin-1-yl)-2-isopropylphenyl)amino)-5-(trifluoromethyl)pyrimidin-4-yl)amino)propyl)-1,4-oxazepan-5-one, 4-(3-((2-((2-methyl-4-(piperazin-1-yl)phenyl)amino)-5-(trifluoromethyl)pyrimidin-4-yl)amino)propyl)-1,4-oxazepan-5-one, 4-(3-((5-bromo-2-((2-ethyl-4-(4-methylpiperazin-1-yl)phenyl)amino)pyrimidin-4-yl)amino)propyl)-1,4-oxazepan-5-one, rac-4-(3-((2-((4-((1R,4R)-2-oxa-5-azabicyclo[2.2.1]heptan-5-yl)-2-methylphenyl)amino)-5-(trifluoromethyl)pyrimidin-4-yl)amino)propyl)-1,4-oxazepan-5-one, 4-(3-((2-((2-ethyl-4-(4-methyl-1,4-diazepan-1-yl)phenyl)amino)-5-(trifluoromethyl)pyrimidin-4-yl)amino)propyl)-1,4-oxazepan-5-one, 4-(3-((5-chloro-2-((2-ethyl-4-(4-methylpiperazin-1-yl)phenyl)amino)pyrimidin-4-yl)amino)propyl)-1,4-oxazepan-5-one, 4-(3-((5-bromo-2-((2-cyclopropyl-4-(4-methylpiperazin-1-yl)phenyl)amino)pyrimidin-4-yl)amino)propyl)-1,4-oxazepan-5-one, 4-(3-((5-chloro-2-((2-cyclopropyl-4-(4-methylpiperazin-1-yl)phenyl)amino)pyrimidin-4-yl)amino)propyl)-1,4-oxazepan-5-one, 4-(3-((5-cyclopropyl-2-((2-ethyl-4-(4-methylpiperazin-1-yl)phenyl)amino)pyrimidin-4-yl)amino)propyl)-1,4-oxazepan-5-one, 4-(3-((2-((2-ethyl-4-(piperazin-1-yl)phenyl)amino)-5-(trifluoromethyl)pyrimidin-4-yl)amino)propyl)-1,4-oxazepan-5-one, 4-(3-((2-((2-cyclopropyl-4-(piperazin-1-yl)phenyl)amino)-5-(trifluoromethyl)pyrimidin-4-yl)amino)propyl)-1,4-oxazepan-5-one, 4-(3-((2-((2-ethyl-5-fluoro-4-(4-methylpiperazin-1-yl)phenyl)amino)-5-(trifluoromethyl)pyrimidin-4-yl)amino)propyl)-1,4-oxazepan-5-one, 4-(3-((5-bromo-2-((2-isopropyl-4-(4-methylpiperazin-1-yl)phenyl)amino)pyrimidin-4-yl)amino)propyl)-1,4-oxazepan-5-one, 4-(3-((5-chloro-2-((2-isopropyl-4-(4-methylpiperazin-1-yl)phenyl)amino)pyrimidin-4-yl)amino)propyl)-1,4-oxazepan-5-one, 4-(3-((5-chloro-2-((2-cyclopropyl-4-(piperazin-1-yl)phenyl)amino)pyrimidin-4-yl)amino)propyl)-1,4-oxazepan-5-one, 4-(3-((2-((2-ethyl-4-((1R,5S)-8-methyl-3,8-diazabicyclo[3.2.1]octan-3-yl)

phenyl)amino)-5-(trifluoromethyl)pyrimidin-4-yl)amino) propyl)-1,4-oxazepan-5-one, rac-(R)-4-(3-((2-((2-ethyl-4-(hexahydropyrrolo[1,2-a]pyrazin-2(1H)-yl)phenyl)amino)-5-(trifluoromethyl)pyrimidin-4-yl)amino)propyl)-1,4-oxazepan-5-one, 1-(3-((2-((2-cyclopropyl-4-(4-methylpiperazin-1-yl)phenyl)amino)-5-(trifluoromethyl) pyridin-4-yl)amino)propyl)piperidin-2-one, 4-(3-((2-((2-ethyl-4-(4-methylpiperazin-1-yl)phenyl)amino)-5-(trifluoromethyl)pyridin-4-yl)amino)propyl)-1,4-oxazepan-5-one, 4-(3-((2-((2-cyclopropyl-4-(4-methylpiperazin-1-yl) phenyl)amino)-5-(trifluoromethyl)pyridin-4-yl)amino) propyl)-1,4-oxazepan-5-one, 3-((3-((2-((4-(4-methylpiperazin-1-yl)phenyl)amino)-5-(trifluoromethyl) pyridin-4-yl)amino)propyl)-1,3-oxazinan-2-one, 1-(3-((2-((4-(4-methylpiperazin-1-yl)phenyl)amino)-5-(trifluoromethyl)pyridin-4-yl)amino)propyl)piperidin-2-one, 1-(3-((2-((4-methyl-6-(4-methylpiperazin-1-yl)pyridin-3-yl)amino)-5-(trifluoromethyl)pyridin-4-yl)amino)propyl) piperidin-2-one, 1-(3-((2-((4-methyl-6-morpholinopyridin-3-yl)amino)-5-(trifluoromethyl)pyridin-4-yl)amino)propyl) piperidin-2-one, 4-(3-((5-chloro-2-((2-cyclopropyl-4-(4-methylpiperazin-1-yl)phenyl)amino)pyridin-4-yl)amino) propyl)-1,4-oxazepan-5-one, 1-(3-((5-cyclopropyl-2-((4-(4-cyclopropylpiperazin-1-yl)phenyl)amino)pyrimidin-4-yl) amino)propyl)-5,5-dimethylpyrrolidin-2-one, 1-(3-((2-((2-methyl-4-(4-methylpiperazin-1-yl)phenyl)amino)-5-(trifluoromethyl)pyrimidin-4-yl)amino)propyl)pyrrolidin-2-one, 1-(3-((2-((2-methyl-4-(piperazin-1-yl)phenyl)amino)-5-(trifluoromethyl)pyrimidin-4-yl)amino)propyl)pyrrolidin-2-one, 1-(3-((2-((2-ethyl-4-(4-methylpiperazin-1-yl)phenyl) amino)-5-(trifluoromethyl)pyrimidin-4-yl)amino)propyl) pyrrolidin-2-one, 1-(3-((2-((4-methyl-6-(4-methylpiperazin-1-yl)pyridin-3-yl)amino)-5-(trifluoromethyl)pyrimidin-4-yl)amino)propyl)piperidin-2-one, 1-(3-((2-((5-(4-methylpiperazin-1-yl)pyridin-2-yl)amino)-5-(trifluoromethyl)pyridin-4-yl)amino)propyl)piperidin-2-one, 4-(3-((2-((4-ethyl-6-(4-methylpiperazin-1-yl)pyridin-3-yl)amino)-5-(trifluoromethyl)pyrimidin-4-yl)amino) propyl)-1,4-oxazepan-3-one, 4-(3-((2-((4-ethyl-6-(4-methylpiperazin-1-yl)pyridin-3-yl)amino)-5-(trifluoromethyl)pyrimidin-4-yl)amino)propyl)-1,4-oxazepan-5-one, (R)-4-(3-((2-((2-cyclopropyl-4-(hexahydropyrrolo[1,2-a]pyrazin-2(1H)-yl)phenyl)amino)-5-(trifluoromethyl)pyrimidin-4-yl)amino)propyl)-1,4-oxazepan-5-one, 4-(3-((2-((2-ethyl-4-((1S,4S)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 3-(3-((2-((2-ethyl-4-((1S,4S)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 4-(3-((2-((2-cyclopropyl-4-((1S,4S)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 3-(3-((2-((2-cyclopropyl-4-((1S,4S)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 4-(3-((2-((2-ethyl-4-((1R,4R)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 4-(3-((2-((2-cyclopropyl-4-((1R,4R)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 3-(3-((2-((2-ethyl-4-((1R,4R)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 1-(3-((2-((2-cyclopropyl-4-(3-(dimethylamino)azetidin-1-yl)phenyl)amino)-5-(trifluoromethyl)pyrimidin-4-yl)amino)propyl)piperidin-2-one, 4-(3-((2-((2-(methoxymethyl)-4-(4-methylpiperazin-1-yl)phenyl)amino)-5-(trifluoromethyl)pyrimidin-4-yl)amino) propyl)-1,4-oxazepan-5-one, 3-(3-((2-((4-ethyl-6-(4-methylpiperazin-1-yl)pyridin-3-yl)amino)-5-(trifluoromethyl)pyrimidin-4-yl)amino)propyl)-1,3-oxazinan-2-one, 2-((2-ethyl-4-(4-methylpiperazin-1-yl)phenyl)amino)-4-((3-(5-oxo-1,4-oxazepan-4-yl)propyl) amino)pyrimidine-5-carbonitrile, 3-(3-((2-((2-cyclopropyl-((1R,4R)-5-methyl-2,5-diazabicyclo[2.2.1]heptan-2-yl) phenyl)amino)-5-(trifluoromethyl)pyrimidin-4-yl)amino) propyl)-1,3-oxazinan-2-one, (S)-2-(4-(3-ethyl-4-((4-((3-(2-oxo-1,3-oxazinan-3-yl)propyl)amino)-5-(trifluoromethyl)pyrimidin-2-yl)amino)phenyl)-1-methylpiperazin-2-yl) acetonitrile, (R)-2-(4-(3-ethyl-4-((4-((3-(2-oxo-1,3-oxazinan-3-yl)propyl)amino)-5-(trifluoromethyl)pyrimidin-2-yl)amino)phenyl)-1-methylpiperazin-2-yl)acetonitrile, (S)-2-(1-methyl-4-(3-methyl-4-((4-((3-(5-oxo-1,4-oxazepan-4-yl)propyl)amino)-5-(trifluoromethyl)pyrimidin-2-yl) amino)phenyl)piperazin-2-yl)acetonitrile, (R)-2-(1-methyl-4-(3-methyl-4-((4-((3-(5-oxo-1,4-oxazepan-4-yl)propyl) amino)-5-(trifluoromethyl)pyrimidin-2-yl)amino)phenyl) piperazin-2-yl)acetonitrile, 4-(3-((5-(difluoromethyl)-2-((2-ethyl-4-(4-methylpiperazin-1-yl)phenyl)amino)pyrimidin-4-yl)amino)propyl)-1,4-oxazepan-5-one, 3434(5-(difluoromethyl)-2-((2-ethyl-4-(4-methylpiperazin-1-yl) phenyl)amino)pyrimidin-4-yl)amino)propyl)-1,3-oxazinan-2-one, 2-((2-ethyl-4-(4-methylpiperazin-1-yl)phenyl) amino)-4-((3-(2-oxo-1,3-oxazinan-3-yl)propyl)amino) pyrimidine-5-carbonitrile, 4-(3-((2-((2-ethyl-4-(1-methylpiperidin-4-yl)phenyl)amino)-5-(trifluoromethyl) pyrimidin-4-yl)amino)propyl)-1,4-oxazepan-5-one, 4-(3-((2-((2-ethyl-4-((1R,5S)-3-methyl-3,8-diazabicyclo[3.2.1] octan-8-yl)phenyl)amino)-5-(trifluoromethyl)pyrimidin-4-yl)amino)propyl)-1,4-oxazepan-5-one, 4-(3-((2-((2-ethyl-4-(9-methyl-3,9-diazabicyclo[3.3.1]nonan-3-yl)phenyl) amino)-5-(trifluoromethyl)pyrimidin-4-yl)amino)propyl)-1, 4-oxazepan-5-one, 4-(3-((2-((2-ethyl-4-(3-methyl-3,9-diazabicyclo[3.3.1]nonan-9-yl)phenyl)amino)-5-(trifluoromethyl)pyrimidin-4-yl)amino)propyl)-1,4-oxazepan-5-one, (S)-4-(3-((2-((4-(3-(dimethylamino) pyrrolidin-1-yl)-2-ethylphenyl)amino)-5-(trifluoromethyl) pyrimidin-4-yl)amino)propyl)-1,4-oxazepan-5-one, (R)-4-(3-((2-((4-(3-(dimethylamino)pyrrolidin-1-yl)-2-ethylphenyl)amino)-5-(trifluoromethyl)pyrimidin-4-yl) amino)propyl)-1,4-oxazepan-5-one, 4-(3-((2-((2-ethyl-4-(1-methylpyrrolidin-3-yl)phenyl)amino)-5-(trifluoromethyl) pyrimidin-4-yl)amino)propyl)-1,4-oxazepan-5-one, 4-(3-((2-((2-ethynyl-4-(4-methylpiperazin-1-yl)phenyl)amino)-5-(trifluoromethyl)pyrimidin-4-yl)amino)propyl)-1,4-oxazepan-5-one, 4-(3-((2-((2-(ethynyl-d)-4-(4-methylpiperazin-1-yl)phenyl)amino)-5-(trifluoromethyl) pyrimidin-4-yl)amino)propyl)-1,4-oxazepan-5-one, 4-(3-((2-((2-(ethyl-d5)-4-(4-methylpiperazin-1-yl)phenyl) amino)-5-(trifluoromethyl)pyrimidin-4-yl)amino)propyl)-1, 4-oxazepan-5-one, 4-(3-((2-((4-(4-methylpiperazin-1-yl)-2-(2,2,2-trifluoroethyl)phenyl)amino)-5-(trifluoromethyl) pyrimidin-4-yl)amino)propyl)-1,4-oxazepan-5-one, 4-(3-((2-((2-(1,1-difluoroethyl)-4-(4-methylpiperazin-1-yl) phenyl)amino)-5-(trifluoromethyl)pyrimidin-4-yl)amino) propyl)-1,4-oxazepan-5-one, 5-(4-methylpiperazin-1-yl)-2-((4-((3-(5-oxo-1,4-oxazepan-4-yl)propyl)amino)-5-(trifluoromethyl)pyrimidin-2-yl)amino)benzonitrile, 2-methyl-2-(5-(4-methylpiperazin-1-yl)-2-((4-((3-(5-oxo-1, 4-oxazepan-2-yl)propyl)amino)-5-(trifluoromethyl)pyrimidin-2-yl)amino)phenyl)propanenitrile, 2-(5-(4-methylpiperazin-1-yl)-2-((4-((3-(5-oxo-1,4-oxazepan-4-yl)propyl)

amino)-5-(trifluoromethyl)pyrimidin-2-yl)amino)phenyl) acetonitrile, 4-(3-((2-((4-(4-methylpiperazin-1-yl)-2-(trifluoromethyl)phenyl)amino)-5-(trifluoromethyl) pyrimidin-4-yl)amino)propyl)-1,4-oxazepan-5-one, 4-(3-((2-((2-(difluoromethyl)-4-(4-methylpiperazin-1-yl)phenyl) amino)-5-(trifluoromethyl)pyrimidin-4-yl)amino)propyl)-1, 4-oxazepan-5-one, 4-(3-((2-((2-bromo-4-(4-methylpiperazin-1-yl)phenyl)amino)-5-(trifluoromethyl) pyrimidin-4-yl)amino)propyl)-1,4-oxazepan-5-one, 4-(3-((2-((2-chloro-4-(4-methylpiperazin-1-yl)phenyl)amino)-5-(trifluoromethyl)pyrimidin-4-yl)amino)propyl)-1,4-oxazepan-5-one, 4-(3-((2-((2-cyclopropyl-4-(3-(dimethylamino)azetidin-1-yl)phenyl)amino)-5-(trifluoromethyl)pyrimidin-4-yl)amino)propyl)-1,4-oxazepan-5-one, 4-(3-((2-((2-cyclopropyl-4-(3-((dimethylamino)methyl)azetidin-1-yl)phenyl)amino)-5-(trifluoromethyl)pyrimidin-4-yl)amino)propyl)-1,4-oxazepan-5-one, 1-(3-((2-((2-ethyl-4-(4-methylpiperazin-1-yl)phenyl)amino)-5-(trifluoromethyl)pyrimidin-4-yl)amino) propyl)-3-methyltetrahydropyrimidin-2(1H)-one, 1-(3-((2-((2-cyclopropyl-4-(4-methylpiperazin-1-yl)phenyl)amino)-5-(trifluoromethyl)pyrimidin-4-yl)amino)propyl)-3-methyltetrahydropyrimidin-2(1H)-one, 3-(3-((2-((2-ethyl-4-(4-methylpiperazin-1-yl)phenyl)amino)-5-(trifluoromethyl) pyrimidin-4-yl)amino)propyl)-1,3-oxazepan-2-one, 3-(3-((2-((2-cyclopropyl-4-(4-methylpiperazin-1-yl)phenyl) amino)-5-(trifluoromethyl)pyrimidin-4-yl)amino)propyl)-1, 3-oxazepan-2-one, 1-(3-((2-((2-ethyl-4-(4-methylpiperazin-1-yl)phenyl)amino)-5-(trifluoromethyl)pyrimidin-4-yl) amino)propyl)-4-methyl-1,4-diazepan-2-one, 1-(3-((2-((2-cyclopropyl-4-(4-methylpiperazin-1-yl)phenyl)amino)-5-(trifluoromethyl)pyrimidin-4-yl)amino)propyl)-4-methyl-1, 4-diazepan-2-one, 4-(3-((2-((2-ethyl-4-(4-methylpiperazin-1-yl)phenyl)amino)-5-(trifluoromethyl)pyrimidin-4-yl) amino)propyl)-1-methyl-1,4-diazepan-5-one, 4-(3-((2-((2-cyclopropyl-4-(4-methylpiperazin-1-yl)phenyl)amino)-5-(trifluoromethyl)pyrimidin-4-yl)amino)propyl)-1-methyl-1, 4-diazepan-5-one, 1-(3-((2-((2-ethyl-4-(4-methylpiperazin-1-yl)phenyl)amino)-5-(trifluoromethyl)pyrimidin-4-yl) amino)propyl)-3-methyl-1,3-diazepan-2-one, 1-(3-((2-((2-cyclopropyl-4-(4-methylpiperazin-1-yl)phenyl)amino)-5-(trifluoromethyl)pyrimidin-4-yl)amino)propyl)-3-methyl-1, 3-diazepan-2-one, 3-(3-((2-((2-cyclopropyl-4-(4-methylpiperazin-1-yl)phenyl)amino)-5-(difluoromethyl) pyrimidin-4-yl)amino)propyl)-1,3-oxazinan-2-one, 3-(3-((5-(difluoromethyl)-2-((2-ethyl-4-(1R,5S)-8-methyl-3,8-diazabicyclo[3.2.1]octan-3-yl)phenyl)amino)pyrimidin-4-yl)amino)propyl)-1,3-oxazinan-2-one, 3-(3-((2-((2-cyclopropyl-4-((1R,5S)-8-methyl-3,8-diazabicyclo[3.2.1] octan-3-yl)phenyl)amino)-5-(difluoromethyl)pyrimidin-4-yl)amino)propyl)-1,3-oxazinan-2-one, 3-(3-((5-(difluoromethyl)-2-((2-ethyl-4-((1S,4S)-5-methyl-2,5-diazabicyclo[2.2.1]heptan-2-yl)phenyl)amino)pyrimidin-4-yl)amino)propyl)-1,3-oxazinan-2-one, 3-(3-((5-(difluoromethyl)-2-((2-ethyl-4-((1R,4R)-5-methyl-2,5-diazabicyclo[2.2.1]heptan-2-yl)phenyl)amino)pyrimidin-4-yl)amino)propyl)-1,3-oxazinan-2-one, (R)-3-(3-((5-(difluoromethyl)-2-((2-ethyl-4-(hexahydropyrrolo[1,2-a] pyrazin-2(1H)-yl)phenyl)amino)pyrimidin-4-yl)amino) propyl)-1,3-oxazinan-2-one, (S)-3-(3-((5-(difluoromethyl)-2-((2-ethyl-4-(hexahydropyrrolo[1,2-a]pyrazin-2(1H)-yl) phenyl)amino)pyrimidin-4-yl)amino)propyl)-1,3-oxazinan-2-one, 3-(3-((5-(difluoromethyl)-2-((2-ethyl-4-(piperazin-1-yl)phenyl)amino)pyrimidin-4-yl)amino)propyl)-1,3-oxazinan-2-one, 3-(3-((2-((2-cyclopropyl-4-(piperazin-1-yl) phenyl)amino)-5-(difluoromethyl)pyrimidin-4-yl)amino) propyl)-1,3-oxazinan-2-one, 1-(3-((5-(difluoromethyl)-2-((2-ethyl-4-(4-methylpiperazin-1-yl)phenyl)amino) pyrimidin-4-yl)amino)propyl)-3-methyltetrahydropyrimidin-2(1H)-one, 1-(3-((2-((2-cyclopropyl-4-(4-methylpiperazin-1-yl)phenyl)amino)-5-(difluoromethyl)pyrimidin-4-yl)amino)propyl)-3-methyltetrahydropyrimidin-2(1H)-one, 4-(3-((5-(difluoromethyl)-2-((2-ethyl-4-(4-methylpiperazin-1-yl) phenyl)amino)pyrimidin-4-yl)amino)propyl)-1,4-oxazepan-3-one, 4-(3-((2-((2-cyclopropyl-4-(4-methylpiperazin-1-yl) phenyl)amino)-5-(difluoromethyl)pyrimidin-4-yl)amino) propyl)-1,4-oxazepan-3-one, 4-(3-((2-((2-cyclopropyl-4-(4-methylpiperazin-1-yl)phenyl)amino)-5-(difluoromethyl) pyrimidin-4-yl)amino)propyl)-1,4-oxazepan-5-one, 3-(3-((5-(difluoromethyl)-2-((2-ethyl-4-(4-methylpiperazin-1-yl) phenyl)amino)pyrimidin-4-yl)amino)propyl)-1,3-oxazepan-2-one, 3-(3-((2-((2-cyclopropyl-4-(4-methylpiperazin-1-yl) phenyl)amino)-5-(difluoromethyl)pyrimidin-4-yl)amino) propyl)-1,3-oxazepan-2-one, 1-(3-((5-(difluoromethyl)-2-((2-ethyl-4-(4-methylpiperazin-1-yl)phenyl)amino) pyrimidin-4-yl)amino)propyl)-4-methyl-1,4-diazepan-2-one, 1-(3-((2-((2-cyclopropyl-4-(4-methylpiperazin-1-yl) phenyl)amino)-5-(difluoromethyl)pyrimidin-4-yl)amino) propyl)-4-methyl-1,4-diazepan-2-one, 4-(3-((5-(difluoromethyl)-2-((2-ethyl-4-(4-methylpiperazin-1-yl) phenyl)amino)pyrimidin-4-yl)amino)propyl)-1-methyl-1,4-diazepan-5-one, 4-(3-((2-((2-cyclopropyl-4-(4-methylpiperazin-1-yl)phenyl)amino)-5-(difluoromethyl) pyrimidin-4-yl)amino)propyl)-1-methyl-1,4-diazepan-5-one, 1-(3-((5-(difluoromethyl)-2-((2-ethyl-4-(4-methylpiperazin-1-yl)phenyl)amino)pyrimidin-4-yl)amino) propyl)-3-methyl-1,3-diazepan-2-one, 1-(3-((2-((2-cyclopropyl-4-(4-methylpiperazin-1-yl)phenyl)amino)-5-(difluoromethyl)pyrimidin-4-yl)amino)propyl)-3-methyl-1, 3-diazepan-2-one, 2-((2-cyclopropyl-4-(4-methylpiperazin-1-yl)phenyl)amino)-4-((3-(2-oxo-1,3-oxazinan-3-yl)propyl) amino)pyrimidine-5-carbonitrile, 24(2-cyclopropyl-4-((1R,5 S)-8-methyl-3,8-diazabicyclo[3.2.1]octan-3-yl) phenyl)amino)-4-((3-(2-oxo-1,3-oxazinan-3-yl)propyl) amino)pyrimidine-5-carbonitrile, 2-((2-ethyl-4-(1R,5 S)-8-methyl-3,8-diazabicyclo[3.2.1]octan-3-yl)phenyl)amino)-4-((3-(2-oxo-1,3-oxazinan-3-yl)propyl)amino)pyrimidine-5-carbonitrile, 2-((2-ethyl-4-((1S,4S)-5-methyl-2,5-diazabicyclo[2.2.1]heptan-2-yl)phenyl)amino)-4-((3-(2-oxo-1,3-oxazinan-3-yl)propyl)amino)pyrimidine-5-carbonitrile, 2-((2-ethyl-((1R,4R)-5-methyl-2,5-diazabicyclo[2.2.1]heptan-2-yl)phenyl)amino)-4-((3-(2-oxo-1,3-oxazinan-3-yl)propyl)amino)pyrimidine-5-carbonitrile, (R)-2-((2-ethyl-4-(hexahydropyrrolo[1,2-a] pyrazin-2(1H)-yl)phenyl)amino)-4-((3-(2-oxo-1,3-oxazinan-3-yl)propyl)amino)pyrimidine-5-carbonitrile, (S)-2-((2-ethyl-4-(hexahydropyrrolo[1,2-a]pyrazin-2(1H)-yl) phenyl)amino)-4-((3-(2-oxo-1,3-oxazinan-3-yl)propyl) amino)pyrimidine-5-carbonitrile, 2-((2-ethyl-4-(piperazin-1-yl)phenyl)amino)-4-((3-(2-oxo-1,3-oxazinan-3-yl)propyl) amino)pyrimidine-5-carbonitrile, 2-((2-cyclopropyl-4-(piperazin-1-yl)phenyl)amino)-4-((3-(2-oxo-1,3-oxazinan-3-yl)propyl)amino)pyrimidine-5-carbonitrile, 2-((2-ethyl-4-(4-methylpiperazin-1-yl)phenyl)amino)-4-((3-(3-methyl-2-oxotetrahydropyrimidin-1(2H)-yl)propyl)amino) pyrimidine-5-carbonitrile, 2-((2-cyclopropyl-4-(4-methylpiperazin-1-yl)phenyl)amino)-4-((3-(3-methyl-2-oxotetrahydropyrimidin-1(2H)-yl)propyl)amino) pyrimidine-5-carbonitrile, 2-((2-ethyl-4-(4-methylpiperazin-1-yl)phenyl)amino)-4-((3-(3-oxo-1,4-oxazepan-4-yl)propyl)amino)pyrimidine-5-carbonitrile, 2-((2-cyclopropyl-4-(4-methylpiperazin-1-yl)phenyl) amino)-4-((3-(3-oxo-1,4-oxazepan-4-yl)propyl)amino)pyrimidine-5-carbonitrile, 2-((2-cyclopropyl-4-(4-methylpiperazin-1-yl)phenyl)amino)-4-((3-(5-oxo-1,4-oxazepan-4-yl)propyl)amino)pyrimidine-5-carbonitrile, 2-((2-ethyl-4-(4-methylpiperazin-1-yl)phenyl)amino)-4-((3-(2-oxo-1,3-oxazepan-3-yl)propyl)amino)pyrimidine-5-carbonitrile, 2-((2-cyclopropyl-4-(4-methylpiperazin-1-yl)phenyl)amino)-4-((3-(2-oxo-1,3-oxazepan-3-yl)propyl)amino)pyrimidine-5-carbonitrile, 2-((2-cyclopropyl-4-(4-methylpiperazin-1-yl)phenyl)amino)-4-((3-(4-methyl-2-oxo-1,4-diazepan-1-yl)propyl)amino)pyrimidine-5-carbonitrile, 2-((2-ethyl-4-(4-methylpiperazin-1-yl)phenyl)amino)-4-((3-(4-methyl-7-oxo-1,4-diazepan-1-yl)propyl)amino)pyrimidine-5-carbonitrile, 2-((2-cyclopropyl-4-(4-methylpiperazin-1-yl)phenyl)amino)-4-((3-(4-methyl-7-oxo-1,4-diazepan-1-yl)propyl)amino)pyrimidine-5-carbonitrile, 2-((2-ethyl-4-(4-methylpiperazin-1-yl)phenyl)amino)-4-((3-(3-methyl-2-oxo-1,3-diazepan-1-yl)propyl)amino)pyrimidine-5-carbonitrile, 2-((2-cyclopropyl-4-(4-methylpiperazin-1-yl)phenyl)amino)-4-((3-(3-methyl-2-oxo-1,3-diazepan-1-yl)propyl)amino)pyrimidine-5-carbonitrile, 1-(3-((2-((2-cyclopropyl-4-((1R,5S)-8-methyl-3,8-diazabicyclo[3.2.1]octan-3-yl)phenyl)amino)-5-(trifluoromethyl)pyrimidin-4-yl)amino)propyl)piperidin-2-one, 1-(3-((2-(2-cyclopropyl-4-((1R,5S)-8-methyl-3,8-diazabicyclo[3.2.1]octan-3-yl)phenyl)amino)-5-(difluoromethyl)pyrimidin-4-yl)amino)propyl)piperidin-2-one, 3-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-6,6-dimethyl-1,3-oxazinan-2-one, 4-(3-((2-((2-cyclopropyl-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-5-one, 4-(3-((2-((2-cyclopropyl-4-(5-methyl-2,5-diazabicyclo[2.2.1]heptan-2-yl)phenyl)amino)-5-(difluoromethyl)pyrimidin-4-yl)amino)propyl)-1,4-oxazepan-5-one, 4-(3-((5-(difluoromethyl)-2-((2-ethyl-4-(5-methyl-2,5-diazabicyclo[2.2.1]heptan-2-yl)phenyl)amino)pyrimidin-4-yl)amino)propyl)-1,4-oxazepan-5-one, 4-(3-((5-(difluoromethyl)-2-((2-ethyl-4-((1R,5S)-8-methyl-3,8-diazabicyclo[3.2.1]octan-3-yl)phenyl)amino)pyrimidin-4-yl)amino)propyl)-1,4-oxazepan-3-one, 4-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-3-one, 4-(3-((5-(difluoromethyl)-2-((2-ethyl-4-(5-methyl-2,5-diazabicyclo[2.2.1]heptan-2-yl)phenyl)amino)pyrimidin-4-yl)amino)propyl)-1,4-oxazepan-3-one, 4-(3-((2-((2-ethyl-4-(5-methyl-2,5-diazabicyclo[2.2.1]heptan-2-yl)phenyl)amino)-5-(trifluoromethyl)pyrimidin-4-yl)amino)propyl)-1,4-oxazepan-3-one, 3-(3-((5-(difluoromethyl)-2-((2-ethyl-4-((1R,5S)-8-methyl-3,8-diazabicyclo[3.2.1]octan-3-yl)phenyl)amino)pyrimidin-4-yl)amino)propyl)-1,3-oxazepan-2-one, 3-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-1,3-oxazepan-2-one, 4-(3-((2-((2-ethyl-4-(4-methylpiperazin-1-yl)phenyl)amino)-5-(trifluoromethyl)pyrimidin-4-yl)amino)propyl)-6,6-dimethyl-1,4-oxazepan-5-one, 3-(3-((2-((2-ethyl-4-(4-methylpiperazin-1-yl)phenyl)amino)-5-(trifluoromethyl)pyrimidin-4-yl)amino)propyl)-6,6-dimethyl-1,3-oxazinan-2-one, 4-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-2,2-dimethyl-1,4-oxazepan-3-one, 4-(3-((2-(2-ethyl-4-(4-methylpiperazin-1-yl)phenyl)amino)-5-(trifluoromethyl)pyrimidin-4-yl)amino)propyl)-2,2-dimethyl-1,4-oxazepan-3-one, 4-(3-((5-(difluoromethyl)-2-((2-ethyl-4-(4-methylpiperazin-1-yl)phenyl)amino)pyrimidin-4-yl)amino)propyl)-6,6-dimethyl-1,4-oxazepan-5-one, 8-(3-((2-((2-ethyl-4-(4-methylpiperazin-1-yl)phenyl)amino)-5-(trifluoromethyl)pyrimidin-4-yl)amino)propyl)-5-oxa-8-azaspiro[2.6]nonan-9-one, 4-(3-((2-((4-(1,4-diazabicyclo[3.2.1]octan-4-yl)-2-ethylphenyl)amino)-5-(trifluoromethyl)pyrimidin-4-yl)amino)propyl)-1,4-oxazepan-5-one, 4-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-6,6-dimethyl-1,4-oxazepan-5-one, 4-(3-((5-(difluoromethyl)-2-((2-ethyl-4-((1R,5S)-8-methyl-3,8-diazabicyclo[3.2.1]octan-3-yl)phenyl)amino)pyrimidin-4-yl)amino)propyl)-6,6-dimethyl-1,4-oxazepan-5-one, 4-(3-((2-((4-(1,4-diazabicyclo[3.2.1]octan-4-yl)-2-ethylphenyl)amino)-5-(trifluoromethyl)pyrimidin-4-yl)amino)propyl)-6,6-dimethyl-1,4-oxazepan-5-one, 4-(3-((2-((4-(1,4-diazabicyclo[3.2.1]octan-4-yl)-2-ethylphenyl)amino)-5-(difluoromethyl)pyrimidin-4-yl)amino)propyl)-6,6-dimethyl-1,4-oxazepan-5-one, 1-(3-((2-((2-ethyl-4-(4-methylpiperazin-1-yl)phenyl)amino)-5-(trifluoromethyl)pyrimidin-4-yl)amino)propyl)azetidin-2-one, 1-(3-((2-((2-ethyl-4-(4-methylpiperazin-1-yl)phenyl)amino)-5-(trifluoromethyl)pyrimidin-4-yl)amino)propyl)-3,3-dimethylazetidin-2-one, 1-(3-((2-((4-(1,4-diazabicyclo[3.2.1]octan-4-yl)-2-ethylphenyl)amino)-5-(trifluoromethyl)pyrimidin-4-yl)amino)propyl)azetidin-2-one, 1-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)azetidin-2-one, 1-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-3,3-dimethylazetidin-2-one, 1-(3-((2-((4-(1,4-diazabicyclo[3.2.1]octan-4-yl)-2-ethylphenyl)amino)-5-(trifluoromethyl)pyrimidin-4-yl)amino)propyl)-3,3-dimethylazetidin-2-one, 1-(3-((2-((2-ethyl-4-(hexahydropyrrolo[1,2-a]pyrazin-2(1H)-yl)phenyl)amino)-5-(trifluoromethyl)pyrimidin-4-yl)amino)propyl)azetidin-2-one, 1-(3-((2-((2-ethyl-4-(hexahydropyrrolo[1,2-a]pyrazin-2(1H)-yl)phenyl)amino)-5-(trifluoromethyl)pyrimidin-4-yl)amino)propyl)-3,3-dimethylazetidin-2-one, 1-(3-((2-((2-ethyl-4-(5-methyl-2,5-diazabicyclo[2.2.1]heptan-2-yl)phenyl)amino)-5-(trifluoromethyl)pyrimidin-4-yl)amino)propyl)azetidin-2-one, 1-(3-((2-((2-ethyl-4-(5-methyl-2,5-diazabicyclo[2.2.1]heptan-2-yl)phenyl)amino)-5-(trifluoromethyl)pyrimidin-4-yl)amino)propyl)-3,3-dimethylazetidin-2-one, 1-(3-((2-((2-ethyl-4-(5-methyl-2,5-diazabicyclo[2.2.1]heptan-2-yl)phenyl)amino)-5-(trifluoromethyl)pyrimidin-4-yl)amino)propyl)pyrrolidin-2-one, 1-(3-((5-(difluoromethyl)-2-((2-ethyl-4-(5-methyl-2,5-diazabicyclo[2.2.1]heptan-2-yl)phenyl)amino)pyrimidin-4-yl)amino)propyl)pyrrolidin-2-one, 1-(3-((2-((2-ethyl-4-(5-methyl-2,5-diazabicyclo[2.2.1]heptan-2-yl)phenyl)amino)-5-(trifluoromethyl)pyrimidin-4-yl)amino)propyl)-3,3-dimethylpyrrolidin-2-one, 1-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)pyrrolidin-2-one, 1-(3-((5-(difluoromethyl)-2-((2-ethyl-4-((1R,5S)-8-methyl-3,8-diazabicyclo[3.2.1]octan-3-yl)phenyl)amino)pyrimidin-4-yl)amino)propyl)pyrrolidin-2-one, 1-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-3,3-dimethylpyrrolidin-2-one, 1-(3-((2-((4-(1,4-diazabicyclo[3.2.1]octan-4-yl)-2-ethylphenyl)amino)-5-(trifluoromethyl)pyrimidin-4-yl)amino)propyl)pyrrolidin-2-one, 1-(3-((2-((4-(1,4-diazabicyclo[3.2.1]octan-4-yl)-2-ethylphenyl)amino)-5-(difluoromethyl)pyrimidin-4-yl)amino)propyl)pyrrolidin-2-one, 1-(3-((2-

((4-(1,4-diazabicyclo[3.2.1]octan-4-yl)-2-ethylphenyl) amino)-5-(trifluoromethyl)pyrimidin-4-yl)amino)propyl)-3,3-dimethylpyrrolidin-2-one, 1-(3-((2-((2-ethyl-4-(hexahydropyrrolo[1,2-a]pyrazin-2(1H)-yl)phenyl)amino)-5-(trifluoromethyl)pyrimidin-4-yl)amino)propyl)pyrrolidin-2-one, 1-(3-((5-(difluoromethyl)-2-((2-ethyl-4-(hexahydropyrrolo[1,2-a]pyrazin-2(1H)-yl)phenyl)amino)pyrimidin-4-yl)amino)propyl)pyrrolidin-2-one, 1-(3-((2-((2-ethyl-4-(hexahydropyrrolo[1,2-a]pyrazin-2(1H)-yl)phenyl)amino)-5-(trifluoromethyl)pyrimidin-4-yl)amino)propyl)-3,3-dimethylpyrrolidin-2-one, 1-(3-((5-chloro-2-((2-ethyl-4-(5-methyl-2,5-diazabicyclo[2.2.1]heptan-2-yl)phenyl)amino)pyrimidin-4-yl)amino)propyl)pyrrolidin-2-one, 1-(3-((5-chloro-2-((2-ethyl-4-((1R,5S)-8-methyl-3,8-diazabicyclo[3.2.1]octan-3-yl)phenyl)amino)pyrimidin-4-yl)amino)propyl)pyrrolidin-2-one, 1-(3-((2-((4-(1,4-diazabicyclo[3.2.1]octan-4-yl)-2-ethylphenyl)amino)-5-chloropyrimidin-4-yl)amino)propyl)pyrrolidin-2-one, 1-(3-((5-chloro-2-((2-ethyl-4-(hexahydropyrrolo[1,2-a]pyrazin-2(1H)-yl)phenyl)amino)pyrimidin-4-yl)amino)propyl)pyrrolidin-2-one, 1-(3-((5-bromo-2-((2-ethyl-4-(5-methyl-2,5-diazabicyclo[2.2.1]heptan-2-yl)phenyl)amino)pyrimidin-4-yl)amino)propyl)pyrrolidin-2-one, 1-(3-((5-bromo-2-((2-ethyl-4-((1R,5S)-8-methyl-3,8-diazabicyclo[3.2.1]octan-3-yl)phenyl)amino)pyrimidin-4-yl)amino)propyl)pyrrolidin-2-one, 1-(3-((2-((4-(1,4-diazabicyclo[3.2.1]octan-4-yl)-2-ethylphenyl)amino)-5-bromopyrimidin-4-yl)amino)propyl)pyrrolidin-2-one, 1-(3-((5-bromo-2-((2-ethyl-4-(hexahydropyrrolo[1,2-a]pyrazin-2(1H)-yl)phenyl)amino)pyrimidin-4-yl)amino)propyl)pyrrolidin-2-one, 4-(3-((2-((4-(3-(diethylamino)propyl)-2-ethylphenyl)amino)-5-(trifluoromethyl)pyrimidin-4-yl)amino)propyl)-1,4-oxazepan-5-one, 4-(3-((2-((2-cyclopropyl-4-(3-morpholinopropyl)phenyl)amino)-5-(trifluoromethyl)pyrimidin-4-yl)amino)propyl)-1,4-oxazepan-3-one, 3-(3-((2-((2-ethyl-4-(2-(pyrrolidin-1-yl)ethyl)phenyl)amino)-5-(trifluoromethyl)pyrimidin-4-yl)amino)propyl)-1,3-oxazinan-2-one, 3-(3-((2-((2-cyclopropyl-4-((dimethylamino)methyl)phenyl)amino)-5-(trifluoromethyl)pyrimidin-4-yl)amino)propyl)-1,3-oxazinan-2-one, 3-(3-((2-((2-cyclopropyl-4-(4-methylpiperazine-1-carbonyl)phenyl)amino)-5-(trifluoromethyl)pyrimidin-4-yl)amino)propyl)-1,3-oxazinan-2-one, 3-methoxy-N-(1-methylpiperidin-4-yl)-4-((4-((3-(5-oxo-1,4-oxazepan-4-yl)propyl)amino)-5-(trifluoromethyl)pyrimidin-2-yl)amino)benzamide, 4-(3-((2-((4-(4-(diethylamino)piperidin-1-yl)-2-ethylphenyl)amino)-5-(trifluoromethyl)pyrimidin-4-yl)amino)propyl)-1,4-oxazepan-3-one, (S)-4-(3-((2-((2-cyclopropyl-4-(3-(dimethylamino)pyrrolidin-1-yl)phenyl)amino)-5-(trifluoromethyl)pyrimidin-4-yl)amino)propyl)-1,4-oxazepan-5-one, 1-(3-((2-((2-cyclopropyl-4-(morpholinomethyl)phenyl)amino)-5-(trifluoromethyl)pyrimidin-4-yl)amino)propyl)piperidin-2-one, 1-(3-((2-((2-ethyl-4-(2-(pyrrolidin-1-yl)propan-2-yl)phenyl)amino)-5-(trifluoromethyl)pyrimidin-4-yl)amino)propyl)piperidin-2-one, 4-(3-((2-((2-ethyl-4-(2-(4-methylpiperazin-1-yl)-2-oxoethyl)phenyl)amino)-5-(trifluoromethyl)pyrimidin-4-yl)amino)propyl)-1,4-oxazepan-5-one, 4-(3-((2-((4-(4-((dimethylamino)methyl)piperidin-1-yl)-2-ethylphenyl)amino)-5-(trifluoromethyl)pyrimidin-4-yl)amino)propyl)-1,4-oxazepan-5-one, 4-(3-((2-((4-(4-(dimethylglycyl)piperazin-1-yl)-2-ethylphenyl)amino)-5-(trifluoromethyl)pyrimidin-4-yl)amino)propyl)-1,4-oxazepan-3-one, 4-(3-((2-((4-(3,3-dimethylpiperazin-1-yl)-2-ethylphenyl)amino)-5-(trifluoromethyl)pyrimidin-4-yl)amino)propyl)-1,4-oxazepan-3-one, 4-(3-((2-((2-ethyl-4-(3,3,5,5-tetramethylpiperazin-1-yl)phenyl)amino)-5-(trifluoromethyl)pyrimidin-4-yl)amino)propyl)-1,4-oxazepan-3-one, 4-(3-((2-(2-cyclopropyl-4-(3,4,5-trimethylpiperazin-1-yl)phenyl)amino)-5-(trifluoromethyl) pyrimidin-4-yl)amino)propyl)-1,4-oxazepan-5-one, 4-(3-((2-((2-ethyl-4-(3,3,4-trimethylpiperazin-1-yl)phenyl)amino)-5-(trifluoromethyl)pyrimidin-4-yl)amino)propyl)-1,4-oxazepan-3-one, 4-(3-((2-((2-ethyl-4-(3,3,4,5,5-pentamethylpiperazin-1-yl)phenyl)amino)-5-(trifluoromethyl)pyrimidin-4-yl)amino)propyl)-1,4-oxazepan-3-one, 1-(3-((2-((2-chloro-4-(3,4-dimethylpiperazin-1-yl)phenyl)amino)-5-(trifluoromethyl)pyrimidin-4-yl)amino)propyl)azepan-2-one, 3-(3-((2-((4-(hexahydropyrrolo[1,2-a]pyrazin-2(1H)-yl)phenyl)amino)-5-(trifluoromethyl)pyridin-4-yl)amino)propyl)-1,3-oxazepan-2-one, 4-(3-((2-((4-(hexahydropyrrolo[1,2-a]pyrazin-2(1H)-yl)phenyl)amino)-5-(trifluoromethyl)pyridin-4-yl)amino)propyl)-1,4-oxazepan-3-one, 4-(3-((2-((4-(octahydro-2H-pyrido[1,2-a]pyrazin-2-yl)phenyl)amino)-5-(trifluoromethyl)pyridin-4-yl)amino)propyl)-1,4-oxazepan-3-one, 3-(3-((2-((4-(4-methylpiperazin-1-yl)phenyl)amino)-5-(trifluoromethyl)pyridin-4-yl)amino)propyl)-1,3-oxazepan-2-one, 4-(3-((2-((4-(4-methylpiperazin-1-yl)phenyl)amino)-5-(trifluoromethyl) pyridin-4-yl)amino)propyl)-1,4-oxazepan-3-one, 4-(3-((2-((4-(5-methyl-2,5-diazabicyclo[2.2.1]heptan-2-yl)phenyl)amino)-5-(trifluoromethyl)pyridin-4-yl)amino)propyl)-1,4-oxazepan-5-one, 3-(3-((2-((2-bromo-4-(4-methylpiperazin-1-yl)phenyl)amino)-5-(trifluoromethyl)pyridin-4-yl)amino)propyl)-1,3-oxazepan-2-one, 4-(3-((2-((2-methyl-4-(4-methylpiperazin-1-yl)phenyl)amino)-5-(trifluoromethyl)pyridin-4-yl)amino)propyl)-1,4-oxazepan-3-one, 4-(3-((2-((6-(5-methyl-2,5-diazabicyclo[2.2.1]heptan-2-yl)pyridin-3-yl)amino)-5-(trifluoromethyl)pyridin-4-yl)amino)propyl)-1,4-oxazepan-5-one, 1-(3-((2-((4-((1R,5S)-8-methyl-3,8-diazabicyclo[3.2.1]octan-3-yl)phenyl)amino)-5-(trifluoromethyl)pyridin-4-yl)amino)propyl)azepan-2-one, 1-(3-((2-((2-cyclopropyl-4-(5-methyl-2,5-diazabicyclo[2.2.1]heptan-2-yl)phenyl)amino)-5-(difluoromethyl)pyridin-4-yl)amino)propyl)pyrrolidin-2-one, 4-(3-((2-((4-(4-methylpiperazin-1-yl)-2-(trifluoromethyl)phenyl)amino)-5-(trifluoromethyl)pyridin-4-yl)amino)propyl)-1,4-oxazepan-5-one, 4-(3-((2-((2-methyl-4-(4-(methylsulfonyl)piperazin-1-yl)phenyl)amino)-5-(trifluoromethyl)pyridin-4-yl)amino)propyl)-1,4-oxazepan-5-one, 4-(3-((2-((4-(4-(dimethylglycyl)piperazin-1-yl)phenyl)amino)-5-(trifluoromethyl)pyridin-4-yl)amino)propyl)-1,4-oxazepan-5-one, 3-(3-((2-((2-ethyl-4-(4-methylpiperazine-1-carbonyl)phenyl)amino)-5-(trifluoromethyl)pyridin-4-yl)amino)propyl)-1,3-oxazinan-2-one, 1-(3-((2-((2-cyclopropyl-4-(morpholinomethyl)phenyl)amino)-5-(trifluoromethyl)pyridin-4-yl)amino)propyl)piperidin-2-one, 3-(3-((2-ethyl-4-(2-(pyrrolidin-1-yl)ethyl)phenyl)amino)-5-(trifluoromethyl)pyridin-4-yl)amino)propyl)-1,3-oxazinan-2-one, 3-(3-((2-((2-fluoro-4-(3-morpholinopropyl)phenyl)amino)-5-(trifluoromethyl)pyridin-4-yl)amino)propyl)-1,3-oxazinan-2-one, 1-(3-((2-((2-cyclopropyl-4-((1,1-dioxidothiomorpholino)methyl)phenyl)amino)-5-(trifluoromethyl)pyridin-4-yl)amino)propyl)piperidin-2-one, 1-(3-((2-((2-cyclopropyl-4-((4-methylpiperazin-1-yl)sulfonyl)phenyl)amino)-5-(trifluoromethyl)pyridin-4-yl)amino)propyl)piperidin-2-one, 3-(3-((2-((4-(3-(diethylamino)propyl)-2-(trifluoromethyl)phenyl)amino)-5-(trifluoromethyl)pyridin-4-yl)amino)propyl)-1,3-oxazinan-2-one, 4-(3-((2-((2-chloro-4-(3,4-dimethylpiperazin-1-yl)phenyl)amino)-5-(trifluoromethyl)pyridin-4-yl)amino)propyl)-1,4-oxazepan-5-one, 1-(3-((2-((2-cyclopropyl-4-

(morpholinosulfonyl)phenyl)amino)-5-(trifluoromethyl)pyridin-4-yl)amino)propyl)piperidin-2-one, 3-(3-((2-((2-(2-hydroxypropan-2-yl)-4-(4-methylpiperazin-1-yl)phenyl)amino)-5-(trifluoromethyl)pyrimidin-4-yl)amino)propyl)-1,3-oxazinan-2-one, 4-(3-((2-((2-(2-hydroxypropan-2-yl)-4-(4-methylpiperazin-1-yl)phenyl)amino)-5-(trifluoromethyl)pyrimidin-4-yl)amino)propyl)-1,4-oxazepan-5-one, 4-(3-((2-((2-(1-hydroxyethyl)-4-(4-methylpiperazin-1-yl)phenyl)amino)-5-(trifluoromethyl)pyrimidin-4-yl)amino)propyl)-1,4-oxazepan-5-one, 4-(3-((2-((2-methyl-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-5-one, 4-(3-((2-((2-chloro-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-5-one, 4-(3-((2-((2-(1-hydroxyethyl)-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-5-one, 4-(3-((2-((2-methyl-4-((1S,4S)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 4-(3-((2-((2-chloro-4-((1S,4S)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 4-(3-((2-((2-(1-hydroxyethyl)-4-((1S,4S)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 4-(3-((2-((2-methyl-4-((1R,4R)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 4-(3-((2-((2-chloro-4-((1R,4R)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 4-(3-((2-((2-(1-hydroxyethyl)-((1R,4R)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 3-(3-((2-((2-chloro-4-(4-methylpiperazin-1-yl)phenyl)amino)-5-(trifluoromethyl)pyrimidin-4-yl)amino)propyl)-1,3-oxazinan-2-one, 3-(3-((2-((2-(1-hydroxyethyl)-4-(4-methylpiperazin-1-yl)phenyl)amino)-5-(trifluoromethyl)pyrimidin-4-yl)amino)propyl)-1,3-oxazinan-2-one, 3-(3-((2-((2-chloro-4-((1R,5S)-8-methyl-3,8-diazabicyclo[3.2.1]octan-3-yl)phenyl)amino)-5-(trifluoromethyl)pyrimidin-4-yl)amino)propyl)-1,3-oxazinan-2-one, 3-(3-((2-((2-(1-hydroxyethyl)-4-((1R,5S)-8-methyl-3,8-diazabicyclo[3.2.1]octan-3-yl)phenyl)amino)-5-(trifluoromethyl)pyrimidin-4-yl)amino)propyl)-1,3-oxazinan-2-one, 3-(3-((2-((2-methyl-4-((1S,4S)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 3-(3-((2-((2-chloro-4-((1S,4S)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 3-(3-((2-((2-(1-hydroxyethyl)-4-((1S,4S)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 3-(3-((2-((2-methyl-4-((1R,4R)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 3-(3-((2-((2-chloro-4-((1R,4R)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 3-(3-((2-((2-(1-hydroxyethyl)-4-((1R,4R)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 4-(3-((2-((2-methyl-4-(4-methylpiperazin-1-yl)phenyl)amino)-5-(trifluoromethyl)pyrimidin-4-yl)amino)propyl)-1,4-oxazepan-3-one, 4-(3-((2-((2-chloro-4-(4-methylpiperazin-1-yl)phenyl)amino)-5-(trifluoromethyl)pyrimidin-4-yl)amino)propyl)-1,4-oxazepan-3-one, 4-(3-((2-((2-(1-hydroxyethyl)-4-(4-methylpiperazin-1-yl)phenyl)amino)-5-(trifluoromethyl)pyrimidin-4-yl)amino)propyl)-1,4-oxazepan-3-one, 4-(3-((2-((2-methyl-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-3-one, 4-(3-((2-((2-chloro-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-3-one, 4-(3-((2-((2-(1-hydroxyethyl)-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-3-one, 4-(3-((2-((4-(4-methylpiperazin-1-yl)-2-(trifluoromethoxy)phenyl)amino)-5-(trifluoromethyl)pyrimidin-4-yl)amino)propyl)-1,4-oxazepan-5-one, 4-(3-((2-((2-(difluoromethoxy)-4-(4-methylpiperazin-1-yl)phenyl)amino)-5-(trifluoromethyl)pyrimidin-4-yl)amino)propyl)-1,4-oxazepan-5-one, 3-(3-((2-((2-(methoxymethyl)-4-(4-methylpiperazin-1-yl)phenyl)amino)-5-(trifluoromethyl)pyrimidin-4-yl)amino)propyl)-1,3-oxazinan-2-one, 3-(3-((2-((2-cyclopropyl-4-(4-methylpiperazin-1-yl)phenyl)amino)-5-(trifluoromethyl)pyrimidin-4-yl)amino)propyl)-6,6-dimethyl-1,3-oxazinan-2-one, 4-(3-((2-((4-((1R,5S)-3,8-diazabicyclo[3.2.1]octan-3-yl)-2-ethylphenyl)amino)-5-(trifluoromethyl)pyrimidin-4-yl)amino)propyl)-1,4-oxazepan-5-one, 1-(3-((2-((2-cyclopropyl-4-(3-((dimethylamino)methyl)azetidin-1-yl)phenyl)amino)-5-(trifluoromethyl)pyrimidin-4-yl)amino)propyl)piperidin-2-one, 4-(3-((2-((4-(3-((dimethylamino)methyl)azetidin-1-yl)-2-ethylphenyl)amino)-5-(trifluoromethyl)pyrimidin-4-yl)amino)propyl)-1,4-oxazepan-5-one, 4-(3-((2-((4-(4-methylpiperazin-1-yl)phenyl)amino)-5-(trifluoromethyl)pyrimidin-4-yl)amino)propyl)-1,4-oxazepan-5-one, and pharmaceutically acceptable salts, enantiomers, stereoisomers, and tautomers thereof.

Methods of Treatment

Compounds described herein can act as inhibitors of autophagy useful in the treatment of a disorder in a patient in need thereof. The disorder, for example, can be a tumor, e.g., a solid tumor. The disorder may also be cancer.

Exemplary disorders also include gastrointestinal stromal tumors, esophageal cancer, gastric cancer, melanomas, gliomas, glioblastomas, ovarian cancer, bladder cancer, pancreatic cancer, prostate cancer, lung cancers, breast cancers, renal cancers, hepatic cancers, osteosarcomas, multiple myelomas, cervical carcinomas, cancers that are metastatic to bone, papillary thyroid carcinoma, non-small cell lung cancer, and colorectal cancers. A cancer treated by the methods described herein may be a metastatic cancer.

In some embodiments, the compounds described herein are useful for the treatment of cancers caused by RAS mutation. In some embodiments, the cancer is caused by a KRAS mutation. In some embodiments, the cancer has additional mutations in tumor suppressor proteins, including mutations in TP53, PTEN, CDN2A/INK4A, p16, or STAG2. In some embodiments, these additional mutations occur in one or more of TP53, PTEN, CDN2A/INK4A, p16, or STAG2. In some embodiments, the cancer is pancreatic ductal adenocarcinoma. In some embodiments, the cancer is lung cancer. In some embodiments, the cancer is colorectal.

In some embodiments, determination of cellular inhibition of autophagy by compounds described herein is determined by monitoring of autophagic flux, for instance by monitoring inhibition of autophagy-mediated clearance of mCherry/GFP-LC3 fusion protein. In some embodiments, determination of cellular inhibition of autophagy by compounds described herein is determined by monitoring of accumulation of autophagic proteins such as p62 or LC-3. In some embodiments, determination of cellular inhibition of autophagy by compounds described herein is determined by decreased clearance of luciferase-tagged LC3 protein. In some embodiments, determination of cellular inhibition of autophagy by compounds described herein is determined by monitoring decreases in cellular autophagosomes, for instance by measurement of fluorescent puncta with the autophagosome marker Cyto-ID.

In some embodiments, cellular inhibition of ULK kinase by compounds described herein is determined by inhibition of phosphorylation of cellular ULK substrates including ATG13, ATG14, Beclin 1, or STING either in tumor cells or in non-tumor host tissues. In some embodiments, cellular inhibition of ULK kinase by compounds described herein is determined in host tissues including immune cells.

In some embodiments, in vivo inhibition of autophagy by compounds described herein is determined by inhibition of phosphorylation of cellular ULK substrates including ATG13, ATG14, Beclin 1, or STING either in tumor cells or in non-tumor host tissues. In some embodiments, in vivo inhibition of ULK kinase by compounds described herein is determined in host tissues including immune cells. In some embodiments, the in vivo inhibition of autophagic flux by compounds described herein can be used as a pharmacodynamic model for monitoring the kinetics and extent of such ULK inhibition. In some embodiments, tin vivo inhibition of ULK kinase by compounds described herein is determined in pancreatic cancer-bearing animals. In some embodiments, in vivo inhibition of ULK kinase by compounds described herein is determined in lung cancer-bearing animals. In some embodiments, in vivo inhibition of ULK kinase is determined in colorectal cancer-bearing animals. In some embodiments, in vivo inhibition of autophagy by compounds described herein is determined by inhibition of autophagic flux in tumor cells, or in non-tumor host tissues by monitoring inhibition of autophagosome formation, or by accumulation of autophagic proteins such as p62 or LC-III. In some embodiments, in vivo inhibition of autophagy is determined in host tissues including immune cells. In some embodiments, the in vivo inhibition of autophagic flux can be used as a pharmacodynamic model for monitoring the kinetics and extent of such ULK inhibition.

In some embodiments, inhibition of autophagy and anti-tumor activity by compounds described herein are evaluated in xenograft studies utilizing human RAS mutant cell lines in immunocompromised mice, for instance in SCID or nude mice. In some embodiments, inhibition of autophagy and anti-tumor activity by compounds described herein are evaluated in xenograft studies utilizing human RAS mutant patient-derived tumor xenografts (PDXs) in immunocompromised mice, for instance in SCID or nude mice. In some embodiments, xenograft studies include evaluation of compounds described herein in pancreatic cancer models. In some embodiments, inhibition of autophagy and anti-tumor activity by compounds described herein are evaluated in syngeneic murine genetically engineered models (GEMs) of mutant RAS cancers. In some embodiments, inhibition of autophagy and anti-tumor activity by compounds described herein are evaluated in the murine GEM syngeneic orthotopic pancreatic cancer model known as the KPC model (LSL-Kras$^{G12D/+}$;LSL-Trp53$^{R172H/+}$;pdx-1-Cre) or variants of the KPC model.

In some embodiments, compounds described herein will be evaluated in xenograft or GEM cancer models in combination with a MEK inhibitor. In some embodiments, compounds described herein will be evaluated in xenograft or GEM cancer models in combination with a RAF inhibitor. In some embodiments, compounds described herein will be evaluated in xenograft or GEM cancer models in combination with an ERK inhibitor. In some embodiments, compounds described herein will be evaluated in xenograft or GEM cancer models in combination with a RAS G12C direct inhibitor.

In some embodiments, inhibition of autophagy and anti-tumor activity by compounds described herein is evaluated in immunocompetent murine cancer models to assess an immunomodulatory component to the mechanism of action of ULK inhibitors. In some embodiments, the immunocompetent murine model is the murine GEM syngeneic orthotopic pancreatic cancer model known as the KPC model (LSL-Kras$^{G12D/+}$;LSL-Trp53$^{R172H/+}$; Pdx-1-Cre) or variants of the KPC model. In some embodiments, immunomodulatory properties of compounds described herein are evaluated in combination with a MEK inhibitor. In some embodiments, immunomodulatory properties of compounds described herein are evaluated in combination with a RAF inhibitor. In some embodiments, immunomodulatory properties of compounds described herein are evaluated in combination with an ERK inhibitor. In some embodiments, immunomodulatory properties of compounds described herein are evaluated in combination with a RAS G12C direct inhibitor.

In some embodiments, the immunomodulatory component of ULK inhibition is an enhanced innate immune response. In some embodiments, the immunomodulatory component of ULK inhibition is an enhanced adaptive immune response. In some embodiments, the immunomodulatory component of ULK inhibition is an enhanced activity of antigen-presenting cells. In some embodiments, the immunomodulatory component of ULK inhibition is an enhanced anti-tumor activity of myeloid cells including macrophages. In some embodiments, the immunomodulatory component of ULK inhibition is an enhanced anti-tumor activity of Natural Killer cells. In some embodiments, the immunomodulatory component of ULK inhibition is an enhanced activity of effector T Cells, including cytotoxic T Cells.

In an embodiment, provided herein is a method of treating a disorder described herein that includes: administering a therapeutically effective amount of compound described herein in a patient in need thereof, and during or after the course of administration (e.g., at discrete time points, such as one week, two weeks, or on month after initial administration of a contemplated compound) detecting the engagement of the compound with an ULK kinase, wherein detecting comprises contacting a sample obtained from the patient (including but not limited to a tumor, blood, saliva, or tissue) with a phospho-ATG13 antibody ELISA assay to detect inhibition of ULK kinase activity, e.g, based on the level of phospho-ATG13 in the sample. In some embodiments, a contemplated method comprises optionally contacting a sample obtained from the patient (including but not limited to a tumor, blood, saliva, or tissue) prior to administration of the compound with a phospho-ATG13 antibody ELISA assay, and comparing the level of phospho-ATG13 in the sample obtained prior to administration with the level of phospho-ATG13 in the sample obtained during or after the course of administration. In some embodiments, the phospho-ATG13 is p-S318ATG13.

In an embodiment, provided herein is a method of treating a disorder described herein that includes: administering a therapeutically effective amount of compound described herein in a patient in need thereof, and during or after the course of administration (e.g., at discrete time points, such as one week, two weeks, or on month after initial administration of a contemplated compound) detecting the engagement of the compound with an ULK kinase, wherein detecting comprises contacting a sample obtained from the patient (including but not limited to a tumor, blood, saliva, or tissue) with a phospho-ATG14 antibody ELISA assay to detect inhibition of ULK kinase activity, e.g, based on the level of phospho-ATG14 in the sample. In some embodiments, a contemplated method comprises optionally contacting a sample obtained from the patient (including but not limited to a tumor, blood, saliva, or tissue) prior to administration of the compound with a phospho-ATG14 antibody ELISA assay, and comparing the level of phospho-ATG14 in the sample obtained prior to administration with the level of phospho-ATG14 in the sample obtained during or after the course of administration. In some embodiments, the phospho-ATG14 is p-ATG14 Ser29.

In an embodiment, provided herein is a method of treating a disorder described herein that includes: administering a therapeutically effective amount of compound described herein in a patient in need thereof, and during or after the course of administration (e.g., at discrete time points, such as one week, two weeks, or on month after initial administration of a contemplated compound) detecting the engagement of the compound with an ULK kinase, wherein detecting comprises contacting a sample obtained from the patient (including but not limited to a tumor, blood, saliva, or tissue) with a p62 antibody ELISA assay to detect inhibition of ULK kinase activity, e.g, based on the level of p62 in the sample. In some embodiments, a contemplated method comprises optionally contacting a sample obtained from the patient (including but not limited to a tumor, blood, saliva, or tissue) prior to administration of the compound with a p62 antibody ELISA assay, and comparing the level of p62 in the sample obtained prior to administration with the level of p62 in the sample obtained during or after the course of administration.

In an embodiment, provided herein is a method of treating a disorder described herein that includes: administering a therapeutically effective amount of compound described herein in a patient in need thereof, and during or after the course of administration (e.g., at discrete time points, such as one week, two weeks, or on month after initial administration of a contemplated compound) detecting the engagement of the compound with an ULK kinase, wherein detecting comprises contacting a sample obtained from the patient (including but not limited to a tumor, blood, saliva, or tissue) with a pBeclin antibody ELISA assay to detect inhibition of ULK kinase activity, e.g, based on the level of pBeclin in the sample. In some embodiments, a contemplated method comprises optionally contacting a sample obtained from the patient (including but not limited to a tumor, blood, saliva, or tissue) prior to administration of the compound with a pBeclin antibody ELISA assay, and comparing the level of pBeclin in the sample obtained prior to administration with the level of pBeclin in the sample obtained during or after the course of administration.

The compounds provided herein may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound provided herein may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result is achieved.

Combination Therapy

Compounds described herein, e.g., a compound of Formula I as defined herein, can be administered in combination with one or more additional therapeutic agents to treat a disorder described herein, such as cancer. For example, provided in the present disclosure is a pharmaceutical composition comprising a compound described herein, e.g., a compound of Formula I as defined herein, one or more additional therapeutic agents, and a pharmaceutically acceptable excipient. In some embodiments, a compound of Formula I as defined herein and one additional therapeutic agent is administered. In some embodiments, a compound of Formula I as defined herein and two additional therapeutic agents are administered. In some embodiments, a compound of Formula I as defined herein and three additional therapeutic agents are administered. Combination therapy can be achieved by administering two or more therapeutic agents, each of which is formulated and administered separately. For example, a compound of Formula I as defined herein and an additional therapeutic agent can be formulated and administered separately. Combination therapy can also be achieved by administering two or more therapeutic agents in a single formulation, for example a pharmaceutical composition comprising a compound of Formula I as one therapeutic agent and one or more additional therapeutic agents such as a MAPKAP pathway inhibitor or chemotherapeutic agent. For example, a compound of Formula I as defined herein and an additional therapeutic agent can be administered in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X—Y—X, X—X—Y, Y—X—Y, Y—Y—X, X—X—Y—Y, etc.

In some embodiments, the one or more additional therapeutic agents that may be administered in combination with a compound provided herein can be a MAPKAP pathway inhibitor. Such MAPKAP pathway inhibitors include, for example, MEK inhibitors, ERK inhibitors, RAF inhibitors, and Ras inhibitors.

Exemplary MEK inhibitors include, but are not limited to, trametinib, selumetinib, cobimetinib, binimetinib, and pharmaceutically acceptable salts thereof. Exemplary ERK inhibitors include, but are not limited to, include, but are not limited to, ulixertinib, SCH772984, LY3214996, ravoxertinib, VX-11e, and pharmaceutically acceptable salts thereof. Exemplary RAF inhibitors include, but are not limited to, LY3009120, LXH254, RAF709, dabrafenib, vemurafenib, and pharmaceutically acceptable salts thereof. Exemplary Ras inhibitors include, but are not limited to, AMG-510, MRTX849, and pharmaceutically acceptable salts thereof.

The compounds described herein may be administered in combination with other therapeutic agents known to treat cancers. Such other therapeutic agents include radiation therapy, anti-tubulin agents, DNA alkylating agents, DNA synthesis-inhibiting agents, DNA intercalating agents, anti-estrogen agents, anti-androgens, steroids, anti-EGFR agents, kinase inhibitors, mTOR inhibitors, PI3 kinase inhibitors, cyclin-dependent kinase inhibitors, CD4/CD6 kinase inhibitors, topoisomerase inhibitors, Histone Deacetylase (HDAC) inhibitors, DNA methylation inhibitors, anti-HER2 agents, anti-angiogenic agents, proteasome inhibitors, PARP inhibitors, cell cycle regulating kinase inhibitors, thalidomide, lenalidomide, antibody-drug-conjugates (ADCs), immunotherapeutic agents including immunomodulating agents, targeted therapeutic agents, cancer vaccines, and CAR-T cell therapy.

In an embodiment, the additional therapeutic agents can be chemotherapeutic agents including but not limited to an anti-tubulin agents (for example, paclitaxel, paclitaxel protein-bound particles for injectable suspension including nab-paclitaxel, eribulin, docetaxel, ixabepilone, vincristine, auristatins, or maytansinoids), vinorelbine, DNA-alkylating agents (including cisplatin, carboplatin, oxaliplatin, cyclophosphamide, ifosfamide, temozolomide), DNA intercalating agents or DNA topoisomerase inhibitors (including anthracyclines such as doxorubicin, pegylated liposomal doxorubicin, daunorubicin, idarubicin, mitoxantrone, or epirubicin, camptothecins such as topotecan, irinotecan, or exatecan), 5-fluorouracil, capecitabine, cytarabine, decitabine, 5-aza cytadine, gemcitabine and methotrexate.

In some embodiments, the additional therapeutic agents can be kinase inhibitors including but not limited to erlotinib, gefitinib, neratinib, afatinib, osimertinib, lapatanib, crizotinib, brigatinib, ceritinib, alectinib, lorlatinib, everolimus, temsirolimus, abemaciclib, LEE011, palbociclib, cabozantinib, sunitinib, pazopanib, sorafenib, regorafenib, sunitinib, axitinib, dasatinib, imatinib, nilotinib, idelalisib, ibrutinib, BLU-667, Loxo 292, larotrectinib, and quizartinib, anti-estrogen agents including but not limited to tamoxifen, fulvestrant, anastrozole, letrozole, and exemestane, anti-androgen agents including but not limited to abiraterone acetate, enzalutamide, nilutamide, bicalutamide, flutamide, cyproterone acetate, steroid agents including but not limited to prednisone and dexamethasone, PARP inhibitors including but not limited to neraparib, olaparib, talazoparib, and rucaparib, topoisomerase I inhibitors including but not limited to irinotecan, camptothecin, exatecan, and topotecan, topoisomerase II inhibitors including but not limited to anthracyclines, etoposide, etoposide phosphate, and mitoxantrone, Histone Deacetylase (HDAC) inhibitors including but not limited to vorinostat, romidepsin, panobinostat, valproic acid, and belinostat, DNA methylation inhibitors including but not limited to DZNep and 5-aza-2'-deoxycytidine, proteasome inhibitors including but not limited to bortezomib and carfilzomib, thalidomide, lenalidomide, pomalidomide, biological agents including but not limited to trastuzumab, ado-trastuzumab, pertuzumab, cetuximab, panitumumab, ipilimumab, tremelimumab, anti-PD-1 agents including pembrolizumab, nivolumab, pidilizumab, and Cemiplimab, anti-PD-L 1 agents including atezolizumab, avelumab, durvalumab and BMS-936559, anti-angiogenic agents including bevacizumab and aflibercept, and antibody-drug-conjugates (ADCs) including DM1, DM4, MMAE, MMAF, or camptothecin payloads, brentuximab vedotin and trastuzumab emtansine, radiotherapy, therapeutic vaccines including but not limited to sipuleucel-T.

In some embodiments, the additional therapeutic agents can be immunomodulatory agents including but not limited to anti-PD-1 or anti-PDL-1 therapeutics including pembrolizumab, nivolumab, atezolizumab, durvalumab, BMS-936559, or avelumab, anti-TIM3 (anti-HAVcr2) therapeutics including but not limited to TSR-022 or MBG453, anti-LAG3 therapeutics including but not limited to relatlimab, LAG525, or TSR-033, anti-4-1BB (anti-CD37, anti-TNFRSF9), CD40 agonist therapeutics including but not limited to SGN-40, CP-870,893 or RO7009789, anti-CD47 therapeutics including but not limited to Hu5F9-G4, anti-CD20 therapeutics, anti-CD38 therapeutics, STING agonists including but not limited to ADU-S100, MK-1454, ASA404, or amidobenzimidazoles, anthracyclines including but not limited to doxorubicin or mitoxantrone, hypomethylating agents including but not limited to azacytidine or decitabine, other immunomodulatory therapeutics including but not limited to epidermal growth factor inhibitors, statins, metformin, angiotensin receptor blockers, thalidomide, lenalidomide, pomalidomide, prednisone, or dexamethasone.

In some embodiments, the additional therapeutic agent is selected from a luteinizing hormone-releasing hormone (LHRH) analog, including goserelin and leuprolide.

In some embodiments, the additional therapeutic agent is selected from the group consisting of selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, of atumtunab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)-ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser (Bu t) 6, Azgly 10] (pyro-Glu-His-Trp-Ser-Tyr-D-Ser(Bu 0-Leu-Arg-Pro-Azgly-NH$_2$ acetate [C$_{59}$H$_{84}$N$_{18}$O$_{14}$-(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutanide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, sspegfilgrastim, erythropoietin, epoetin alfa and darbepoetin alfa, ipilumumab, vemurafenib, and mixtures thereof.

Pharmaceutical Compositions and Kits

Another aspect of this disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions may be used in the form of a pharmaceutical preparation, for example, in solid, semisolid or liquid form, which contains one or more of the compounds described herein, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound provided herein, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of the present disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

In another aspect, provided are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5.

Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives described herein.

Advantageously, provided herein are kits for use by a e.g. a consumer in need of treatment of cancer. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

The following abbreviation are used in this disclosure and have the following definitions: "ADP" is adenosine diphosphate, "Boc" is t-butylcarbonate, "CDI" is carbodiimidazole, "conc." is concentrated, "$Cs_2CO_3$" is cesium carbonate, "CuI" is copper (I) iodide, "DBU" is 1,8-diazabicyclo[5.4.0]undec-7-ene, "DCC" is N,N'-Dicyclohexylcarbodiimide, "DCE" is dichloroethane, "DCM" is dichloromethane, "DIEA" is N,N-diisopropylethylamine, "DMA" is N,N-dimethylacetamide, "DMAP" is 4-(dimethylamino)pyridine, "DMF" is N,N-dimethylformamide, "dppf" is 1,1'-bis(diphenylphosphino)ferrocene, "DMEM" is Dulbecco's Modified Eagle Media, "DMSO" is dimethylsulfoxide, "DPPA" is diphenylphosphryl azide, "EDC" is 1-Ethyl-3-(3-dimethylaminopropyl)carbodiimide, "ESI" is electrospray ionization, "$Et_2O$" is diethylether, "EtOAc" is ethyl acetate, "EtOH" is ethanol, "GST" is glutathione S-transferase, "h" is hour or hours, "HBTU" is (2-(1H-benzotriazol-1-yl)-1,1,3,3-tetramethyluronium hexafluorophosphate, "$H_2$" is hydrogen gas, "HCl" is hydrochloric acid, "Hex" is hexane, "$H_2O$" is water, "HOBt" is Hydroxybenzotriazole "$IC_{50}$" is half maximal inhibitory concentration, "$K_2CO_3$" is potassium carbonate, "$K_3PO_4$" is potassium phosphate, "LiMHDS" is lithium bis(trimethylsilyl)amide, "MeCN" is acetonitrile, "MeOH" is methanol, "$Me_4tBuXPhos$" is di-tert-butyl(2',4',6'-triisopropyl-3,4,5,6-tetramethyl-[1,1'-biphenyl]-2-yl)phosphine, "$MgSO_4$" is magnesium sulfate, "MHz" is megahertz, "min" is minute or minutes, "MS" is mass spectrometry, "MTBE" is methyl tert-butyl ether, "NADH" is nicotinamide adenine dinucleotide, "NaH" is sodium hydride, "$NaHCO_3$" is sodium bicarbonate, "$Na_2SO_4$" is sodium sulfate, "$NH_4Cl$" is ammonium chloride, "NaSMe" is sodium thiomethoxide, "NBS" is N-bromosuccinimide, "NMR" is nuclear magnetic resonance, "PBS" is phosphate buffered saline, "Pd/C" is palladium on carbon, "$Pd_2(dba)_3$" is tris(dibenzylideneacetone)dipalladium(0), "$Pd(OAc)_2$" is palladium (II) acetate, "$Pd(PPh_3)_4$" is tetrakis(triphenylphosphine)palladium (0), "prep-HPLC" is preparative high performance liquid chromatography, "PyBOP" is benzotriazol-1-yl-oxytripyrrolidinophosphonium hexafluorophosphate, "rt" is room temperature which is also known as "ambient temp," which will be understood to consist of a range of normal laboratory temperatures ranging from 15-25° C., "satd." is saturated, "$T_3P$" is n-propanephosphonic acid anhydride, "TEA" is triethylamine, "TFA" is trifluoroacetic acid, "THF" is tetrahydrofuran, "TMS" is trimethylsilyl, "Tris" is tris(hydroxymethyl)aminomethane, "Xantphos" is 4,5-bis(diphenylphosphino)-9,9-dimethylxanthene, "X-Phos" is 2-dicyclohexylphosphino-2',4',6'-triisopropylbiphenyl and "$ZnCl_2$" is zinc chloride.

General Chemistry

Exemplary compounds described herein are available by the general synthetic methods illustrated in the Schemes below, Intermediate preparations, and the accompanying Examples.

Synthetic Schemes

Scheme 1

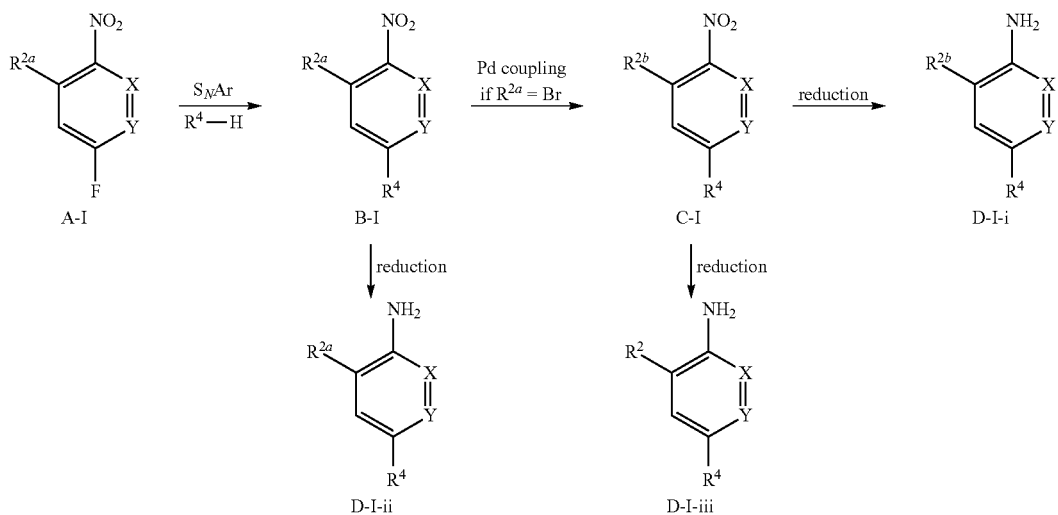

Scheme 1 illustrates an exemplary preparation of amines D-I-i, D-I-ii, and D-I-iii. Treatment of A-I with amine $R^4$—H, which can be aliphatic or heterocyclic, in the presence of a base (e.g. $Cs_2CO_3$ or $K_2CO_3$) affords compound B—I. Further treatment of B—I where $R^{2a}$ is Br with commercially available boronic esters/boronic acids/trifluoroborates in the presence of a palladium catalyst (Suzuki coupling) or Sonogashira coupling reaction affords compound C—I. Intermediate C—I may be selectively converted to amine D-I-i where $R^{2b}$ is alkenyl, alkynyl, or cycloalkyl by mild reducing conditions for example, zinc or iron metal with ammonium chloride. Intermediate C—I can be fully reduced to D-I-iii by palladium catalyzed hydrogenation. Intermediate B—I where $R^{2a}$ is Cl, Br, alkyl, CN or alkoxy may be reduced to D-I-ii by mild reducing conditions for example, zinc or iron metal with ammonium chloride.

In Scheme 1, examples of X include N and CH, examples of Y include N, CH, and C—F where X and Y are not both N, examples of $R^2$ include alkyl and cycloalkyl, and examples of $R^4$ include an N-linked alkyl and N-linked heterocylcyl with suitable optional substituents as exemplified by the tables of intermediates below.

Scheme 2

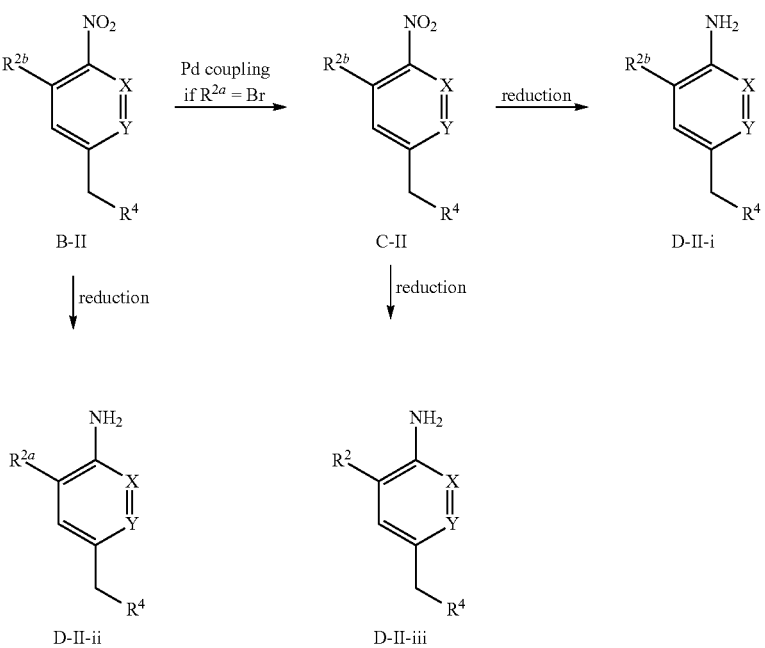

Scheme 2 illustrates an exemplary preparation of amine D-II-i, D-II-ii and D-II-iii. Reaction of A-II (commercially available starting materials) and amine $R^4$—H under reductive amination conditions (e.g. sodium cyanoborohydride or sodium triacetoxyborohydride in the presence of a catalytic amount of acetic acid in polar solvents like MeOH) affords compound B-II. Further treatment of B-II where $R^{2a}$ is Br with commercially available boronic esters/boronic acids/trifluoroborates in the presence of a palladium catalyst (Suzuki coupling) or Sonogashira coupling reaction affords compound C-II. Intermediate C-II may be selectively converted to amine D-II-i where $R^{2b}$ is alkenyl, alkynyl, cycloalkyl by mild reducing conditions for example, zinc or iron metal with ammonium chloride. Intermediate C-II can be fully reduced to D-II-iii by palladium catalyzed hydrogenation. Intermediate B-II where $R^{2a}$ is Cl, Br, alkyl, CN or alkoxy may be reduced to D-II-ii by mild reducing conditions for example, zinc or iron metal with ammonium chloride.

In Scheme 2, examples of X include N and CH, examples of Y include N, CH, and C—F where X and Y are not both N, examples of $R^1$ include alkyl and cycloalkyl, and examples of $R^4$ include an N-linked alkyl and N-linked heterocylcyl with suitable optional substituents as exemplified by the tables of interemediates below.

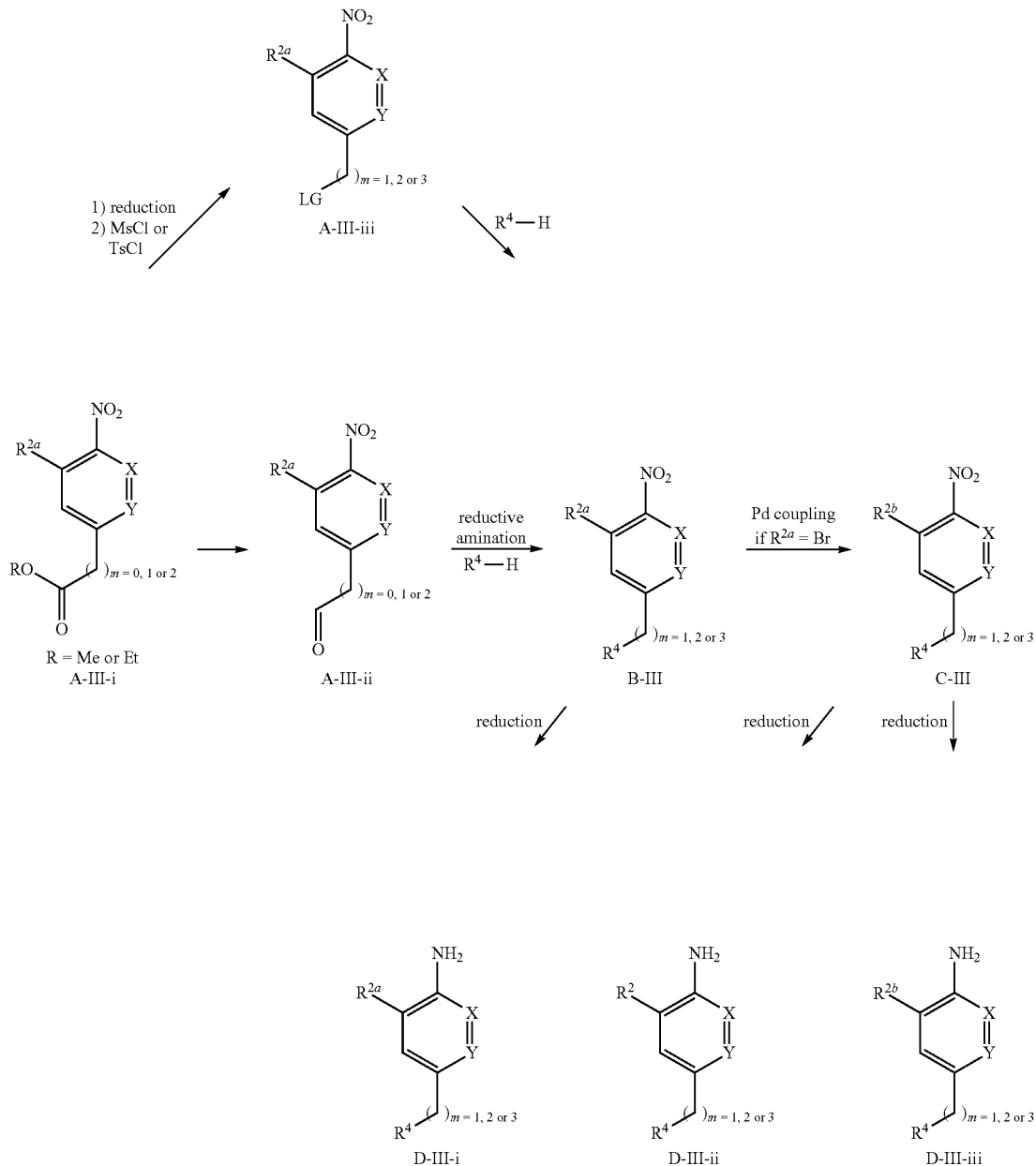

Scheme 3 illustrates an exemplary preparation of amine D-III-i, D-III-ii and D-III-iii. Reduction of A-III-i with reducing reagents such as DIBAL affords aldehyde A-III-ii. Another way to prepare A-III-ii is reduction of A-III-i to the corresponding alcohol followed by mild oxidation conditions such as using $MnO_2$. Reaction of A-III-ii and amine $R^4$—H under reductive amination conditions (e.g. sodium cyanoborohydride or sodium triacetoxyborohydride in the presence of a catalytic amount of acetic acid in polar solvents like MeOH) affords compound B-III Another way to prepare B-III is reduction of to the alcohol followed by conversion of the alcohol to the sulfonates A-III-iii. Reaction of A-III-iii with amine $R^4$—H in the presence of base such as triethylamine, Hunig's base, or cesium carbonate affords B-III Further treatment of B-III where $R^{2a}$ is Br with commercially available boronic esters/boronic acids/trifluoroborates in the presence of a palladium catalyst (Suzuki coupling) or Sonogashira coupling reaction affords compound C-III. Intermediate C-III may be selectively converted to amine D-III-iii where $R^{2b}$ is alkenyl, alkynyl, or cycloalkyl by mild reducing conditions for example, zinc or iron metal with ammonium chloride. Intermediate C-III can be fully reduced to D-III-ii by palladium catalyzed hydrogenation. Intermediate B-III where $R^{2a}$ is Cl, Br, alkyl, CN or alkoxy may be reduced to D-III-i by mild reducing conditions for example, zinc or iron metal with ammonium chloride.

In Scheme 3, examples of X include N and CH, examples of Y include N, CH, and C—F where X and Y are not both N, examples of R include methyl and ethyl, examples of $R^2$ include alkyl and cycloalkyl, examples of $R^4$ include an N-linked alkyl and N-linked heterocylcyl with suitable optional substituents as exemplified by the tables of interemediates below, and examples of LG include mesylate and tosylate.

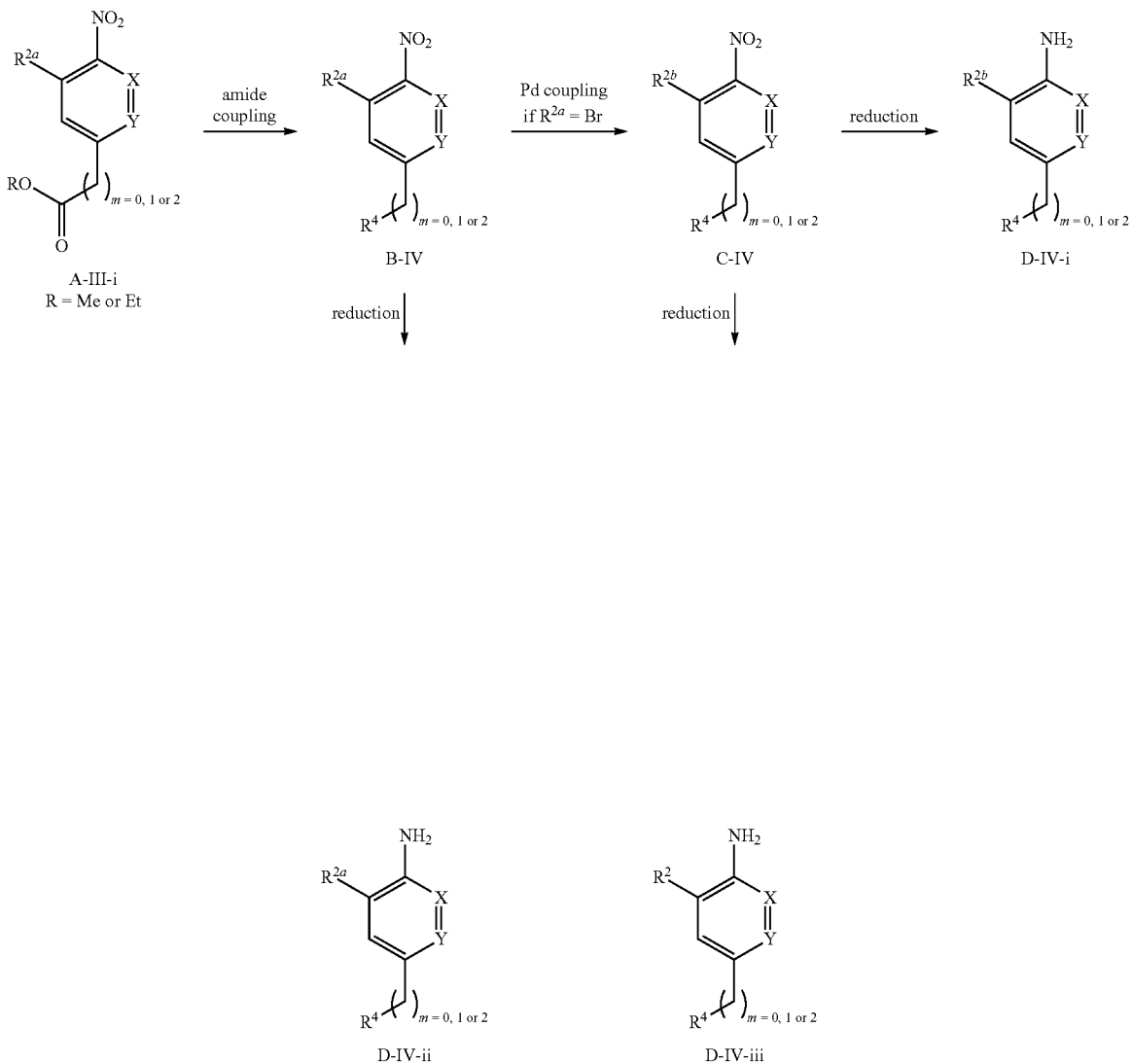

Scheme 4 illustrates an exemplary preparation of amine D-IV. Reaction of A-III-i and various amines under amide coupling reagents (e.g. CDI, DCC, EDC, HOBt, HBTU, PyBOP, or T$_3$P) in the presence of a catalytic amount of DMAP, if needed, affords amide B-IV. Further treatment of B-IV where R$^{2a}$ is Br with commercially available boronic esters/boronic acids/trifluoroborates in the presence of a palladium catalyst (Suzuki coupling) or Sonogashira coupling reaction affords compound C-IV. Intermediate C-IV may be selectively converted to amine D-IV-i where R$^{2b}$ is alkenyl, alkynyl, or cycloalkyl by mild reducing conditions for example, zinc or iron metal with ammonium chloride. Intermediate C-IV can be fully reduced to D-IV-iii by palladium catalyzed hydrogenation. Intermediate B-IV where R$^{2a}$ is Cl, Br, alkyl, CN or alkoxy may be reduced to D-IV-ii by mild reducing conditions for example, zinc or iron metal with ammonium chloride.

In Scheme 4, examples of X include N and CH, examples of Y include N, CH, and C—F where X and Y are not both N, examples of R include methyl and ethyl, examples of R$^2$ include alkyl and cycloalkyl, and examples of R$^4$ include —C(O)-alkyl and —C(O)-heterocylcyl, where the alkyl and heterocyclyl moieties are N-linked with suitable optional substituents as exemplified by the tables of interemediates below.

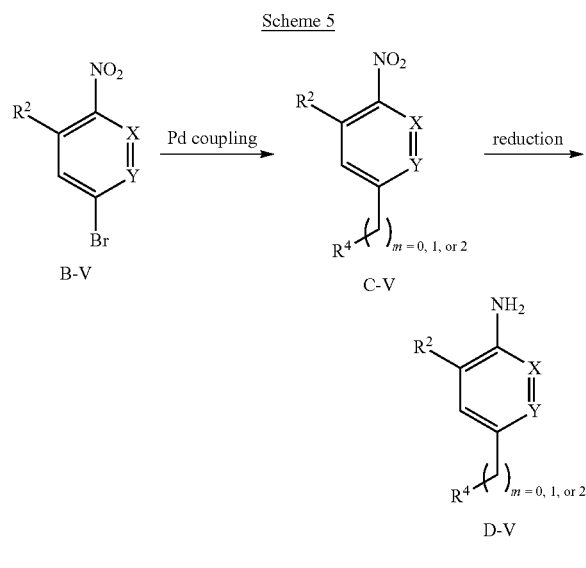

Scheme 5 illustrates an exemplary preparation of amine D-V. B-V reacts with boronic esters/boronic acids/trifluoroborates in the presence of a palladium catalyst (Suzuki coupling) to afford compound C-V. Many boronic esters/boronic acids/trifluoroborates are commercially available and those that are not can be readily prepared from the corresponding carboxylic acids (see Scheme 7). Intermediate C-V may be converted to amine D-V by standard reducing conditions, for example, by palladium catalyzed hydrogenation or by mild reducing conditions including zinc metal and ammonium chloride.

In Scheme 5, examples of X include N and CH, examples of Y include N, CH, and C-F, examples of R$^2$ include alkyl and cycloalkyl, and examples of R$^4$ include a C-linked heterocylcyl and heteroaryl with suitable optional substituents as exemplified by the tables of interemediates below.

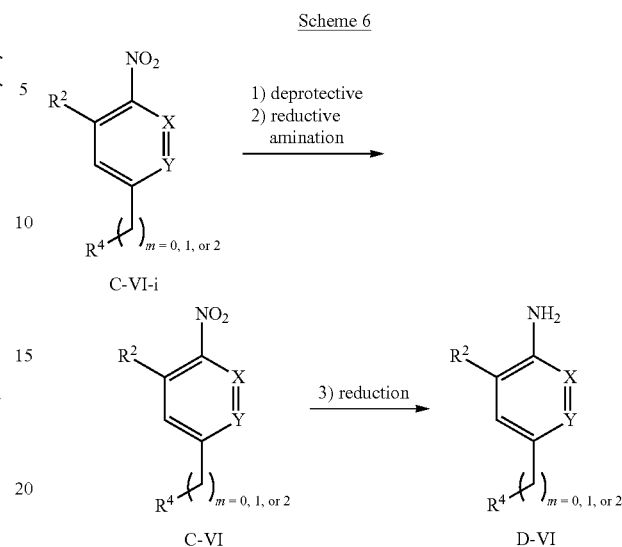

Scheme 6 illustrates an exemplary preparation of D-VI from C-VI-i where, in C-VI-i, R$^4$ contains a nitrogen protecting group, e.g. a Boc group. C-VI-i can be deprotected under acidic conditions to provide the amine salt. Further treatment of the salt with sodium cyanoborohydride or sodium triacetoxyborohydride and an aldehyde or ketone in the presence of a catalytic amount of acetic acid in polar solvents such as MeOH (reductive amination conditions) affords C-VI. Intermediate C-VI may be converted to aniline D-VI by standard reducing conditions, for example, by palladium catalyzed hydrogenation or by mild reducing conditions including zinc metal and ammonium chloride.

In Scheme 6, examples of X include N and CH, examples of Y include N, CH, and C—F where X and Y are not both N, examples of R$^2$ include alkyl and cycloalkyl, and examples of R$^4$ include heterocylcyl with suitable optional substituents as exemplified by the tables of interemediates below.

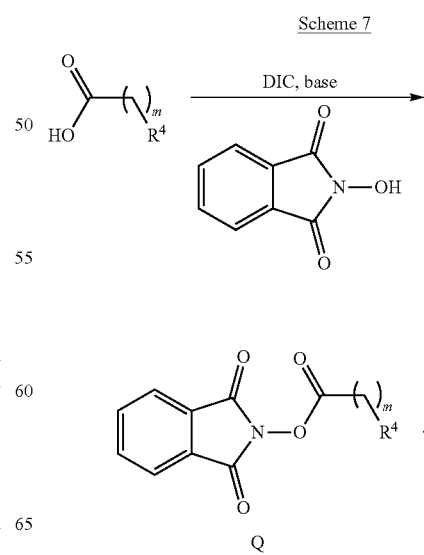

-continued

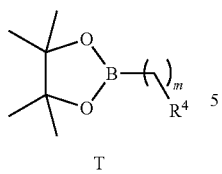

T

Scheme 7 illustrates an exemplary preparation of boronic acid/boronic ester T, which are not commercially available. These compounds can be readily prepared from the substituted carboxylic acid. The starting material carboxylic acid can be activated by 2-hydroxyisoindoline-1,3-dione in the presence of coupling reagent (e.g. DCI or Et$_3$N/HATU) to afford Q. Intermediate Q may be converted to boronic ester T by nickel-catalyzed decarboxylation borylation with the [B$_2$pin$_2$Me]Li complex, which is premixed with methyllithium and B$_2$pin$_2$ (Science, 356, 1045 (2017), JACS, 138, 2174 (2016)).

In Scheme 7, examples of m include 0, 1, and 2, and examples of R$^4$ include alkyl, cycloalkyl, and heterocyclyl with suitable optional substituents as exemplified by the tables of interemediates below.

Scheme 8

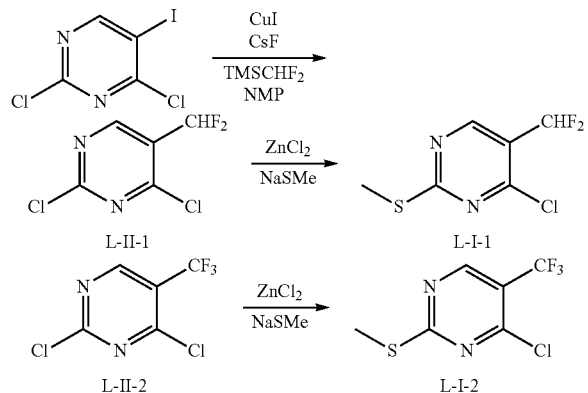

Scheme 8 illustrates an exemplary preparation of L-I-1 and L-I-2. Commercially available 2,4-dichloro-5-iodopyrimidine reacts with TMSCF2H in a solvent such as NMP or DMF in the presence of CuI and CsF to produce difluoromethylpyrimidine L-II-1 (US20150284341). Difluoromethylpyrimidine L-II-1 can be converted to thiomethyletherpyrimidine L-I-1 by treatment with sodium thiomethoxide and zinc chloride in diethyl ether at temperatures lower than 10° C. (WO2012110773). In a similar manner to L-I-1, trifluoromethylpyrimidine L-I-2 can be prepared from the commercially available 2,4-dichloro-5-(trifluoromethyl)pyrimidine, L-II-2.

Scheme 9

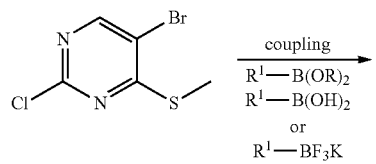

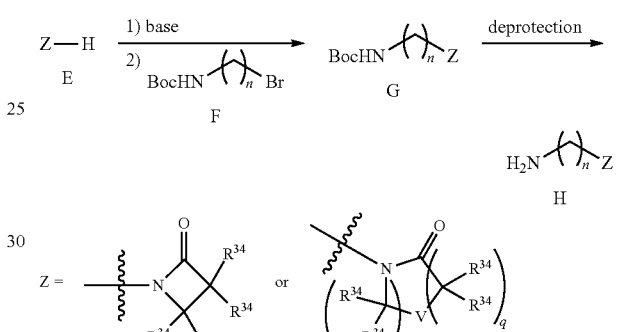

Scheme 9 illustrates an exemplary preparation of sulfonylpyrimidine L-III (t=2) where R$^1$ can be cycloalkyl. Treatment of commercially available 5-bromo-2-chloro-4-(methylthio)pyrimidine with commercially available boronic esters/boronic acids/trifluoroborates (see scheme 7) in the presence of a palladium catalyst (Suzuki coupling) affords thiopyrimidine L-III (t=0). The intermediate thiopyrimidine L-III (t=0) may be converted to sulfonylpyrimidine L-III (t=2) by standard oxidations, for example, by mCPBA.

Scheme 10

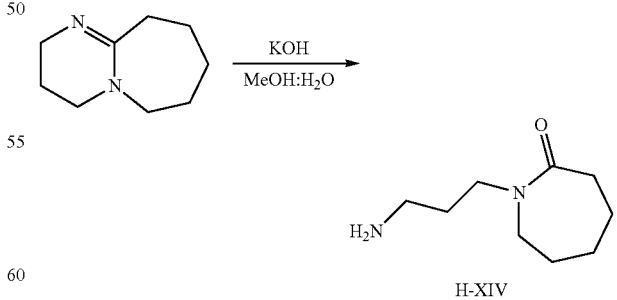

Scheme 10 illustrates an exemplary preparation of intermediate H (I-XIII) using a widely known method. Treatment of commercially available lactam/cyclic-carbamate/oxolactam/cyclic-urea/diazepanone E with (Boc)-protected bromo-intermediate F in the presence of base, for example sodium hydride or potassium tert-butoxide, provides G. The Boc protecting group of G may be removed upon exposure to acid, for example HCl or TFA.

In Scheme 10, q can be 0, 1, 2, or 3, r can be 2, 3, or 4, V can be C(R$^{34}$)$_2$, O, or NR$^6$, where R$^6$ is alkyl, n can be 2, 3, or 4, each R$^{34}$ can, independently, be H, C$_1$-C$_6$alkyl, or two R$^{34}$ can be taken together to form a cycloalkyl.

Scheme 11

H-XIV

In another embodiment to prepare H, H-XIV can be prepared from DBU via one step process as illustrated in Scheme 11. DBU can be hydrolyzed by potassium hydroxide in the solution of methanol and water at ambient temperature to provide H-XIV.

Scheme 12

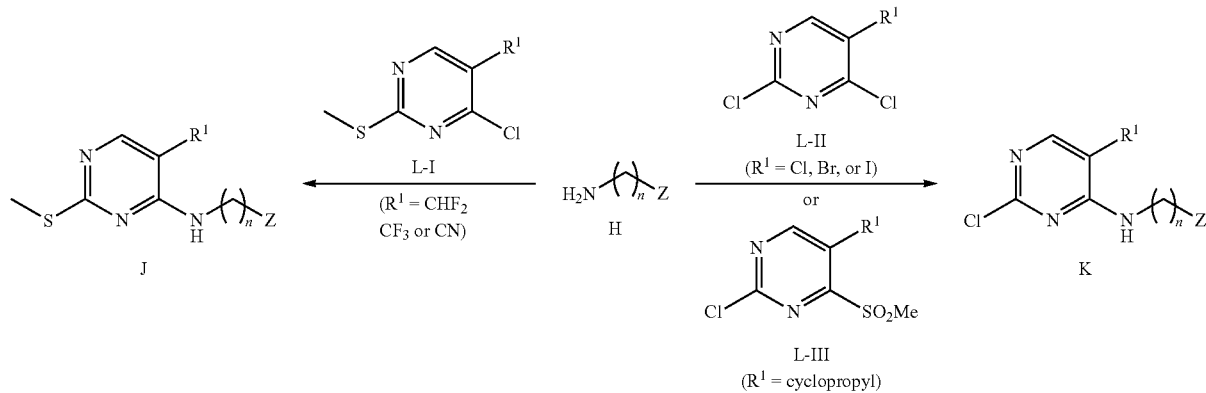

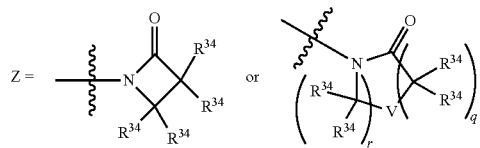

Scheme 12 illustrates an exemplary preparation of key intermediates J and K. Key intermediate J can be prepared from H (either free base or acid addition salt) by reacting with thiopyrimidine L-I in the presence of an organic base (e.g. triethylamine or DIEA) and optional heating. In a similar manner, key intermediate K can be prepared from H with either L-II or L-III.

In Scheme 12, q can be 0, 1, 2, or 3, r can be 2, 3, or 4, V can be $C(R^{34})_2$, O, or $NR^6$, where $R^6$ is alkyl, n can be 2, 3, or 4, each $R^{34}$ can, independently, be H, $C_1$-$C_6$alkyl, or two $R^{34}$ can be taken together to form a cycloalkyl group.

Scheme 13

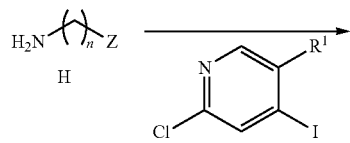

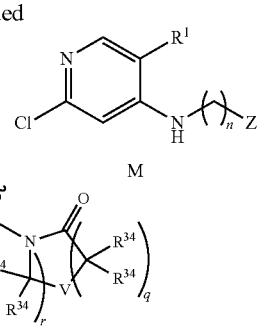

-continued

Scheme 13 illustrates an exemplary preparation of key intermediate M. Treatment of H with commercially available iodopyridine under Buchwald-Hartwig coupling conditions ($Cs_2CO_3$, Xantphos and $Pd(OAc)_2$), typically performed in an aprotic solvent (e.g. DME, DME, DMSO, or NMP) at temperatures ranging from ambient temp to 140° C., provides key intermediate M.

In Scheme 13, $R^1$ can be Br, Cl, alkyl optionally substituted by one or more fluorine atoms, or cycloalkyl, q can be 0, 1, 2, or 3, r can be 2, 3, or 4, V can be $C(R^{34})_2$, O, or $NR^6$, where $R^6$ is alkyl, n can be 2, 3, or 4, each $R^{34}$ can, independently, be H, $C_1$-$C_6$alkyl, or two $R^{34}$ can be taken together to form a cycloalkyl.

Scheme 14

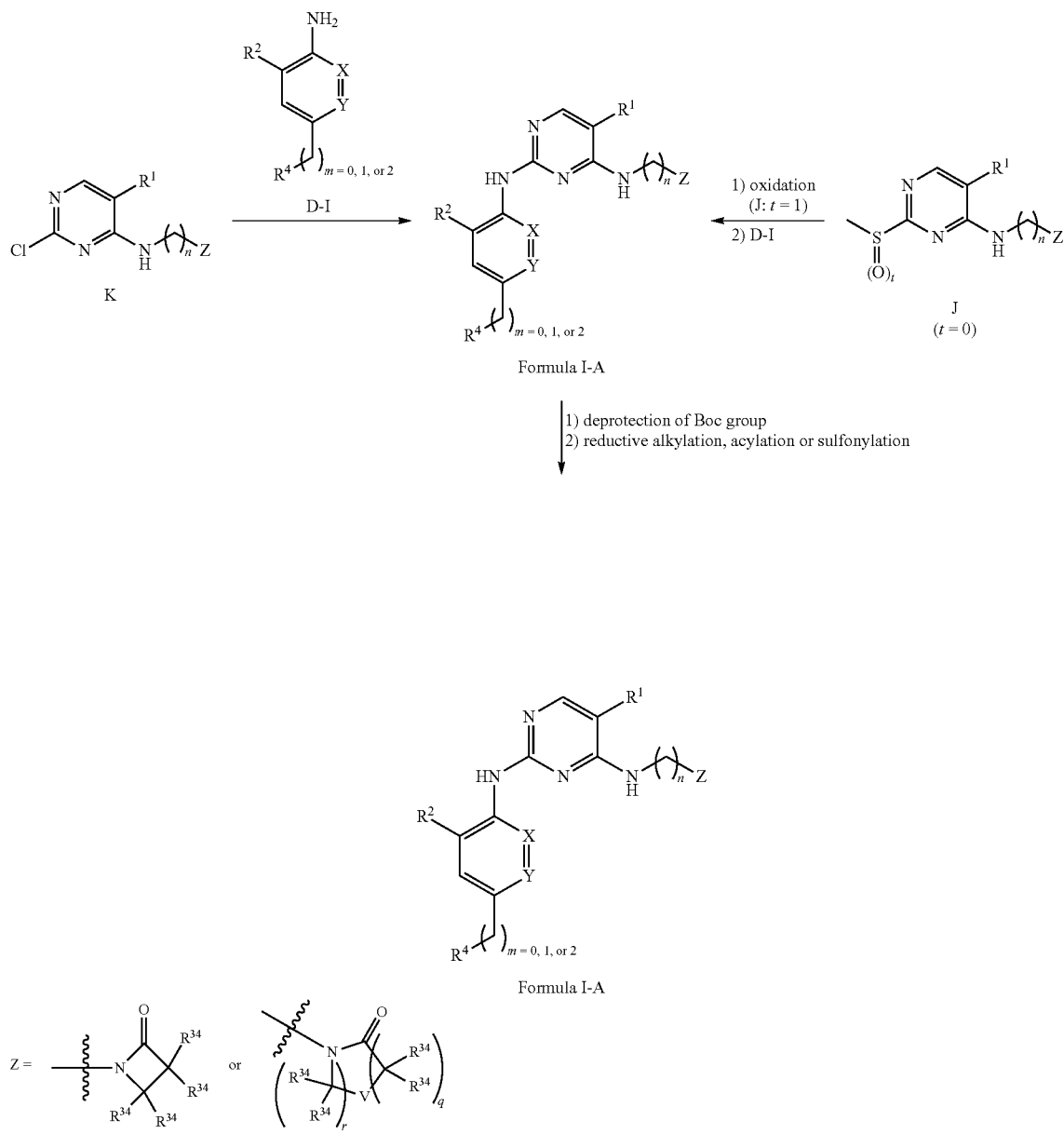

Formula I-A

Scheme 14 illustrates an exemplary preparation of compounds of Formula I from substituted anilines or aminopyridines (D-I). The preparation of Formula I-A can be accomplished from key intermediates K and J. First, a nucleophilic substitution reaction of K with amine D can be typically performed in an aprotic solvent at temperatures ranging from ambient temp to 150° C., in some embodiments with microwave heating, optionally in the presence of an acid for example 4 N HCl in 1,4-dioxane to provide Formula I-A. Compounds D-I, which are not commercially available, can be readily prepared from substituted nitrobenzenes or nitropyridines (see schemes 1-6). An alternative general synthesis of Formula I-A is via a two-step process by first converting J(t=0) to sulfoxide (J(t=1, major product) by oxidation using various oxidants, for example mCPBA. The sulfoxide reacts with amine D-I by a nucleophilic substitution reaction, typically performed in an aprotic solvent at temperatures ranging from ambient temp to 150° C., in some embodiments with microwave heating, optionally in the presence of an acid for example 4 N HCl in 1,4-dioxane or pTSA. Formula I-A which contains a nitrogen protecting group such as a Boc group, can be deprotected under acidic conditions to provide Formula I-A containing a free NH on $R^4$ (free amine or acid addition salt). Further treatment of Formula I-A (free base or acid addition salt) with sodium cyanoborohydride or sodium triacetoxyborohydride and an aldehyde or ketone in the presence of a catalytic amount of acetic acid in polar solvents such as MeOH (reductive amination conditions) affords $R^4$ N-substituted Formula I-A. For acylation and sulfonylation, the free amine (or salt) can be treated with commercially available acyl chloride or sulfonyl chloride to afford N-substituted Formula I-A.

Scheme 15
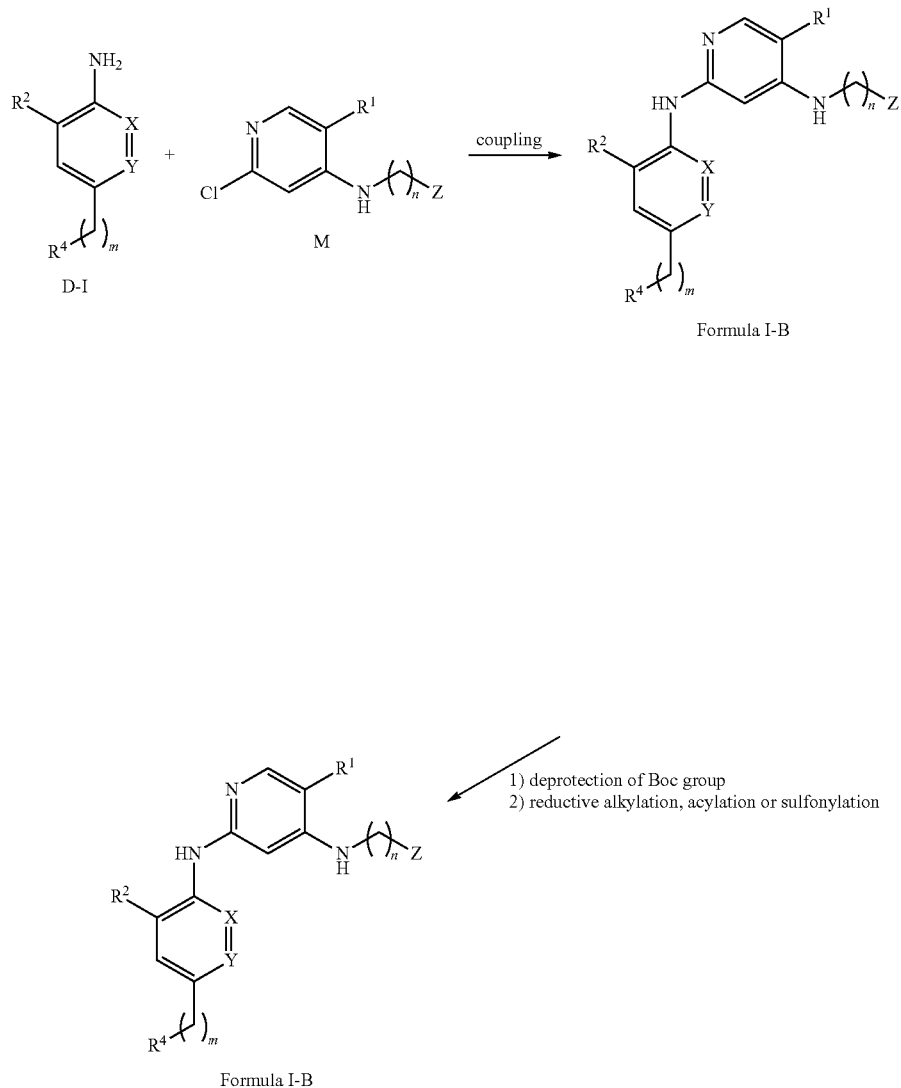
Formula I-B
1) deprotection of Boc group
2) reductive alkylation, acylation or sulfonylation
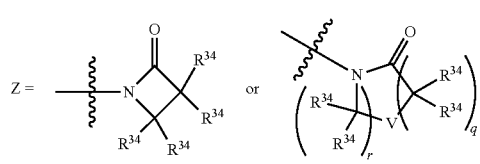

Scheme 15 illustrates exemplary preparations of compounds of Formula I-B. The preparation of Formula I-B can be accomplished by Buchwald-Hartwig coupling reaction with D-I and M. Amines D-I which are not commercially available can be readily prepared from substituted nitrobenzene or nitropyridine (see schemes 1-6). Formula I-B which contains a nitrogen protecting group such as a Boc group can be deprotected under an acidic condition to provide Formula I-B containing a free NH on $R^4$ (free amine or acid addition salt). Further treatment of Formula I-B (free base or acid addition salt) with sodium cyanoborohydride or sodium triacetoxyborohydride and an aldehyde or ketone in the presence of a catalytic amount of acetic acid in polar solvents such as MeOH (reductive amination conditions) affords $R^4$ N-substituted Formula I-B. In a same manner as Scheme 14, the free amine (or acid addition salt) can be treated with commercially available acyl chloride or sulfonyl chloride to afford N-substituted Formula I-B.

PREPARATION OF INTERMEDIATES

Using the synthetic procedures and methods described herein and methods known to those skilled in the art, the following compounds were made:

General Method A: Aromatic Nucleophilic Substitution

Intermediate B-I-8:
1-(3-bromo-4-nitrophenyl)-4-methylpiperazine

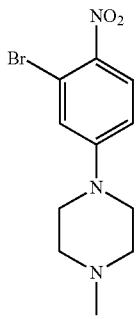

A mixture of 2-bromo-4-fluoro-1-nitrobenzene (50 g, 227 mmol) and 1-methylpiperazine (24 g, 250 mmol) in DMF (400 mL) was treated with $K_2CO_3$ (63 g, 455 mmol) at RT and the reaction mixture was stirred at 60° C. for 16 h. The reaction mixture was diluted with ice water (500 mL) and the precipitated solid was filtered. The solid was further triturated with $Et_2O$ and n-pentane to obtained 1-(3-bromo-4-nitrophenyl)-4-methylpiperazine (58 g, 85% yield) as a yellow solid. $^1$H NMR (400 MHz, DMSO-d6): δ 7.98 (d, J=9.4 Hz, 1H), 7.24 (d, J=2.1 Hz, 1H), 7.01 (dd, J=2.2 and 9.4 Hz, 1H), 3.42 (m, 4H), 2.40 (m, 4H), 2.19 (s, 3H); LC-MS (ESI) m/z: 299.0 (M+H$^+$).

General Method B: Deprotection and Reductive Amination

Intermediate B-I-24: 3-(3-bromo-4-nitrophenyl)-8-methyl-3,8-diazabicyclo[3.2.1]octane

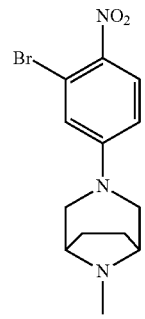 [SMILES: CN1C2CCC1CN(c1ccc([N+](=O)[O-])c(Br)c1)C2]

A solution of tert-butyl 3-(3-bromo-4-nitrophenyl)-3,8-diazabicyclo[3.2.1]octane-8-carboxylate (B-I-14, 2.57 g, 6.2 mol) in MeOH (30 mL) was treated with 4 N HCl in 1,4-dioxanes (16 mL, 62 mmol) and the reaction mixture was stirred at rt 16 h. The reaction mixture was concentrated to dryness under vacuum to provide 3-(3-bromo-4-nitrophenyl)-3,8-diazabicyclo[3.2.1]octane hydrochloride (2.17 g, 100% yield) as a white solid. Material was carried forward without further purification. A suspension of 3-(3-bromo-4-nitrophenyl)-3,8-diazabicyclo[3.2.1]octane hydrochloride (1.92 g, 5.5 mmol) in DCE (25 mL) was treated with DIEA (2.9 mL, 17 mmol) and formaldehyde (1.2 mL, 17 mmol). The yellow suspension became a clear orange solution. The reaction mixture was stirred for 10 min at rt and then acetic acid (0.63 mL, 11 mmol) was added. The orange solution became a yellow suspension which was stirred for 20 min. Sodium triacetoxyborohydride (2.33 g, 11 mmol) was added and the reaction mixture was stirred at rt for 4 h. The reaction mixture was diluted with aqueous NaHCO$_3$ (50 mL) and the solution was extracted with DCM (3×50 mL). The combined organics were dried over anhydrous Na$_2$SO$_4$, filtered, and concentrated to afford a brown solid. The brown solid was purified using silica gel column chromatography (0 to 15% MeOH/DCM) to afford 3-(3-bromo-4-nitrophenyl)-8-methyl-3,8-diazabicyclo[3.2.1]octane (1.71 g, 95% yield) as a yellow solid. $^1$H NMR (400 MHz, DMSO-d6): δ 7.98 (d, J=9.4 Hz, 1H), 7.10 (d, J=2.7 Hz, 1H), 6.89 (dd, J=9.5 and 2.7 Hz, 1H), 3.54 (d, J=11.6 Hz, 2H), 3.22 (brs, 2H), 2.99-3.04 (m, 2H), 2.22 (s, 3H), 1.92-1.95 (m, 2H), 1.52-1.56 (m, 2H); LC-MS (ESI) m/z: 326.0 (M+H$^+$).

General Method C: Alkylation

Intermediate B-I-23: 1-(2-fluoroethyl)-4-(3-methyl-4-nitrophenyl)piperazine

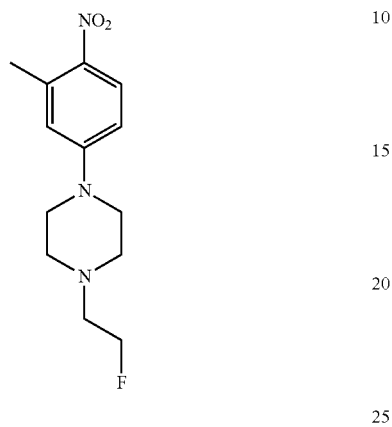

A mixture of 1-(3-methyl-4-nitrophenyl)piperazine hydrochloride (Boc-deprotected product of B-I-3 1.5 g, 0.58 mmol) and $K_2CO_3$ (4.0 g, 2.9 mmol) in 1,4-dioxane (20 mL) was treated with 1-fluoro-2-iodoethane (2.0 mL, 2.6 mmol) [Note: material described as prone to instability—some solids present in the orange liquid], capped tightly and heated to 100° C. for 24 h. The mixture was cooled to rt and the solids ($K_2CO_3$) were removed via filtration, rinsed with DCM and the filtrate was concentrated to dryness to afford 1-(2-fluoroethyl)-4-(3-methyl-4-nitrophenyl)piperazine (1.52 g, 98% yield) as a yellow oil which solidified upon standing to an amber solid. $^1$H NMR (400 MHz, DMSO-$d_6$): δ 7.97 (d, J=9.6 Hz, 1H), 6.87-6.89 (m, 2H), 4.61 (t, J=4.9 Hz, 1H), 4.52 (t, J=4.9 Hz, 1H), 3.41 (m, 4H), 2.69 (t, J=4.9 Hz, 1H), 2.63 (t, J=4.9 Hz, 1H), 2.54-2.56 (m, 7H); LC-MS (ESI) m/z: 268.2 (M+H$^+$).

Using the General Methods A-C above, the following Intermediates in Table A were prepared.

TABLE A

| Intermediate | Structure | Method | Yield (%) | $^1$H NMR (400 MHz, DMSO-$d_6$): δ | LC-MS (m/z: (M + H$^+$) |
|---|---|---|---|---|---|
| B-I-1 | 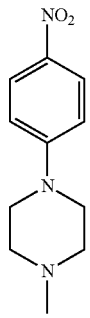 [SMILES: CN1CCN(c2ccc([N+](=O)[O-])cc2)CC1] | A | 90 | 8.04 (d, J = 9.4 Hz, 2H), 7.02 (d, J = 9.4 Hz, 2H), 3.44 (brs, 4H), 2.41 (brs, 4H), 2.21 (s, 3H). | 222.1 |

TABLE A-continued

| Intermediate | Structure | Method | Yield (%) | $^1$H NMR (400 MHz, DMSO-d$_6$): δ | LC-MS (m/z: (M + H$^+$) |
|---|---|---|---|---|---|
| B-I-2 | 4-nitrophenyl-piperazine-cyclopropyl | A | 81 | 8.03 (d, 2H), 7.01 (d, 2H), 3.40 (t, J = 5.0 Hz, 4H), 2.63 (t, J = 5.0 Hz, 4H), 1.63-1.67 (m, 1H), 0.42-0.45 (m, 2H), 0.33-0.36 (m, 2H). | 248.2 |
| B-I-3 | 3-methyl-4-nitrophenyl-piperazine-Boc | A | 96 | 7.99 (d, J = 9.0 Hz, 1H), 6.86-6.88 (m, 2H), 3.43 (s, 8H), 2.54 (s, 3H), 1.41 (s, 9H). | 322.2 |
| B-I-4 | 3-methyl-4-nitrophenyl-piperazine-cyclopropyl | A | 90 | 7.97 (d, J = 9.6 Hz, 1H), 6.87 (m, 2H), 3.37 (brs, 4H), 2.62 (brs, 4H), 2.54 (s, 3H), 1.64 (m, 1H), 0.43 (m, 2H), 0.36 (m, 2H). | 262.3 |
| B-I-5 | 3-methyl-4-nitrophenyl-oxabicyclic | A | 87 | 7.99 (d, J = 9.2 Hz, 1H), 6.58 (brs, 2H), 4.82 (s, 1H), 4.69 (s, 1H), 3.78 (m, 1H), 3.63 (m, 1H), 3.52 (m, 1H), 3.16 (d, J = 10.0 Hz, 1H), 2.54 (s, 3H), 1.91 (m, 2H). | 235.1 |

TABLE A-continued
| Intermediate | Structure | Method | Yield (%) | $^1$H NMR (400 MHz, DMSO-$d_6$): δ | LC-MS (m/z: (M + H$^+$)) |
|---|---|---|---|---|---|
| B-I-6 | 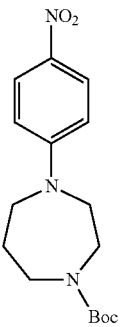 | A | 80 | No NMR Data | 322.2 |
| B-I-7 | 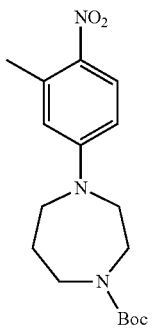 [SMILES: Cc1cc(N2CCCN(C(=O)OC(C)(C)C)CC2)ccc1[N+](=O)[O-]] | A | 54 | 7.95-7.98 (m, 1H), 6.72-6.74 (m, 2H), 3.73 (t, J = 6.0 Hz, 1H), 3.68 (t, J = 5.6 Hz, 1H), 3.58-3.62 (m, 2H), 3.54 (t, J = 6.0 Hz, 1H), 3.47 (t, J = 5.6 Hz, 1H), 3.26 (t, J = 5.2 Hz, 1H), 3.19 (t, J = 5.7 Hz, 1H), 2.54 (d, J = 3.3 Hz, 3H), 1.80 (t, J = 6.3 Hz, 1H), 1.73 (s, 1H), 1.28 (s, 4H), 1.14 (s, 5H). | 358.2 (M + Na + H$^+$) |
| B-I-9 | 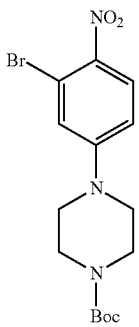 [SMILES: CC(C)(C)OC(=O)N1CCN(c2ccc([N+](=O)[O-])c(Br)c2)CC1] | A | 100 | 8.01 (d, J = 9.3 Hz, 1H), 7.24 (m, 1H), 7.01 (m, 1H), 3.44 (brs, 8H), 1.41 (s, 9H). | 408.0 410.0 (M + Na + H$^+$) (M + Na + 3H$^+$) |
| B-I-10 | 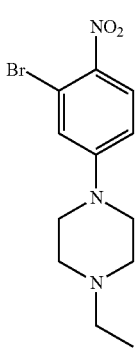 [SMILES: CCN1CCN(c2ccc([N+](=O)[O-])c(Br)c2)CC1] | B | 92 | 7.98 (d, J = 9.4 Hz, 1H), 7.24 (d, J = 2.7 Hz, 1H), 7.01 (dd, J = 9.4 and 2.7 Hz, 1H), 3.42 (t, J = 5.0 Hz, 4H), 2.44 (t, J = 5.0 Hz, 4H), 2.35 (q, J = 7.2 Hz, 2H), 1.01 (t, J = 7.2 Hz, 3H). | No data |

TABLE A-continued

| Intermediate | Structure | Method | Yield (%) | $^1$H NMR (400 MHz, DMSO-d$_6$): δ | LC-MS (m/z: (M + H$^+$) |
|---|---|---|---|---|---|
| B-I-11 | 4-bromo-1-nitro-4-(4-isopropylpiperazin-1-yl)benzene | B | 95 | No NMR Data | 328.0 330.0 |
| B-I-12 | 3-bromo-4-nitro-phenyl morpholine | A | 58 | 8.02 (d, J = 8.0 Hz, 1H), 7.27 (d, J = 2.0 Hz, 1H), 7.05 (dd, J = 8.0 and 2.0 Hz, 1H), 3.73 (m, 2H), 3.41 (m, 2H). | 287.0 289.0 |
| B-I-13 | 4-(3-bromo-4-nitrophenyl)-1-methylpiperazin-2-one | A | 53 | 8.0 (d, J = 9.2 Hz, 1H), 7.24 (s, 1H), 6.99 (m, 1H), 4.02 (s, 2H), 3.72 (brs, 2H), 3.45 (d, J = 4.0, 2H), 2.90 (s, 3H). | 313.0 315.0 |
| B-I-14 | tert-butyl 3-(3-bromo-4-nitrophenyl)-3,8-diazabicyclo[3.2.1]octane-8-carboxylate | A | 76 | 7.99 (d, J = 9.5 Hz, 1H), 7.19 (s, 1H), 6.95-6.97 (m, 1H), 4.16-4.23 (m, 2H), 3.72 (d, J = 12.1Hz, 2H), 2.99 (d, J = 12.1 Hz, 2H), 1.85 (brs, 2H), 1.67 (d, J = 7.5 Hz, 2H), 1.41 (s, 9H). | No Data |
| B-I-15 | 3-(5-bromo-2-fluoro-4-nitrophenyl)-3,8-diazabicyclo[3.2.1]octane | A | 37 | 7.99 (d, J = 9.4 Hz, 1H), 7.18 (d, J = 2.7 Hz, 1H), 6.96 (dd, J = 9.4 and 2.8 Hz, 1H), 4.57 (t, J = 4.2 Hz, 1H), 3.44 (dd, J = 12.9 and 5.6 Hz, 1H), 3.01-3.07 (m, 1H), 2.88-2.97 (m, 3H), 2.80-2.86 (m, 1H), 2.71 (dd, J = 13.3, 4.9 Hz, 1H), 2.51 (s, 1H), 1.85-1.92 (m, 1H), 1.69-1.75 (m, 1H). | No Data |

TABLE A-continued

| Intermediate | Structure | Method | Yield (%) | $^1$H NMR (400 MHz, DMSO-$d_6$): δ | LC-MS (m/z: (M + H$^+$) |
|---|---|---|---|---|---|
| B-I-16 | 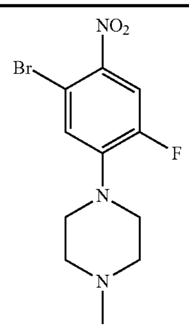 | A | 87 | 8.02 (m, 1H), 7.33 (m, 1H), 3.26 (m, 4 H), 2.43 (m, 4 H), 2.20 (s, 3 H). | 318.0 320.0 |
| B-I-17 | 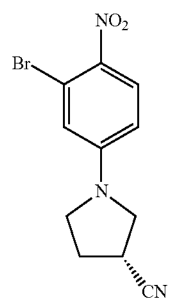 | A | 20 | 8.03 (d, J = 9.2 Hz, 1H), 6.93 (s, 1H), 6.69 (d, J = 9.3 Hz, 1H), 3.72 (t, J = 8.5 Hz, 1H), 3.58-3.66 (m, 2H), 3.52 (t, J = 7.8 Hz, 1H), 3.41-3.46 (m, 1H), 2.35-2.42 (m, 1H), 2.23-2.30 (m, 1H). | No Data |
| B-I-18 | 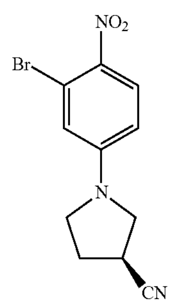 [SMILES: N#C[C@H]1CCN(c2ccc([N+](=O)[O-])c(Br)c2)C1] | A | 76 | 8.03 (d, J = 9.2 Hz, 1H), 6.93 (d, J = 2.6 Hz, 1H), 6.68 (dd, J = 9.3, 2.6 Hz, 1H), 3.70-3.73 (m, 1H), 3.58-3.66 (m, 2H), 3.53 (dt, J = 10.3 and 6.8 Hz, 1H), 3.41-3.46 (m, 1H), 2.36-2.41 (m, 1H), 2.23-2.30 (m, 1H). | No Data |
| B-I-19 | 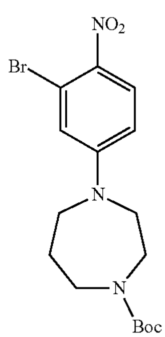 | A | 77 | 7.97 (dd, J = 9.4 and 4.1 Hz, 1H), 7.07 (s, 1H), 6.86 (d, J = 9.6 Hz, 1H), 3.47-3.76 (m, 6 H), 3.21-3.28 (m, 2H), 1.67-1.81 (m, 2H), 1.21 (s, 9H). | 422.2 424.2 |
| B-I-20 | 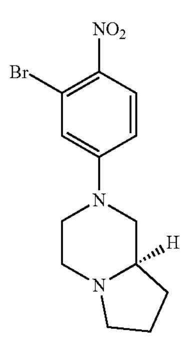 [SMILES: O=[N+]([O-])c1ccc(N2CCN3CCC[C@@H]3C2)cc1Br] | A | 36 | 7.98 (d, J = 9.4 Hz, 1H), 7.26 (d, J = 2.8 Hz, 1H), 7.03 (dd, J = 9.4, 2.8 Hz, 1H), 4.11 (d, J = 12.2 Hz, 1H), 3.95 (d, J = 12.7 Hz, 1H), 2.92-3.05 (m, 3H), 2.63 (t, J = 11.3 Hz, 1H), 2.15 (t, J = 11.3 Hz, 1H), 2.06 (q, J = 8.7 Hz, 1H), 1.91-2.00 (m, 1H), 1.80-1.86 (m, 1H), 1.64-1.73 (m, 2H), 1.30-1.40 (m, 1H). | 326.0 328.0 |

TABLE A-continued

| Intermediate | Structure | Method | Yield (%) | $^1$H NMR (400 MHz, DMSO-d$_6$): δ | LC-MS (m/z: (M + H$^+$) |
|---|---|---|---|---|---|
| B-I-21 | (structure: 3-bromo-4-nitrophenyl octahydropyrrolo[1,2-a]pyrazine) | A | 64 | 7.98 (d, J = 9.4 Hz, 1H), 7.26 (d, J = 2.8 Hz, 1H), 7.03 (dd, J = 9.4, 2.8 Hz, 1H), 4.11 (d, J = 12.2 Hz, 1H), 3.95 (d, J = 12.7 Hz, 1H), 2.92-3.05 (m, 3H), 2.63 (t, J = 11.3 Hz, 1H), 2.15 (t, J = 11.3 Hz, 1H), 2.06 (q, J = 8.7 Hz, 1H), 1.91-2.00 (m, 1H), 1.80-1.86 (m, 1H), 1.64-1.73 (m, 2H), 1.30-1.40 (m, 1H). | 326.0 328.0 |
| B-I-22 | (structure: 3-methyl-4-nitrophenyl-4-methylpiperazine) | A | 86 | 7.97 (d, J = 9.6 Hz, 1H), 6.88 (d, J = 8.0 Hz, 2H), 3.40 (brs, 4H), 2.54 (s, 3H), 2.40 (brs, 4H), 2.20 (s, 3H). | 236.2 |
| B-I-25 | (structure: 3-bromo-4-nitrophenyl-3-(dimethylamino)azetidine) | A | 41 | 8.00 (d, J = 9.1 Hz, 1H), 6.69 (d, J = 2.5 Hz, 1H), 6.44 (dd, J = 9.1 and 2.5 Hz, 1H), 4.05 (m, 2H), 3.81 (dd, J = 9.1, 5.1 Hz, 2H), 2.11 (s, 6H). | 300.2 302.2 |
| B-I-26 | (structure: 3-bromo-4-nitrophenyl-5-methyl-2,5-diazabicyclo[2.2.1]heptane) | B | 44 | 7.99 (d, J = 9.3 Hz, 1H), 6.60-6.91 (brm, 2H), 4.59 (s, 1H), 3.49 (s, 1H), 3.34 (s, 2H), 2.81 (dd, J = 9.6 and 2.0 Hz, 1H), 2.42, (d, J = 9.7 Hz, 1H), 2.27 (s, 3H), 1.90 (m, 1H), 1.75 (m, 1H). | 312.0 314.0 |
| B-I-27 | (structure: 4-methyl-5-nitro-2-morpholinopyridine) | A | 90 | 8.86 (s, 1H), 6.83 (s, 1H), 3.68 (brs, 8H), 2.51 (s, 3H). | 224.33 |

TABLE A-continued
| Intermediate | Structure | Method | Yield (%) | $^1$H NMR (400 MHz, DMSO-d$_6$): δ | LC-MS (m/z: (M + H$^+$) |
|---|---|---|---|---|---|
| B-I-28 | 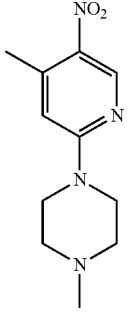 [SMILES: Cc1cc(N2CCN(C)CC2)ncc1[N+](=O)[O-]] | A | 99 | 8.84 (s, 1H), 6.83 (s, 1H), 3.71 (brs, 4H), 2.52 (s, 3H), 2.37 (brs, 4H), 2.20 (s, 3H). | 237.2 |
| B-I-29 | 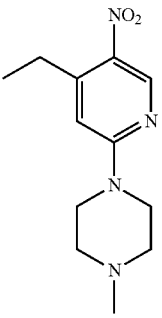 | A | 83 | 8.84 (s, 1H), 6.79 (s, 1H), 3.71 (brs, 4H), 2.89 (q, 2H), 2.38 (brs, 4H), 2.21 (s, 3H), 1.19 (t, J = 7.4 Hz, 3H). | 251.2 |
| B-I-30 | 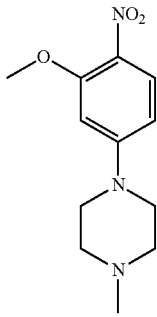 | A | 74 | 7.87 (d, J = 9.2 Hz, 1H), 6.59 (d, J = 9.2 Hz, 1H), 6.53 (s, 1H), 3.90 (s, 3H), 3.43 (s, 4H), 2.41 (s, 4H), 2.21 (s, 3H), | 252.1 |
| B-I-31 | 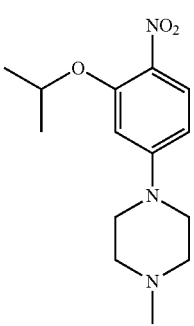 [SMILES: CC(C)Oc1cc(N2CCN(C)CC2)ccc1[N+](=O)[O-]] | A | 71 | 7.82 (d, J = 9.2 Hz, 1H), 6.51 (m, 2H), 4.82 (m, 1H), 3.92 (m, 4H), 2.40 (m, 4H), 2.21 (s, 3H), 1.28 (d, J = 6.0 Hz, 6H). | 280.1 |

TABLE A-continued
| Intermediate | Structure | Method | Yield (%) | ¹H NMR (400 MHz, DMSO-d₆): δ | LC-MS (m/z: (M + H⁺) |
|---|---|---|---|---|---|
| B-I-32 | 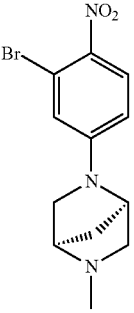 [SMILES: CN1C[C@H]2C[C@@H]1CN2c1ccc([N+](=O)[O-])c(Br)c1] | B | 87 | 7.99 (d, J = 9.3 Hz, 1H), 6.60-6.91 (brm, 2H), 4.59 (s, 1H), 3.49 (s, 1H), 3.34 (s, 2H), 2.81 (dd, J = 9.6 and 2.0 Hz, 1H), 2.42, (d, J = 9.7 Hz, 1H), 2.27 (s, 3H), 1.90 (m, 1H), 1.75 (m, 1H). | 312.0 314.0 |
| B-I-A | 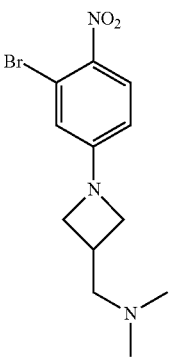 [SMILES: CN(C)CC1CN(c2ccc([N+](=O)[O-])c(Br)c2)C1] | A | 57 | 7.88 (d, J = 9.1 Hz, 1H), 5.98 (dd, J = 9.1, 2.2 Hz, 1H), 5.80 (d, J = 2.3 Hz, 1H), 4.20 (t, J = 8.3 Hz, 2H), 3.83 (t, J = 7.1 Hz, 2H), 3.47 (d, J = 7.2 Hz, 2H), 3.27 (m, 1H), 2.81 (s, 6H). | 314.0 316.0 |
| B-I-B | 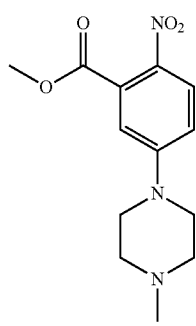 [SMILES: COC(=O)c1cc(N2CCN(C)CC2)ccc1[N+](=O)[O-]] | A | crude | No NMR Data | 280.2 |
| B-I-C | 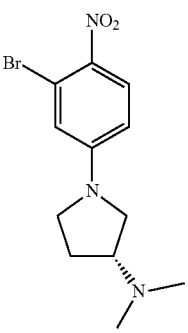 [SMILES: CN(C)[C@@H]1CCN(c2ccc([N+](=O)[O-])c(Br)c2)C1] | A | 70 | 8.01 (d, J = 9.3 Hz, 1H), 6.86 (d, J = 2.6 Hz, 1H), 6.61 (dd, J = 2.6 and 9.3 Hz, 1H), 3.54 (m, 1H), 3.44 (m, 1H), 3.35 (m, 1H), 3.12 (m, 1H), 2.77 (m, 1H), 2.18 (s, 6H), 2.14 (m, 1H), 1.80 (m, 1H). | 314.2 316.2 |

TABLE A-continued

| Intermediate | Structure | Method | Yield (%) | $^1$H NMR (400 MHz, DMSO-$d_6$): δ | LC-MS (m/z: (M + H$^+$) |
|---|---|---|---|---|---|
| B-I-D | ![structure] | A | 58 | 8.01 (d, J = 9.3 Hz, 1H), 6.86 (d, J = 2.6 Hz, 1H), 6.61 (dd, J = 2.6 and 9.3 Hz, 1H), 3.54 (m, 1H), 3.44 (m, 1H), 3.35 (m, 1H), 3.12 (m, 1H), 2.77 (m, 1H), 2.18 (s, 6H), 2.14 (m, 1H), 1.80 (m, 1H). | 336.2 338.2 (Na) |
| B-I-E | ![structure] | A | 57 | No NMR Data | 314.2 |
| B-I-F | ![structure] | A | 74 | 7.99 (d, J = 9.4 Hz, 1H), 7.07 (d, J = 2.7 Hz, 1H), 6.96 (dd, J = 2.7 and 9.5 Hz, 1H), 3.42 (t, J = 5.1 Hz, 4H), 2.39 (t, J = 5.1 Hz, 4H), 2.20 (s, 3H). | 256.0 |

Intermediate B-I-33: 1-(3-bromo-4-nitrophenyl)-4-methylpiperazin 2-one

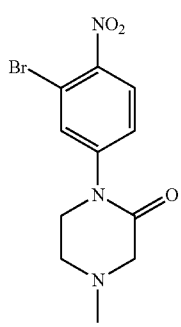 [SMILES: CN1CCN(c2ccc([N+](=O)[O-])c(Br)c2)C(=O)C1]

A mixture of tert-butyl (2-aminoethyl) (methyl)carbamate (4.3 g, 24 mmol) and potassium carbonate (3.8 g, 27 mmol) in DMF (50 mL) was treated with 4-fluoro-2-bromo-1-nitrobenzene (5 g, 22 mmol) at rt under N$_2$ atmosphere and the mixture was stirred at 90° C. for 16 h. The reaction mixture was diluted with water (200 mL) and the solution was extracted with EtOAc (2×100 mL), The combined organics were dried over anhydrous Na$_2$SO$_4$, filtered and concentrated. The crude was purified by silica gel column chromatography (2% MeOH/DCM, 10 CV's) to give tert-butyl (2-((3-bromo-4-nitrophenyl)amino)ethyl)(methyl)carbamate (5.6 g, 66% yield) as a yellow liquid. $^1$H NMR (400 MHz, DMSO-$d_6$): δ 7.98 (d, J=9.0 Hz, 1H), 6.77 (S, 1H), 6.46 (d, J=9.0 Hz, 1H), 3.54 (s, 2H), 3.31 (t, J=6.0 Hz, 2H), 2.90 (s, 3H), 1.47 (s, 9H); LC-MS (ESI) m/z: 374.1 (M+H$^+$).

A mixture of tert-butyl (2-((3-bromo-4-nitrophenyl)amino)ethyl)(methyl)carbamate (5.6 g, 15 mmol) and TEA (7.6 g, 75 mmol) in DCM (100 mL) was treated with chloroacetylchloride (5.1 g, 45 mmol) at 0° C. under N$_2$ atmosphere and the mixture was stirred at rt for 16 h. The reaction mixture was diluted with water (100 mL) and the solution was extracted with DCM (2×100 mL). The combined organics were evaporated under reduced pressure and the crude was purified by silica gel column chromatography (2% MeOH/DCM, 10 CV's) to obtain tert-butyl (2-(N-(3- bromo-4-nitrophenyl)-2-chloroacetamido)ethyl)(methyl) carbamate (5.6 g, 66% yield) as a yellow liquid. $^1$H NMR (400 MHz, DMSO-d$_6$): δ 8.12 (d, J=8.6 Hz, 1H), 7.97 (s, 1H), 6.66 (d, J=7.4 Hz, 1H), 4.24 (m, 2H), 3.82 (s, 2H), 3.18 (s, 2H), 2.70 (s, 3H), 1.41 (s, 9H); LC-MS (ESI) m/z: 374.1 (M+H$^+$).

A solution of N-(3-bromo-4-nitrophenyl)-2-chloro-N-(2-(methylamino)ethyl)acetamide hydrochloride (5.6 g, 12 mmol) in dioxane (100 mL) was treated with 4 N HCl in 1,4-dioxane (100 mL) at 0° C. under N$_2$ atmosphere and the reaction mixture was stirred at rt for 16 h. The reaction mixture evaporated under reduced pressure and the crude was purified by crystallization in Et$_2$O (100 mL) to obtain N-(3-bromo-4-nitrophenyl)-2-chloro-N-(2-(methylamino)ethyl)acetamide hydrochloride (4.79 g, 99% yield) as a yellow solid. $^1$H NMR (400 MHz, DMSO-d$_6$): δ 8.75 (brs, 2H), 8.16 (m, 2H), 7.83 (d, J=7.8 Hz, 1H), 4.20 (s, 2H), 3.98 (t, 2H), 3.20 (s, 2H), 2.56 (s, 3H), 1.41 (s, 9H); LC-MS (ESI) m/z: 374.1 (M+H$^+$).

A solution of N-(3-bromo-4-nitrophenyl)-2-chloro-N-(2-(methylamino)ethyl)acetamide hydrochloride (5.0 g, 12 mmol) in DMF (50 mL) was added to NaH in 60% mineral oil (1.1 g, 25 mmol) at 0° C. under N$_2$ atmosphere and the reaction mixture was stirred at rt for 2 h. The reaction mixture was diluted with water (100 mL) and the solution was extracted with EtOAc (2×50 mL), The combined organics were evaporated under reduced pressure and the crude was purified by silica gel column chromatography (2% MeOH/DCM, 10 CV's) to give 1-(3-bromo-4-nitrophenyl)-4-methylpiperazin-2-one (3.1 g, 76% yield) as a yellow solid. $^1$H NMR (400 MHz, DMSO-d$_6$): δ 8.0 (d, J=9.4 Hz, 1H), 7.24 (d, J=2.3 Hz, 1H), 6.99 (dd, J=2.3 and 9.3 Hz, 1H), 4.0 (s, 2H), 3.72 (t, J=5.4 Hz, 2H), 3.45 (t, J=5.4 Hz, 2H), 2.90 (s, 3H); LC-MS (ESI) m/z: 314.2 (M+H$^+$).

Intermediate B-I-34: 1-(3-(methoxymethyl)-4-nitrophenyl)-4-methylpiperazine

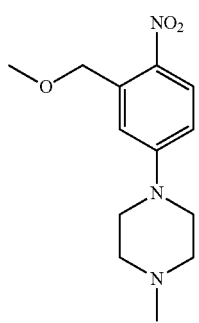 [SMILES: COCc1cc(N2CCN(C)CC2)ccc1[N+](=O)[O-]]

A solution of (5-(4-methylpiperazin-1-yl)-2-nitrophenyl)methanol (1.0 g, 4.0 mmol) in DMF (30 mL) was cooled to 0° C. Sodium hydride (0.80 g, 60% in mineral) was added in portions and the mixture was stirred under the same conditions. Iodomethane (1.7 g, 12 mmol) was added at 0° C. and the mixture was slowly warmed to rt and stirred for 2 h. The reaction was diluted with EtOAc and carefully quenched with ice water. The mixture was extracted with EtOAc (3×30 mL) and the combined organic extracts were dried over anhydrous Na$_2$SO$_4$, filtered and concentrated under the reduced pressure to obtain the crude. The crude was purified by silica gel column chromatography (hexane/EtOAc) 1-(3-(methoxymethyl)-4-nitrophenyl)-4-methylpiperazine (0.76 g, 72% yield). $^1$H NMR (400 MHz, DMSO-d$_6$): δ 8.03 (m, 1H), 7.08 (s, 1H), 6.96 (m, 1H), 4.76 (s, 2H), 3.45 (brs, 4H), 3.40 (s, 3H), 2.42 (brs, 4H), 2.22 (s, 3H); LC-MS (ESI) m/z: 266.2 (M+H$^+$).

General Method D: Suzuki Coupling Reaction

Intermediate C-V-4: 1-methyl-4-(3-methyl-4-nitrophenyl)-1H-imidazole

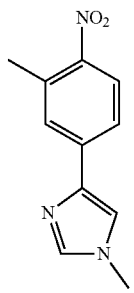

A suspension of 4,4,5,5-tetramethyl-2-(3-methyl-4-nitrophenyl)-1,3,2-dioxaborolane (0.80 g, 3.0 mmol) and 4-bromo-1-methyl-1H-imidazole (0.49 g, 3.0 mmol) in a mixture of 1,4-dioxane (12 mL) and water (0.5 mL) was treated with potassium carbonate (1.26 g, 9.1 mmol) and the suspension was allowed to stir. The reaction mixture was degassed by bubbling argon for two minutes and treated with Pd(dppf)Cl$_2$.DCM adduct (0.50 g, 0.61 mmol). The resulting reaction mixture was heated at 100° C. 16 h. The reaction was diluted with water and extracted with DCM (4×25 mL). The organics were combined and dried over anhydrous Na$_2$SO$_4$, filtered and concentrated to dryness under vacuum to afford a black oil. The black oil was purified using silica gel (0 to 15% MeOH/DCM, 15 CV's) to obtain 1-methyl-4-(3-methyl-4-nitrophenyl)-1H-imidazole (0.31 g, 47% yield). $^1$H NMR (400 MHz, DMSO-d$_6$): δ 8.02 (d, J=8.6 Hz, 1H), 7.84 (d, J=7.7 Hz, 2H), 7.77 (d, J=8.6 Hz, 1H), 7.72 (s, 1H), 3.70 (s, 3H), 2.57 (s, 3H); LC-MS (ESI) m/z: 218.2 (M+H$^+$).

Using the General Method D above, the following Intermediates of Table B were prepared.

TABLE B

| Intermediate | Structure | Method | Yield (%) | $^1$H NMR (400 MHz, DMSO-d$_6$): δ | LC-MS (m/z: (M + H$^+$) |
|---|---|---|---|---|---|
| C-V-1 | 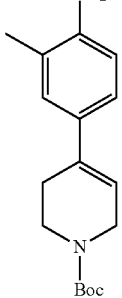 | D | 62 | No NMR Data | 319.2 |

TABLE B-continued

| Intermediate | Structure | Method | Yield (%) | $^1$H NMR (400 MHz, DMSO-$d_6$): δ | LC-MS (m/z: (M + H$^+$) |
|---|---|---|---|---|---|
| C-V-2 | ![structure] | D | 64 | No NMR Data | 233.2 |
| C-V-3 | ![structure] | D | 72 | 8.34 (s, 1H), 8.02 (s, 1H), 8.00 (s, 1H), 7.72 (s, 1H), 7.63 (m, 1H), 3.88 (s, 3H), 2.56 (s, 3H). | 218.2 |

General Method E: Suzuki Coupling Reaction

Intermediate C-I-1:
1-(3-cyclopropyl-4-nitrophenyl)-4-methylpiperazine

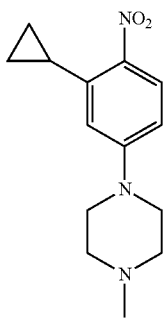 [SMILES: CN1CCN(c2ccc([N+](=O)[O-])c(C3CC3)c2)CC1]

A mixture of 1-(3-bromo-4-nitrophenyl)-4-methylpiperazine (B-I-8, 20 g, 67 mmol) and cyclopropylboronic acid (8.6 g, 100 mmol) in toluene: H$_2$O (9:1) (200 mL) was treated with K$_3$PO$_4$ (43 g, 200 mmol) and the reaction mixture was purged with nitrogen for 20 min. Tricyclohexyl phosphine (3.7 g, 13 mmol) and Pd(OAc)$_2$ (2.2 g, 10 mmol) were added into the reaction mixture and then the reaction mixture was stirred at 100° C. for 5 h. the reaction mixture was diluted with water (100 mL) and the solution was extracted with EtOAc (3×200 mL). The combined organic extracts were washed with brine (50 mL), dried over anhydrous Na$_2$SO$_4$, filtered and concentrated. The crude was purified by silica gel column chromatography (0 to 80% EtOAc/hexane, 15 CV's) to obtain 1-(3-cyclopropyl-4-nitrophenyl)-4-methylpiperazine (12 g, 69% yield) as a yellow solid. $^1$H NMR (400 MHz, DMSO-$d_6$): δ 7.89 (d, J=9.3 Hz, 1H), 6.85 (dd, J=2.4 and 9.4 Hz 1H), 6.55 (s, 1H), 3.36 (m, 4H), 2.45 (m, 1H), 2.40 (m, 4H), 2.20 (s, 3H), 0.94 (m, 2H), 0.75 (m, 2H); LC-MS (ESI) m/z: 261.3 (M+H$^+$).

General Method F: Suzuki Coupling Reaction

Intermediate C-I-12:
1-methyl-4-(4-nitro-3-vinylphenyl) piperazine

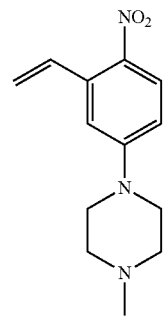 [SMILES: C=Cc1cc(N2CCN(C)CC2)ccc1[N+](=O)[O-]]

A mixture of 1-(3-bromo-4-nitrophenyl)-4-methylpiperazine (B-I-8, 30 g, 100 mmol) and potassium trifluorovinyl borate (20 g, 150 mmol) in DMSO (210 mL) was treated with K$_2$CO$_3$ (42 g, 301 mmol) at rt and the reaction mixture was purged with nitrogen for 15 min. PdCl$_2$(dppf) (3.7 g, 5.0 mmol) was added into the reaction mixture and the reaction mixture was stirred at 80° C. for 3 h. The reaction mixture was diluted with cold water (300 mL) and the solution was extracted with EtOAc (3×250 mL). The combined organic extracts were washed with brine (200 mL), dried over anhydrous Na$_2$SO$_4$, filtered and concentrated under reduced pressure. The crude was purified by silica gel column chromatography (0 to 80% EtOAc/hexane, 10 CV's) to obtain 1-methyl-4-(4-nitro-3-vinylphenyl) piperazine. (20 g, 81% yield) as a yellow solid. $^1$H NMR (400 MHz, DMSO-$d_6$): δ 7.96 (d, J=9.2 Hz, 1H), 7.21 (m, 1H), 6.98 (m, 2H), 5.77 (t, J=17.2 Hz, 1H), 5.41 (d, J=11.2 Hz, 1H), 3.44 (t, J=4.8 Hz, 4H), 2.42 (t, J=4.8 Hz, 4H), 2.21 (s, 3H); LC-MS (ESI) m/z: 247.3 (M+H$^+$).

The General Method E or General Method F for the Suzuki reaction was used to prepare the following intermediates in Table C.

TABLE C

| Intermediate | Structure | Method | Yield (%) | $^1$H NMR (400 MHz, DMSO-d$_6$): δ | LC-MS (m/z: (M + H$^+$)) |
|---|---|---|---|---|---|
| C-I-2 | (cyclopropyl, NO$_2$, phenyl, piperazine-Boc) | E | 43 | 7.90 (d, J = 9.3 Hz, 1H), 6.84 (dd, J = 9.3 and 2.7 Hz, 1H), 6.53 (d, J = 2.7 Hz, 1H), 3.36-3.45 (m, 8H), 2.44-2.47 (m, 1H), 1.41 (s, 9H), 0.93-0.97 (m, 2H), 0.73-0.76 (m, 2H). | No MS Data |
| C-I-3 | (cyclopropyl, NO$_2$, phenyl, 4-ethylpiperazine) | E | 91 | No NMR Data | 276.2 |
| C-I-4 | (cyclopropyl, NO$_2$, F, phenyl, 4-methylpiperazine) | E | 62 | 7.83 (d, J = 5.9 Hz, 1H), 6.63 (d, J = 5.9 Hz, 1H), 3.21 (s, 4H), 2.43 (s, 4H), 2.38 (m, 1H), 2.20 (s, 3H), 0.96 (m, 2H), 0.74 (m, 2H). | 280.2 |
| C-I-5 | (cyclopropyl, NO$_2$, phenyl, 4-methyl-2-oxopiperazine) | E | 53 | 7.91 (d, J = 9.2 Hz, 1H), 6.84 (m, 1H), 6.49 (m, 1H), 3.98 (s, 2H), 3.68 (m, 2H), 3.45 (m, 2H), 2.9 (s, 3H), 2.47 (s, 1H), 0.94 (m, 2H), 0.78 (m, 2H). | 276.1 |

TABLE C-continued

| Intermediate | Structure | Method | Yield (%) | $^1$H NMR (400 MHz, DMSO-$d_6$): δ | LC-MS (m/z: (M + H$^+$)) |
|---|---|---|---|---|---|
| C-I-6 | 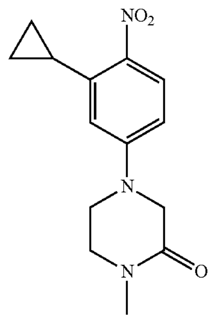 [SMILES: CN1CCN(c2ccc([N+](=O)[O-])c(C3CC3)c2)CC1=O] | E | 78 | 7.91 (d, J = 9.2 Hz, 1H), 6.84 (m, 1H), 6.49 (m, 1H), 3.98 (s, 2H), 3.68 (m, 2H), 3.45 (m, 2H), 2.8 (s, 3H), 2.47 (s, 1H), 0.94 (m, 2H), 0.78 (m, 2H). | 276.1 |
| C-I-7 | 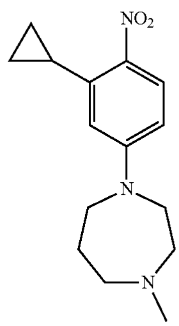 [SMILES: CN1CCCN(c2ccc([N+](=O)[O-])c(C3CC3)c2)CC1] | E | 44 | 7.91 (d, J = 9.3 Hz, 1H), 6.66 (dd, J = 2.6 and 9.4 Hz 1H), 6.32 (d, J = 2.4 Hz, 1H), 3.59 (m, 2H), 3.53 (m, 2H), 3.28 (m, 1H), 2.58 (m, 2H), 2.44 (m, 2H), 2.24 (s, 3H), 1.87 (m, 2H), 0.95 (dd, J = 1.6 and 8.4 Hz, 2H), 0.73 (m, 2H). | 276.1 |
| C-I-8 | 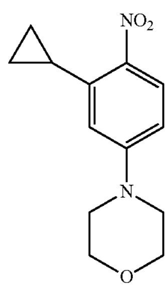 | E | 93 | 7.90 (d, J = 9.3 Hz, 1H), 6.86 (dd, J = 9.3 and 2.6 Hz, 1H), 6.55 (d, J = 2.6 Hz, 1H), 3.70 (t, J = 4.8 Hz, 4H), 3.30-3.33 (m, 4H), 2.46-2.48 (m, 1H), 0.93-0.96 (m, 2H), 0.73-0.76 (m, 2H). | No Data |
| C-I-9 | 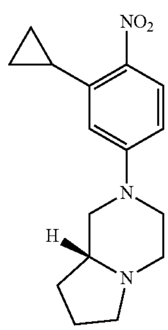 | E | 58 | 7.89 (d, J = 8.5 Hz, 1H), 6.87 (m, 1H), 6.55 (d, J = 2.6 Hz, 1H), 3.99 (m, 2H), 2.97-3.04 (m, 2H), 2.88 (m, 1H), 2.55 (m, 1H), 2.45-2.47 (m, 1H), 2.15 (m, 1H), 2.05 (m, 1H), 1.95 (m, 1H), 1.80-1.85 (m, 1H), 1.63-1.74 (m, 2H), 1.35 (m, 1H), 0.92-0.96 (m, 2H), 0.72-0.75 (m, 2H). | 288.2 |
| C-I-10 | 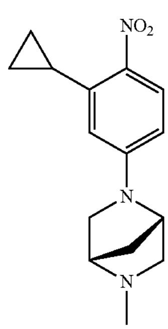 | E | 64 | 7.91 (d, J = 9.2 Hz, 1H), 6.50 (s, 1H), 6.18 (s, 1H), 4.55 (s, 1H), 3.48 (s, 1H), 2.80 (d, J = 9.5 Hz, 1H), 2.53 (m, 1H), 2.41 (d, J = 9.8 Hz, 1H), 2.27 (s, 3H), 1.89 (d, J = 9.3 Hz, 1H), 1.73 (d, J = 9.7 Hz, 1H), 0.94 (m, 2H), 0.71 (m, 2H). | 274.2 |

TABLE C-continued

| Intermediate | Structure | Method | Yield (%) | $^1$H NMR (400 MHz, DMSO-d$_6$): δ | LC-MS (m/z: (M + H$^+$) |
|---|---|---|---|---|---|
| C-I-11 | 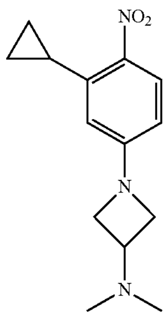 | E | 78 | 7.90 (d, J = 9.0 Hz, 1H), 6.28 (dd, J = 9.1 and 2.4 Hz, 1H), 6.01 (s, 1H), 4.01 (t, J = 7.8 Hz, 2H), 3.75 (dd, J = 8.6 and 5.2 Hz, 2H), 3.12 (m, 1H), 2.10 (s, 6 H), 0.95 (m, 2H), 0.8 (m, 2H). | 262.2 |
| C-I-13 | 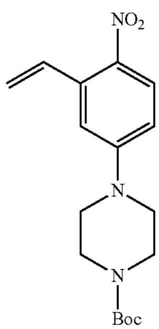 [SMILES: C=Cc1cc(N2CCN(C(=O)OC(C)(C)C)CC2)ccc1[N+](=O)[O-]] | F | 87 | 7.98 (d, J = 9.3 Hz, 1H), 7.21 (dd, J = 17.2 and 10.9 Hz, 1H), 6.95-6.97 (m, 2H), 5.79 (d, J = 17.2 Hz, 1H), 5.42 (d, J = 11.0 Hz, 1H), 3.46 (s, 8H), 1.41 (s, 9H). | 356.2 (M + Na + H$^+$). |
| C-I-14 | 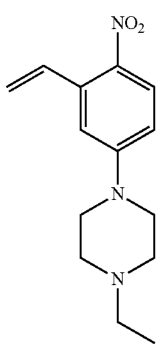 [SMILES: C=Cc1cc(N2CCN(CC)CC2)ccc1[N+](=O)[O-]] | F | 77 | No NMR Data | 262.2 |
| C-I-15 | 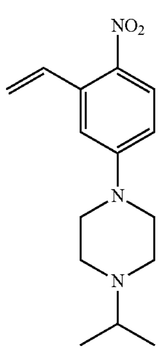 [SMILES: C=Cc1cc(N2CCN(C(C)C)CC2)ccc1[N+](=O)[O-]] | F | 96 | No NMR Data | 276.2 |

TABLE C-continued

| Intermediate | Structure | Method | Yield (%) | ¹H NMR (400 MHz, DMSO-d$_6$): δ | LC-MS (m/z: (M + H$^+$) |
|---|---|---|---|---|---|
| C-I-16 | 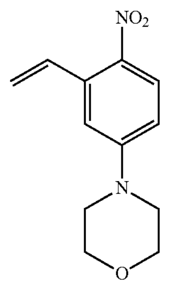 [SMILES: C=Cc1cc(N2CCOCC2)ccc1[N+](=O)[O-]] | F | 90 | 7.98 (d, J = 9.0 Hz, 1H), 7.21 (dd, J = 17.3 and 10.9 Hz, 1H), 7.00 (m 1H), 6.98 (s, 1H), 5.80 (d, J = 17.2 Hz, 1H), 5.42 (d, J = 11.0 Hz, 1H), 3.72 (t, J = 4.8 Hz, 4H), 3.41 (t, J = 4.8 Hz, 4H). | 235.2 |
| C-I-17 | 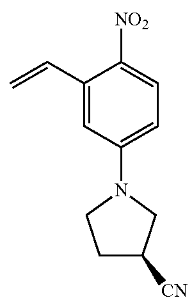 [SMILES: C=Cc1cc(N2CC[C@H](C#N)C2)ccc1[N+](=O)[O-]] | F | 81 | 8.01 (d, J = 9.1 Hz, 1H), 7.25 (dd, J = 17.3 and 10.9 Hz, 1H), 6.62-6.65 (m, 2H), 5.78 (d, J = 17.3 Hz, 1H), 5.41 (d, J = 11.0 Hz, 1H), 3.73-3.77 (m, 1H), 3.46-3.70 (m, 4H), 2.35-2.43 (m, 1H), 2.24-2.31 (m, 1H). | No Data |
| C-I-18 | 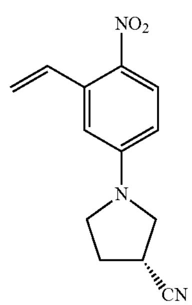 [SMILES: C=Cc1cc(N2CC[C@@H](C#N)C2)ccc1[N+](=O)[O-]] | F | 72 | 8.01 (d, J = 9.1 Hz, 1H), 7.25 (dd, J = 17.3 and 10.9 Hz, 1H), 6.62-6.65 (m, 2H), 5.78 (d, J = 17.3 Hz, 1H), 5.41 (d, J = 11.0 Hz, 1H), 3.73-3.77 (m, 1H), 3.46-3.70 (m, 4H), 2.35-2.43 (m, 1H), 2.24-2.31 (m, 1H). | No Data |
| C-I-19 | 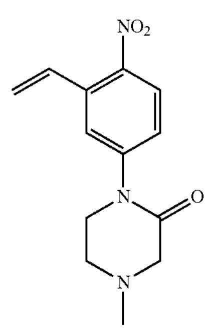 [SMILES: C=Cc1cc(N2CCN(C)CC2=O)ccc1[N+](=O)[O-]] | F | 32 | 7.99 (d, J = 9.2 Hz, 1H), 7.24 (m, 1H), 6.96 (m, 2H), 5.86 (d, J = 18.1 Hz, 1H), 5.44 (d, J = 11.9 Hz, 1H), 4.05 (s, 2H), 3.75 (t, J = 5.2 Hz, 2H), 3.47 (t, J = 5.4 Hz, 2H), 2.91 (s, 3H). | 262.2 |
| C-I-20 | 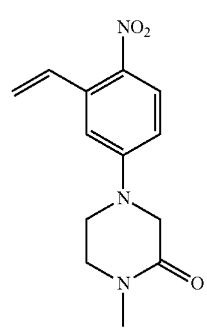 [SMILES: C=Cc1cc(N2CCN(C)C(=O)C2)ccc1[N+](=O)[O-]] | F | 42 | 7.99 (d, J = 9.2 Hz, 1H), 7.22 (m, 1H), 6.96 (m, 2H), 5.85 (m, 1H), 5.44 (d, J = 11.0 Hz, 1H), 4.04 (s, 2H), 3.75 (t, J = 5.2 Hz, 2H), 3.47 (t, J = 5.6 Hz, 2H), 2.92 (s, 3H). | 262.3 |

TABLE C-continued

| Intermediate | Structure | Method | Yield (%) | $^1$H NMR (400 MHz, DMSO-d$_6$): δ | LC-MS (m/z: (M + H$^+$) |
|---|---|---|---|---|---|
| C-I-21 | 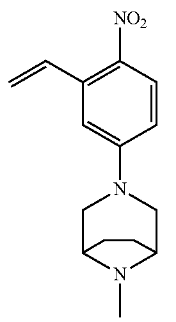 [SMILES: C=Cc1cc(N2CC3CCC(C2)N3C)ccc1[N+](=O)[O-]] | F | 87 | 7.96 (d, J = 9.3 Hz, 1H), 7.23 (dd, J = 17.2 and 10.9 Hz, 1H), 6.84 (m, 2H), 5.76 (d, J = 17.2 Hz, 1H), 5.39 (d, J = 11.0 Hz, 1H), 3.60 (d, J = 11.4 Hz, 2H), 3.23 (brs, 2H), 3.03 (d, J = 11.4 Hz, 2H), 2.23 (s, 3H), 1.95 (m, 2H), 1.56 (m, 2H). | 274.2 |
| C-I-22 | 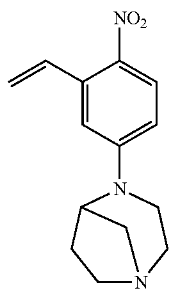 [SMILES: C=Cc1cc(N2CCN3CCC2C3)ccc1[N+](=O)[O-]] | F | 56 | No NMR Data | 260.2 |
| C-I-23 | 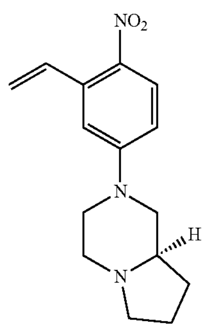 [SMILES: C=Cc1cc(N2CCN3CCC[C@@H]3C2)ccc1[N+](=O)[O-]] | F | 95 | 7.96 (d, J = 9.3 Hz, 1H), 7.21 (dd, J = 17.2 and 10.9 Hz, 1H), 7.00 (dd, J = 9.4 and 2.9 Hz, 1H), 6.96 (d, J = 2.8 Hz, 1H), 5.79 (dd, J = 17.2 and 1.2 Hz, 1H), 5.41 (d, J = 11.0 Hz, 1H), 4.15 (d, J = 12.1 Hz, 1H), 3.99 (d, J = 12.6 Hz, 1H), 2.91-3.06 (m, 3H), 2.62 (t, J = 11.2 Hz, 1H), 2.18 (td, J = 11.3 and 3.3 Hz, 1H), 2.06 (q, J = 8.7 Hz, 1H), 1.98 (m, 1H), 1.84 (m, 1H), 1.63-1.76 (m, 2H), 1.34-1.42 (m, 1H). | 274.2 |
| C-I-24 | 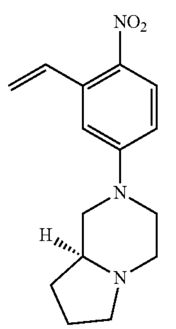 [SMILES: C=Cc1cc(N2CCN3CCC[C@H]3C2)ccc1[N+](=O)[O-]] | F | 100 | 7.96 (d, J = 9.3 Hz, 1H), 7.21 (dd, J = 17.2 and 10.9 Hz, 1H), 7.00 (dd, J = 9.4 and 2.9 Hz, 1H), 6.96 (d, J = 2.8 Hz, 1H), 5.79 (dd, J = 17.2 and 1.2 Hz, 1H), 5.41 (dd, J = 11.0 and 1.2 Hz, 1H), 4.15 (d, J = 12.1 Hz, 1H), 3.99 (d, J = 12.6 Hz, 1H), 3.06 (d, J = 11.2 Hz, 1H), 2.92-3.03 (m, 2H), 2.62 (t, J = 11.2 Hz, 1H), 2.17 (td, J = 11.3 and 3.3 Hz, 1H), 2.06 (q, J = 8.7 Hz, 1H), 1.98 (m, 1H), 1.84 (m, 1H), 1.63-1.74 (m, 2H), 1.37 (m, 1H). | 274.2 |
| C-I-25 | 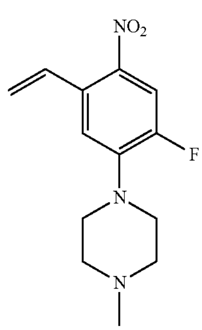 | F | 79 | 7.90 (d, J = 13.6 Hz, 1H), 7.06-7.15 (m, 2H), 5.83 (d, J = 17.3 Hz, 1H), 5.47 (d, J = 11.0 Hz, 1H), 3.26-3.30 (m, 4H), 2.44-2.47 (m, 4H), 2.22 (s, 3H). | 266.2 |

TABLE C-continued

| Intermediate | Structure | Method | Yield (%) | $^1$H NMR (400 MHz, DMSO-$d_6$): δ | LC-MS (m/z: (M + H$^+$) |
|---|---|---|---|---|---|
| C-I-26 | 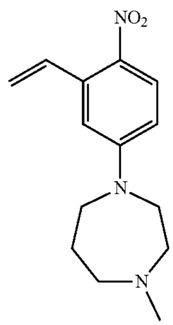 [SMILES: C=Cc1cc(N2CCCN(C)CC2)ccc1[N+](=O)[O-]] | F | 75 | 7.98 (d, J = 9.4 Hz, 1H), 7.27 (m, 1H), 6.80 (dd, J = 2.9 and 9.3 Hz, 1H), 6.71 (d, J = 2.3 Hz, 1H), 5.70 (d, J = 18.4 Hz, 1H), 5.39 (d, J = 11.2 Hz, 1H), 3.66 (m, 2H), 3.59 (m, 2H), 2.63 (m, 2H), 2.45 (m, 2H) 2.25 (s, 3H), 1.89 (m, 2H). | 262.2 |
| C-I-27 | 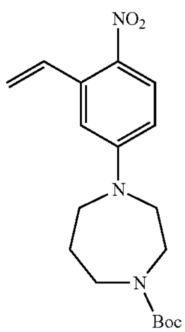 [SMILES: C=Cc1cc(N2CCCN(C(=O)OC(C)(C)C)CC2)ccc1[N+](=O)[O-]] | F | 92 | 7.98 (d, J = 9.4 Hz, 1H), 7.26 (dd, J = 17.2 and 10.9 Hz, 1H), 6.84 (d, J = 9.6 Hz, 1H), 6.77 (d, J = 9.1 Hz, 1H), 5.75 (d, J = 17.2 Hz, 1H), 5.42 (d, J = 11.0 Hz, 1H), 3.52-3.81 (m, 6H), 3.23-3.31 (m, 2H), 1.72-1.90 (m, 2H), 1.22 (s, 9H). | |
| C-I-28 | 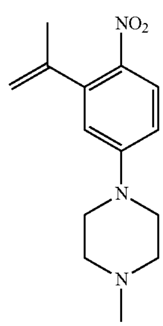 [SMILES: C=C(C)c1cc(N2CCN(C)CC2)ccc1[N+](=O)[O-]] | F | 57 | 7.93 (d, J = 9.3 Hz, 1H), 6.95 (dd, J = 2.7 and 9.3 Hz, 1H), 6.69 (d, J = 2.7 Hz, 1H), 5.07 (s, 1H), 4.83 (s, 1H), 3.40 (brs, 4H), 2.41 (brs, 4H), 2.21 (s, 3H), 1.82 (s, 3H). | 262.3 |
| C-I-29 | 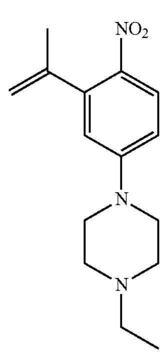 [SMILES: C=C(C)c1cc(N2CCN(CC)CC2)ccc1[N+](=O)[O-]] | F | 88 | 7.93 (d, J = 9.2 Hz, 1H), 6.94 (m, 1H), 6.69 (d, J = 2.0 Hz, 1H), 5.07 (s, 1H), 4.83 (s, 1H), 3.40 (m, 4H), 2.45 (m, 4H), 2.35 (q, J = 6.8 Hz, 2H), 1.98 (s, 3H), 1.02 (t, J = 6.8 Hz, 3H). | 276.3 |

TABLE C-continued

| Intermediate | Structure | Method | Yield (%) | $^1$H NMR (400 MHz, DMSO-d$_6$): δ | LC-MS (m/z: (M + H$^+$) |
|---|---|---|---|---|---|
| C-I-30 | 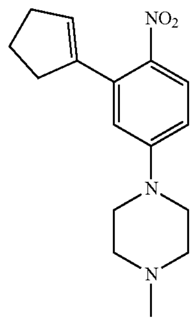 [SMILES: CN1CCN(c2ccc([N+](=O)[O-])c(C3=CCCC3)c2)CC1] | F | 92 | 7.90 (d, J = 9.2 Hz, 1H), 6.94 (d, J = 9.3 Hz, 1H), 6.72 (d, J = 2.2 Hz, 1H), 5.71 (s, 1H), 3.37 (m, 4H), 2.41 (m, 8H), 2.20 (s, 3H), 1.95 (m, 2H). | 289.2 |
| C-I-31 | 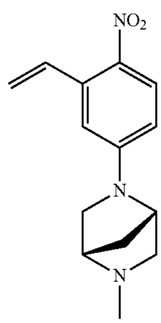 [SMILES: C=Cc1cc(N2C[C@@H]3C[C@H]2CN3C)ccc1[N+](=O)[O-]] | F | 91 | 7.97 (d, J = 9.3 Hz, 1H), 7.24 (dd, J = 17.2 and 10.9 Hz, 1H), 6.61 (d, J = 23.0 Hz, 2H), 5.73 (d, J = 17.2 Hz, 1H), 5.38 (d, J = 11.0 Hz, 1H), 4.60 (s, 1H), 3.49 (s, 1H), 3.31 (s, 2H), 2.82 (dd, J = 9.6 and 2.0 Hz, 1H), 2.44 (m, 1H), 2.28 (s, 3H), 1.71-1.90 (m, 2H). | 260.2 |
| C-I-32 | 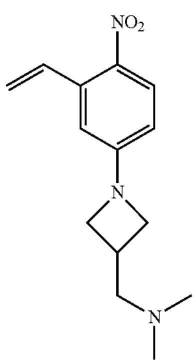 [SMILES: C=Cc1cc(N2CC(CN(C)C)C2)ccc1[N+](=O)[O-]] | F | 63 | No NMR Data | 262.2 |
| C-I-34 | 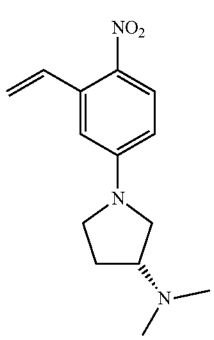 | F | 74 | No NMR Data | 262.2 |

TABLE C-continued

| Intermediate | Structure | Method | Yield (%) | ¹H NMR (400 MHz, DMSO-d$_6$): δ | LC-MS (m/z: (M + H⁺) |
|---|---|---|---|---|---|
| C-I-35 | 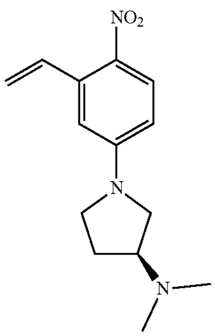 [SMILES: C=Cc1cc(N2CC[C@H](N(C)C)C2)ccc1[N+](=O)[O-]] | F | 63 | No NMR Data | 262.2 |
| C-I-36 | 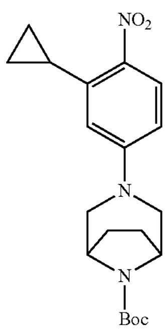 [SMILES: CC(C)(C)OC(=O)N1C2CCC1CN(c1ccc([N+](=O)[O-])c(C3CC3)c1)C2] | E | 89 | 7.90 (d, J = 9.2 Hz, 1H), 6.78 (dd, J = 2.5 and 9.3 Hz, 1H), 6.47 (s, 1H), 4.51 (brm, 2 H), 3.61 (brm, 2 H), 3.05 (brm, 1H), 2.90 (brm, 1H), 1.93 (s, 2H), 1.71 (m, 2H), 1.38 (s, 9H), 0.94 (m, 2 H), 0.75 (m, 2H). | 396.2 (M + Na + H⁺). |
| C-I-37 | 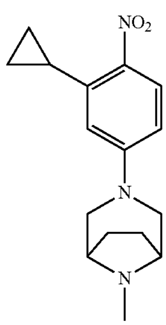 | E | crude | No data | 288.2 |
| C-I-38 | 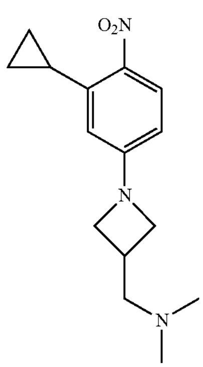 [SMILES: CN(C)CC1CN(c2ccc([N+](=O)[O-])c(C3CC3)c2)C1] | E | 68 | No Data | 276.2 |

General Method G: Reduction

Intermediate D-I-1:
2-cyclopropyl-4-(4-methylpiperazin-1-yl) aniline

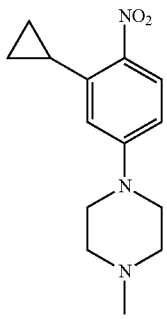 [SMILES: CN1CCN(c2ccc([N+](=O)[O-])c(C3CC3)c2)CC1]

A solution of 1-(3-cyclopropyl-4-nitrophenyl)-4-methylpiperazine (C-I-1, 12 g, 46 mmol) in MeOH (60 mL) at 0° C., was treated with NH$_4$Cl (73 g, 14 mmol) and the reaction mixture was stirred at 0° C. for 10 min. Zinc dust (30 g, 459 mmol) was added slowly (internal temperature increased to 20° C.) into the reaction mixture under an ice-water bath. After 15 minutes of stirring, the reaction mixture was warmed to rt and allowed to stir vigorously at rt for 16 h. The mixture was filtered through a pad of Celite and washed with THF (500 mL). The filtrate was concentrated under reduced pressure to afford 2-cyclopropyl-4-(4-methylpiperazin-1-yl) aniline (10 g, 95%) as a dark brown sticky solid. $^1$H NMR (400 MHz, DMSO-d$_6$): δ 6.52 (m, 2H), 6.43 (d, J=2.0 Hz, 1H), 4.52 (brs, 2H), 2.88 (m, 4H), 2.42 (m, 4H), 2.20 (s, 3H), 1.65 (m, 1H), 0.813 (m, 2H), 0.471 (m, 2H); LC-MS (ESI) m/z: 213.2 (M+H$^+$).

General Method H: Reduction

Intermediate D-I-11:
2-ethyl-4-(4-methylpiperazin-1-yl)aniline

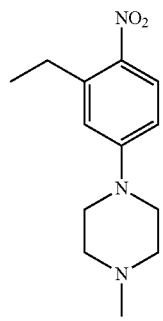 [SMILES: CCc1cc(N2CCN(C)CC2)ccc1[N+](=O)[O-]]

A solution of 1-methyl-4-(4-nitro-3-vinylphenyl) piperazine (C-I-12, 20 g, 81 mmol) in EtOAc (200 mL) was treated with Pd/C (20 g, 10% w/w, 50% moisture) under nitrogen atmosphere and the mixture was then stirred under hydrogen balloon pressure at rt for 3 h. After general work up, 2-ethyl-4-(4-methylpiperazin-1-yl)aniline (16 g, 90% yield) was obtained as a brown sticky solid. $^1$H NMR (400 MHz, DMSO-d$_6$): δ 6.61 (s, 1H), 6.52 (m, 2H), 4.25 (brs, 2H), 2.89 (t, J=4.4 Hz, 4H), 2.41 (m, 6H), 2.19 (s, 3H), 1.09 (t, J=7.6 Hz, 3H); LC-MS (ESI) m/z: 219.3 (M+H$^+$).

Using the General Method G or H for preparing D-I-1 or D-I-11, the following intermediates in Table D were prepared.

TABLE D

| Intermediate | Structure | Method | Yield (%) | $^1$H NMR (400 MHz, DMSO-d$_6$): δ | LC-MS (m/z: (M + H$^+$) |
|---|---|---|---|---|---|
| D-I-2 | 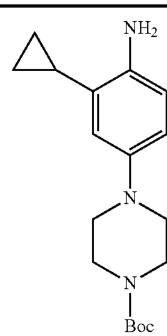 | G | 76 | 6.56 (d, J = 8.6 Hz, 1H), 6.51 (d, J = 8.5 Hz, 1H), 6.45 (s, 1H), 4.53 (s, 2H), 3.39 (s, 4H), 2.80 (s, 4H), 1.63 (s, 1H), 1.39 (s, 9H), 0.80 (d, J = 8.0 Hz, 2H), 0.47 (d, J = 5.2 Hz, 2H). | No Data |
| D-I-3 | 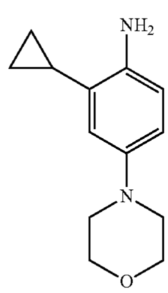 | G | 100 | 6.51-6.56 (m, 2H), 6.43 (s, 1H), 4.49 (s, 2H), 3.67 (t, J = 4.6 Hz, 4H), 2.85 (t, J = 4.5 Hz, 4H), 1.65 (m, 1H), 0.80 (m, 2H), 0.46 (m, 2H). | 219.2 |

TABLE D-continued

| Intermediate | Structure | Method | Yield (%) | $^1$H NMR (400 MHz, DMSO-$d_6$): δ | LC-MS (m/z: M + H$^+$) |
|---|---|---|---|---|---|
| D-I-4 | 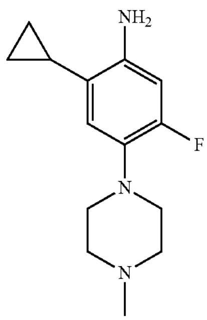 [SMILES: CN1CCN(c2cc(C3CC3)c(N)cc2F)CC1] | G | 100 | 6.49 (d, J = 5.1 Hz, 1H), 6.38 (d, J = 5.1 Hz, 1H), 4.85 (s, 2H), 2.80 (s, 4H), 2.40 (s, 4H), 2.18 (s, 3H), 0.80 (m, 2H), 0.44 (m, 2H). | 250.2 |
| D-I-5 | 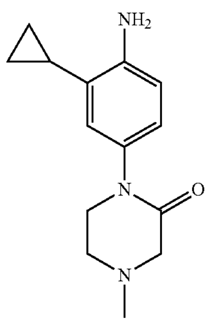 [SMILES: CN1CCN(c2ccc(N)c(C3CC3)c2)C(=O)C1] | G | 96 | 6.56 (m, 2H), 6.46 (s, 1H), 4.56 (s, 2H), 3.48 (s, 2H), 3.32 (s, 2H), 3.18 (s, 2H), 2.85 (s, 3H), 1.65 (m, 1H), 0.83 (m, 2H), 0.50 (m, 2H). | 246.1 |
| D-I-6 | 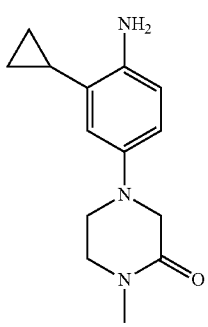 [SMILES: CN1CCN(c2ccc(N)c(C3CC3)c2)CC1=O] | G | 70 | 6.55 (m, 2H), 6.46 (s, 1H), 4.55 (brs, 2H), 3.48 (s, 2H), 3.32 (s, 2H), 3.17 (s, 2H), 2.85 (s, 3H), 1.65 (s, 1H), 0.82 (m, 2H), 0.50 (m, 2H). | 246.2 |
| D-I-7 | 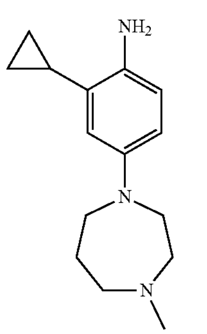 [SMILES: CN1CCCN(c2ccc(N)c(C3CC3)c2)CC1] | G | 74 | 6.63 (m, 1H), 6.46 (m, 1H), 6.27 (s, 1H), 3.54 (brm, 2H), 3.32 (m, 6H) 3.16 (m, 2H), 2.82 (s, 3H), 2.11 (brs, 2H), 1.70 (s, 1H), 0.84 (brm, 2H), 0.51 (brm, 2H). | 246.2 |

TABLE D-continued

| Intermediate | Structure | Method | Yield (%) | ¹H NMR (400 MHz, DMSO-d₆): δ | LC-MS (m/z: (M + H⁺) |
|---|---|---|---|---|---|
| D-I-8 | 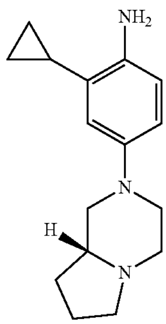 [SMILES: Nc1ccc(N2CCN3CCC[C@@H]3C2)cc1C1CC1] | G | 100 | 6.57 (m, 2H), 6.44 (m, 1H), 4.48 (brs, 2H), 3.40 (m, 1H), 3.26 (m, 1H), 2.96 (m, 2H), 2.56 (m, 1H), 2.18-2.26 (m, 2H), 2.04 (m, 2H), 1.62-1.80 (m, 4H), 1.32 (m, 1H), 0.81 (m, 2H), 0.45 (m, 2H). | 258.2 |
| D-I-9 | 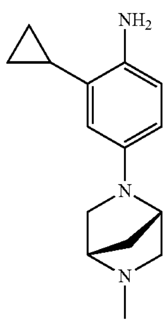 [SMILES: CN1C[C@@H]2C[C@H]1CN2c1ccc(N)c(C2CC2)c1] | G | 91 | 6.51 (d, J = 8.6 Hz, 1H), 6.24 (s, 1H), 6.08 (s, 1H), 4.19 (s, 1H), 3.63 (s, 1H), 3.31 (s, 2H), 3.05-3.05 (m, 1H), 2.80 (brs, 2H), 2.39 (s, 3H), 1.91 (s, 1H), 1.81 (s, 1H), 1.66 (brs, 1H), 0.81 (m, 2H), 0.46 (m, 2H). | 244.2 |
| D-I-10 | 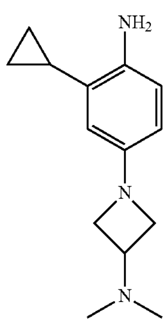 [SMILES: CN(C)C1CN(c2ccc(N)c(C3CC3)c2)C1] | G | 100 | No NMR Data | 232.2 |
| D-I-12 | 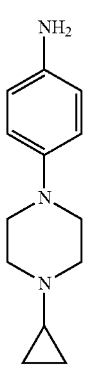 | H | 100 | 6.65 (d, 2H), 6.46 (d, J = 8.5 Hz, 2H), 4.53 (s, 2H), 2.83 (t, J = 4.8 Hz, 4H), 2.62 (t, J = 4.8 Hz, 4H), 1.62 (m, 1H), 0.40 (m, 2H), 0.29 (m, 2H). | 218.2 |

TABLE D-continued

| Intermediate | Structure | Method | Yield (%) | $^1$H NMR (400 MHz, DMSO-d$_6$): δ | LC-MS (m/z: M + H$^+$) |
|---|---|---|---|---|---|
| D-I-13 | 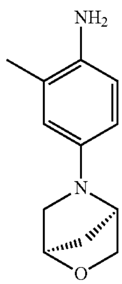 | H | 92 | 6.50 (d, J = 8.0 Hz, 1H), 6.29 (brs, 1H), 6.24 (d, J = 7.6 Hz, 1H), 4.50 (s, 1H), 4.31 (s, 1H), 4.11 (brs, 2H), 3.64 (brs, 2H), 3.39 (m, 1H), 2.79 (d, J = 8.8 Hz, 1H), 2.01 (s, 3H), 1.85 (m, 1H), 1.74 (m, 1H). | 205.1 |
| D-I-14 | 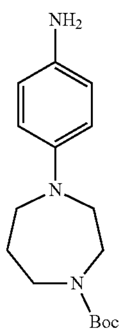 [SMILES: CC(C)(C)OC(=O)N1CCCN(c2ccc(N)cc2)CC1] | H | 100 | No NMR Data | 292.2 |
| D-I-15 | 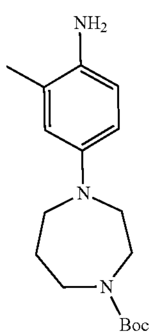 [SMILES: Cc1cc(N2CCCN(C(=O)OC(C)(C)C)CC2)ccc1N] | H | 72 | 6.48 (d, J = 8.4 Hz, 1H), 6.40 (d, J = 7.2 Hz, 1H), 6.35 (m, 1H), 4.07 (brs, 2H), 3.33-3.48 (m, 4H), 3.00-3.31 (m, 2H), 2.52-2.71 (m, 1H), 2.00 (s, 3H), 1.43-1.80 (m, 3H), 1.31 (s, 9H). | 306.2 |
| D-I-16 | 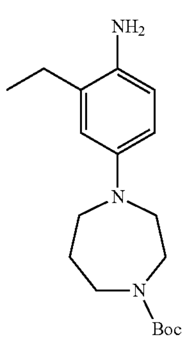 [SMILES: CCc1cc(N2CCCN(C(=O)OC(C)(C)C)CC2)ccc1N] | H | 82 | split into two isomers. | 320.2 |

TABLE D-continued

| Intermediate | Structure | Method | Yield (%) | ¹H NMR (400 MHz, DMSO-d₆): δ | LC-MS (m/z: (M + H⁺) |
|---|---|---|---|---|---|
| D-I-17 | 4-methylpiperazinyl-2-methylaniline | H | 97 | 6.58 (brs, 1H), 6.52 (m, 2H), 4.34 (brs, 2H), 2.88 (m, 4H), 2.49 (m, 4H), 2.19 (s, 3H), 2.01 (s, 3H). | 206.1 |
| D-I-18 | 4-(4-(2-fluoroethyl)piperazin-1-yl)-2-methylaniline | H | 100 | 6.58 (s, 1H), 6.48-6.53 (m, 2H), 4.59 (t, J = 4.9 Hz, 1H), 4.50 (t, J = 4.9 Hz, 1H), 4.35 (brs, 2H), 2.89 (t, J = 4.7 Hz, 4H), 2.67 (t, J = 4.7 Hz, 1H), 2.61 (t, J = 4.8 Hz, 1H), 2.55 (t, J = 4.7 Hz, 4H), 2.01 (s, 3H). | 238.2 |
| D-I-19 | 4-(4-cyclopropylpiperazin-1-yl)-2-methylaniline | H | 44 | 6.58 (s, 1H), 6.49 (m, 2H), 4.33 (brs, 2H), 2.84 (brs, 4H), 2.63 (brs, 4H), 2.01 (s, 3H), 1.62 (m, 1H), 0.42 (m, 2H), 0.31 (m, 2H). | 232.3 |
| D-I-20 | tert-butyl 4-(4-amino-3-methylphenyl)piperazine-1-carboxylate | H | 99 | No NMR Data | 292.2 |

TABLE D-continued

| Intermediate | Structure | Method | Yield (%) | ¹H NMR (400 MHz, DMSO-d₆): δ | LC-MS (m/z: (M + H⁺) |
|---|---|---|---|---|---|
| D-I-21 | 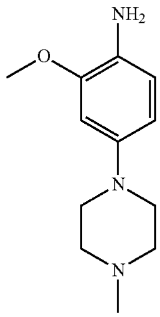 [SMILES: COc1cc(N2CCN(C)CC2)ccc1N] | H | 92 | 6.49 (m, 2H), 6.27 (dd, J = 2.0 and 8.0 Hz, 1H), 4.19 (brs, 2H), 3.73 (s, 3H), 2.93 (m, 4H), 2.42 (m, 4H), 2.20 (s, 3H). | 222.1 |
| D-I-22 | 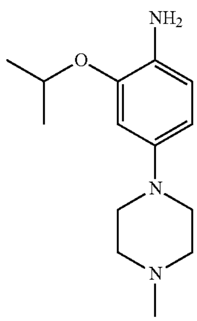 [SMILES: CC(C)Oc1cc(N2CCN(C)CC2)ccc1N] | H | 100 | 6.52 (d, J = 8.4 Hz, 1H), 6.46 (m, 1H), 6.28 (m, 1H), 4.46 (m, 1H), 4.25 (brs, 2H), 2.91 (m, 4H), 2.41 (m, 4H), 2.13 (s, 3H), 1.17 (d, J = 8.4 Hz, 6H) | 250.3 |
| D-I-23 | 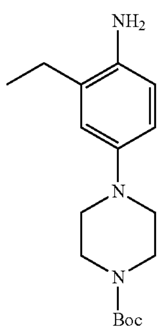 [SMILES: CCc1cc(N2CCN(C(=O)OC(C)(C)C)CC2)ccc1N] | H | 100 | 6.63 (m, 1H), 6.53 (m, 2H), 4.39 (brs, 2H), 3.41 (brs, 4H), 2.83 (brs, 4H), 2.30 (q, 2H), 1.40 (s, 9H), 1.09 (t, J = 7.4 Hz, 3H). | 306.2 |
| D-I-24 | 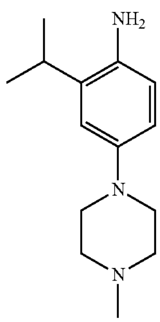 [SMILES: CC(C)c1cc(N2CCN(C)CC2)ccc1N] | H | 92 | 6.63 (s, 1H), 6.52 (s, 2H), 4.47 (brs, 2H), 2.91 (m, 5H), 2.42 (brs, 4H), 2.19 (s, 3H), 1.12 (d, J = 6.8 Hz, 6H). | 234.2 |

TABLE D-continued

| Intermediate | Structure | Method | Yield (%) | $^1$H NMR (400 MHz, DMSO-$d_6$): δ | LC-MS (m/z: M + H$^+$) |
|---|---|---|---|---|---|
| D-I-25 | 4-(4-ethylpiperazin-1-yl)-2-isopropylaniline | H | 93 | 6.63 (s, 1H), 6.51 (m, 2H), 4.37 (brs, 2H), 2.92 (m, 5H), 2.47 (m, 4H), 2.33 (q, J = 7.2 Hz, 2H), 1.12 (d, J = 6.8 Hz, 6H), 1.01 (t, J = 7.2 Hz, 3H). | 248.3 |
| D-I-26 | 2-ethyl-4-morpholinoaniline | H | 100 | No NMR Data | 207.2 |
| D-I-27 | (R)-1-(4-amino-3-ethylphenyl)pyrrolidine-3-carbonitrile | H | 98 | 6.52 (d, J = 8.5 Hz, 1H), 6.26-6.30 (m, 2H), 4.16 (s, 2H), 3.24-3.45 (m, 4H), 3.10-3.14 (m, 1H), 2.41 (q, J = 7.8 Hz, 2H), 2.28-2.32 (m, 1H), 2.13-2.17 (m, 1H), 1.10 (t, J = 7.6 Hz, 3H). | 216.2 |
| D-I-28 | (S)-1-(4-amino-3-ethylphenyl)pyrrolidine-3-carbonitrile | H | 95 | 6.52 (d, J = 8.5 Hz, 1H), 6.26-6.30 (m, 2H), 4.16 (s, 2 H), 3.24-3.45 (m, 4H), 3.10-3.14 (m, 1H), 2.41 (q, J = 7.8 Hz, 2H), 2.30 (m, 1H), 2.13-2.17 (m, 1H), 1.10 (t, J = 7.6 Hz, 3H). | 216.2 |
| D-I-29 | 2-ethyl-5-fluoro-4-(4-methylpiperazin-1-yl)aniline | H | 91 | No NMR Data | 238.2 |

TABLE D-continued

| Intermediate | Structure | Method | Yield (%) | ¹H NMR (400 MHz, DMSO-d₆): δ | LC-MS (m/z: (M + H⁺)) |
|---|---|---|---|---|---|
| D-I-30 | 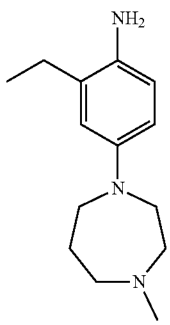 [SMILES: CCc1cc(N2CCCN(C)CC2)ccc1N] | H | 87 | 6.49 (brs, 1H), 6.40 (m, 2H), 3.48 (m, 6H), 2.57 (m, 2H), 2.45 (m, 4H) 2.30 (s, 3H), 1.85 (m, 2H), 1.09 (t, J = 7.6 Hz, 3H). | 233.2 |
| D-I-31 | 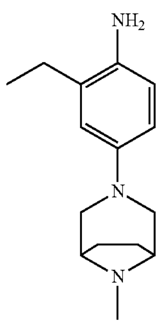 [SMILES: CCc1cc(N2CC3CCC(C2)N3C)ccc1N] | H | 100 | No NMR Data | 246.2 |
| D-I-32 | 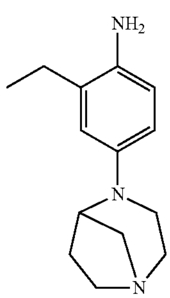 [SMILES: CCc1cc(N2CCN3CCC2C3)ccc1N] | H | 97 | 6.45-6.50 (m, 3H), 4.28 (brs, 2H), 3.94 (s, 1H), 2.91 (m, 2H), 2.81 (m, 1H), 2.75 (t, J = 7.5 Hz, 3H), 2.62 (m, 1H), 2.4-2.5 (m, 1H), 2.39 (q, J = 7.5 Hz, 2H), 1.57 (m, 2H), 1.09 (t, J = 7.5 Hz, 3H). | 232.2 |
| D-I-33 | 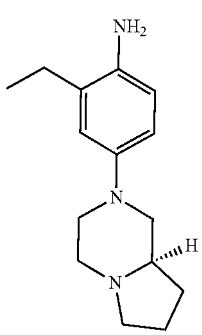 [SMILES: CCc1cc(N2CCN3CCC[C@@H]3C2)ccc1N] | H | 85 | No NMR Data | 246.2 |

TABLE D-continued

| Intermediate | Structure | Method | Yield (%) | $^1$H NMR (400 MHz, DMSO-$d_6$): δ | LC-MS (m/z: (M + H$^+$) |
|---|---|---|---|---|---|
| D-I-34 | 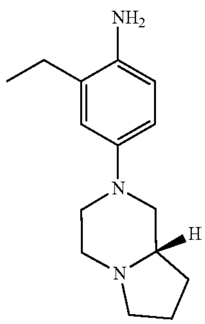 [SMILES: CCc1cc(N2CCN3CCC[C@H]3C2)ccc1N] | H | 100 | No NMR Data | 246.2 |
| D-I-35 | 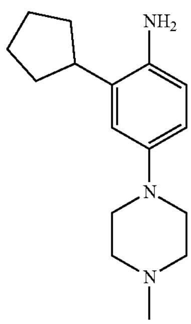 [SMILES: CN1CCN(c2ccc(N)c(C3CCCC3)c2)CC1] | H | 76 | 6.66 (m, 2H), 6.51 (s, 1H), 4.57 (brs, 2H), 2.96 (m, 4H), 2.89 (m, 8H), 2.43 (s, 3H), 2.20 (m, 3H), 1.90 (m, 2H). | 260.3 |
| D-I-36 | 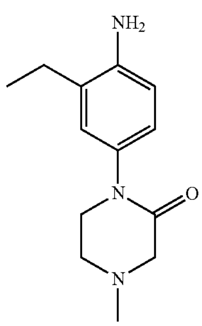 [SMILES: CCc1cc(N2CCN(C)CC2=O)ccc1N] | H | 88 | 6.90 (s, 1H), 6.77 (m, 1H), 6.50 (s, 1H), 4.75 (brs, 2H), 3.98 (s, 2H), 2.82 (s, 4H), 2.16 (m, 2H), 1.95 (m, 1H), 1.88 (m, 1H), 1.81 (m, 1H), 1.32 (t, J = 7.4 Hz, 3H). | 234.2 |
| D-I-37 | 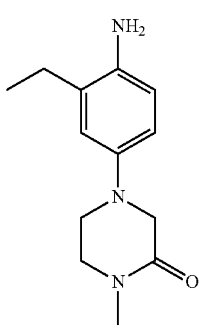 [SMILES: CCc1cc(N2CCN(C)C(=O)C2)ccc1N] | H | 77 | 6.89 (s, 1H), 6.78 (m, 1H), 6.52(s, 1H), 4.93 (brs, 2H), 3.39 (s, 2H), 2.86 (s, 4H), 2.16 (m, 2H), 1.98 (m, 1H), 1.89 (m, 1H), 1.80 (m, 1H), 1.35 (t, J = 7.5 Hz, 3H). | 234.2 |

TABLE D-continued

| Intermediate | Structure | Method | Yield (%) | $^1$H NMR (400 MHz, DMSO-d$_6$): δ | LC-MS (m/z: (M + H$^+$) |
|---|---|---|---|---|---|
| D-I-38 | 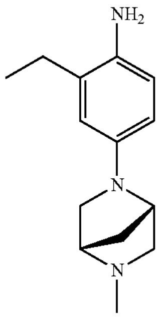 [SMILES: CCc1cc(N2C[C@@H]3C[C@H]2CN3C)ccc1N] | H | 77 | No NMR Data | 232.2 |
| D-I-39 | 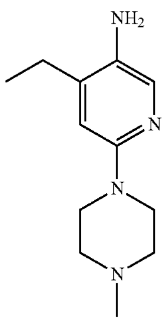 [SMILES: CCc1cc(N2CCN(C)CC2)ncc1N] | H | 90 | 7.56 (s, 1H), 6.48 (s, 1H), 4.33 (brs, 2H), 3.21 (brs, 4H), 2.41 (q, 2H), 2.37 (brs, 4H), 2.19 (s, 3H), 1.11 (t, J = 7.4 Hz, 3H). | 221.1 |
| D-I-40 | 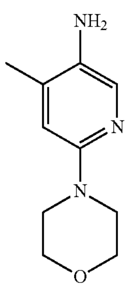 | H | 92 | 7.57 (s, 1H), 6.53 (s, 1H), 4.37 (brs, 2H), 3.67 (brs, 4H), 3.16 (brs, 4H), 2.05 (s, 3H). | 194.2 |
| D-I-41 | 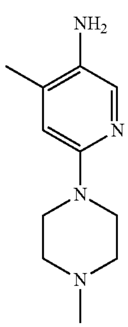 | H | 96 | 7.55 (s, 1H), 6.52 (s, 1H), 4.33 (brs, 2H), 3.33 (brs, 4H), 2.31 (brs, 4H), 2.19 (s, 3H), 2.02 (s, 3H). | 207.2 |
| D-I-42 | 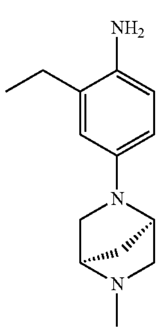 [SMILES: CCc1cc(N2C[C@H]3C[C@@H]2CN3C)ccc1N] | H | 93 | No NMR Data | 232.2 |

TABLE D-continued

| Intermediate | Structure | Method | Yield (%) | ¹H NMR (400 MHz, DMSO-d$_6$): δ | LC-MS (m/z: (M + H⁺) |
|---|---|---|---|---|---|
| D-I-43 | 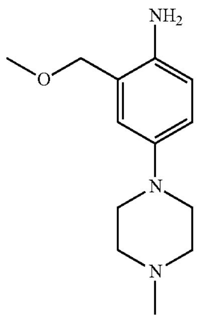 [SMILES: COCc1cc(N2CCN(C)CC2)ccc1N] | H | 80 | 6.76 (m, 1H), 6.66 (m, 2H), 6.56 (d, J = 8.4 Hz, 1H), 6.47 (d, J = 8.6 Hz, 1H), 4.27 (s, 2H), 3.23 (s, 3H), 2.90 (brs, 4H), 2.41 (brs, 4H), 2.19 (s, 3H). | 236.3 |
| D-I-44 | 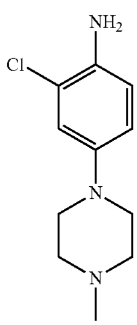 | G | 96 | No NMR data | 226.2 |
| D-I-45 | 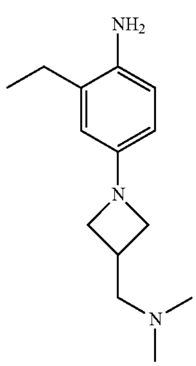 [SMILES: CCc1cc(N2CC(CN(C)C)C2)ccc1N] | H | 100 | No NMR Data | 234.0 |
| D-I-46 | 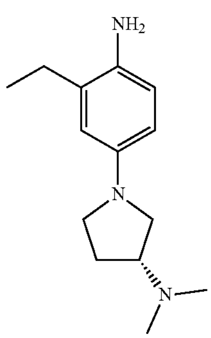 [SMILES: CCc1cc(N2CC[C@@H](N(C)C)C2)ccc1N] | H | 93 | No NMR Data | 234.2 |

TABLE D-continued

| Intermediate | Structure | Method | Yield (%) | ¹H NMR (400 MHz, DMSO-d₆): δ | LC-MS (m/z: (M + H⁺) |
|---|---|---|---|---|---|
| D-I-47 | 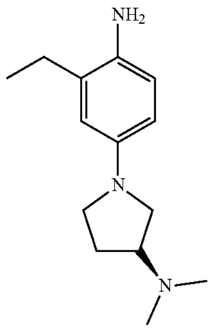 | H | 100 | No NMR Data | 234.2 |
| D-I-48 | 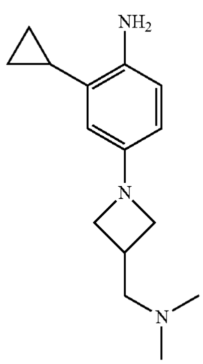 [SMILES: CN(C)CC1CN(c2ccc(N)c(C3CC3)c2)C1] | G | 82 | No NMR Data | No data |
| D-I-49 | 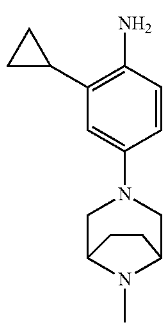 [SMILES: CN1C2CCC1CN(c1ccc(N)c(C3CC3)c1)C2] | G | 88 | No NMR Data | 258.2 |
| D-V-1 | 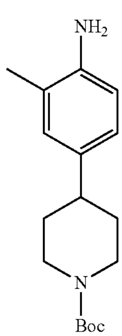 [SMILES: Cc1cc(C2CCN(C(=O)OC(C)(C)C)CC2)ccc1N] | H | 100 | 6.74 (brm, 1H), 6.71 (m, 1H), 6.49 (m, 1H), 4.57 (brs, 2H), 4.00 (brm, 2H), 2.73 (brm, 2H), 2.33 (m, 1H), 1.99 (s, 3H), 1.83 (m, 2H), 1.38 (s, 9H), 1.32 (m, 2H). | 313.2 (M + Na + H⁺). |

TABLE D-continued

| Intermediate | Structure | Method | Yield (%) | ¹H NMR (400 MHz, DMSO-d₆): δ | LC-MS (m/z: (M + H⁺) |
|---|---|---|---|---|---|
| D-V-2 | 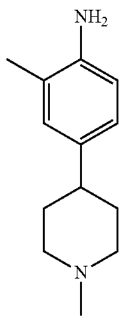 | H | 100 | 6.99 (brm, 1H), 6.95 (m, 1H), 6.54 (m, 1H), 5.85 (brm, 1H), 4.82 (brs, 2H), 3.92 (brm, 2H), 3.16 (s, 3H), 2.96 (brm, 2H), 2.54 (m, 2H), 2.38 (m, 2H), 2.03 (s, 3H). | 185.2 |
| D-V-3 | 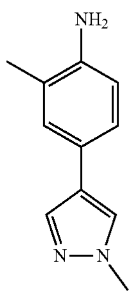 | H | 93 | 7.84 (s, 1H), 7.62 (s, 1H), 7.11 (s, 1H), 7.06 (d, J = 8.0 Hz, 1H), 6.57 (d, J = 8.0 Hz, 1H), 4.76 (brs, 2H), 3.80 (s, 3H), 2.02 (s, 3H). | 188.4 |
| D-V-4 | 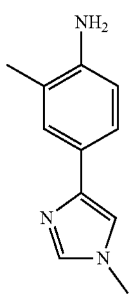 | H | 93 | 7.51 (s, 1H), 7.32 (s, 1H), 7.26 (m, 2H), 6.57 (d, J = 8.1 Hz, 1H), 4.78 (brs, 2H), 3.64 (s, 3H), 2.07 (s, 3H). | 264.2 |
| D-V-5 | 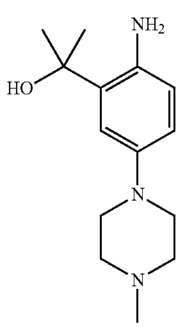 [SMILES: CN1CCN(c2ccc(N)c(C(C)(C)O)c2)CC1] | Grignard | crude | No NMR Data | 250.2 |

Intermediate D-V-6:
2-ethyl-4-(1-methylpyrrolidin-3-yl)aniline

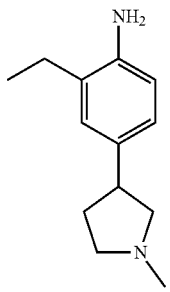

A solution of tert-butyl 3-(4,4,5,5-tetramethyl-1,3,2-dioxaborolan-2-yl)-2,5-dihydro-1H-pyrrole-1-carboxylate (0.25 g, 0.85 mmol),4-bromo-2-ethylaniline (0.121 g, 0.60 mmol) in a mixture of 1,4-dioxane (5 mL) and water (1 mL) was treated with $K_2CO_3$ (0.251 g, 1.8 mmol). The mixture was degassed with Ar for 2 min and then bis(triphenylphosphine)palladium(II) dichloride (0.042 g, 0.06 mmol) was added. The reaction mixture was heated at 95° C. overnight under microwave. The reaction mixture was cooled to rt and the mixture extracted with EtOAC (2x). The combined organic extracts were dried over anhydrous $Na_2SO_4$, filtered and concentrated under reduced pressure to obtain the crude. The crude was purified by silica gel column chromatography (0 to 60% EtOAc/hexanes, 15CVs) to give tert-butyl 3-(4-amino-3-ethylphenyl)-2,5-dihydro-1H-pyrrole-1-carboxylate (0.12 g, 70% yield) which was carried forward without further purification. LC-MS m/z: 289.2 (M+H$^+$).

A solution of tert-butyl 3-(4-amino-3-ethylphenyl)-2,5-dihydro-1H-pyrrole-1-carboxylate (0.12 g, 0.42 mmol) in MeOH (20 mL) was treated with Pd-C(0.040 g, 0.0424 mmol). The reaction mixture was under a balloon overnight. The mixture was filtered through a pad of celite and the filtrate was concentrated under reduced pressure to give tert-butyl 3-(4-amino-3-ethylphenyl)pyrrolidine-1-carboxylate (0.12 g, 97% yield) as a colorless sticky oil. $^1$H NMR (400 MHz, DMSO-d$_6$): δ 6.81 (s, 1H), 6.80 (m, 1H), 6.53 (d, J=8.0 Hz, 1H), 4.68 (s, 2H), 3.57 (m, 1H), 3.41 (m, 1H), 3.11-3.29 (m, 2H), 3.04 (m, 1H), 2.40 (q, J=7.5 Hz, 2H), 2.08 (brm, 1H), 1.75 (brm, 1H), 1.39 (s, 9H), 1.09 (t, J=7.5 Hz, 3H); LC-MS m/z: 313.2 (M+H+Na$^+$).

A solution of tert-butyl 3-(4-amino-3-ethylphenyl)pyrrolidine-1-carboxylate (0.12 g, 0.40 mmol) in a biphasic mixture of EtOAc (25 mL) and Sat'd NaHCO$_3$ (aq) (25 mL) was treated with benzyl chloroformate (0.086 mL, 0.60 mmol). The mixture was stirred at rt overnight. The mixture was partitioned between EtOAc and sat'd NaHCO$_3$ and extracted EtOAc (2×25 mL). The combined organic extracts were dried over anhydrous Na$_2$SO$_4$, filtered and concentrated under reduced pressure to obtain tert-butyl 3-(4-(((benzyloxy)carbonyl)amino)-3-ethylphenyl)pyrrolidine-1-carboxylate (0.18 g, 100% yield) which was carried forward without further purification. LC-MS m/z: 447.2 (M+H+Na$^+$).

A solution of tert-butyl 3-(4-(((benzyloxy)carbonyl)amino)-3-ethylphenyl)pyrrolidine-1-carboxylate (0.18 g, 0.44 mmol) in DCM (3 mL) was treated with TFA (2 mL). The mixture was stirred for 1 h at rt. The solvent was removed to give the crude TFA salt. The crude was suspended in DCM and TEA (1 mL) was added. The solvent was removed under reduced pressure and dried under vacuum. The resulting mixture was suspended in DCM and AcOH (3 drops). Formaldehyde (5 drops) was added and the mixture was stirred at rt for 1 h. Sodium triacetoxyborohydride (0.37 g, 1.7 mmol) was added and the mixture was stirred overnight at rt. The mixture was partitioned between DCM and sat'd NaHCO$_3$ and stirred for 1 h. The mixture was extracted with DCM (2×25 mL). The combined organic extracts were dried over anhydrous Na$_2$SO$_4$, filtered and concentrated under reduced pressure to give benzyl (2-ethyl-4-(1-methylpyrrolidin-3-yl)phenyl)carbamate (0.14 g, 94% yield) which was carried forward without further purification. LC-MS m/z: 339.2 (M+H$^+$).

A solution of benzyl (2-ethyl-4-(1-methylpyrrolidin-3-yl)phenyl)carbamate (0.14 g, 0.41 mmol) in EtOAc (20 mL) was flushed with Ar. Palladium on carbon (0.022 g, 0.02 mmol) was added and the mixture was hydrogenated under a balloon overnight at rt. The mixture was filtered through a pad of celite and the filtrate was concentrated under reduced pressure to give (2-ethyl-4-(1-methylpyrrolidin-3-yl)aniline (0.10 g, 119% yield) which was carried forward without further purification. LC-MS m/z: 205.2 (M+H$^+$).

General Method of Alkylation of Z Lactams and Deprotection of Boc Group

Intermediate H-VII-1

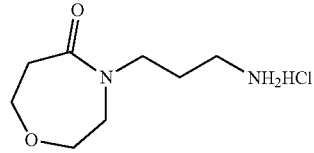

A solution of 1, 4-oxazepan-5-one (10 g, 87 mmol) in dry THF (400 mL) at 0° C. was treated with sodium hydride (3.0 g, 130 mmol) portion wise under nitrogen atmosphere. The reaction mixture was stirred for 15 min at 0° C. then tert-butyl (3-bromopropyl) carbamate (21 g, 87 mmol) was added. The solution was continued stirred from 0° C. rt for 16 h. The reaction mixture was quenched with saturated solution of NH$_4$Cl (200 mL) and then the solution was extracted with EtOAc (2×150 mL). The combined organic extract was washed with brine (150 mL), dried over anhydrous Na$_2$SO$_4$, and filtered under reduced pressure. The crude was purified by silica gel column chromatography (40 to 50% EtOAc/hexane, 15 CV's) to obtain tert-butyl (3-(5-oxo-1,4-oxazepan-4-yl)propyl carbamate (12 g, 50% yield) as yellow liquid. The product was dissolved in DCM (50 mL) and treated with 4 N HCl in 1,4-dioxane (4 eq). The mixture was stirred at rt for 3 h and concentrated, dried under high vacuum to obtain 4-(3-aminopropyl)-1,4-oxazepan-5-one HCl salt (100% yield). $^1$H NMR (400 MHz, DMSO-d$_6$): δ 8.09 (brs, 3H), 3.62 (m, 4H), 3.49 (m, 2H), 3.35 (t, J=6.8 Hz, 2H), 2.73 (m, 2H), 2.62 (t, J=4.8 Hz, 2H), 1.78 (m, 2H); MS (ESI) m/z: 173.2 (M+H$^+$).

Using the General Method for the preparation of H-VII-1, the following intermediates H-II-1 through H-VI-1 in Table E were prepared.

TABLE E
| Intermediate | Structure | Yield (%) | ¹H NMR (400 MHz, DMSO-$d_6$): δ | LC-MS (m/z: (M + H⁺) |
|---|---|---|---|---|
| H-I-1 | 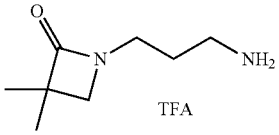 TFA | crude | No Data | 157.2 |
| H-II-1 | 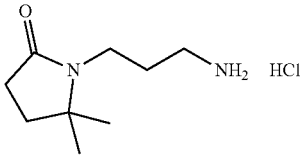 HCl | 52 | Boc: 4.17 (m, 2H), 3.26 (m, 2H), 2.52 (m, 2H), 2.23 (m, 2H), 1.80 (m, 2H), 1.71 (m, 2H), 1.39 (s, 6H), 1.17 (s, 9H). | 171.2 |
| H-III-1 | 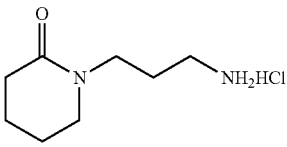 NH₂HCl | 36 | Boc: 6.76 (t, J = 5.7 Hz, 1H), 3.20 (m, 4H), 2.86 (m, 2H), 2.17 (m, 2H), 1.67 (m, 4H), 1.53 (m, 2H), 1.35 (s, 9H). | 157.2 |
| H-IV-1 | 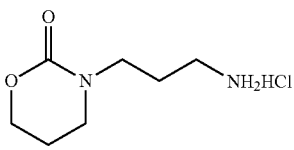 NH₂HCl | 64 | Boc: 4.14 (m, 2H), 3.25 (m, 2H), 3.18 (m, 2H), 2.92 (m, 2H), 1.92 (m, 2H), 1.62 (m, 2H), 1.36 (s, 9H). | 159.2 |
| H-XIII-1 | 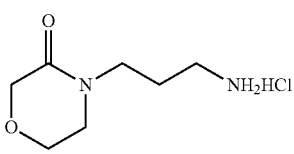 NH₂HCl | 84 | Boc: 3.99 (m, 2H), 3.48 (m, 2H), 3.30 (m, 4H), 2.91 (m, 2H), 1.58 (m, 2H), 1.36 (s, 9H). | 159.2 |
| H-VI-1 | 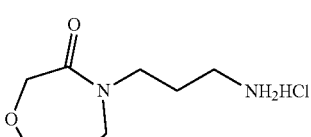 NH₂HCl | 57 | Boc: 6.74 (s, 1H), 4.08 (s, 2H), 3.73 (t, J = 5.5 Hz, 2H), 3.46 (m, 2H), 3.25 (m, 2H), 2.88 (q, J = 6.5 Hz, 2H), 1.98 (s, 1H), 1.78 (m, 2H), 1.53 (m, 2H), 1.36 (s, 9H). | 173.2 |
| H-IV-2 | 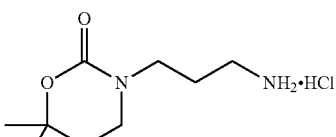 NH₂·HCl | crude | No NMR Data | 187.2 |
| H-VII-2 | 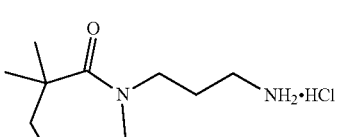 NH₂·HCl | crude | No NMR Data | 201.2 |

Intermediate H-XIV: 1-(3-aminopropyl) azepan-2-one

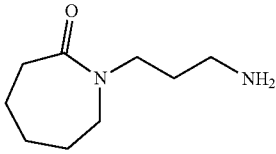 [SMILES: NCCCN1CCCCCC1=O]

A suspension of DBU (22 g, 145 mmol) in MeOH: H₂O (1:1) (130 mL) was treated with KOH (12 g, 217 mmol) at 0° C. under N₂ atmosphere and the reaction mixture was stirred at rt for 16 h. The reaction mixture was evaporated under reduced pressure and the residue was diluted with water (200 mL). The solution was extracted with 10% MeOH in DCM (3×250 mL) and the combined organic extracts were dried over anhydrous sodium sulphate, filtered and concentrated under reduced pressure to obtain 1-(3-aminopropyl) azepan-2-one (21 g, 85% yield) as a liquid oil. ¹H NMR (400 MHz, CDCl3): δ 3.45 (t, J=3.5 Hz, 2H), 3.31 (t, J=4.4 Hz, 2H), 2.68 (t, J=6.5 Hz, 2H), 2.51 (t, J=5.8 Hz, 2H), 1.70 (m, 2H), 1.65 (m, 8H); LC-MS (ESI) m/z: 171.4 (M+H⁺).

Intermediate L-III-1: 2-chloro-5-cyclopropyl-4-(methylsulfonyl)pyrimidine

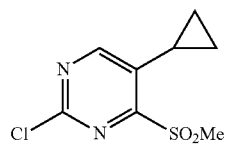

(A) A suspension of 5-bromo-2-chloro-4-(methylthio) pyrimidine (25.0 g, 105 mmol) and cyclopropylboronic acid (13.7 g, 158 mmol) in toluene: H₂O (9:1) (650 mL) was treated with K₃PO₄ (66.7 g, 315 mmol) was added. The reaction mixture was purged with nitrogen for 20 min and then added tricyclohexyl phosphine (5.9 g, 21 mmol) and Pd(OAc)₂ (2.35 g, 10.50 mmol). The reaction mixture was stirred at 90° C. for 16 h. The reaction mixture was diluted with water (200 mL) and extracted with EtOAc (3×300 mL). The combined organic extracts were washed with brine (200 mL), dried over anhydrous Na₂SO₄, filtered and concentrated under reduced pressure. The crude was purified by silica gel column chromatography (0 to 10% EtOAc/hexane) to obtain 2-chloro-5-cyclopropyl-4-(methylthio) pyrimidine (14.0 g, 66% yield) as a yellow oil. ¹H NMR (400 MHz, DMSO-d₆): δ 7.92 (s, 1H), 2.58 (s, 3H), 1.67 (m, 1H), 1.03 (m, 2H), 0.67 (m, 2H); LC-MS (ESI) m/z: 201.0 (M+H⁺).

(B) A solution of 2-chloro-5-cyclopropyl-4-(methylthio) pyrimidine (4.0 g, 20 mmol) in DCM (60 mL) at 0° C. was treated with m-CPBA (4.8 g, 28 mmol). The reaction mixture was warmed to rt and stirred for 3 h. The reaction mixture was washed with saturated aq. NaHCO₃ (2×40 mL). The organic layer was dried over anhydrous Na₂SO₄, filtered and concentrated under reduced pressure to obtain 2-chloro-5-cyclopropyl-4-(methylsulfonyl)pyrimidine (3.6 g, 86% yield) as a yellow solid. ¹H NMR (400 MHz, DMSO-d₆): δ 8.57 (s, 1H), 2.89 (s, 3H), 2.16 (m, 1H), 1.16 (m, 2H), 0.93 (m, 2H); LC-MS (ESI) m/z: 217.0 (M+H⁺).

Intermediate L-I-2: 4-chloro-2-(methylthio)-5(trifluoromethyl)pyrimidine

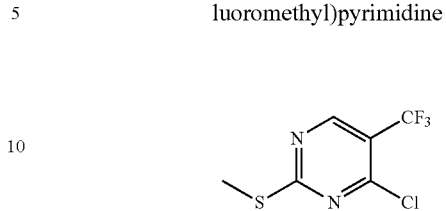

A solution of 2,4-dichloro-5-(trifluoromethyl) pyrimidine (100 g, 0.46 mol) in diethyl ether (2 L) was treated with ZnCl₂ (1.0 N in ether) (555 mL, 0.56 mol) dropwise at 0° C. and the reaction mixture was stirred for 2 h. Sodium thiomethoxide (49 g, 0.94 mol) was added at 0° C. and the reaction mixture was warmed to rt and stirred for 48 h. The reaction mixture was quenched with 2 N HCl under an ice-water bath and then the solution was extracted with Et₂O (3×500 mL). The combined organic extracts were washed with water (500 mL), dried over anhydrous Na₂SO₄, filtered, and concentrated under reduced pressure at 35° C. to obtain 4-chloro-2-(methylthio)-5-(trifluoromethyl)pyrimidine (100 g, 95% yield) as a colorless liquid. 41 NMR (400 MHz, DMSO-d₆): δ 9.01 (s 1H), 2.62 (s 3H).

General Method for Substitution Reaction

Intermediate J-7: 4-(3-((2-(methylthio)-5-(trifluoromethyl) pyrimidin-4-yl)amino)propyl)-1,4-oxazepan-5-one

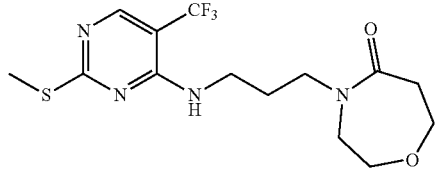 [SMILES: CSc1ncc(C(F)(F)F)c(NCCCN2CCOCCC2=O)n1]

A solution of 4-(3-aminopropyl) 1,4-oxazepan-5-one hydrochloride (H-VII-1, 3.0 g, 17.4 mmol) in DMF (60 mL) was treated with DIEA (15.5 ml, 87.2 mmol) at 0° C. and stirred for 15 min. Then 4-chloro-2-(methylthio)-5-(trifluoromethyl) pyrimidine (L-I-2, 6.0 g, 26.2 mmol) was added and stirring continued from 0° C. to rt for 16 h. The reaction mixture was quenched with ice water (120 mL) and extracted with ethyl acetate (3×50 mL). The combined organic extracts were washed with brine (50 mL), dried over anhydrous Na₂SO₄, and filtered. The filtrate was concentrated under reduced pressure and the crude was purified by silica gel column chromatography (40 to 50% EtOAc/hexane, 15 CV's) to obtain 4-(3-((2-(methylthio)-5-(trifluoromethyl) pyrimidin-4-yl)amino)propyl)-1,4-oxazepan-5-one (3.0 g, 47% yield) as yellow liquid. ¹H NMR (400 MHz, DMSO-d₆): δ 8.25 (s, 1H), 7.52 (bs, 1H), 3.64 (m, 4H), 3.47 (m, 2H), 3.42 (m, 2H), 3.32 (m, 2H), 2.63 (t, J=4.8 Hz, 2H), 2.47 (s, 3H), 1.68 (m, 2H); LC-MS (ESI) m/z: 365.3 (M+H⁺).

Using the General Method for preparation of Intermediate J-7, the following intermediates of Table F were prepared.

TABLE F
| Intermediate | Structure | Yield (%) | ¹H NMR (400 MHz, DMSO-d₆): δ | LC-MS (m/z: (M + H⁺)) |
|---|---|---|---|---|
| K-1 | 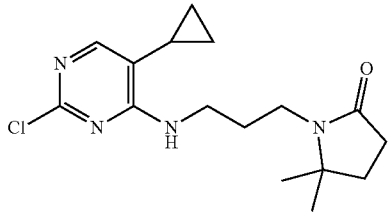 [SMILES: CC1(C)CCC(=O)N1CCCNc1nc(Cl)ncc1C1CC1] | 31 | No NMR Data | 323.2 |
| K-2 | 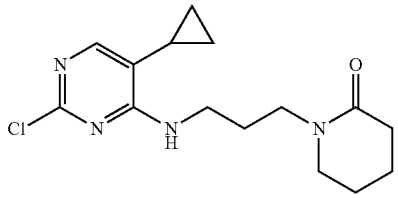 [SMILES: O=C1CCCCN1CCCNc1nc(Cl)ncc1C1CC1] | 82 | 7.69 (s, 1H), 7.51 (t, J = 5.9 Hz, 1H), 3.34 (t, J = 6.4 Hz, 3H), 3.24 (m, 2H), 2.22 (t, J = 6.3 Hz, 2H), 1.68-1.73 (m, 6H), 1.46-1.56 (m, 2H), 0.86-0.90 (m, 2H), 0.54 (m, 2H). | 309.2 |
| K-3 | 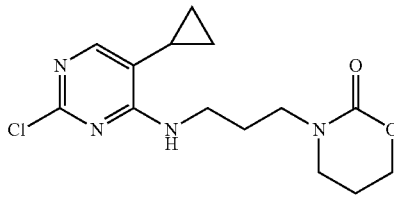 | 47 | 7.69 (s, 1H), 7.43 (s, 1H), 4.17 (m, 2H), 3.39 (m, 2H), 3.29 (m, 4H), 1.94 (m, 2H), 1.77 (m, 2H), 1.48 (m, 1H), 0.89 (m, 2H), 0.56 (m, 2H). | 311.3 |
| K-4 | 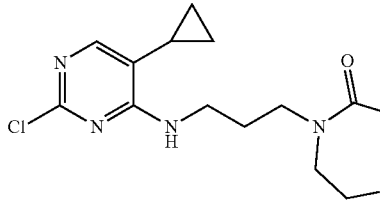 | 42 | 7.69 (s, 1H), 7.45 (s, 1H), 3.66 (m, 4H), 3.56 (brs, 2H), 3.35 (m, 4H), 2.64 (m, 2H), 1.69 (m, 2H), 1.50 (m, 1H), 0.88 (m, 2H), 0.56 (m, 2H). | 325.3 |
| K-5 | 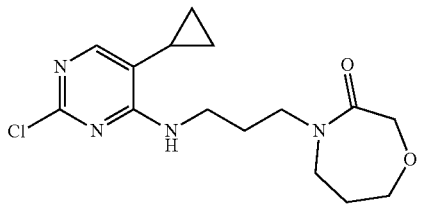 [SMILES: O=C1COCCCN1CCCNc1nc(Cl)ncc1C1CC1] | 51 | 7.70 (s, 1H), 7.45 (brs, 1H), 4.12 (s, 2H), 3.76 (t, J = 5.2 Hz, 2H), 3.50 (m, 2H), 3.37 (m, 4H), 1.85 (m, 2H), 1.72 (m, 2H), 1.51 (m, 1H), 0.89 (m, 2H), 0.55 (m, 2H). | 325.1 |
| K-6 | 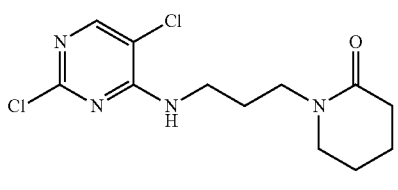 [SMILES: O=C1CCCCN1CCCNc1nc(Cl)ncc1Cl] | 37 | 8.15 (s, 1H), 7.94 (m, 1H), 3.35 (m, 2H), 3.30 (m, 2H), 3.25 (m, 2H), 2.21 (m, 2H), 1.72 (m, 6H). | 303.20 |
| K-7 | 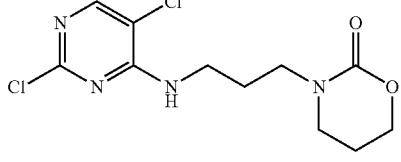 | 64 | 8.15 (s, 1H), 7.90 (brs, 1H), 4.16 (m, 2H), 3.37 (m, 2H), 3.27 (m, 4H), 1.94 (m, 2H), 1.77 (m, 2H). | 305.2 |

TABLE F-continued
| Intermediate | Structure | Yield (%) | ¹H NMR (400 MHz, DMSO-d₆): δ | LC-MS (m/z: (M + H⁺) |
|---|---|---|---|---|
| K-8 | 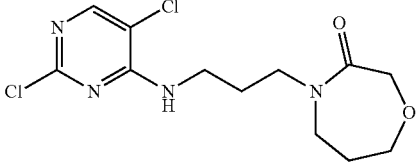 | 47 | 8.20 (s, 1H), 7.88 (m, 1H), 4.11 (s, 2H), 3.76 (m, 2H), 3.50 (m, 2H), 3.36 (m, 4H), 1.84 (m, 2H), 1.72 (m, 2H). | 319.1 |
| K-9 | 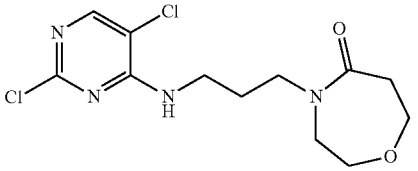 | 51 | 8.15 (s, 1H), 7.91 (brs, 1H), 3.65 (m, 4H), 3.48 (m, 2H), 3.35 (m, 4H), 2.63 (m, 2H), 1.66 (m, 2H). | 319.0 |
| K-10 | 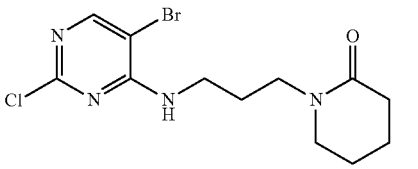 [SMILES: O=C1CCCCN1CCCNc1nc(Cl)ncc1Br] | 39 | 8.23 (s, 1H), 7.58 (brs, 1H), 3.33 (m, 2H), 3.31 (m, 2H), 3.25 (m, 2H), 2.22 (m, 2H), 1.71 (m, 6H). | 347.1 |
| K-11 | 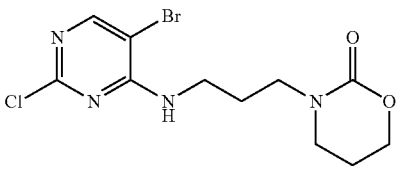 [SMILES: O=C1OCCCN1CCCNc1nc(Cl)ncc1Br] | 56 | 8.23 (s, 1H), 7.72 (brs, 1H), 4.16 (m, 2H), 3.36 (m, 2H), 3.28 (m, 4H), 1.95 (m, 2H), 1.76 (m, 2H). | 349.0 |
| K-12 | 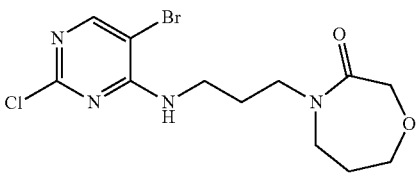 | 48 | 8.23 (s, 1H), 7.72 (m, 1H), 4.11 (s, 2H), 3.76 (m, 2H), 3.49 (m, 2H), 3.33 (m, 4H), 1.83 (m, 2H), 1.71 (m, 2H). | 363.0 |
| K-13 | 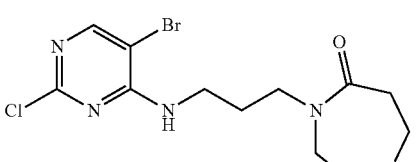 | 50 | 8.23 (s, 1H), 7.74 (brs, 1H), 3.66 (brs, 4H), 3.48 (m, 2H), 3.34 (m, 4H), 2.63 (m, 2H), 1.67 (m, 2H). | 363.2 |
| J-1 | 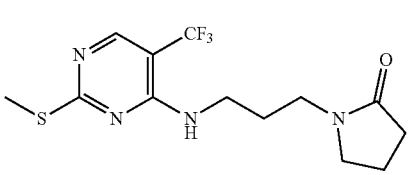 [SMILES: CSc1ncc(C(F)(F)F)c(NCCCN2CCCC2=O)n1] | 100 | 7.53 (t, J = 5.7 Hz, 1H), 3.40 (q, J = 6.5 Hz, 2H), 3.34 (t, J = 7.0 Hz, 2H), 3.19 (t, J = 6.8 Hz, 2H), 2.46 (s, 3H), 2.21 (t, J = 8.1 Hz, 2H), 1.91 (p, J = 7.5 Hz, 2H), 1.71 (m, 2H). | 335.2 |
| J-2 | 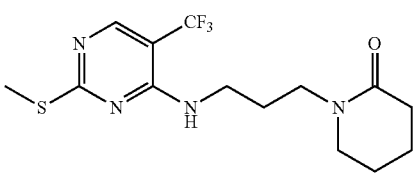 [SMILES: CSc1ncc(C(F)(F)F)c(NCCCN2CCCCC2=O)n1] | 91 | 8.24 (s, 1H), 7.58 (t, J = 5.8 Hz, 1H), 3.40 (q, J = 6.5 Hz, 2H), 3.21-3.28 (m, 4 H), 2.46 (s, 3H), 2.21 (t, J = 6.2 Hz, 2H), 1.65-1.75 (m, 6H). | 349.2 |

TABLE F-continued

| Intermediate | Structure | Yield (%) | ¹H NMR (400 MHz, DMSO-d₆): δ | LC-MS (m/z: (M + H⁺) |
|---|---|---|---|---|
| J-3 | 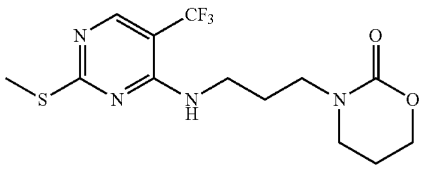 [SMILES: CSc1ncc(C(F)(F)F)c(NCCCN2CCCOC2=O)n1] | 65 | 8.25 (d, J = 1.1 Hz, 1H), 7.51 (t, J = 5.8 Hz, 1H), 4.15 (t, J = 5.3 Hz, 2H), 3.44 (q, J = 6.6 Hz, 2H), 3.22-3.27 (m, 4H), 2.46 (s, 3H), 1.89-1.95 (m, 2H), 1.73-1.80 (m, 2H). | 351.2 |
| J-4 | 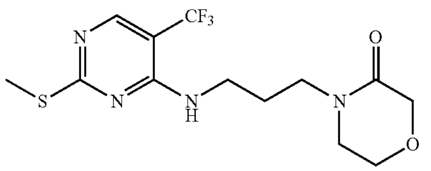 [SMILES: CSc1ncc(C(F)(F)F)c(NCCCN2CCOCC2=O)n1] | 77 | 8.25 (s, 1H), 1.54 (t, J = 5.2 Hz, 1H), 4.02 (s, 2H), 3.82 (t, J = 5.2 Hz, 2H), 3.44 (q, 2H), 3.34 (m, 4H), 2.47 (s, 3H), 1.77 (m, 2H). | 351.1 |
| J-5 | 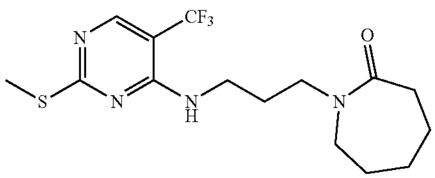 [SMILES: CSc1ncc(C(F)(F)F)c(NCCCN2CCCCCC2=O)n1] | 65 | 8.26 (s, 1H), 7.53 (m, 1H), 3.45 (m, 2H), 3.34 (m, 4H), 2.48 (s, 3H), 2.43 (m, 2H), 1.66 (m, 4H), 1.52 (m, 4H). | 363.2 |
| J-6 | 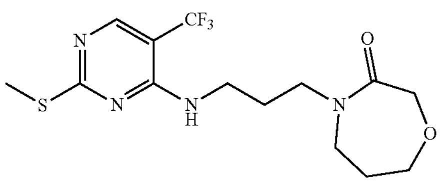 [SMILES: CSc1ncc(C(F)(F)F)c(NCCCN2CCCOCC2=O)n1] | 64 | 8.25 (s, 1H), 7.52 (brs, 1H), 4.11 (s, 2H), 3.75 (t, J = 5.6 Hz, 2H), 3.48 (m, 2H), 3.45 (m, 2H), 3.34 (m, 2H), 2.47 (s, 3H), 1.82 (m, 2H), 1.72 (m, 2H). | 365.3 |
| J-7 | 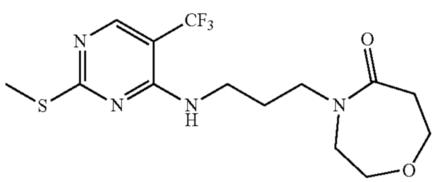 [SMILES: CSc1ncc(C(F)(F)F)c(NCCCN2CCOCCC2=O)n1] | 47 | 8.25 (s, 1H), 7.52 (bs, 1H), 3.64 (m, 4H), 3.47 (m, 2H), 3.42 (m, 2H), 3.32 (m, 2H), 2.63 (t, J = 4.8 Hz, 2H), 2.47 (s, 3H), 1.68 (m, 2H). | 365.3 |
| J-8 | 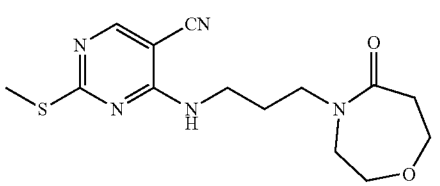 [SMILES: CSc1ncc(C#N)c(NCCCN2CCOCCC2=O)n1] | 89 | 8.25 (s, 1H), 7.51 (t, J = 5.8 Hz, 1H), 3.64 (m, 4H), 3.46 (m, 2H), 3.42 (q, J = 6.5 Hz, 2H), 3.31 (m, 2H), 2.62 (m, 2H), 2.46 (s, 3H), 1.68 (m, 2H). | 322.2 |
| J-A | 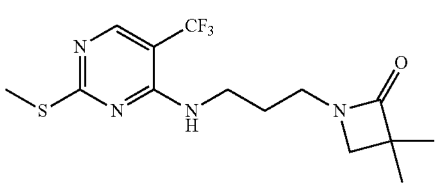 | 81 | 8.26 (s, 1H), 7.53 (t, J = 5.7 Hz, 1H), 3.39 (m, 2H), 3.09 (m, 2H), 3.06 (s, 2H), 2.46 (s, 3H), 1.74 (m, 2H), 1.17 (s, 6H). | 349.2 |
| J-B | 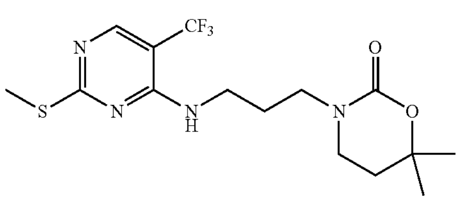 | crude | No NMR Data | 379.2 |

TABLE F-continued

| Intermediate | Structure | Yield (%) | ¹H NMR (400 MHz, DMSO-$d_6$): δ | LC-MS (m/z: (M + H⁺) |
|---|---|---|---|---|
| J-C | (structure) | crude | No NMR Data | 393.2 |

General Method of Pd Coupling Reaction

Intermediate M-1: 4-(3-((2-(methylthio)-5-(trifluoromethyl) pyrimidin-4-yl)amino)propyl)-1,4-oxazepan-5-one

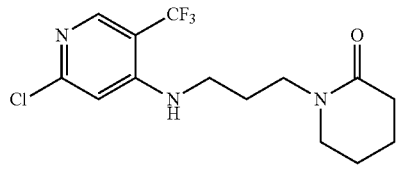 [SMILES: O=C1CCCCN1CCCNc1cc(Cl)ncc1C(F)(F)F]

A solution of 1-(3-aminopropyl) piperidin-2-one hydrochloride (H-III-1, 9.0 g, 29.3 mmol) and 2-chloro-4-iodo-5-(trifluoromethyl) pyridine (6.19 g, 32.2 mmol) in toluene (180 mL) was treated with cesium carbonate (23.9 g, 73.2 mmol). The mixture was purged with Ar for 15 min. Then, PdCl$_2$(dppf) DCM (2.39 g, 2.93 mmol) was added and the mixture was purged with Ar for a further 5 min. The seal tube was closed and conventionally heated in a pre-heated oil bath at 90° C. for 16 h. The reaction mixture was cooled to rt, poured into water (100 mL). The solution was extracted with EtOAc (3×100 mL). The combined organic extracts were washed with brine, dried over anhydrous Na$_2$SO$_4$, filtered and concentrated under reduced pressure. The residue was purified by silica gel column chromatography (40 to 45% EtOAc/hexane, 12 CV's) to obtain 1-(3-((2-chloro-5-(trifluoromethyl) pyridin-4-yl) amino) propyl) piperidin-2-one (2.6 g, 26% yield) as brown solid. ¹H NMR (400 MHz, DMSO-$d_6$): δ 8.18 (s, 1H), 6.98 (t, J=6 Hz, 1H), 6.88 (s, 1H), 3.29 (m, 2H), 3.15 (m, 4H), 2.22 (t, J=6.4 Hz, 2H), 1.67 (m, 6H); LC-MS (ESI) m/z: 336.1 (M+H⁺).

Using the General Method for preparation of Intermediate M-1, the following intermediates of Table G were prepared.

TABLE G

| Intermediate | Structure | Yield (%) | ¹H NMR (400 MHz, DMSO-$d_6$): δ | LC-MS (m/z: (M + H⁺) |
|---|---|---|---|---|
| M-2 | (structure) | 26 | 8.18 (s, 1H), 6.90 (s, 1H), 6.87 (brs, 1H), 4.16 (m, 2H), 3.25 (m, 6H), 1.92 (m, 2H), 1.72 (m, 2H). | 338.2 |
| M-3 | (structure) | 27 | 8.18 (s, 1H), 6.90 (brs, 2H), 3.64 (brs, 4H), 3.48 (m, 2H), 3.26 (m, 4H), 2.63 (m, 2H), 1.63 (m, 2H). | 351.1 |
| M-4 | (structure) | 19 | 7.99 (s, 1H), 6.75 (s, 2H), 3.62 (m, 4H), 3.49 (m, 2H), 3.35 (m, 2H), 3.20 (m, 2H), 2.94 (brs, 2H), 1.65 (m, 2H). | 318.2 |

General Method of Oxidation to Sulfinyl Intermediates

Intermediate J-14: 4-(3-((2-(methyl sulfinyl)-5-(trifluoromethyl)pyrimidin-4-yl)amino)propyl)-1,4-oxazepan-5-one

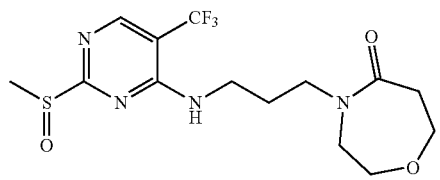

A solution of 4-(3-((2-(methylthio)-5-(trifluoromethyl)pyrimidin-4-yl)amino)propyl)-1,4-oxazepan-5-one (J-7, 3.0 g, 8.2 mmol) in DCM (60 mL) at 0° C., m-CPBA (2.0 g, 11.5 mmol) was added and stirred from 0° C. to room temperature for 3 h. The reaction mixture was washed with saturated aq. sodium bicarbonate (2×90 mL). Organic layer was dried over anhydrous $Na_2SO_4$ and filtered. The filtrate was concentrated under reduced pressure to obtain mixture of 4-(3-((2-(methylsulfinyl)-5-(trifluoromethyl)pyrimidin-4-yl)amino)propyl)-1,4-oxazepan-5-one and 4-(3-((2-(methylsulfonyl)-5-(trifluoromethyl)pyrimidin-4-yl)amino)propyl)-1,4-oxazepan-5-one (3.0 g, 95%, 9:1) as light yellow semi-solid. $^1$H NMR (400 MHz, DMSO-$d_6$): δ 8.59 (s, 1H), 7.94 (brs, 1H), 3.60 (m, 4H), 3.45 (m, 4H), 3.36 (m, 2H), 2.88 (s, 3H), 2.63 (m, 2H), 1.70 (m, 2H); LC-MS (ESI) m/z: 381.3 (M+H$^+$).

Using the General Method for preparation of Intermediate J-14, the following intermediates of Table H were prepared.

TABLE H

| Intermediate | Structure | Yield (%) | $^1$H NMR (400 MHz, DMSO-$d_6$): δ | LC-MS (m/z): (M + H$^+$) |
|---|---|---|---|---|
| J-8-A | 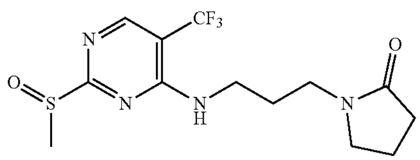 [SMILES: CS(=O)c1ncc(C(F)(F)F)c(NCCCN2CCCC2=O)n1] | 90 | 8.58 (s, 1H), 8.01 (s, 1H), 3.46 (m, 2H), 3.35 (m, 2H), 3.20 (m, 2H), 2.83 (s, 3H), 2.22 (m, 2H), 1.96 (m, 2H), 1.71 (m, 2H). | 351.2 |
| J-9 | 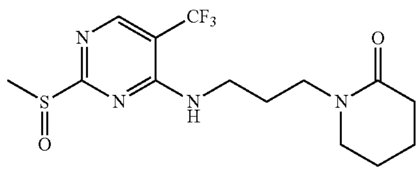 [SMILES: CS(=O)c1ncc(C(F)(F)F)c(NCCCN2CCCCC2=O)n1] | 96 | 8.58 (s, 1H), 8.06 (s, 1H), 3.46 (m, 2H), 3.35 (m, 2H), 3.24 (m, 2H), 2.72 (s, 3H), 2.23 (m, 2H), 1.73 (m, 6H). | 365.3 |
| J-10 | 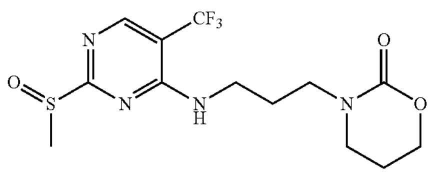 [SMILES: CS(=O)c1ncc(C(F)(F)F)c(NCCCN2CCCOC2=O)n1] | 92 | 8.58 (s, 1H), 7.99 (brs, 1H), 4.16 (m, 2H), 3.48 (m, 2H), 3.26 (m, 4H), 2.83 (s, 3H), 1.92 (m, 2H), 1.78 (m, 2H). | 367.2 |
| J-11 | 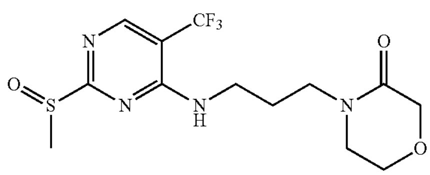 [SMILES: CS(=O)c1ncc(C(F)(F)F)c(NCCCN2CCOCC2=O)n1] | 96 | 8.59 (s, 1H), 8.00 (brs, 1H), 4.03 (s, 2H), 3.84 (m, 2H), 3.48 (m, 2H), 3.35 (m, 4H), 2.84 (s, 3H), 1.79 (m, 2H). | 367.1 |
| J-12 | 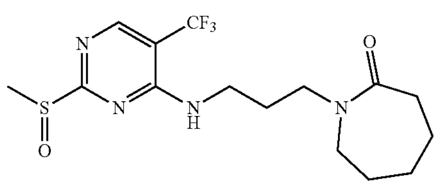 | 83 | 8.58 (s, 1H), 8.02 (brs, 1H), 3.45 (m, 2H), 3.34 (m, 4H), 2.83 (s, 3H), 2.43 (m, 2H), 1.69 (m, 4H), 1.56 (m, 4H). | 379.4 |
| J-13 | 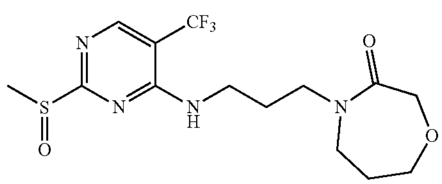 [SMILES: CS(=O)c1ncc(C(F)(F)F)c(NCCCN2CCCOCC2=O)n1] | 96 | 8.58 (s, 1H), 7.98 (s, 1H), 4.12 (s, 2H), 3.74 (m, 2H), 3.48 (m, 4H), 3.34 (m, 2H), 2.83 (s, 3H), 1.77 (m, 2H), 1.73 (m, 2H). | 381.3 |

TABLE H-continued

| Intermediate | Structure | Yield (%) | ¹H NMR (400 MHz, DMSO-d₆): δ | LC-MS (m/z: (M + H⁺) |
|---|---|---|---|---|
| J-14 | 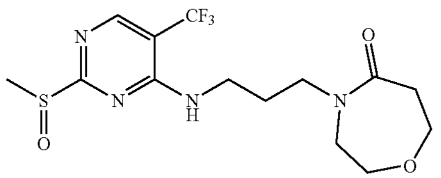 [SMILES: CS(=O)c1ncc(C(F)(F)F)c(NCCCN2CCOCCC2=O)n1] | 95 | 8.59 (s, 1H), 7.94 (brs, 1H), 3.60 (m, 4H), 3.45 (m, 4H), 3.36 (m, 2H), 2.88 (s, 3H), 2.63 (m, 2H), 1.70 (m, 2H). | 381.3 |
| J-15 | 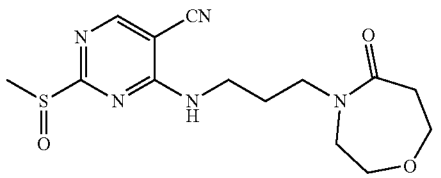 [SMILES: CS(=O)c1ncc(C#N)c(NCCCN2CCOCCC2=O)n1] | 100 | No NMR Data | 338.2 |
| J-16 | 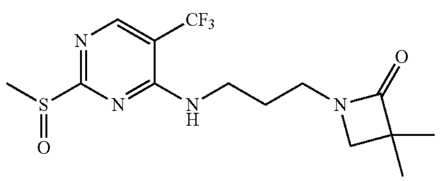 | crude | No NMR Data | 365.2 |
| J-17 | 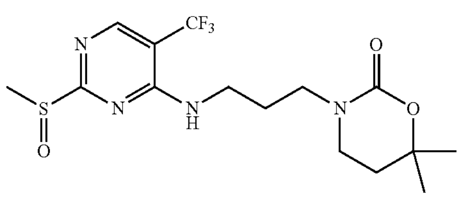 | crude | No NMR Data | 395.2 |
| J-18 | 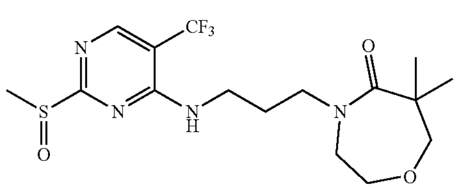 | crude | No NMR Data | 409.2 |

189

Exemplary Compounds:

Using the methods described above the following compounds of Formula I-A and Formula I-B were prepared. Exemplary compounds of Formula I-A and Formula I-B are shown below in Table I. Exemplary methods for the preparation of the compounds are also provided below.

General Method I: Substitution Reaction

Example 23: 1-(3-((5-bromo-2-((2-ethyl-4-(4-methylpiperazin-1-yl)phenyl)amino)pyrimidin-4-yl)amino)propyl)piperidin-2-one

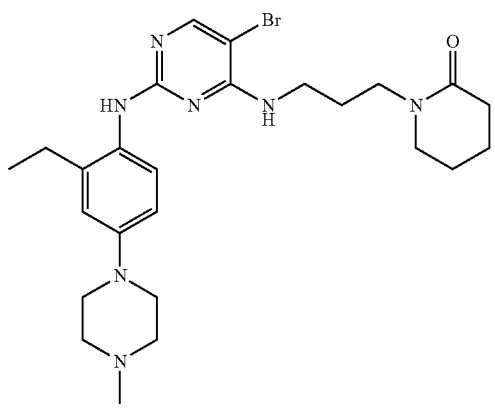

A solution of 1-(3-((5-bromo-2-chloropyrimidin-4-yl)amino)propyl)piperidin-2-one (K-10, 4.0 g, 11.6 mmol) in 2-butanol (80 mL) at rt was treated with 2-ethyl-4-(4-methylpiperazin-1-yl)aniline (D-I-11, 2.53 g, 11.6 mmol). The reaction mixture was treated with 4N HCl in 1,4-dioxane (3.5 mL, 13.9 mmol) and stirred at 95° C. for 72 h. The reaction mixture was cooled to rt and then basified with sat' d aqueous NaHCO$_3$. The solution was extracted with DCM (3×50 mL) and the combined organics were dried over anhydrous Na$_2$SO$_4$, filtered and concentrated under reduced pressure. The crude was purified silica gel column chromatography (4 to 5% MeOH/DCM, 10 CV's). The product was dissolved in DCM (200 mL) and added QuadraSil-MP resin (w/w) in order to remove residual palladium. The solution was stirred for 4 h and filtered. The filtrate was evaporated to obtain 1-(3-((5-bromo-2-((2-ethyl-4-(4-methylpiperazin-1-yl)phenyl)amino)pyrimidin-4-yl)amino)propyl)piperidin-2-one (1.70 g, 28% yield) as off white solid. $^1$H NMR (400 MHz, DMSO-d$_6$): δ 8.09 (s, 1H), 7.81 (s, 1H), 7.13 (d, J=8.5 Hz, 1H), 6.80 (m, 1H), 6.74 (m, 1H), 6.71 (m, 1H), 3.21 (m, 4H), 3.14 (m, 2H), 3.07 (m, 5H), 2.43 (m, 5H), 2.21 (s, 5H), 1.67 (s, 4H), 1.61 (m, 2H), 1.05 (t, J=7.4 Hz, 3H); LC-MS (ESI) m/z: 530.3 (M+H$^+$).

190

General Method J: Substitution Reaction tert-butyl 4-(4-((4-((3-(2-oxopiperidin-1-yl)propyl)amino)-5-(trifluoromethyl)pyrimidin-2-yl)amino)phenyl)-1,4-diazepane-1-carboxyl

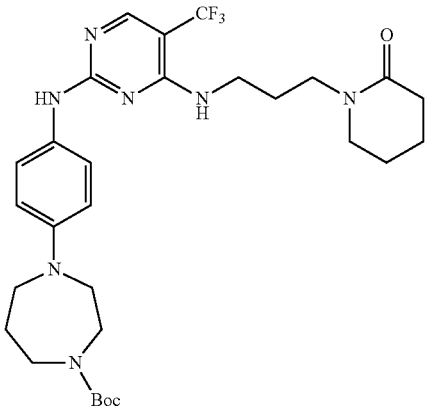 [SMILES: CC(C)(C)OC(=O)N1CCCN(c2ccc(Nc3ncc(C(F)(F)F)c(NCCCN4CCCCC4=O)n3)cc2)CC1]

A solution of tert-butyl 4-(4-aminophenyl)-1,4-diazepane-1-carboxylate (D-I-12, 0.21 g, 0.57 mmol) and 1-(3-((2-(methylsulfinyl)-5-(trifluoromethyl)pyrimidin-4-yl)amino)propyl)piperidin-2-one (J-9, 0.17 g, 0.57 mmol) in DMF (3.0 mL) was sealed and heated at 90° C. for 12 h. The mixture was concentrated and the crude was purified by silica gel column chromatography (0 to 4% MeOH/DCM, 12 CV's) to provide product tert-butyl 4-(4-((4-((3-(2-oxopiperidin-1-yl)propyl)amino)-5-(trifluoromethyl)pyrimidin-2-yl)amino)phenyl)-1,4-diazepane-1-carboxylate (0.20 g, 60% yield). LC-MS (ESI) m/z: 592.4 (M+H$^+$).

General Method K: Deprotection of Boc Group of R$^4$ Moieties

Example 9: 1-(3-((2-((4-(1,4-diazepan-1-yl)phenyl)amino)-5-(trifluoromethyl)pyrimidin-4-yl)amino)propyl)piperidin-2-one

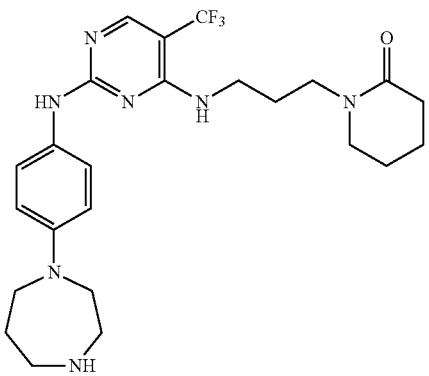 [SMILES: O=C1CCCCN1CCCNc1nc(Nc2ccc(N3CCCNCC3)cc2)ncc1C(F)(F)F]

A solution of tert-butyl 4-(4-((4-((3-(2-oxopiperidin-1-yl)propyl)amino)-5-(trifluoromethyl)pyrimidin-2-yl)amino)phenyl)-1,4-diazepane-1-carboxylate (0.20 g, 0.34 mmol) in DCM (3 mL) was treated with 4 N HCl in 1,4-dioxane (1.0 mL). The mixture was stirred at rt for 2 h. The solution was concentrated and the residue was dissolved in water (1.0 mL) and acetonitrile (1 mL), frozen and lyophilized to obtain 1-(3-((2-((4-(1,4-diazepan-1-yl)phenyl)amino)-5-(trifluoromethyl)pyrimidin-4-yl)amino)propyl)piperidin-2-one hydrochloride (0.12 g, 67% yield). $^1$H NMR (400 MHz, DMSO-d$_6$): δ 9.23 (brs, 1H), 8.27 (s, 1H, FA), 8.08 (s, 1H), 7.47 (d, J=8.5 Hz, 2H), 7.06 (s, 1H), 6.67 (d, J=8.5 Hz, 2H), 3.51 (t, J=5.0 Hz, 2H), 3.47 (t, J=6.2 Hz, 3H), 3.34-3.37 (m, 3H), 3.30 (t, J=6.9 Hz, 3H), 3.20 (s, 3H), 2.98 (t, J=4.9 Hz, 2H), 2.80 (t, J=5.6 Hz, 2H), 2.21 (t, J=6.0 Hz, 2H), 1.87-1.90 (m, 2H), 1.69-1.75 (m, 7H); LC-MS (ESI) m/z: 492.4 (M+H$^+$).

General Method L: Reductive Alkylation of R$^4$ Moieties

Example 10: 1-(3-((2-((4-(4-ethyl-1,4-diazepan-1-yl)phenyl)amino)-5-(trifluoromethyl)pyrimidin-4-yl)amino)propyl)piperidin-2-one

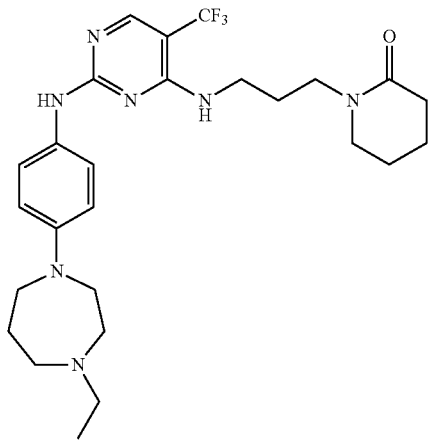 [SMILES: CCN1CCCN(c2ccc(Nc3ncc(C(F)(F)F)c(NCCCN4CCCCC4=O)n3)cc2)CC1]

A solution of 1-(3-((2-((4-(1,4-diazepan-1-yl)phenyl)amino)-5-(trifluoromethyl)pyrimidin-4-yl)amino)propyl)piperidin-2-one (9, 0.10 g, 0.20 mmol)) in methanol (0.5 mL) was treated with acetaldehyde (0.1 mL 1.8 mmol), and acetic acid (2 drops). Sodium cyanoborohydride (0.026 g, 0.41 mmol) was added and the mixture was stirred at rt 6 h. The solution was treated with brine and then extracted with EtOAc (3×15 mL). The combined organics were dried over anhydrous Na$_2$SO$_4$, filtered and concentrated. The crude was purified by reverse-phase column chromatography (0% to 20% CH$_3$CN/H$_2$O (0.1% FA), 15 CV's) to obtain 1-(3-((2-((4-(4-ethyl-1,4-diazepan-1-yl)phenyl)amino)-5-(trifluoromethyl)pyrimidin-4-yl)amino)propyl)piperidin-2-one (56 mg, 49% yield). $^1$H NMR (400 MHz, DMSO-d$_6$): δ 9.21 (brs, 1H), 8.17 (s, 1H, FA), 8.08 (s, 1H), 7.45 (d, J=8.3 Hz, 2H), 7.05 (s, 1H), 6.63 (d, J=8.7 Hz, 2H), 3.47 (t, J=4.9 Hz, 3H), 3.36-3.42 (m, 5H), 3.30 (t, J=6.9 Hz, 3H), 3.19 (s, 3H), 2.72 (t, J=4.7 Hz, 2H), 2.53-2.56 (m, 4H), 2.21 (t, J=5.9 Hz, 2H), 1.83-1.88 (m, 2H), 1.68-1.73 (m, 7H), 0.98 (t, J=7.1 Hz, 3H); MS (ESI) m/z: 520.4 (M+H$^+$).

General Method of Acylation of R$^4$ Moieties

Example 36: 1-(3-((2-((4-(4-acetylpiperazin-1-yl)-2-cyclopropylphenyl)amino)-5-(trifluoromethyl)pyrimidin-4-yl)amino)propyl)piperidin-2-one

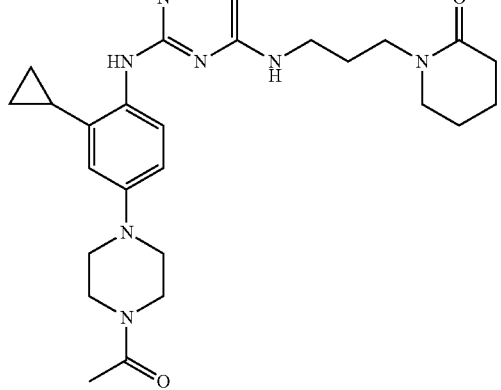

A solution of 1-(3-((2-((2-cyclopropyl-4-(piperazin-1-yl)phenyl)amino)-5-(trifluoromethyl)pyrimidin-4-yl)amino)propyl)piperidin-2-one (34, 0.21 g, 0.40 mmol) in 2.5 mL of 30% MeCN: water was treated with acetic anhydride (1.0 eq) at rt. The reaction mixture was stirred at rt for 30 min and the solution was diluted with water (15 mL). The solution was extracted with EtOAc (3×20 mL) and the combined organics were washed with sat' d NaHCO$_3$ (15 mL). The organic layer was dried with MgSO$_4$, filtered and concentrated under reduced pressure. The crude was purified by silica gel column chromatography (0 to 10% DCM/MeOH, 25CV) to yield 1-(3-((2-((4-(4-acetylpiperazin-1-yl)-2-cyclopropylphenyl)amino)-5-(trifluoromethyl)pyrimidin-4-yl)amino)propyl)piperidin-2-one (0.13 g, 57% yield) as a clear glassy solid. $^1$H NMR (400 MHz, DMSO-d$_6$): δ 8.64 (brs, 1H), 8.04 (s, 1H), 7.27 (s, 1H), 7.05 (brs, 1H), 6.75 (d, 1H), 6.46 (s, 1H), 3.54 (d, 4H), 3.01-3.24 (m, 10H), 2.18-2.19 (m, 2H), 2.02 (s, 3H), 1.91-1.96 (m, 1H), 1.61-1.67 (m, 6H), 0.82 (d, 2H), 0.58 (d, 2H); LC-MS (ESI) m/z: 560.4 (M+H$^+$).

General Method M: Pd Coupling Reaction

Example 97: 1-(3-((2-((5-(4-methylpiperazin-1-yl)pyridin-2-yl)amino)-5-(trifluoromethyl)pyrimidin-4-yl)amino)propyl)piperidin-2-one

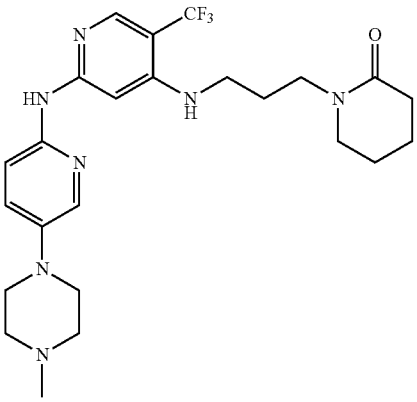 [SMILES: CN1CCN(c2ccc(Nc3cc(NCCCN4CCCCC4=O)c(C(F)(F)F)cn3)nc2)CC1]

A mixture of commercially available 5-(4-methylpiperazin-1-yl)pyridin-2-amine (0.13 g, 0.66 mmol) and 1-(3-((2-chloro-5-(trifluoromethyl)pyridin-4-yl)amino)propyl)piperidin-2-one (M-1, 0.20 g, 0.60 mmol) in 1,4-dioxane (3 mL) was treated with cesium carbonate (0.39 g, 1.2 mmol). The solution was sparged with Ar and treated with Pd$_2$(dba)$_3$ (0.055 g, 0.06 mmol) and Xantphos (0.069 g, 0.12 mmol). The mixture was sparged again with Ar, capped tightly and heated at 90° C. 15 h. The mixture was cooled to rt, diluted with DCM (20 mL) and water (10 mL). The black solid was filtered off and then the filtrate was treated with brine. The solution was extracted with additional DCM (3×25 mL). The combined organics were dried over anhydrous Na$_2$SO$_4$, filtered and concentrated under reduced pressure to obtain 1-(3-((2-((5-(4-methylpiperazin-1-yl)pyridin-2-yl)amino)-5-(trifluoromethyl)pyridin-4-yl)amino)propyl)piperidin-2-one (0.18 g, 57% yield) as an orange solid. $^1$H NMR (400 MHz, DMSO-d$_6$): δ 9.35 (s, 1H), 8.01 (s, 1H), 7.90 (d, J=3.0 Hz, 1H), 7.55 (d, J=9.1 Hz, 1H), 7.37 (dd, J=9.1 and 3.1 Hz, 1H), 7.11 (s, 1H), 6.19-6.21 (m, 1H), 3.31-3.35 (m, 2H), 3.22-3.26 (m, 2H), 3.13 (q, J=6.5 Hz, 2H), 3.05-3.10 (m, 4H), 2.44-2.49 (m, 4H), 2.20-2.23 (m, 5H), 1.66-1.76 (m, 6H); LC-MS (ESI) m/z: 492.2 (M+H$^+$).

TABLE I

Exemplary compounds.

| Example Number | Product | Method | Yield (%) | $^1$H NMR (400 MHz, DMSO-d$_6$): δ | LC-MS (m/z: M + H$^+$) |
|---|---|---|---|---|---|
| 1 | | I | 20 | 8.58 (1H, s), 8.14 (s, 1H), 7.56 (m, 3H), 6.89 (t, J = 6.0 Hz, 1H), 6.81 (d, J = 8.7 Hz, 2H), 3.43 (m, 2H), 3.16 (t, 2H, J = 7.2 Hz), 2.96 (d, J = 5.3 Hz, 4H), 2.65 (t, J = 4.8 Hz, 4H), 2.26 (t, J = 7.8 Hz, 2H), 1.77 (t, J = 7.8 Hz, 2H), 1.72 (m, 2H), 1.63 (m, 1H), 1.43 (m, 1H), 1.16 (s, 6H), 0.80 (m, 2H), 0.43 (m, 4H), 0.32 (m, 2H). | 504.4 |
| 2 | 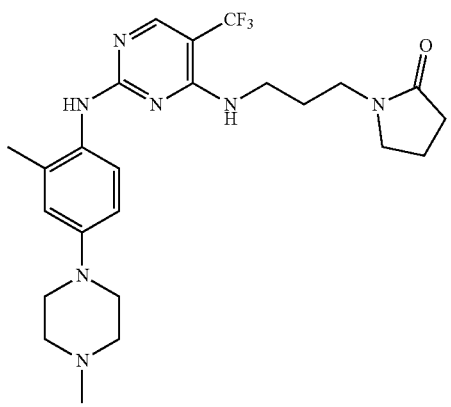 [SMILES: Cc1cc(N2CCN(C)CC2)ccc1Nc1ncc(C(F)(F)F)c(NCCCN2CCCC2=O)n1] | J | 20 | 8.32 (s, 1H), 8.03 (s, 1H), 7.20 (d, J = 8.6 Hz, 1H), 6.77 (brs, 1H), 6.74 (m, 1H), 6.63 (m, 1H), 3.26 (m, 4H), 3.13 (m, 6H), 2.56 (brs, 4H), 2.31 (s, 3H), 2.20 (m, 2H), 2.16 (s, 3H), 1.90 (m, 2H), 1.64 (m, 2H). | 492.4 |

TABLE I-continued

Exemplary compounds.

| Example Number | Product | Method | Yield (%) | $^1$H NMR (400 MHz, DMSO-$d_6$): δ | LC-MS (m/z: M + H$^+$) |
|---|---|---|---|---|---|
| 3 | (structure) | J | 22 | 9.72 (s, 1H), 9.24 (brs, 1H), 8.26 (s, 1H), 7.89 (brs, 1H), 7.32 (d, J = 8.6 Hz, 1H), 6.91 (brs, 1H), 6.86 (dd, J = 2.4, 8.7 Hz, 1H), 3.41 (m, 4H), 3.32 (m, 2H), 3.27 (m, 2H), 3.21 (brs, 4H), 3.12 (m, 2H), 2.23 (s, 3H), 2.20 (m, 2H), 1.90 (m, 2H), 1.67 (m, 2H). | 478.4 |
| 4 | (structure) | J | 64 | 8.60 (brs, 1H), 8.02 (brs, 1H), 7.09 (d, J = 8.4 Hz, 1H), 6.86 (m, 1H), 6.76 (brs, 1H), 6.72 (dd, J = 2.5 and 8.5 Hz, 1H), 3.21 (brs, 4H), 3.09 (brs, 6H), 2.49 (m, 2H), 2.44 (m, 4H), 2.19 (m, 5H), 1.87 (m, 2H), 1.57 (brs, 2H), 1.05 (t, J = 7.4 Hz, 3H). | 506.4 |
| 5 | (structure) | I & K | 47 | 8.32 (s, 1H, FA), 8.20 (s, 1H), 7.80 (s, 1H), 7.44 (d, J = 8.2 Hz, 1H), 7.06 (t, J = 6.1 Hz, 1H), 7.00 (s, 1H), 6.97 (m, 1H), 3.24-3.32 (m, 6H), 3.18 (m, 2H), 2.90 (m, 2H), 2.71 (m 2H), 2.20 (m, 2H), 2.18 (s, 3H), 1.86 (m, 2H), 1.76 (m, 2H), 1.67 (m, 6H). | 457.4 |

TABLE I-continued

Exemplary compounds.

| Example Number | Product | Method | Yield (%) | $^1$H NMR (400 MHz, DMSO-$d_6$): δ | LC-MS (m/z: (M + H$^+$) |
|---|---|---|---|---|---|
| 6 | | I | 65 | 8.20 (brs, 1H, FA), 8.16 (s, 1H), 7.79 (s, 1H), 7.40 (d, J = 8.2 Hz, 1H), 7.04 (t, J = 6.1 Hz, 1H), 7.01 (s, 1H), 6.98 (m, 1H), 3.24-3.30 (m, 4H), 3.17 (m, 2H), 2.98 (m, 2H), 2.43 (m, 1H), 2.29 (m, 3H), 2.13-2.20 (m, 4H), 2.17 (s, 3H), 1.6-1.8 (m, 10H). | 471.4 |
| 7 | | J & K | 80 | 8.74 (s, 1H), 8.32 (s, 1H, FA), 8.06 (s, 1H), 7.36 (d, J = 8.0 Hz, 1H), 6.9-7.1 (m, 2H), 3.19-3.32 (m, 6H), 3.15 (m, 2H), 2.90 (m, 2H), 2.73 (m, 1H), 2.18 (s, 3H), 2.18-2.20 (m, 2H), 2.18 (s, 3H), 1.86 (m, 2H), 1.76 (m, 2H), 1.60-1.70 (m, 6H). | 491.4 |
| 8 | | J | 42 | 8.71 (s, 1H), 8.20 (s, 1H, FA), 8.05 (s, 1H), 7.33 (d, J = 8.1 Hz, 1H), 7.04 (s, 1H), 7.03 (d, J = 8.4 Hz, 1H), 7.00 (m, 1H), 3.19-3.25 (m, 4H), 3.15 (m, 2H), 2.97 (m, 2H), 2.44 (m, 1H), 2.29 (s, 3H), 2.1-2.2 (m, 4H), 2.17 (s, 3H), 1.6-1.8 (m, 10H). | 505.4 |

TABLE I-continued
Exemplary compounds.
| Example Number | Product | Method | Yield (%) | $^1$H NMR (400 MHz, DMSO-$d_6$): δ | LC-MS (m/z: (M + H$^+$)) |
|---|---|---|---|---|---|
| 11 | 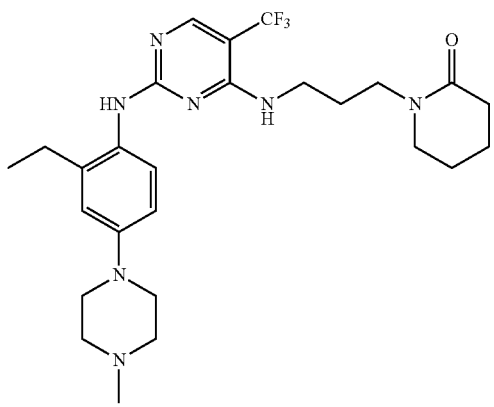 [SMILES: CCc1cc(N2CCN(C)CC2)ccc1Nc1ncc(C(F)(F)F)c(NCCCN2CCCCC2=O)n1] | J | 7 | 8.60 (s, 1H), 8.34 (s, 1H: FA), 8.01 (s, 1H), 7.10 (m, 1H), 6.95 (m, 1H), 6.76 (s, 1H), 6.70 (m 1H), 3.1-3.4 (brm, 6H), 3.09 (m, 2H), 2.50 (m, 3H), 2.44 (m, 5H), 2.21 (s, 3H), 2.20 (m, 2H), 1.65 (brm, 4H), 1.54 (brm, 2H), 1.06 (t, J = 7.4 Hz, 3H). | 520.4 |
| 12 | 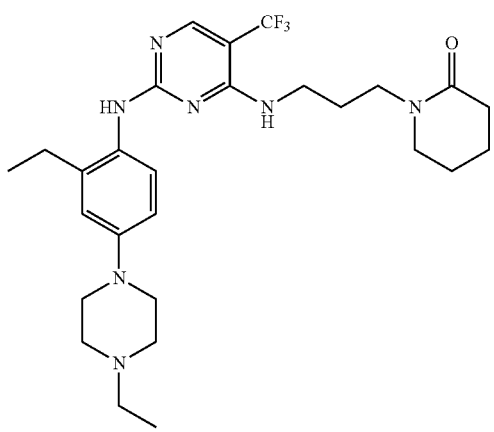 [SMILES: CCc1cc(N2CCN(CC)CC2)ccc1Nc1ncc(C(F)(F)F)c(NCCCN2CCCCC2=O)n1] | J, K & L | 5 | 8.60 (brs, 1H), 8.01 (brs, 1H), 7.10 (brm, 1H), 6.95 (t, 1H, J = 5.8 Hz), 6.76 (m, 1H), 6.72 (m, 1H), 3.19 (brs, 4H), 3.05-3.10 (m, 6H), 2.50 (m, 4H), 2.48 (m, 6H), 2.33-2.37 (m, 2H), 2.18 (m, 2H), 1.66 (brm, 4H), 1.58 (brm, 2H), 1.06 (t, J = 7.4 Hz, 3H), 1.01 (t, J = 7.2 Hz, 3H). | 534.4 |
| 13 | 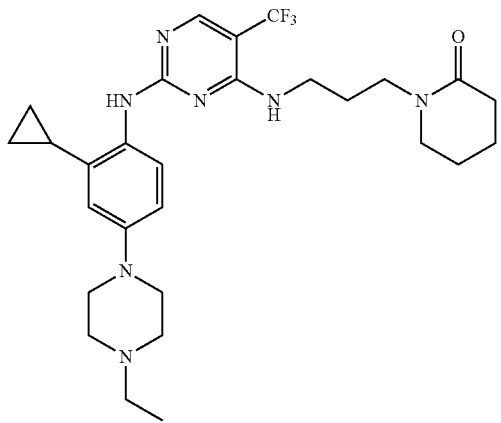 [SMILES: CCN1CCN(c2ccc(Nc3ncc(C(F)(F)F)c(NCCCN4CCCCC4=O)n3)c(C3CC3)c2)CC1] | J, K & L | 20 | 8.57 (s, 1H), 8.03 (s, 1H), 7.24 (brm, 1H), 6.98 (d, J = 6.3 Hz, 1H), 6.71 (d, J = 8.9 Hz, 1H), 6.43 (s, 1H), 3.22 (brm, 4H), 3.12 (brm, 2H), 3.09 (brm, 4H), 2.41 (brm, 4H), 2.35 (brm, 3H), 2.18-2.19 (m, 2H), 1.93 (m, 1H), 1.66 (brm, 4H), 1.60 (brm, 2H), 1.02 (brm, 3H), 0.81 (m, 2H), 0.57 (m, 2H). | 546.4 |

TABLE I-continued

Exemplary compounds.

| Example Number | Product | Method | Yield (%) | $^1$H NMR (400 MHz, DMSO-$d_6$): δ | LC-MS (m/z: $(M + H^+)$) |
|---|---|---|---|---|---|
| 14 | (structure) | J | 29 | 8.57 (s, 1H), 8.17 (s, 1H, FA), 8.03 (s, 1H), 7.24 (brm, 1H), 6.98 (m, 1H), 6.71 (m, 1H), 6.42 (d, J = 2.7 Hz, 1H), 3.12-3.24 (m, 10H), 3.06 (t, J = 4.8 Hz, 4H), 2.43 (m, 4H), 2.18-2.20 (m, 5H), 1.94 (m, 1H), 1.66 (brm, 4H), 1.60 (brm, 2H), 0.81 (m, 2H), 0.56 (m, 2H). | 578.4 |
| 15 | (structure) | I | 6 | 8.10 (s, 1H), 7.79 (s, 1H), 7.03 (d, J = 8.6 Hz, 1H), 6.78 (m, 2H), 6.70 (dd, J = 2.2 and 8.6 Hz, 1H), 3.19 (m, 4H), 3.09 (m, 7H), 2.45 (brs, 4H), 2.21 (s, 3H), 2.19 (m, 2H), 1.67 (brs, 4H), 1.59 (m, 2H), 1.09 (d, J = 6.8 Hz, 6H). | 544.4 546.4 |
| 16 | (structure) | J | 68 | 10.18 (brs, 1H), 9.26 (brs, 2H), 8.50 (brs, 1H), 7.32 (t, J = 8.56 Hz, 1H), 6.94 (s, 1H), 6.89 (d, J = 8.56 Hz, 1H), 3.38 (brs, 4H), 3.20 (brs, 10H), 2.21 (brs, 5H), 1.63 (brs, 6H). | 492.4 |

TABLE I-continued

Exemplary compounds.

| Example Number | Product | Method | Yield (%) | $^1$H NMR (400 MHz, DMSO-$d_6$): δ | LC-MS (m/z: M + H$^+$) |
|---|---|---|---|---|---|
| 17 | | J, K & L | 26 | 8.62 (s, 1H), 8.03 (s, 1H), 7.17 (brs, 1H), 6.98 (s, 1H), 6.75 (m, 2H), 3.21 (brs, 4H), 3.14 (brs, 2H), 3.06 (brm, 4H), 2.55 (m, 2H), 2.20 (brm, 2H), 2.14 (s, 3H), 1.63 (m, 7H), 1.19 (brm, 2H), 1.00 (brm, 6H). | 534.5 |
| 18 | | J | 43 | 8.60 (s, 1H), 8.02 (s, 1H), 7.13-7.20 (m, 1H), 6.97 (t, J = 5.8 Hz, 1H), 6.77 (s, 1H), 6.72 (d, J = 8.9 Hz, 1H), 4.61 (t, J = 4.9 Hz, 1H), 4.51 (t, J = 4.9 Hz, 1H), 3.11-3.25 (m, 6H), 3.06-3.10 (m, 4H), 2.68 (t, J = 4.9 Hz, 1H), 2.62 (t, J = 4.9 Hz, 1H), 2.57 (t, J = 4.7 Hz, 4H), 2.19-2.20 (m, 2H), 2.13 (s, 3H), 1.59-1.66 (m, 6H). | 538.4 |
| 19 | | J, K & L | 26 | 8.61 (s, 1H), 8.03 (s, 1H), 7.16 (d, J = 7.0 Hz, 1H), 6.98 (brs, 1H), 6.76 (s, 1H), 6.72 (d, J = 8.4 Hz, 1H), 3.20 (brs, 4H), 3.14 (brs, 2H), 3.08 (brs, 4H), 2.49 (m, 4H), 2.34 (m, 2H), 2.19 (brs, 2H), 2.13 (s, 3H), 1.63 (m, 6H), 1.02 (t, J = 7.0 Hz, 3H). | 520.5 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 20 | (structure) | J | 30 | 8.60 (s, 1H), 8.03 (s, 1H), 7.16 (d, J = 7.9 Hz, 1H), 6.96 (brs, 1H), 6.77 (s, 1H), 6.72 (d, J = 8.6 Hz, 1H), 3.20 (brs, 4H), 3.14 (brs, 2H), 3.08 (brs, 4H), 2.43 (brs, 4H), 2.20 (brs, 5H), 2.13 (s, 3H), 1.63 (m, 6H). | 506.4 |
| 21 | (structure) | J, K & L | 12 | 8.30 (s, 1H), 8.03 (s, 1H), 7.20 (d, J = 8.6 Hz, 1H), 6.76 (s, 1H), 6.71 (m, 2H), 3.27 (m, 4H), 3.15 (m, 2H), 3.10 (brs, 4H), 2.81 (m, 1H), 2.41 (brs, 4H), 2.20 (m, 2H), 2.16 (s, 3H), 2.00 (m, 2H), 1.85 (m, 2H), 1.66 (m, 8H). | 546.5 |
| 22 | (structure) | J, K & L | 19 | 8.61 (s, 1H), 8.02 (s, 1H), 7.15 (brs, 1H), 6.97 (brs, 1H), 6.76 (s, 1H), 6.71 (d, J = 7.8 Hz, 1H), 3.21 (m, 5H), 3.04 (brs, 4H), 2.65 (brs, 4H), 2.19 (brs, 2H), 2.13 (s, 3H), 1.67 (m, 8H), 0.42 (m, 2H), 0.33 (m, 2H). | 532.4 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 24 | | J | 16 | 8.52 (s, 1H), 8.02 (s, 1H), 7.11 (brs, 1H), 6.96 (s, 1H) 6.47 (d, J = 6.8 Hz, 1H), 6.13 (s, 1H), 3.46 (brs, 2H), 3.37 (m, 2H), 3.17 (m, 8H), 2.58 (brs, 2H), 2.43 (brs, 2H), 2.25 (s, 3H), 2.19 (s, 2H), 1.87 (m, 1H), 1.58 (m, 6H), 0.79 (m, 2H), 0.54 (m, 2H). | 546.6 |
| 25 | | J | 72 | 8.67 (brs, 1H), 8.12 (s, 1H, FA), 8.03 (brs, 1H), 7.23 (d, J = 8.6 Hz, 1H), 6.91 (brm, 1H), 6.84 (s, 1H), 6.79 (d, J = 8.9 Hz, 1H), 4.13 (t, J = 5.2 Hz, 2H), 3.10-3.40 (m, 14H), 2.76 (brs, 3H), 2.15 (s, 3H), 1.87-1.92 (m, 2H), 1.62-1.69 (brm, 2H). | 508.2 |
| 26 | | I | 6 | 8.02 (s, 1H), 7.85 (s, 1H), 7.35 (d, J = 8.72 Hz, 1H), 6.86 (t, J = 5.76 1H), 6.71 (dd, J = 2.5 and 8.7 Hz, 1H), 6.44 (d, J = 2.4 Hz, 1H), 3.25 (m, 4H), 3.15 (m, 2H), 3.05 (brs, 4H), 2.44 (brs, 4H), 2.20 (m, 5H), 1.94 (m, 1H), 1.65 (m, 6H), 0.82 (m, 2H), 0.56 (m, 2H). | 544.3 546.3 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 27 | [structure: 2-(2-cyclopropyl-4-(4-methylpiperazin-1-yl)phenylamino)-5-chloro-4-(3-(2-oxopiperidin-1-yl)propylamino)pyrimidine] | I | 13 | 8.02 (s, 1H), 7.78 (s, 1H), 7.35 (d, J = 8.72 Hz, 1H), 7.03 (t, 1H), 6.70 (dd, J = 2.5 and 8.8 Hz, 1H), 6.44 (d, J = 2.44 Hz, 1H), 3.24 (m, 4H), 3.15 (m, 2H), 3.04 (brs, 4H), 2.42 (brs, 4H), 2.42 (m, 5H), 1.94 (m, 1H), 1.66 (m, 6H), 0.82 (m, 2H), 0.56 (m, 2H). | 498.4 |
| 28 | [structure: 2-(2-isopropyl-4-(4-ethylpiperazin-1-yl)phenylamino)-5-trifluoromethyl-4-(3-(2-oxopiperidin-1-yl)propylamino)pyrimidine] | J | 18 | 8.30 (s, 1H), 8.01 (s, 1H), 7.08 (d, J = 8.6 Hz, 1H), 6.80 (d, J = 2.6 Hz, 1H) 6.72 (dd, J = 2.6 and 8.6 Hz, 1H), 6.66 (m, 1H), 3.23 (m, 4H), 3.12 (brs, 8H), 2.50 (m, 3H), 2.39 (m, 2H), 2.19 (m, 2H), 1.69 (t, J = 3.4 Hz, 4H), 1.59 (t, J = 6.8 Hz, 2H), 1.13 (d, J = 6.8 Hz, 6H), 1.04 (t, J = 7.1 Hz, 3H). | 548.5 |
| 29 | [structure: 2-(2-isopropyl-4-(4-ethylpiperazin-1-yl)phenylamino)-5-chloro-4-(3-(2-oxopiperidin-1-yl)propylamino)pyrimidine] | I | 10 | 8.08 (s, 1H), 7.72 (s, 1H), 7.03 (d, J = 8.6 Hz, 1H), 6.94 (t, J = 5.7 Hz, 1H), 6.78 (d, J = 2.4 Hz, 1H), 6.69 (dd, J = 2.4 and 8.6 Hz, 1H), 3.16 (m, 14H), 2.35 (m, 2H), 2.19 (d, J = 5.8 Hz, 2H), 1.8 (m, 1H), 1.62 (m, 6H), 1.09 (d, J = 6.8 Hz, 6H), 1.03 (t, J = 7.1 Hz, 3H). | 514.5 |

TABLE I-continued

Exemplary compounds.

| Example Number | Product | Method | Yield (%) | $^1$H NMR (400 MHz, DMSO-$d_6$): δ | LC-MS (m/z: M + H$^+$) |
|---|---|---|---|---|---|
| 30 | (structure) | I | 9 | 8.09 (s, 1H), 7.79 (s, 1H), 7.03 (d, J = 8.6 Hz, 1H), 6.78 (brs, 2H), 6.67 (dd, J = 8.5 and 16.6 Hz, 1H), 3.15 (m, 14H), 2.47 (m, 1H), 2.36 (q, 2H), 2.19 (brs, 2H), 1.62 (m, 6H), 1.09 (d, J = 6.8 Hz, 6H), 1.03 (t, J = 7.0 Hz, 3H). | 558.4 560.4 |
| 31 | (structure) | J, K & L | 6 | 8.24 (brs, 1H), 8.00 (s, 1H), 7.05 (d, J = 8.3 Hz, 1H), 6.69 (brs, 1H), 6.53 (s, 1H), 6.50 (m, 1H), 3.50 (m, 2H), 3.43 (m, 2H), 3.23 (m, 4H), 3.09 (m, 4H), 2.68 (m, 2H), 2.53 (m, 2H), 2.31 (s, 3H), 2.20 (m, 2H), 1.91 (m, 2H), 1.64 (m, 6H), 1.08 (t, J = 7.4 Hz, 3H). | 534.4 |
| 32 | (structure) | I | 50 | 11.4 (brs, 1H), 10.10 (s, 1H), 8.75 (s, 1H), 8.19 (brs, 1H), 7.30 (brs, 1H), 6.86-6.90 (m, 2H), 3.81 (d, J = 11.3 Hz, 2H), 3.43 (d, J = 10.4 Hz, 2H), 3.2-3.05 (m, 10 H), 2.75 (d, J = 4.4 Hz, 3H), 2.54 (d, J = 8.6 Hz, 2H), 2.15 (s, 2H), 1.63 (s, 6H), 1.08 (t, J = 7.5 Hz, 3H). | 486.2 |

TABLE I-continued

Exemplary compounds.

| Example Number | Product | Method | Yield (%) | $^1$H NMR (400 MHz, DMSO-$d_6$): δ | LC-MS (m/z: (M + H$^+$) |
|---|---|---|---|---|---|
| 33 | (structure: 2-isopropyl-4-(4-methylpiperazin-1-yl)phenyl-NH-pyrimidine(CF$_3$)-NH-propyl-piperidin-2-one) | J | 11 | 8.30 (s, 1H), 8.01 (s, 1H), 7.08 (d, J = 8.6 Hz, 1H), 6.80 (d, J = 2.4 Hz, 1H), 6.72 (dd, J = 2.5 and 8.6 Hz, 1H), 6.66 (brs, 1H), 3.24 (m, 5H), 3.14 (m, 8H), 2.50 (m, 2H), 2.25 (s, 3H), 2.20 (m, 2H), 1.69 (m, 4H), 1.61 (m, 2H), 1.13 (d, J = 6.8 Hz, 6H). | 534.5 |
| 34 | (structure: 2-cyclopropyl-4-(piperazin-1-yl)phenyl-NH-pyrimidine(CF$_3$)-NH-propyl-piperidin-2-one) | I & K | 49 | 8.59 (s, 1H), 8.03 (s, 1H), 7.25 (s, 1H), 6.99 (s, 1H), 6.72 (d, J = 8.9 Hz, 1H), 6.43 (s, 1H), 3.10-3.25 (m, 7H), 3.06 (t, 4H), 2.93 (m, 4H), 2.18 (m, 2H), 1.91-1.95 (m, 1H), 1.59-1.70 (m, 6H), 0.81 (m, 2H), 0.57 (m, 2H). | 518.2 |
| 35 | (structure: 2-cyclopropyl-5-fluoro-4-(4-methylpiperazin-1-yl)phenyl-NH-pyrimidine(CF$_3$)-NH-propyl-piperidin-2-one) | I | 39 | 8.63 (s, 1H), 8.11 (s, 1H), 7.45 (d, J = 14.4 Hz, 1H), 7.15 (s, 1H), 6.55 (d, J = 9.6 Hz, 1H), 3.28 (s, 1H), 3.22 (m, 2H), 3.15 (s, 3H), 3.01 (brs, 4H), 2.19 (m, 2H), 1.92-1.98 (m, 1H), 1.66 (m, 6 H), 0.85 (m, 2H), 0.57 (m, 2H). | 550.2 |

TABLE I-continued

Exemplary compounds.

| Example Number | Product | Method | Yield (%) | ¹H NMR (400 MHz, DMSO-$d_6$): δ | LC-MS (m/z: (M + H⁺) |
|---|---|---|---|---|---|
| 37 | (structure) | J & K | 48 | 10.3 (brs, 1H), 9.37 (brs, 1H), 8.49 (brs, 1H), 7.37 (brs, 1H), 6.94 (s, 1H), 6.89 (d, J = 9.0 Hz, 1H), 4.09-4.15 (m, 2H), 3.55 (brs, 4H), 3.35-3.42 (m, 4H), 3.08-3.23 (m, 6H), 2.22 (s, 3H), 1.85-1.92 (m, 2H), 1.62-1.73 (brm, 2H). | 494.2 |
| 38 | (structure) | J | 30 | 8.60 (s, 1H), 8.04 (s, 1H), 7.25 (d, J = 8.0 Hz, 1H), 6.98 (d, J = 5.6 Hz, 1H), 6.73 (d, J = 8.0 Hz, 1H), 6.44 (d, J = 2.0 Hz, 1H), 3.23 (brs, 6H), 3.12 (brs, 4H), 2.59 (brs, 4H), 2.39 (d, J = 9.6 Hz, 2H), 2.33 (brs, 3H), 1.94 (m, 1H), 1.58 (m, 8H), 0.81 (m, 2H), 0.59 (m, 2H). | 546.5 |
| 39 | (structure) | J | 29 | 8.67 (s, 1H), 8.02 (s, 1H), 7.15 (d, J = 8.4 Hz, 1H), 6.89 (s, 1H), 6.76-6.81 (m, 2H), 4.12 (t, J = 5.2 Hz, 2H), 3.25-3.38 (m, 7H), 3.13 (brs, 4H), 2.97 (brs, 4H), 2.51-2.59 (m, 4H), 1.88 (t, J = 6.1 Hz, 2H), 1.63 (brs, 2H), 1.06 (t, J = 7.5 Hz, 3H). | 522.4 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 40 | (structure: 5-Br pyrimidine with 2-cyclopropyl-4-(4-methylpiperazin-1-yl)phenylamino and propyl-1,3-oxazinan-2-one) | I | 12 | 8.05 (s, 1H), 7.86 (s, 1H), 7.34 (d, J = 8.5 Hz, 1H), 6.82 (m, 1H), 6.71 (d, J = 8.2 Hz, 1H), 6.44 (s, 1H), 4.12 (s, 2H), 3.27 (m, 2H), 3.17 (brs, 4H), 3.04 (brs, 4H), 2.42 (brs, 4H), 2.20 (s, 3H), 1.91 m, 2H), 1.69 (brs, 2H), 1.03 (m, 1H), 0.82 (m, 2H), 0.57 (m, 2H). | 544.5 |
| 41 | (structure: 5-CF₃ pyrimidine with 2-cyclopropyl-4-(4-methylpiperazin-1-yl)phenylamino and propyl-1,3-oxazinan-2-one) | J | 13 | 8.25 (s, 1H), 8.05 (s, 1H), 7.34 (d, J = 8.7 Hz, 1H), 6.73 (dd, J = 2.6 and 8.7 Hz, 1H), 6.65 (brs, 1H), 6.49 (d, J = 2.5 Hz, 1H), 4.13 (t, J = 5.2 Hz, 2H), 3.33 (q, J = 6.4 Hz, 2H), 3.19 (m, 4H), 3.09 (m, 4H), 2.45 (m, 4H), 2.23 (s, 3H), 1.92 (m, 3H), 1.71 (m, 2H), 0.84 (m, 2H), 0.59 (m, 2H). | 534.2 |
| 41 | (structure: 5-CF₃ pyrimidine with 2-cyclopropyl-4-(4-methylpiperazin-1-yl)phenylamino and propyl-1,3-oxazinan-2-one) | J | 44 | 10.6 (brs, 1H), 7.32 (brs, 1H), 6.84 (d, J = 8.8 Hz, 1H), 6.54 (s, 1H), 4.12 (s, 2H), 3.79-3.82 (m, 2H), 3.48-3.45 (m, 2H), 3.30 (brs, 2H), 2.99-3.14 (m, 8H), 2.80 (s, 3H), 1.87-1.94 (m, 4H), 1.68 (brs, 1H), 0.87 (m, 2H), 0.65 (m, 2H). | 534.2 |

TABLE I-continued

Exemplary compounds.

| Example Number | Product | Method | Yield (%) | $^1$H NMR (400 MHz, DMSO-$d_6$): δ | LC-MS (m/z: (M + H$^+$) |
|---|---|---|---|---|---|
| 42 | | J | 6 | 8.58 (s, 1H), 8.04 (s, 1H), 7.23 (s, 1H), 6.90 (s, 1H), 6.73 (dd, J = 8.8 and 2.7 Hz, 1H), 6.43 (d, J = 2.7 Hz, 1H), 4.11 (m, 2H), 3.69 (m, 1H), 3.55 (m, 1H), 3.29 (m, 1H), 3.13 (s, 4H), 3.02 (d, 2H), 2.66 (m, 1H), 2.32 (m, 1H), 2.20 (m, 1H), 1.70-2.07 (brm, 11H), 1.35 (m, 1H), 0.81 (m, 2H), 0.57 (m, 2H). | 560.3 |
| 43 | | I | 7 | 8.08 (s, 1H), 7.74 (s, 1H), 7.13 (d, J = 8.5 Hz, 1H), 6.92 (m, 1H), 6.74 (d, J = 2.3 Hz, 1H), 6.71 (dd, J = 2.5 and 8.6 Hz, 1H), 4.12 (t, J = 5.1 Hz, 2H), 3.25 (m, 2H), 3.16 (m, 4H), 3.07 (m, 4H), 2.52 (m, 2H), 2.43 (m, 4H), 2.21 (s, 3H), 1.88 (m, 2H), 1.67 (m, 2H), 1.05 (t, J = 7.2 Hz, 3H). | 488.2 |
| 44 | | I | 9 | 7.83 (s, 1H), 7.74 (s, 1H), 7.20 (d, J = 8.6 Hz, 1H), 6.75 (d, J = 2.6 Hz, 1H), 6.71 (dd, J = 2.7 and 8.6 Hz, 1H), 6.49 (m, 1H), 4.14 (t, J = 5.3 Hz, 2H), 3.29 (m, 2H), 3.21 (m, 4H), 3.11 (m, 4H), 2.56 (m, 2H), 2.46 (m, 4H), 2.24 (s, 3H), 1.93 (m, 2H), 1.71 (m, 2H), 1.10 (t, J = 7.5 Hz, 3H). | 532.2 534.2 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 45 | (structure) | I | 11 | 7.71 (brs, 1H), 7.43 (s, 1H), 7.24 (d, J = 8.6 Hz, 1H), 6.72 (m, 3H), 4.13 (m, 2H), 3.3 (m, 4H), 3.21 (m, 4H), 3.09 (brs, 4H), 2.53 (m, 4H), 2.26 (s, 3H), 1.90 (m, 2H), 1.71 (m, 2H), 1.38 (m, 1H), 1.06 (t, J = 8.6 Hz, 3H), 0.77 (m, 2H), 0.39 (m, 2H). | 494.5 |
| 46 | (structure) | J & K | 49 | 10.1 (brs, 1H), 9.28 (brs, 2H), 8.36 (brs, 1H), 7.31 (brs, 1H), 6.88-6.92 (m, 2H), 4.12 (brs, 2H), 2.96-3.46 (m, 12H), 2.52-2.61 (m, 2H), 2.50-2.52 (m, 2H), 1.88 (s, 2H), 1.69 (brs, 2H), 1.11 (t, J = 7.5 Hz, 3H). | 508.2 |
| 47 | (structure) | J | 52 | 8.25 (s, 1H), 8.05 (s, 1H), 7.33 (d, J = 8.7 Hz, 1H), 6.73 (dd, J = 2.6 and 8.7 Hz, 1H), 6.68 (brs, 1H), 6.49 (d, J = 2.4 Hz, 1H), 4.00 (s, 2H), 3.79 (t, J = 5.0 Hz, 2H), 3.25 (m, 6H), 3.08 (m, 4H), 2.46 (m, 4H), 2.23 (s, 3H), 1.94 (m, 1H), 1.71 (m, 2H), 0.84 (m, 2H), 0.58 (m, 2H). | 534.3 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 47 | | J | 55 | 10.5 (brs, 1H), 8.65 (s, 1H), 8.11 (s, 1H), 7.40 (d, J = 8.7 Hz, 1H), 7.00 (brs, 1H), 6.81 (dd, J = 2.6 and 8.6 Hz, 1H), 6.56 (d, J = 2.6 Hz, 1H), 4.00 (s, 2H), 3.80 (m, 2H), 3.74 (brs, 2H), 3.46 (brs, 6H), 3.33 (m, 2H), 3.28 (m, 4H), 2.82 (s, 3H), 1.96 (m, 1H), 1.72 (m, 2H), 0.87 (m, 2H), 0.63 (m, 2H). | 534.3 |
| 48 | | J | 24 | 8.66 (brs, 1H), 8.01 (brs, 1H), 7.06 (brs, 2H), 6.40-6.43 (m, 2H), 3.51-3.56 (m, 2H), 3.25-3.48 (m, 7H), 3.0-3.2 (brm, 4H), 2.32-2.38 (m, 1H), 2.17-2.24 (m, 3H), 1.57-1.66 (m, 6H), 1.06 (t, J = 7.5 Hz, 3H). | 516.2 |
| 49 | | J | 33 | 8.62 (s, 1H), 8.04 (s, 1H), 7.27 (d, J = 7.3 Hz, 1H), 7.01 (brs, 1H), 6.73 (dd, J = 2.2, 8.6 Hz, 1H), 6.43 (d, J = 2.0 Hz, 1H), 3.69 (s, 2H), 3.41 (brs, 4H), 3.20 (m, 4H), 3.07 (brs, 2H), 2.88 (s, 3H), 2.19 (brs, 2H), 1.94 (m, 1H), 1.61 (brs, 6H), 0.82 (m, 2H), 0.61 (m, 2H). | 546.5 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 50 | (structure: 2-(2-ethyl-4-morpholinophenylamino)-4-[3-(3-oxo-1,4-oxazepan-4-yl)propylamino]-5-trifluoromethylpyrimidine) | J | 36 | 8.62 (s, 1H), 8.02 (s, 1H), 7.13 (m, 1H), 6.90 (m, 1H), 6.76 (m, 1H), 6.72 (m, 1H), 4.08 (s, 2H), 3.74 (m, 6H), 3.35 (brm, 2H), 3.20 (brm, 4H), 3.06 (m, 4H), 2.50 (m, 2H), 1.76 (brm, 2H), 1.57 (brm, 2H, ), 1.06 (t, J = 7.5 Hz, 3H). | 523.4 |
| 51 | (structure: 2-(2-cyclopropyl-4-morpholinophenylamino)-4-[3-(3-oxo-1,4-oxazepan-4-yl)propylamino]-5-trifluoromethylpyrimidine) | J | 48 | 8.59 (s, 1H), 8.04 (s, 1H), 7.27 (m, 1H), 6.94 (brm, 1H), 6.74 (m, 1H), 6.44 (m, 1H), 4.08 (s, 2H), 3.74 (m, 6H), 3.36 (brm, 2H), 3.23 (brm, 4H), 3.05 (m, 4H), 1.96(m, 1H), 1.76 (brm, 2H), 1.60 (brm, 2H, ), 0.82 (m, 2H), 0.60 (m, 2H). | 535.4 |
| 52 | (structure: 2-(2-cyclopropyl-4-(4-methylpiperazin-1-yl)phenylamino)-4-[3-(3-oxo-1,4-oxazepan-4-yl)propylamino]-5-trifluoromethylpyrimidine) | J | 37 | 8.57 (s, 1H), 8.18 (s, 1H, FA), 8.04 (s, 1H), 7.24 (m, 1H), 6.93 (m, 1H), 6.73 (m, 1H), 6.43 (m, 1H), 4.08 (s, 2H), 3.2-3.7 (m, 6H), 3.20 (brm, 2H), 3.06 (m, 4H), 2.44 (m, 4H), 2.20 (s, 3H), 1.95 (m, 1H), 1.75 (brm, 2H), 1.60 (brm, 2H), 0.82 (m, 2H), 0.59 (m, 2H). | 594.4 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 52 | | J | 36 | 11.1 (brs, 1H), 10.23 (brs, 1H), 8.46 (brs, 1H), 7.36 (brs, 1H), 6.87 (d, J = 8.8 Hz, 1H), 6.56 (s, 1H), 4.08 (s, 2H), 3.83 (d, J = 8.8 Hz, 2H), 3.70-3.76 (m, 2H), 3.09-3.45 (brm, 12H), 2.78 (d, J = 4.4 Hz, 3H), 1.93 (brs, 1H), 1.75 (s, 2H), 1.63 (brs, 2H), 0.90 (m, 2H), 0.69 (m, 2H). | 594.4 |
| 53 | | J | 7 | 10.6 (brs, 1H), 9.69 (brs, 1H), 8.10 (brs, 3H), 6.93 (s, 1H), 4.39 (d, J = 13.7 Hz, 2H), 4.09 (s, 2H), 3.75 (d, J = 5.0 Hz, 2H), 3.49 (d, J = 11.3 Hz, 2H), 3.40 (brs, 2H), 3.24 (m, 6H), 3.07 (m, 2H), 2.80 (s, 3H), 2.54 (m, 2H), 1.77 (brs, 2H), 1.59 (brs, 2H), 1.12 (t, J = 7.5 Hz, 3H). | 537.55 |
| 54 | | J | 53 | 8.60 (s, 1H), 8.17 (s, 1H, FA), 8.01 (m, 1H), 7.10 (m, 1H), 6.90 (m, 1H), 6.74 (m, 1H), 6.73 (m, 1H), 4.08 (s, 2H), 3.74 (m, 2H), 3.40 (brm, 2H), 3.20 (brm, 4H), 3.06 (m, 4H), 2.4-2.6 (m, 6H), 2.21 (s, 3H), 1.75 (brm, 2H), 1.57 (brm, 2H, ), 1.07 (t, J = 7.5 Hz, 3H). | 536.4 |

TABLE I-continued
Exemplary compounds.
| Example Number | Product | Method | Yield (%) | $^1$H NMR (400 MHz, DMSO-$d_6$): δ | LC-MS (m/z: (M + H$^+$) |
|---|---|---|---|---|---|
| 55 | 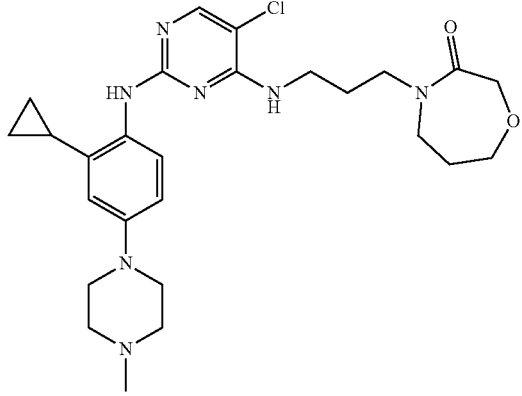 | I | 32 | 10.6 (brs, 1H), 8.19 (brs, 1H), 7.82 (s, 1H), 7.42 (d, J = 8.6 Hz, 1H), 7.13 (brs, 1H), 6.77 (dd, J = 2.3 and 8.7 Hz, 1H), 6.51 (d, J = 2.1 Hz, 1H), 4.09 (s, 2H), 3.74 (t, J = 5.2 Hz, 2H), 3.41 (m, 2H), 3.32 (m, 3H), 3.28 (m, 5H), 3.01 (brs, 4H), 2.79 (s, 3H), 1.96 (m, 1H), 1.77 (m, 2H), 1.66 (m, 2H), 0.84 (m, 2H), 0.60 (m, 2H). | 514.4 |
| 56 | 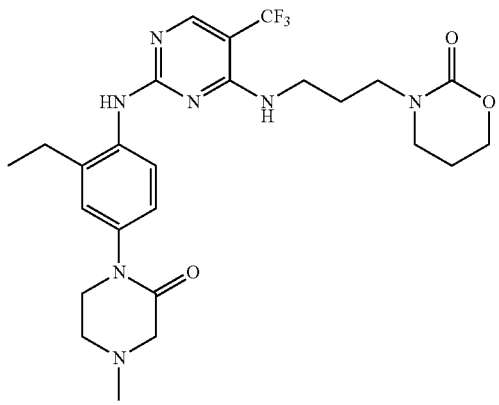 | I | 14 | 8.65 (s, 1H), 8.02 (s, 1H), 7.14 (d, J = 8.0 Hz, 1H), 6.88 (brs, 1H), 6.77 (m, 2H), 4.12 (m, 2H), 3.72 (s, 2H), 3.42 (m, 4H), 3.30 (m, 2H), 3.14 (brs, 4H), 2.89 (s, 3H), 2.50 (m, 2H), 1.89 (d, J = 7.2 Hz, 2H), 1.63 (brs, 2H), 1.07 (t, J = 7.2 Hz, 3H). | 536.43 |
| 57 | 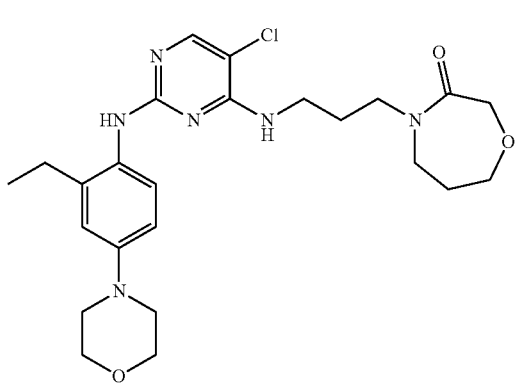 | I | 36 | 8.07 (s, 1H), 7.74 (s, 1H), 7.16 (d, J = 8.6 Hz, 1H), 6.94 (t, J = 5.9 Hz, 1H), 6.76 (s, 1H), 6.71-6.73 (m, 1H), 4.08 (s, 2H), 3.71-3.74 (m, 6H), 3.37-3.39 (m, 2H), 3.21-3.26 (m, 4H), 3.03-3.07 (m, 4H), 2.51-2.55 (m, 2H), 1.74-1.77 (m, 2H), 1.59-1.65 (m, 2H), 1.06 (t, J = 7.5 Hz, 3H). | 489.4 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 58 | (structure: 5-chloro-N2-(2-ethyl-4-(4-methylpiperazin-1-yl)phenyl)-N4-(3-(3-oxo-1,4-oxazepan-4-yl)propyl)pyrimidine-2,4-diamine) | I | 25 | 8.14 (s, 1H, FA), 8.05 (s, 1H), 7.74 (s, 1H), 7.14 (d, J = 8.6 Hz, 1H), 6.93 (t, J = 5.9 Hz, 1H), 6.75 (d, J = 2.7 Hz, 1H), 6.71 (dd, J = 8.7 and 2.7 Hz, 1H), 4.08 (s, 2H), 3.73 (t, J = 5.5 Hz, 2H), 3.37-3.39 (m, 2H), 3.21-3.25 (m, 4H), 3.08 (t, J = 4.8 Hz, 4H), 2.51-2.52 (m, 2H), 2.47 (s, 4H), 2.23 (s, 3H), 1.76 (t, J = 5.6 Hz, 2H), 1.63 (m, 2H), 1.05 (t, J = 7.5 Hz, 3H). | 502.4 |
| 59 | (structure: 5-chloro-N2-(2-cyclopropyl-4-morpholinophenyl)-N4-(3-(3-oxo-1,4-oxazepan-4-yl)propyl)pyrimidine-2,4-diamine) | I | 40 | 8.02 (s, 1H), 7.78 (s, 1H), 7.38 (d, J = 8.8 Hz, 1H), 7.00 (t, J = 5.8 Hz, 1H), 6.72 (dd, J = 8.8, 2.7 Hz, 1H), 6.46 (d, J = 2.7 Hz, 1H), 4.08 (s, 2H), 3.70-3.74 (m, 6H), 3.39-3.41 (m, 2H), 3.26 (q, J = 7.0 Hz, 4H), 3.02 (t, J = 4.6 Hz, 4H), 1.93 (m, 1H), 1.76 (t, J = 5.6 Hz, 2H), 1.65 (p, J = 6.9 Hz, 2H), 0.82 (m, 2H), 0.56 (m, 2H). | 502.4 |
| 60 | (structure: N2-(4-(4-ethylpiperazin-1-yl)-2-isopropylphenyl)-N4-(3-(3-oxo-1,4-oxazepan-4-yl)propyl)-5-(trifluoromethyl)pyrimidine-2,4-diamine) | J | 29 | 8.61 (s, 1H), 8.00 (s, 1H), 7.03 (d, J = 8.1 Hz, 1H), 6.88 (m, 1H), 6.80 (d, J = 2.4 Hz, 1H), 6.71 (dd, J = 2.4 and 8.7 Hz, 1H), 4.08 (s, 2H), 3.73 (m, 2H), 3.34 (m, 2H), 3.19 (brs, 4H), 3.10 (brs, 6H), 2.92 (m, 1H), 2.35 (m, 2H), 1.90 (s, 2H), 1.76 (m, 2H), 1.56 (m, 2H), 1.10 (d, J = 6.9 Hz, 6H), 1.03 (t, J = 7.1 Hz, 3H). | 564.6 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 61 | | I | 9 | ¹H NMR (400 MHz, DMSO-d₆ at HT): 7.74 (brs, 1H), 7.44 (s, 1H), 7.32 (d, J = 8.6 Hz, 1H), 6.78 (m, 2H), 6.74 (dd, J = 2.4, 8.6 Hz, 1H), 4.11 (s, 2H), 3.75 (t, J = 5.6 Hz, 2H), 3.42 (m, 2H), 3.35 (m, 4H), 3.16 (m, 4H), 2.65 (m, 4H), 2.54 (m, 2H), 2.37 (s, 3H), 1.82 (m, 2H), 1.72 (m, 2H), 1.45 (m, 1H), 1.11 (t, J = 7.4 Hz, 3H), 0.82 (m, 2H), 0.46 (m, 2H). | 508.3 |
| 62 | | J & K | 72 | 8.58 (s, 1H), 8.04 (s, 1H), 7.25 (s, 1H), 6.94 (s, 1H), 6.72 (d, J = 9.0 Hz, 1H), 6.43 (s, 1H), 4.08 (s, 3H), 3.74 (m, 2H), 3.16 (d, 3H), 3.03 (m, 4H), 2.88 (s, 4H), 1.90-1.95 (m, 1H), 1.76 (s, 2H), 1.60 (s, 2H), 0.80 (m, 2H), 0.56 (m, 2H). | 534.2 |
| 63 | | J, K & L | 23 | 8.20 (s, 1H), 8.01 (s, 1H), 7.06 (d, J = 8.4 Hz, 1H), 6.60 (m, 1H), 6.52 (m, 2H), 4.09 (s, 2H), 3.74 (t, J = 5.5 Hz, 2H), 3.49 (m, 2H), 3.44 (m, 2H), 3.38 (m, 2H), 3.24 (m, 4H), 2.64 (m, 2H), 2.54 (m, 2H), 2.28 (s, 3H), 1.90 (m, 4H), 1.80 (m, 2H), 1.64 (q, J = 6.4 Hz, 2H), 1.09 (t, J = 7.5 Hz, 3H). | 550.4 |

TABLE I-continued
Exemplary compounds.
| Example Number | Product | Method | Yield (%) | $^1$H NMR (400 MHz, DMSO-$d_6$): δ | LC-MS (m/z: (M + H$^+$) |
|---|---|---|---|---|---|
| 64 | 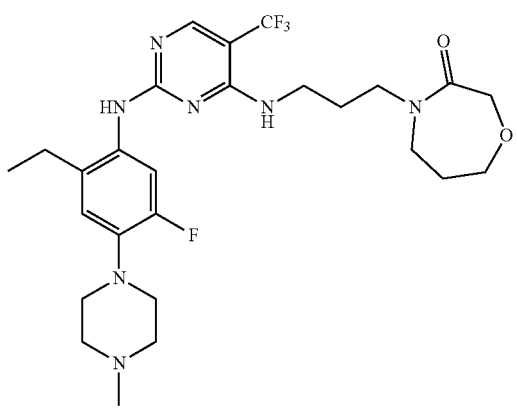 | J | 33 | 8.74 (s, 1H), 8.07 (s, 1H), 7.19 (d, J = 14.2 Hz, 1H), 7.01 (s, 1H), 6.82 (d, J = 9.8 Hz, 1H), 4.08 (s, 2H), 3.73 (s, 2H), 3.20-3.42 (m, 7 H), 3.00 (s, 4H), 2.51-2.5 (m, 4H), 2.26 (brs, 3H), 1.76 (brs, 2H), 1.61 (brs, 2H), 1.05 (t, J = 7.8 Hz, 3H). | 554.2 |
| 65 | 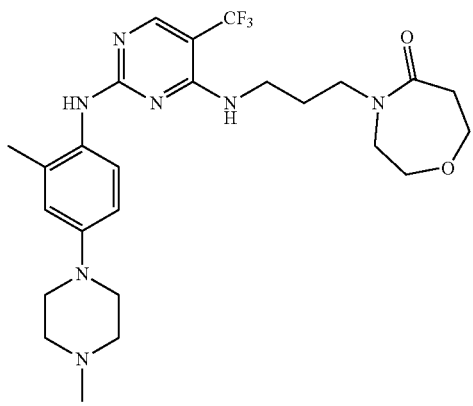 | J | 30 | 8.61 (brs, 1H), 8.15 (s, 1H, FA), 8.03 (brs, 1H), 7.16 (brm, 1H), 6.92(brm, 1H), 6.77 (s, 1H), 6.72 (m, 1H), 3.57-3.63 (m, 4H), 3.32-3.40 (m, 3H), 3.17-3.28 (m, 3H), 3.08 (m, 4H), 2.57-2.65 (m, 2H), 2.42-2.52 (m, 4H), 2.23 (s, 3H), 2.13 (s, 3H), 1.55 (brm, 2H). | 522.4 |
| 66 | 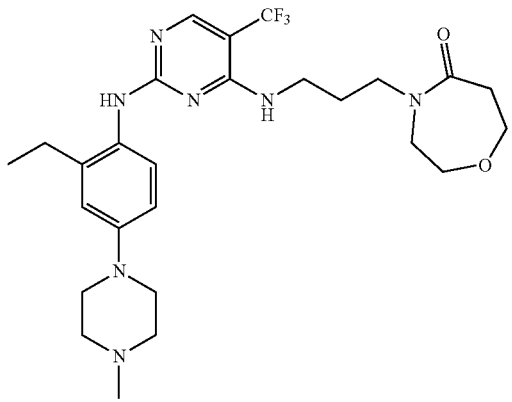 | J | 42 | 8.62 (s, 1H), 8.02 (s, 1H), 7.11 (brs, 1H), 6.92 (m, 1H), 6.77 (m, 1H), 6.73 (d, J = 8.6 Hz, 1H), 3.60 (brs, 4H), 3.20 (brs, 4H), 3.09 (brs, 5H), 2.60 (brs, 3H), 2.36 (brs, 6H), 2.21 (s, 3H), 1.54 (m, 2H), 1.05 (t, J = 7.4 Hz, 3H). | 536.2 |

TABLE I-continued
Exemplary compounds.
| Example Number | Product | Method | Yield (%) | $^1$H NMR (400 MHz, DMSO-$d_6$): δ | LC-MS (m/z: (M + H$^+$) |
|---|---|---|---|---|---|
| 67 | 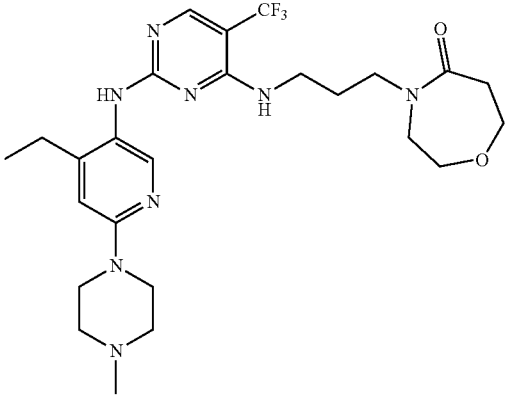 | J | 10 | 10.8 (brs, 1H), 9.12 (s, 1H), 8.14 (s, 1H), 8.09 (s, 1H), 7.30 (brs, 1H), 6.86 (s, 1H), 4.36 (m, 2H), 3.63 (m, 4H), 3.50 (m, 4H), 3.40 (m, 2H), 3.24 (m, 4H), 3.08 (brs, 2H), 2.82 (s, 3H), 2.60 (m, 4H), 1.62 (m, 2H), 1.14 (t, J = 7.5 Hz, 3H). | 537.6 |
| 68 | 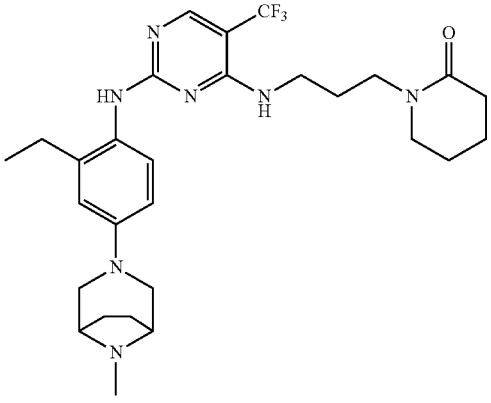 | J | 48 | 8.59 (s, 1 H), 7.99 (s, 1H), 7.07 (brs, 1H), 6.94 (s, 1H), 6.64 (brs, 2H), 2.62-3.28 (m, 12H), 1.95-2.38 (s, 8H), 1.50-1.80 (m, 9H), 1.04 (t, J = 7.5 Hz, 3H). | 546.4 |
| 69 | 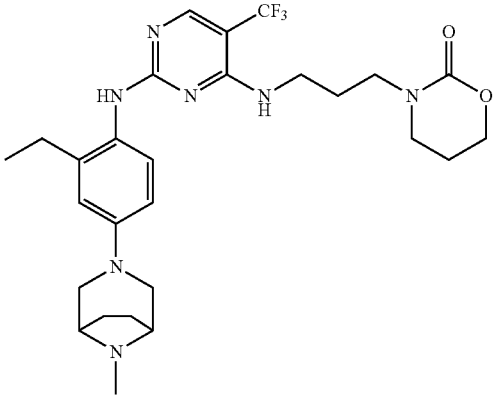 | J | 41 | 11.0 (brs, 1H), 10.10 (brs, 1H), 8.36 (brs, 1H), 7.30 (brd, J = 16.6 Hz, 1H), 6.83 (t, J = 10.0 Hz, 2H), 3.92-4.19 (m, 4H), 3.70 (brd, 2H), 3.05-3.54 (brm, 7 H), 2.72 (d, J = 4.8 Hz, 3H), 2.56 (brs, 2H), 2.16-2.21 (m, 3H), 1.64-1.93 (brm, 6H), 1.10 (t, J = 7.5 Hz, 3H). | 548.3 |

TABLE I-continued

Exemplary compounds.

| Example Number | Product | Method | Yield (%) | $^1$H NMR (400 MHz, DMSO-$d_6$): δ | LC-MS (m/z: (M + H$^+$) |
|---|---|---|---|---|---|
| 70 | | J | 18 | 11.2 (brs, 1H), 10.3 (brs, 1H), 8.52 (brs, 1H), 7.31 (brm, 1H), 6.88 (d, J = 8.8 Hz, 1H), 6.56 (s, 1H), 3.78-3.87 (m, 2H), 3.0-3.7 (m, 16H), 2.78 (s, 3H), 2.55-2.64 (m, 2H), 1.88-1.97 (m, 1H), 1.5-1.7 (m, 2H), 0.90 (m, 2H), 0.70 (m, 2H). | 548.4 |
| 71 | | J | 56 | 8.59 (s, 1H), 8.04 (s, 1H), 7.26 (d, J = 8.6 Hz, 1H), 6.92-6.93 (m, 1H), 6.72 (dd, J = 8.8, 2.6 Hz, 1H), 6.44 (s, 1H), 3.71 (t, J = 4.5 Hz, 4H), 3.56-3.64 (m, 4H), 3.32-3.39 (m, 2H), 3.17-3.29 (m, 4H), 3.04 (t, J = 4.5 Hz, 4H), 2.58-2.62 (m, 2H), 1.90-1.96 (m, 1H), 1.51-1.62 (m, 2H), 0.81 (m, 2H), 0.58 (m, 2H). | 535.4 |
| 72 | | J | 34 | 8.62 (s, 1H), 8.02 (s, 1H), 7.13 (d, J = 8.5 Hz, 1H), 6.90 (t, J = 5.7 Hz, 1H), 6.78 (d, J = 2.7 Hz, 1H), 6.73 (m, 1H), 3.72 (t, J = 4.6 Hz, 4H), 3.55-3.64 (m, 4H), 3.32-3.39 (m, 2H), 3.12-3.28 (m, 4H), 3.06 (t, J = 4.6 Hz, 4H), 2.56-2.64 (m, 2H), 2.52 (q, J = 7.5 Hz, 2H), 1.54 (brm, 2H), 1.06 (t, J = 7.5 Hz, 3H). | 523.4 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 73 | | J | 16 | 8.62 (s, 1H), 8.00 (s, 1H), 7.03 (d, J = 8.0 Hz, 1H), 6.88 (m, 1H), 6.81 (d, J = 1.8 Hz, 1H), 6.72 (d, J = 8.6 Hz, 1H), 3.60 (brs, 4H), 3.31 (s, 2H), 3.19 (brs, 5H), 3.10 (s, 6H), 2.60 (brs, 2H), 2.36 (d, J = 6.8 Hz, 4H), 1.52 (brs, 2H), 1.09 (d, J = 6.8 Hz, 6H), 1.03 (t, J = 7.5 Hz, 3H). | 564.1 |
| 74 | | J | 51 | 8.62 (s, 1H), 8.02 (s, 1H), 7.11 (brs, 1H), 6.92 (s, 1H), 6.67 (m, 2H), 3.42-3.70 (m, 7H), 2.61-3.39 (brm, 12H), 1.5-2.4 (m, 10H), 1.07 (t, J = 7.5 Hz, 3H). | 562.4 |
| 75 | | J & K | 81 | 10.2 (brs, 1H), 9.26 (brs, 1H), 8.42 (brs, 1H), 7.33 (brs, 1H), 6.94 (s, 1H), 6.89 (brd, J = 8.7 Hz, 1H), 3.1-3.7 (brm, 18H), 2.57-2.65 (brm, 2H), 2.21 (s, 3H), 1.50-1.65 (m, 2H). | 508.2 |

TABLE I-continued

Exemplary compounds.

| Example Number | Product | Method | Yield (%) | ¹H NMR (400 MHz, DMSO-$d_6$): δ | LC-MS (m/z: (M + H⁺) |
|---|---|---|---|---|---|
| 76 | | I | 5 | 8.10 (s, 1H), 7.81 (s, 1H), 7.13 (d, J = 8.6 Hz, 1H), 6.69-6.80 (m, 3H), 3.60 (t, J = 6.8 Hz, 4H), 3.37 (s, 3H), 3.12-3.25 (m, 8 H), 2.52-2.61 (m, 6H), 2.27 (s, 3H), 1.57 (t, J = 7.1 Hz, 2H), 1.05 (t, J = 7.5 Hz, 3H). | 546.4 |
| 77 | | I | 8 | 8.09 (s, 1H), 7.80 (s, 1H), 7.04 (d, J = 8.6 Hz, 1H), 6.76 (m, 2H), 6.70 (dd, J = 2.5, 8.7 Hz, 1H), 4.08 (s, 2H), 3.74 (m, 2H), 3.36 (m, 2H), 3.22 (m, 4H), 3.09 (m, 4H), 2.53 (m, 1H), 2.44 (m, 4H), 2.21 (s, 3H), 1.76 (m, 2H), 1.59 (m, 2H), 1.09 (d, J = 6.8 Hz, 6H). | 560.5 562.5 |
| 78 | | J | 20 | 9.58 (brs, 1H), 8.18 (s, 1H), 7.90 (s, 1H), 7.17 (d, J = 8.5 Hz, 1H), 6.54 (s, 1H), 6.50 (d, J = 8.5 Hz, 1H), 4.61 (s, 1H), 4.53 (s, 1H), 3.77 (d, J = 7.1 Hz, 1H), 3.69 (d, J = 7.2 Hz, 1H), 3.62 (m, 4H), 3.48 (d, J = 9.2 Hz, 1H), 3.37 (m, 4H), 3.25 (m, 2H), 3.01 (d, J = 9.2 Hz, 1H), 2.61 (m, 2H), 2.18 (s, 3H), 1.92 (m, 1H), 1.85 (m, 1H), 1.65 (m, 2H). | 521.4 |

TABLE I-continued
Exemplary compounds.
| Example Number | Product | Method | Yield (%) | $^1$H NMR (400 MHz, DMSO-$d_6$): δ | LC-MS (m/z: (M + H$^+$) |
|---|---|---|---|---|---|
| 79 | 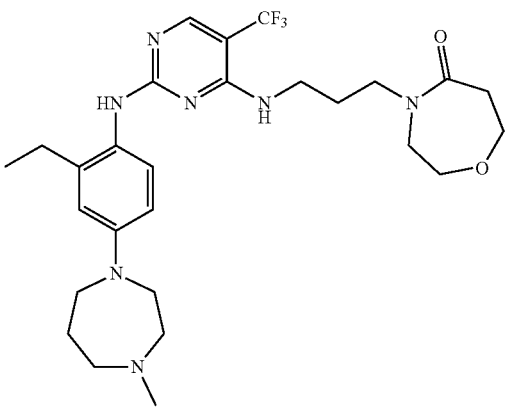 | J, K & L | 14 | 8.25 (s, 1H), 8.01 (s, 1H), 7.11 (d, J = 8.3 Hz, 1H), 6.57 (m, 3H), 3.62 (m, 6H), 3.47 (t, J = 6.0 Hz, 2H), 3.38 (m, 2H), 3.26 (m, 4H), 3.13 (brs, 4H), 2.65 (s, 3H), 2.61 (m, 2H), 2.53 (m, 2H), 2.10 (m, 2H), 1.61 (q, J = 6.7 Hz, 2H), 1.10 (t, J = 7.4 Hz, 3H). | 550.5 |
| 80 | 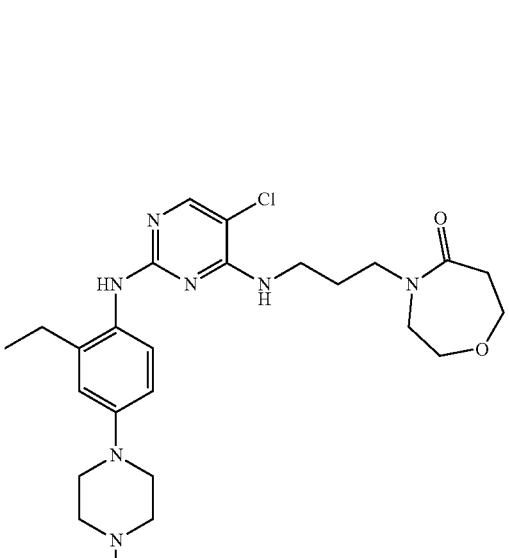 | I | 52 | 8.14 (s, 1H, FA), 8.05 (s, 1H), 7.73 (s, 1H), 7.13 (d, J = 8.6 Hz, 1H), 6.93 (t, J = 5.9 Hz, 1H), 6.75 (d, J = 2.8 Hz, 1H), 6.71 (dd, J = 8.7 and 2.8 Hz, 1H), 3.58-3.63 (m, 4H), 3.36-3.39 (m, 2H), 3.21-3.27 (m, 4H), 3.09 (m, 4H), 2.59 (m, 2H), 2.51-2.54 (m, 6H), 2.24 (s, 3H), 1.55-1.62 (m, 2H), 1.05 (t, J = 5.3 Hz, 3H). | 502.4 |
| 81 | 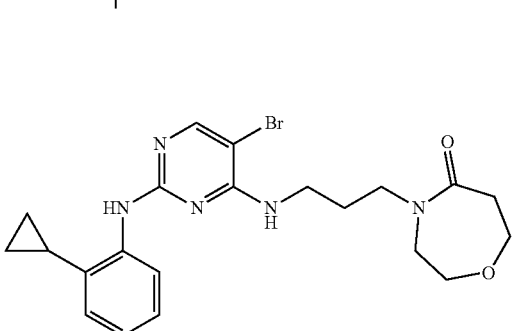 | I | 34 | 8.14 (s, 1H, FA), 8.02 (s, 1H), 7.85 (s, 1H), 7.34 (d, J = 8.7 Hz, 1H), 6.83 (t, J = 5.9 Hz, 1H), 6.70 (d, J = 8.9 Hz, 1H), 6.44 (s, 1H), 3.60 (brs, 4H), 3.38 (brs, 2H), 3.26 (t, J = 7.4 Hz, 4H), 3.04-3.04 (m, 4H), 2.59-2.62 (m, 2H), 2.43 (brs, 4H), 2.21 (s, 3H), 1.89-1.93 (m, 1H), 1.56-1.64 (m, 2H), 0.81 (m, 2H), 0.56 (m 2H). | 556.2 |

TABLE I-continued

Exemplary compounds.

| Example Number | Product | Method | Yield (%) | $^1$H NMR (400 MHz, DMSO-$d_6$): δ | LC-MS (m/z: (M + H$^+$) |
|---|---|---|---|---|---|
| 82 | | I | 44 | 8.15 (s, 1H, FA), 8.00 (s, 1H), 7.78 (s, 1H), 7.35 (d, J = 8.7 Hz, 1H), 6.99 (t, J = 5.9 Hz, 1H), 6.70 (dd, J = 8.8, 2.7 Hz, 1H), 6.44 (d, J = 2.7 Hz, 1H), 3.61 (m, 4H), 3.38 (m, 2H), 3.28 (bm, 4H), 3.04 (4H, m), 2.59-2.61 (m, 2H), 2.45 (t, J = 4.8 Hz, 4H), 2.22 (s, 3H), 1.92 (m, 1H), 1.59-1.65 (m, 2H), 0.81 (m, 2H), 0.55 (m, 2H). | 514.2 |
| 83 | | I | 32 | 9.65 (s, 1H), 8.36 (s, 1H), 7.34 (brs, 1H), 7.22 (d, J = 8.3 Hz, 1H), 6.95 (s, 1H), 6.90 (m, 1H), 3.87 (m, 4H), 3.61 (brs, 4H), 3.53 (m, 2H), 3.41 (brs, 2H), 3.36 (brs, 2H), 3.29 (brs, 2H), 3.14 (m, 2H), 2.94 (m, 2H), 2.88 (s, 3H), 2.61 (m, 2H), 1.65 (m, 2H), 1.49 (m, 1H), 1.10 (t, J = 7.4 Hz, 3H), 0.89 (m, 2H), 0.54 (m, 2H). | 508.3 |
| 84 | | J & K | 95 | 8.59 (s, 1H), 8.01 (s, 1H), 7.10 (s, 1H), 6.90 (t, J = 5.7 Hz, 1H), 6.75 (s, 1H), 6.71 (d, J = 8.9 Hz, 1H), 3.57-3.64 (m, 4H), 3.32-3.41 (m, 2H), 3.10-3.27 (m, 4H), 2.99 (t, J = 4.8 Hz, 4H), 2.81 (t, J = 4.7 Hz, 4H), 2.56-2.63 (m, 2H), 2.50-2.54 (m, 2H), 1.54 (brs, 2H), 1.05 (t, J = 7.5 Hz, 3H) [Note: spectrum as free base, one NH missing] | 522.2 |

TABLE I-continued

Exemplary compounds.

| Example Number | Product | Method | Yield (%) | $^1$H NMR (400 MHz, DMSO-$d_6$): δ | LC-MS (m/z: (M + H$^+$) |
|---|---|---|---|---|---|
| 85 | | J & K | 86 | 10.2 (brs, 1H), 9.29 (brs, 1H), 8.50 (brs, 1H), 7.35 (brs, 1H), 6.86 (d, J = 8.7 Hz, 1H), 6.56 (s, 1H), 3.55-3.64 (m, 6H), 3.35-3.43 (m, 6H), 3.15-3.23 (m, 6H), 2.54-2.64 (m, 2H), 1.88-1.96 (m, 1H), 1.52-1.65 (m, 2H), 0.85-0.93 (m, 2H), 0.68 (m, 2H). | 534.2 |
| 86 | | J | 10 | 8.77 (s, 1H), 8.09 (s, 1H), 7.22 (d, J = 14.1 Hz, 1H), 7.04 (t, J = 5.8 Hz, 1H), 6.86 (d, J = 9.8 Hz, 1H), 3.63 (d, J = 8.9 Hz, 5H), 3.36-3.43 (m, 2H), 3.23-3.32 (m, 4H), 2.92-3.05 (brm, 4H), 2.61-2.65 (m, 4H), 2.54-2.59 (m, 2H), 2.37 (brs, 4H), 1.60 (t, J = 7.3 Hz, 2H), 1.25 (s, 1H), 1.08 (t, J = 7.5 Hz, 3H). | 554.3 |
| 87 | | I | 26 | 8.10 (s, 1H), 7.79 (s, 1H), 7.03 (d, J = 8.6 Hz, 1H), 6.78 (m, 2H), 6.69 (dd, J = 2.5, 8.6 Hz, 1H), 3.61 (brs, 4H), 3.36 (brs, 2H), 3.21 (m, 4H), 3.09 (m, 5H), 2.60 (m, 2H), 2.44 (m, 4H), 2.21 (s, 3H), 1.56 (m, 2H), 1.09 (d, J = 6.8 Hz, 6H). | 560.5 562.5 |

TABLE I-continued

Exemplary compounds.

| Example Number | Product | Method | Yield (%) | $^1$H NMR (400 MHz, DMSO-$d_6$): δ | LC-MS (m/z: (M + H$^+$)) |
|---|---|---|---|---|---|
| 88 | | I | 10 | 8.08 (s, 1H), 7.72 (s, 1H), 7.03 (d, J = 8.6 Hz, 1H), 6.92 (brs, 1H), 6.78 (d, J = 2.3 Hz, 1H), 6.69 (dd, J = 2.4 and 8.8 Hz, 1H), 3.61 (brs, 4H), 3.36 (brs, 2H), 3.23 (brs, 4H), 3.08 (brs, 5H), 2.60 (m, 2H), 2.44 (brs, 4H), 2.21 (s, 3H), 1.57 (m, 2H), 1.09 (d, J = 6.8 Hz, 6H). | 516.4 |
| 89 | | I & K | 10 | 9.12 (brs, 2H), 8.67 (brs, 1H), 7.94 (s, 1H), 7.28 (brs, 1H), 6.85 (d, J = 8.8 Hz, 1H), 6.55 (s, 1H), 3.70 (m, 2H), 3.66 (m, 2H), 3.57-3.63 (m, 4H), 3.49 (m, 2H), 3.46 (m, 2H), 3.25-3.36 (m, 2H), 3.16-3.23 (m, 4H), 2.57-2.63 (m, 2H), 1.88 (m, 1H), 1.65 (m, 2H), 0.88 (m, 2H), 0.67 (m, 2H). | 500.2 |
| 90 | | J | 12 | 8.44 (s, 1H), 8.02 (d, J = 7.4 Hz, 2H), 6.74 (m, 1H), 6.67 (s, 1H), 3.70 (m, 4H), 3.41 (m, 4H), 3.25 (m, 4H), 3.16 (m, 2H), 2.21 (m, 2H), 2.14 (s, 3H), 1.65 (m 6H). | 494.34 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 91 | | J | 21 | 8.70 (s, 1H), 8.03 (s, 1H), 7.96 (s, 1H), 7.02 (s, 1H), 6.70 (s, 1H), 3.42 (brs, 4H), 3.15 (brs, 5H), 2.38 (brs, 4H), 2.20 (s, 5H), 2.11 (s, 3H), 1.62 (m, 7H). | 507.4 |
| 92 | | M | 25 | 8.07 (s, 1H), 7.86 (s, 1H), 7.07 (d, J = 8.5 Hz, 1H), 6.80 (s, 1H), 6.75 (m, 1H), 5.94 (brs, 1H), 5.57 (s, 1H), 3.61 (m, 4H), 3.39 (m, 2H), 3.27 (m, 2H), 3.10 (m, 4H), 2.98 (m, 2H), 2.60 (m, 2H), 2.54 (m, 2H), 2.44 (brs, 4H), 2.21 (s, 3H), 1.57 (m, 2H), 1.06 (t, J = 7.4 Hz, 3H). | 535.5 |
| 93 | | J | 31 | 8.05 (s, 1H), 7.09 (brs, 1H), 6.42-6.45 (m, 2H), 3.15-3.57 (m, 13H), 2.42-2.46 (m, 2H), 2.32-2.37 (m, 1H), 2.18-2.25 (m, 3H), 1.64-1.67 (s, 6H), 1.07 (t, J = 7.5 Hz, 3H). | 516.2 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 94 | | M | 21 | 8.12 (s, 1H), 7.88 (s, 1H), 7.10 (d, J = 8.6 Hz, 1H), 6.71 (dd, J = 2.4 and 8.6 Hz, 1H), 6.38 (d, J = 2.2 Hz, 1H), 5.97 (brs, 1H), 5.63 (s, 1H), 3.24 (m, 2H), 3.15 (brs, 2H), 3.07 (brs, 4H), 2.97 (m, 2H), 2.44 (brs, 4H), 2.21 (s, 3H), 2.19 (m, 2H), 1.91 (m, 1H), 1.63 (m, 6H), 0.82 (m, 2H), 0.60 (m, 2H). | 531.3 |
| 95 | | M | 18 | 8.14 (s, 1H), 7.95 (s, 1H), 7.86 (s, 1H), 6.72 (s, 1H), 6.03 (brs, 1H), 5.65 (s, 1H), 3.42 (brs, 4H), 3.27 (m, 2H), 3.18 (m, 2H), 3.01 (m, 2H), 2.38 (m, 4H), 2.20 (brs, 5H), 2.09 (s, 3H), 1.68 (m, 6H). | 506.5 |
| 96 | | M | 11 | 8.18 (s, 1H), 7.98 (s, 1H), 7.86 (s, 1H), 6.73 (s, 1H), 6.05 (brs, 1H), 5.68 (s, 1H), 3.69 (m, 4H), 3.38 (m, 4H), 3.27 (m, 2H), 3.19 (m, 2H), 3.02 (m, 2H), 2.20 (m, 2H), 2.11 (s, 3H), 1.67 (m, 6H). | 493.4 |

TABLE I-continued

Exemplary compounds.

| Example Number | Product | Method | Yield (%) | $^1$H NMR (400 MHz, DMSO-$d_6$): δ | LC-MS (m/z: (M + H$^+$)) |
|---|---|---|---|---|---|
| 98 | | I | 17 | 7.98 (s, 1H), 7.81 (s, 1H), 7.29 (d, J = 8.7 Hz, 1H), 6.78 (t, J = 5.9 Hz, 1H), 6.66 (dd, J = 8.8 and 2.8 Hz, 1H), 6.39 (d, J = 2.8 Hz, 1H), 4.04 (s, 2H), 3.68 (t, J = 5.5 Hz, 2H), 3.34 (m, 2H), 3.21(m, 4H), 3.00 (t, J = 4.8 Hz, 4H), 2.38 (t, J = 4.8 Hz, 4H), 2.15 (s, 3H), 1.84-1.9 (m, 1H), 1.70-1.73 (m, 2H), 1.59 (m, 2H), 0.75-0.79 (m, 2H), 0.49-0.52 (m, 2H). | 546.2 548.2 |
| 99 | | J & K | 41 | 9.24 (brs, 2H), 6.85 (dd, J = 8.8 and 2.7 Hz, 1H), 6.55 (d, J = 2.7 Hz, 1H), 4.12 (brs, 2H), 3.33-3.40 (brs, 6H), 3.06-3.26 (m, 9H), 1.89 (brs, 3H), 1.68 (brs, 2H), 0.89 (d, J = 8.0 Hz, 2H), 0.67 (m, 2H). | 520.2 |
| 100 | | I | 34 | 8.07 (s, 1H), 7.80 (s, 1H), 7.12 (d, J = 8.6 Hz, 1H), 6.68-6.77 (m, 3H), 4.07 (s, 2H), 3.72 (t, J = 5.5 Hz, 2H), 3.37(m, 2H), 3.24(m, 4H), 3.07 (t, J = 4.8 Hz, 4H), 2.52 (m, 2H), 2.43 (t, J = 4.8 Hz, 4H), 2.20 (s, 3H), 1.75 (t, J = 5.6 Hz, 2H), 1.60 (m, 2H), 1.03 (t, J = 6.4 Hz, 3H). | 546.2 548.2 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 101 | [structure] | J | 26 | 8.15 (s, 1H), 7.88 (s, 1H), 7.10 (d, J = 8.4 Hz, 1H), 6.71 (d, J = 7.4 Hz, 1H), 6.38 (s, 1H), 5.95 (brs, 1H), 5.62 (s, 1H), 3.60 (brs, 4H), 3.39 (m, 2H), 3.27 (m, 2H), 3.03 (m, 6H), 2.60 (m, 2H), 2.43 (m, 4H), 2.21 (s, 3H), 1.91 (m, 1H), 1.58 (m, 2H), 0.82 (m, 2H), 0.62 (m, 2H). | 547.6 |
| 102 | [structure] | M | 23 | 8.77 (s, 1H), 7.97 (s, 1H), 7.39 (d, J = 8.8 Hz, 2H), 6.86 (d, J = 8.9 Hz, 2H), 5.95 (m, 2H), 4.15 (m, 2H), 3.25 (m, 4H), 3.13 (m, 2H), 3.06 (m, 4H), 2.54 (m, 4H), 2.27 (s, 3H), 1.92 (m, 2H), 1.76 (m, 2H). | 493.4 |
| 103 | [structure] | M | 12 | 8.74 (s, 1H), 7.96 (s, 1H), 7.37 (d, J = 8.9 Hz, 2H), 6.86 (d, J = 8.9 Hz, 2H), 6.06 (m, 1H), 5.93 (s, 1H), 3.30 (m, 2H), 3.22 (m, 2H), 3.05 (m, 6H), 2.44 (m, 4H), 2.22 (m, 5H), 1.70 (m, 6H). | 491.4 |

TABLE I-continued

Exemplary compounds.

| Example Number | Product | Method | Yield (%) | ¹H NMR (400 MHz, DMSO-$d_6$): δ | LC-MS (m/z: (M + H⁺) |
|---|---|---|---|---|---|
| 104 | | M | 5 | 7.67 (s, 1H), 7.64 (s, 1H), 7.16 (d, J = 8.6 Hz, 1H), 6.69 (dd, J = 2.4, 8.6 Hz, 1H), 6.38 (d, J = 2.3 Hz, 1H), 5.93 (m, 1H), 5.72 (s, 1H), 3.61 (brs, 4H), 3.41 (brs, 2H), 3.31 (m, 2H), 3.05 (brs, 4H), 2.98 (m, 2H), 2.60 (m, 2H), 2.43 (brs, 4H), 2.20 (s, 3H), 1.92 (m, 1H), 1.62 (m, 2H), 0.82 (m, 2H), 0.59 (m, 2H). | 513.5 |
| 105 | | J | 45 | 8.59 (s, 1H), 8.01 (s, 1H), 7.10 (s, 1H), 6.89 (t, J = 5.7 Hz, 1H), 6.78 (d, J = 2.8 Hz, 1H), 6.73 (dd, J = 8.7 and 2.8 Hz, 1H), 3.73 (d, J = 11.0 Hz, 1H), 3.53-3.62 (m, 5 H), 3.34-3.45 (brm, 2H), 3.03-3.29 (brm, 6H), 2.66-2.71 (m, 1H), 2.57-2.62 (m, 2H), 2.51-2.53 (m, 2H), 2.35 (t, J = 10.6 Hz, 1H), 2.21 (td, J = 11.1 and 3.2 Hz, 1H), 2.00-2.07 (m, 2H), 1.78-1.83 (m, 1H), 1.60-1.73 (m, 2H), 1.54 (brs, 2H), 1.30-1.40 (m, 1H), 1.05 (t, J = 7.5 Hz, 3H). | 562.4 |
| 106 | | J | 41 | 8.60 (s, 1H), 8.01 (s, 1H), 7.10 (d, 1H), 6.86 (t, 1H), 6.78 (d, J = 2.8 Hz, 1H), 6.74 (dd, J = 8.7 and 2.8 Hz, 1H), 4.12 (t, J = 5.2 Hz, 2H), 3.73 (d, J = 11.0 Hz, 1H), 3.58 (d, J = 11.6 Hz, 1H), 2.99-3.27 (m, 8H), 2.68 (dt, J = 11.6 and 3.2 Hz, 1H), 2.51-2.53 (m, 2H), 2.33-2.37 (m, 1H), 2.20 (td, J = 11.1 and 3.2 Hz, 1H), 1.99-2.07 (m, 2H), 1.75-1.88 (m, 3H), 1.61-1.73 (m, 4H), 1.30-1.40 (m, 1H), 1.05 (t, J = 7.5 Hz, 3H). | 548.4 |

TABLE I-continued

Exemplary compounds.

| Example Number | Product | Method | Yield (%) | $^1$H NMR (400 MHz, DMSO-$d_6$): δ | LC-MS (m/z: (M + H$^+$) |
|---|---|---|---|---|---|
| 107 | | J | 40 | 8.58 (s, 1H), 8.04 (s, 1H), 7.25 (s, 1H), 6.94 (s, 1H), 6.74 (d, J = 8.7 Hz, 1H), 6.45 (s, 1H), 3.57-3.68 (m, 5H), 3.35 (brs, 2H), 3.19-3.26 (m, 4H), 3.08 (brs, 1H), 2.59 (m, 2H), 1.91-1.94 (m, 1H), 1.57-1.90 (m, 2H), 0.81 (m, 2H), 0.59 (m, 2H). | 574.3 |
| 108 | | J | 27 | 8.77 (s, 1H), 8.08 (s, 1H), 8.06 (s, 1H), 7.80 (s, 1H), 7.41 (d, J = 7.6 Hz, 2H), 7.34 (d, J = 8.0 Hz, 1H), 7.05 (m, 1H), 3.85 (s, 3H), 3.23 (m, 4H), 3.12 (brs, 2H), 2.22 (s, 3H), 2.18 (m, 2H), 1.64 (m, 6H). | 488.3 |
| 109 | | J | 35 | 8.76 (s, 1H), 8.08 (s, 1H), 7.58 (d, J = 6.7 Hz, 2H), 7.51 (d, J = 7.0 Hz, 2H), 7.40 (d, J = 8.3 Hz, 1H), 6.99 (t, J = 5.7 Hz, 1H), 3.66 (s, 3H), 3.54-3.63 (m, 5H), 3.46-3.47 (m, 1H), 3.19-3.28 (m, 4H), 2.57-2.63 (m, 2H), 2.22 (s, 3H), 1.60 (m, 2H). | 504.4 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 110 | | M | 24 | 8.76 (brs, 1H), 7.97 (brs, 1H), 7.39 (d, J = 8.8 Hz, 2H), 6.87 (d, J = 8.8 Hz, 2H), 6.00 (brs, 1H), 5.93 (s, 1H), 3.62 (brs, 4H), 3.46 (brs, 2H), 3.35 (m, 2H), 3.09 ( t, J = 6.8 Hz, 6H), 2.63 (m, 2H), 2.55 (brs, 4H), 2.29 (brs, 3H), 1.67 (t, J = 6.4 Hz, 2H). | 507.3 |
| 111 | | J | 28 | 8.62 (s, 1H), 8.02 (s, 1H), 7.05 (d, J = 8.08 Hz, 1H), 6.86 (brs, 1H), 6.81 (d, J = 2.4 Hz, 1H), 6.73 (d, J = 2.4, 1H), 4.12 (t, J = 4.7 Hz, 2H), 3.10 (brs, 15H), 2.25 (s, 3H), 1.88 (brs, 4H), 1.61 (brs, 2H), 1.54 (m, 6H). | 562.3 |
| 112 | | J | 16 | 8.59 (brs, 1H), 8.01 (brs, 1H), 7.06 (d, J = 8.4 Hz, 1H), 6.89 (m, 1H), 6.79 (brs, 1H), 6.73 (dd, J = 8.8 Hz & 2.32 Hz, 1H), 3.60 (m, 4H), 3.16 (m, 4H), 3.08 (m, 4H), 3.01 (M, 3 h), 2.59 (t, J = 6.8 Hz, 2H), 2.44 (m, 4H), 2.21 (s, 3H), 1.88 (t, J = 8.8 Hz, 2H), 1.73 (m, 2H), 1.52 (m, 6H). | 576.3 |

TABLE I-continued

Exemplary compounds.

| Example Number | Product | Method | Yield (%) | $^1$H NMR (400 MHz, DMSO-$d_6$): δ | LC-MS (m/z: (M + H$^+$)) |
|---|---|---|---|---|---|
| 113 | | J | 21 | 8.61 (s, 1H), 8.01 (s, 1H), 7.06 (d, J = 7.6 Hz, 1H), 6.95 (t, J = 5.4 Hz, 1H), 6.79 (s, 1H), 6.73 (d, J = 8.6 Hz, 1H), 3.00 (brs, 13H), 2.24 (s, 3H), 2.18 (brs, 2H), 1.88 (brs, 2H), 1.69 (m, 6H), 1.51 (m, 8H). | 560.4 |
| 114 | | J | 16 | 8.65 (brs, 1H), 8.02 (brs, 1H), 7.14 (d, J = 8.0 Hz, 1H), 6.88 (m, 1H), 6.76 (dd, J = 8.8 and 2.4 Hz, 2H), 4.12 (t, J = 5.2 Hz, 2H), 3.72 (s, 2H), 3.42 (dd, J = 9.6 Hz & 4.4 Hz, 4H), 3.25 (m, 5H), 3.14 (brs, 2H), 2.89 (s, 2H), 2.55 (d, J = 7.6 Hz, 2H), 1.88 (t, J = 5.2 Hz, 2H), 1.63 (brs, 2H), 1.08 (m, 3H). | 536.2 |
| 115 | | J | 9 | 8.65 (brs, 1H), 8.03 (brs, 1H), 1H), 7.15 (d, J = 7.2 Hz, 1H), 6.92 (m, 1H), 6.81 (s, 1H), 6.76 (dd, J = 11.2 and 2.4 Hz, 1H), 3.73 (s, 2H), 3.60 (m, 4H), 3.43 (m, 4H), 3.32 (m, 2H), 3.22 (brs, 4H), 2.90 (s, 3H), 2.59 (brs, 2H), 2.53 (brs, 2H), 1.56 (brs, 2H), 1.08 (t, J = 7.5 Hz, 3H). | 550.3 |

TABLE I-continued

Exemplary compounds.

| Example Number | Product | Method | Yield (%) | $^1$H NMR (400 MHz, DMSO-$d_6$): δ | LC-MS (m/z: (M + H$^+$) |
|---|---|---|---|---|---|
| 116 | | J | 54 | 8.52 (s, 1H), 8.02 (s, 1H), 7.10 (brs, 1H), 6.89 (s, 1H), 6.36 (dd, J = 8.6 and 2.6 Hz, 1H), 6.03 (s, 1H), 4.26 (s, 1H), 3.59 (t, J = 11.8 Hz, 4H), 3.34-3.35 (m, 3H), 3.15-3.26 (brs, 4 H), 3.10 (d, J = 9.1 Hz, 1H), 2.77 (d, J = 9.4 Hz, 1H), 2.59 (s, 2H), 2.27 (s, 3H), 1.86-1.92 (m, 2H), 1.75 (s, 1H), 1.55 (brs, 2H), 0.79 (m, 2H), 0.55 (m, 2H). | 560.4 |
| 117 | | J | 48 | 8.54 (s, 1H), 8.02 (s, 1H), 7.12 (brs, 1H), 6.86 (s, 1H), 6.38 (d, J = 8.6 Hz, 1H), 6.04 (s, 1H), 4.29 (s, 1H), 4.12 (t, J = 5.3 Hz, 2H), 3.09-3.28 (m, 6H), 2.80 (s, 1H), 2.32 (brs, 3H), 1.90 (m, 4H), 1.78 (brs, 1H), 1.64 (brs, 2H), 0.80 (m, 2H), 0.55 (m, 2H). | 546.2 |
| 118 | | I | 14 | 8.01 (t, J = 1.0 Hz, 1H), 7.82 (s, 1H), 7.19 (d, J = 8.5 Hz, 1H), 6.82 (t, J = 6.0 Hz, 1H), 6.19 (m, 1H), 5.92 (d, J = 2.6 Hz, 1H), 3.84 (t, J = 7.0 Hz, 2H), 3.44 (t, J = 6.5 Hz, 2H), 3.22 (t, J = 7.0 Hz, 3H), 3.13 (m, 3H), 2.19 (t, J = 6.1 Hz, 2H), 2.07 (s, 6H), 1.90 (m, 1H), 1.61-1.68 (m, 6H), 0.80 (m, 2H), 0.53 (m, 2H). | 542.2 544.4 |

TABLE I-continued

Exemplary compounds.

| Example Number | Product | Method | Yield (%) | $^1$H NMR (400 MHz, DMSO-$d_6$): δ | LC-MS (m/z: M + H$^+$) |
|---|---|---|---|---|---|
| 119 | | J | 19 | 8.53 (s, 1H), 8.00 (s, 1H), 7.01 (brs, 1H), 6.87 (s, 1H), 6.37-6.39 (m, 2H), 4.27 (s, 1H), 3.60 (brs, 5H), 3.43 (brs, 4H), 3.13-3.24 (brm, 4H), 2.78 (brs, 1H), 2.59-2.62 (m, 3H), 2.15-2.47 (m, 5H), 1.53-1.88 (brm, 4H), 1.05 (t, J = 7.5 Hz, 3H). | 548.4 |
| 120 | | J | 12 | 8.53 (s, 1H), 8.00 (s, 1H), 7.01 (s, 1H), 6.83-6.87 (m, 1H), 6.37-6.39 (m, 2H), 4.26 (s, 1H), 4.09-4.15 (m, 2H), 3.36-3.48 (brm, 2H), 3.12-3.27 (m, 6H), 2.78 (s, 1H), 2.45-2.47 (m, 3H), 2.28 (brs, 3H), 1.61-1.88 (brm, 7H), 1.05 (t, J = 7.5 Hz, 3H). | 534.2 |
| 121 | | J | 40 | 8.60 (s, 1H), 8.01 (s, 1H), 7.10 (s, 1H), 6.86 (s, 1H), 6.78 (d, J = 2.7 Hz, 1H), 6.74 (dd, J = 8.8 and 2.8 Hz, 1H), 4.12 (t, J = 5.2 Hz, 2H), 3.73 (d, J = 11.0 Hz, 1H), 3.58 (d, J = 11.6 Hz, 1H), 3.23 (brs, 3 H), 2.97-3.17 (brm, 6H), 2.63-2.71 (m, 1H), 2.50-2.53 (m, 2H), 2.35 (t, J = 10.6 Hz, 1H), 2.21 (t, J = 11.1 Hz, 1H), 2.02-2.08 (m, 2H), 1.85-1.91 (m, 2H), 1.77-1.85 (m, 1H), 1.56-1.75 (m, 4 H), 1.31-1.39 (m, 1H), 1.05 (t, J = 7.5 Hz, 3H). | 548.2 |

TABLE I-continued

Exemplary compounds.

| Example Number | Product | Method | Yield (%) | $^1$H NMR (400 MHz, DMSO-$d_6$): δ | LC-MS (m/z: (M + H$^+$) |
|---|---|---|---|---|---|
| 122 | | J | 29 | 8.59 (s, 1H), 8.01 (s, 1H), 7.10 (s, 1H), 6.90 (t, J = 5.7 Hz, 1H), 6.78 (d, J = 2.8 Hz, 1H), 6.74 (dd, J = 8.7 and 2.8 Hz, 1H), 3.73 (d, J = 11.0 Hz, 1H), 3.54-3.64 (m, 5 H), 3.32-3.37 (m, 2 H), 3.13-3.27 (m, 4 H), 2.98-3.04 (m, 2H), 2.68 (d, J = 11.6 Hz, 1H), 2.56-2.63 (m, 2H), 2.49-2.55 (m, 2H), 2.35 (t, J = 10.6 Hz, 1H), 2.21 (t, J = 11.1 Hz, 1H), 2.02-2.07 (m, 2H), 1.79-1.85 (m, 1H), 1.65-1.73 (m, 2H), 1.54 (brs, 2H), 1.32-1.40 (m, 1H), 1.05 (t, J = 7.5 Hz, 3H). | 562.2 |
| 123 | | J | 17 | 8.52 (s, 1H), 8.00 (s, 1H), 7.00 (brs, 1H), 6.83 (s, 1H), 6.37 (m, 2H), 4.23 (s, 1H), 4.11 (s, 2H), 3.31-3.40 (m, 2H), 2.91-3.29 (m, 8H), 2.74 (d, J = 9.3 Hz, 1H), 2.45 (m, 2H), 2.23 (s, 3H), 1.80-1.93 (m, 3H), 1.73 (d, J = 9.3 Hz, 1H), 1.43-1.70 (brm, 2H), 1.05 (t, J = 7.5 Hz, 3H). | 534.2 |
| 124 | | J | 23 | 8.52 (s, 1H), 8.00 (s, 1H), 7.01 (brs, 1H), 6.87 (s, 1H), 6.37-6.39 (m, 2H), 4.25 (s, 1H), 3.60 (brs, 4H), 3.33-3.51 (m, 3H), 2.99-3.27 (m, 5H), 2.73-2.80 (m, 1H), 2.51-2.64 (m, 3H), 2.43 (m, 2H), 2.26 (s, 3H), 1.81-1.90 (m, 1H), 1.75 (d, J = 9.4 Hz, 1H), 1.52 (brs, 2H), 1.05 (t, J = 7.5 Hz, 3H). | 548.2 |

TABLE I-continued

Exemplary compounds.

| Example Number | Product | Method | Yield (%) | $^1$H NMR (400 MHz, DMSO-$d_6$): δ | LC-MS (m/z: (M + H$^+$)) |
|---|---|---|---|---|---|
| 125 | | J | 57 | 8.51 (s, 1H), 8.05 (d, J = 16.2 Hz, 1H), 7.10 (brs, 1H), 6.89 (s, 1H), 6.36 (dd, J = 8.6 and 2.6 Hz, 1H), 6.02 (d, J = 2.6 Hz, 1H), 4.23 (s, 1H), 3.60 (d, J = 12.3 Hz, 4H), 3.35 (brs, 3H), 3.15-3.29 (m, 5H), 3.08 (m, 1H), 2.73 (d, J = 9.3 Hz, 1H), 2.58 (m, 2H), 2.44 (d, J = 10.1 Hz, 1H), 2.22 (s, 3H), 1.86-1.93 (m, 1H), 1.82 (d, J = 9.2 Hz, 1H), 1.71 (d, J = 9.2 Hz, 1H), 1.55 (brs, 2H), 0.79 (m, 2H), 0.54 (m, 2H). | 560.4 |
| 126 | | J | 14 | 8.55 (s, 1H), 8.02 (s, 1H), 7.12 (s, 1H), 6.95 (t, J = 5.8 Hz, 1H), 6.21 (dd, J = 8.5 and 2.5 Hz, 1H), 5.91 (d, J = 2.5 Hz, 1H), 3.85 (t, J = 7.0 Hz, 2H), 3.45 (t, J = 6.5 Hz, 2H), 3.13 (m, 4 H), 2.19 (m, 2H), 2.07 (s, 6 H), 1.90 (m, 1H), 1.67 (m, 4 H), 0.80 (t, J = 8.1 Hz, 2H), 0.54 (m, 2H). | 531.4 |
| 127 | | J | 7 | 8.49 (s, 1H), 8.07 (s, 1H), 7.45 (d, J = 9.0 Hz, 1H), 7.02 (t, J = 5.4 Hz, 1H), 6.92 (d, J = 2.5 Hz, 1H), 6.87 (dd, J = 2.5 and 8.80 Hz, 1H), 4.39 (s, 2H), 3.62 (m, 4H), 3.37 (s, 2H), 3.32 (m, 3H), 3.27 (s, 2H), 3.09 (m, 4H), 2.61 (m, 2H), 2.49 (m, 4H), 2.24 (s, 3H), 1.91 (s, 2H), 1.59 (m, 2H). | 552.3 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 128 | | J | 16 | 8.71 (brs, 1H), 8.10 (brs, 1H), 7.93 (brs, 1H), 6.93 (brs, 1H), 6.69 (s, 1H), 4.13 (m, 2H), 3.46 (m, 4H), 3.16 (m, 6H), 2.54 (m, 2H), 2.44 (m, 4H), 2.26 (brs, 3H), 1.89 (m, 2H), 1.57 (m, 2H), 1.07 (t, J = 7.5 Hz, 3H). | 523.3 |
| 129 | | J | 45 | 8.77 (s, 1H), 8.09 (s, 1H), 7.22 (d, J = 14.1 Hz, 1H), 7.04 (t, J = 5.8 Hz, 1H), 6.86 (d, J = 9.8 Hz, 1H), 3.63 (d, J = 8.9 Hz, 5H), 3.40 (m, 2H), 3.23-3.32 (m, 4H), 2.92-3.05 (brm, 4H), 2.63 (m, 4H), 2.57 (m, 2H), 2.37 (brs, 4H), 1.60 (t, J = 7.3 Hz, 2H), 1.25 (s, 1H), 1.08 (t, J = 7.5 Hz, 3H). | 493.3 |
| 130 | | J | 27 | 8.52 (s, 1H), 8.03 (s, 1H), 7.13 (brm, 1H), 6.96 (brm, 1H), 6.58 (d, J = 8.7 Hz, 1H), 6.27 (s, 1H), 4.16 (s, 2H), 3.05-3.27 (m, 7H), 2.42 (m, 2H), 2.21 (m, 4H), 2.04 (s, 3H), 1.82 (m, 4H), 1.59-1.66 (m, 7H), 0.79 (m, 2H), 0.55 (m, 2H). | 558.4 |

TABLE I-continued

Exemplary compounds.

| Example Number | Product | Method | Yield (%) | ¹H NMR (400 MHz, DMSO-$d_6$): δ | LC-MS (m/z: (M + H⁺) |
|---|---|---|---|---|---|
| 131 | (structure: 2-(2-bromo-4-(4-methylpiperazin-1-yl)phenylamino)-5-trifluoromethyl-pyrimidine with 4-NH-propyl-1,4-oxazepan-5-one) | J | 30 | 8.64 (s, 1H), 8.06 (s, 1H), 7.34 (d, J = 8.8 Hz, 1H), 7.13 (d, J = 2.7 Hz, 1H), 7.00 (t, J = 5.8 Hz, 1H), 6.94 (dd, J = 2.8 and 8.9 Hz, 1H), 3.60-3.62 (m, 4H), 3.37 (m, 2H) 3.15-3.29 (m, 4H), 3.12 (t, J = 4.8 Hz, 4H), 2.60 (m, 2H), 2.42 (t, J = 4.8 Hz, 4H), 2.20 (s, 3H), 1.56 (s, 2H). | 586.2 588.2 |
| 132 | (structure: 2-(2-chloro-4-(4-methylpiperazin-1-yl)phenylamino)-5-trifluoromethyl-pyrimidine with 4-NH-propyl-1,4-oxazepan-5-one) | J | 44 | 8.68 (s, 1H), 8.06 (s, 1H), 7.38 (d, J = 8.8 Hz, 1H), 7.01 (t, J = 5.9 Hz, 1H), 6.98 (d, J = 2.8 Hz, 1H), 6.90 (dd, J = 2.8 and 8.9 Hz, 1H), 3.61 (m, 4H), 3.38 (s, 2H), 3.14-3.25 (m, 8H), 2.60 (m, 2H), 2.45 (brs, 4H), 2.23 (s, 3H), 1.57 (t, J = 7.4 Hz, 2H). | 542.2 |
| 133 | (structure: 2-(2-cyclopropyl-4-(3-methyl-3,6-diazabicyclo[3.1.1]heptan-6-yl)phenylamino)-5-trifluoromethyl-pyrimidine with 4-NH-propyl-1,4-oxazepan-5-one) | J | 29 | 8.52 (s, 1H), 8.03 (s, 1H), 7.13 (s, 1H), 6.90 (s, 1H), 6.59 (d, J = 8.7 Hz, 1H), 6.27 (s, 1H), 4.17 (s, 2H), 3.60 (s, 4H), 3.36 (s, 2H), 3.22 (brm, 4H), 2.59 (s, 2H), 2.42 (d, J = 10.7 Hz, 2H), 2.24 (d, J = 10.6 Hz, 2H), 2.04 (s, 3H), 1.79-1.90 (m, 5H), 1.55 (brm, 2H), 0.79 (m, 2H), 0.54 (m, 2H). | 574.3 |

TABLE I-continued
Exemplary compounds.
| Example Number | Product | Method | Yield (%) | $^1$H NMR (400 MHz, DMSO-$d_6$): δ | LC-MS (m/z: (M + H$^+$) |
|---|---|---|---|---|---|
| 134 | 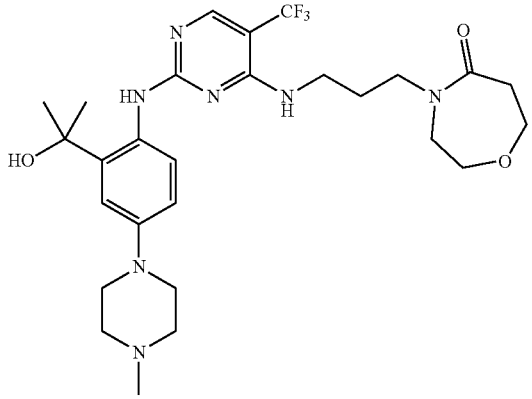 | J | 4 | 9.70 (brs, 1H), 8.09 (s, 1H), 7.98 (brs, 1H), 7.1 (m, 1H), 6.83 (m, 2H), 5.8 (s, 1H), 3.63 (m, 4H), 3.41 (m, 2H), 3.36 (m, 4H), 3.06 (m, 4H), 2.63 (m, 2H), 2.46 (m, 4H), 2.21 (s, 3H), 1.68 (m, 2H), 1.50 (s, 6H). | 566.3 |
| 135 | 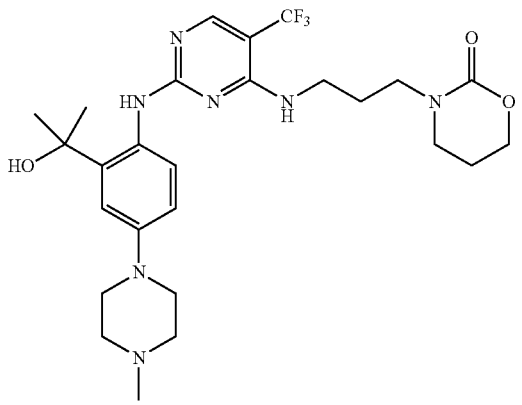 | J | 7 | 9.71 (brs, 1H), 8.09 (s, 1H), 8.00 (d, J = 5.7 Hz, 1H), 7.0 (brs, 1H), 6.85 (brs, 1H), 6.83 (s, 1H), 5.8 (s, 1H), 4.13 (t, J = 5.1 Hz, 2H), 3.37 (m, 2H), 3.23 (m, 4H), 3.06 (m, 4H), 2.44 (m, 4H), 2.21 (s, 3H), 1.89 (m, 2H), 1.76 (m, 2H), 1.50 (s, 6H). | 552.3 |
| 136 | 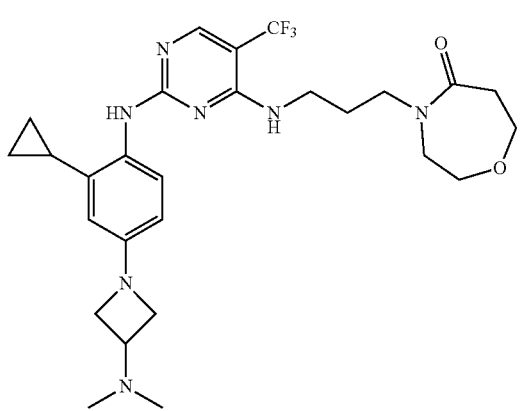 | J | 25 | 8.61 (s, 1H), 8.07 (s, 1H), 7.18 (s, 1H), 6.95 (t, J = 5.8 Hz, 1H), 6.27 (dd, J = 2.6 and 8.5 Hz, 1H), 5.97 (d, J = 2.6 Hz, 1H), 3.92 (t, J = 7.0 Hz, 2H), 3.65 (d, J = 10.9 Hz, 4H), 3.54 (t, J = 6.5 Hz, 2H), 3.40 (m, 2H), 3.25 (m, 5H), 2.65 (m, 2H), 2.17 (s, 6H), 1.94 (m, 1H), 1.60 (brs, 2H), 0.85 (m, 2H), 0.57 (m, 2H). | 548.4 |

TABLE I-continued

Exemplary compounds.

| Example Number | Product | Method | Yield (%) | $^1$H NMR (400 MHz, DMSO-$d_6$): δ | LC-MS (m/z: (M + H$^+$)) |
|---|---|---|---|---|---|
| 137 | | J | 18 | 8.61 (s, 1H), 8.07 (s, 1H), 7.18 (s, 1H), 6.95 (s, 1H), 6.27 (m, 1H), 5.95 (d, J = 2.6 Hz, 1H), 3.95 (t, J = 7.4 Hz, 2H), 3.66 (d, J = 9.4 Hz, 4H), 3.49 (t, J = 6.6 Hz, 2H), 3.35-3.45 (m, 7H), 2.98 (m, 2H), 2.90 (brm, 2H), 2.65 (m, 2H), 2.44 (s, 6H), 1.95 (m, 1H), 1.61 (brs, 2H), 0.85 (m, 2H), 0.58 (m, 2H). | 562.4 |
| 138 | | J | 30 | 8.54 (s, 1H), 8.01 (s, 1H), 7.02 (d, J = 8.4 Hz, 1H), 6.88 (t, J = 5.8 Hz, 1H), 6.64 (d, J = 2.6 Hz, 1H), 6.59-6.63 (m, 1H), 4.18 (s, 2H), 4.07 (s, 2H), 3.73 (t, J = 5.4 Hz, 2H), 3.19 (brs, 4H), 2.40-2.47 (m, 4H), 2.29 (m, 2H), 2.04 (s, 3H), 1.74-1.87 (m, 6H), 1.55 (brs, 2H), 1.04 (t, J = 7.5 Hz, 3H). | 562.4 |
| 139 | | J | 50 | 8.53 (s, 1H), 8.02 (s, 1H), 7.00 (d, J = 8.4 Hz, 1H), 6.87 (brm, 1H), 6.64 (s, 1H), 6.60 (d, J = 8.7 Hz, 1H), 4.18 (s, 2H), 3.21 (m, 4H), 2.92 (brs, 2H), 2.44 (m, 4H), 2.28 (m, 2H), 2.05 (m, 3H), 1.84 (m, 4H), 1.59 (brs, 2H), 1.13 (s, 6H), 1.04 (t, J = 7.5 Hz, 3H). | 546.4 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 140 | | J | 53 | 8.53 (s, 1H), 8.01 (s, 1H), 7.02 (s, 1H), 6.87 (s, 1H), 6.64 (s, 1H), 6.60 (d, J = 8.8 Hz, 1H), 4.18 (s, 2H), 3.15 (m, 6H), 2.43 (m, 4H), 2.28 (m, 2H), 2.05 (s, 3H), 1.83 (m, 6H), 1.62 (brs, 2H), 1.25 (s, 6H), 1.04 (t, J = 7.5 Hz, 3H). | 576.4 |
| 141 | | J | 11 | 8.61 (brs, 1H), 8.02 (s, 1H), 7.08 (d, J = 8.8 Hz, 1H), 6.8 (t, J = 5.8 Hz, 1H), 6.77 (d, J = 2.5 Hz, 1H), 6.73 (dd, J = 2.7 and 8.7 Hz, 1H), 3.21 (brs, 4H), 3.10 (m, 4H), 2.91 (m, 4H), 2.44 (m, 4H), 2.21 (s, 3H), 1.60 (brs, 2H), 1.14 (s, 6H), 1.05 (t, J = 7.5 Hz, 3H). | 520.3 |
| 142 | | J | 24 | 8.62 (s, 1H), 8.02 (s, 1H), 7.11 (d, J = 8.6 Hz, 1H), 6.8 (t, J = 5.9 Hz, 1H), 6.78 (d, J = 2.5 Hz, 1H), 6.73 (dd, J = 2.5 and 8.6 Hz, 1H), 3.61 (brs, 2H), 3.35 (s, 2H), 3.19 (m, 4H), 3.10 (m, 6H), 2.54 (q, 2H), 2.45 (m, 4H), 2.21 (s, 3H), 1.54 (brs, 2H), 1.06 (s, 6H), 1.06 (t, J = 6.8 Hz, 3H). | 564.3 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 143 | | J | 24 | 8.73 (s, 1H), 8.04 (s, 1H), 7.27 (d, J = 8.1 Hz, 1H), 7.09 (m, 2H), 6.96 (m, 1H), 3.60 (m, 4H), 3.36 (brm, 2H), 3.1-3.2 (brm, 4H), 2.97 (t, J = 8.9 Hz, 1H), 2.73 (brm, 2H), 2.52-2.62 (m, 4H), 2.40 (m, 4H), 2.24 (m, 1H), 1.76 (m, 2H), 1.55 (s, 2H), 1.08 (t, J = 7.5 Hz, 3H). | 521.2 |
| 144 | | J | 18 | 8.53 (brs, 1H), 7.99 (brs, 1H), 7.02 (brs, 1H), 6.86 (brm, 1H), 6.35 (m, 2H), 3.58 (m, 4H), 3.41 (m, 4H), 3.32 (m, 4H), 3.21 (m, 2H), 3.02 (t, J = 8.5 Hz, 2H), 2.78 (m, 1H), 2.57 (m, 2H), 2.21 (s, 6H), 2.14 (m, 2H), 1.80 (m, 2H), 1.05 (t, J = 7.5 Hz, 3H). | 550.4 |
| 145 | | J | 26 | 8.53 (brs, 1H), 7.99 (brs, 1H), 7.02 (brs, 1H), 6.86 (brm, 1H), 6.35 (m, 2H), 3.58 (m, 4H), 3.41 (m, 4H), 3.32 (m, 4H), 3.21 (m, 2H), 3.02 (t, J = 8.5 Hz, 2H), 2.78 (m, 1H), 2.57 (m, 2H), 2.21 (s, 6H), 2.14 (m, 2H), 1.80 (m, 2H), 1.05 (t, J = 7.5 Hz, 3H). | 550.4 |

TABLE I-continued

Exemplary compounds.

| Example Number | Product | Method | Yield (%) | ¹H NMR (400 MHz, DMSO-d₆): δ | LC-MS (m/z: (M + H⁺) |
|---|---|---|---|---|---|
| 146 | | J | 21 | 8.72 (s, 1H), 8.04 (s, 1H), 7.27 (d, J = 8.1 Hz, 1H), 7.07 (s, 1H), 7.02 (m, 1H), 6.96 (t, J = 5.9 Hz, 1H), 3.62 (m, 4H), 3.1-3.6 (brm, 8H), 3.00 (m, 2H), 2.53-2.61 (m, 4H), 2.32 (m, 3H), 2.21 (t, J = 12.2 Hz, 2H), 1.78 (m, 2H), 1.68 (m, 2H), 1.56 (m, 2H), 1.08 (t, J = 7.6 Hz, 3H). | 535.2 |
| 147 | | J | 15 | 8.5 (s, 1H), 8.06 (s, 1H), 7.45 (d, J = 7.8 Hz, 1H), 6.9 (m, 1H), 6.90 (s, 1H), 6.87 (dd, J = 1.6 and 8.8 Hz Hz, 1H), 5.25 (brs, 2H), 4.39 (s, 2H), 4.12 (t, J = 4.8 Hz, 2H), 3.27 (s, 3H), 3.17 (m, 4H), 3.09 (m, 4H), 2.44 (m, 4H), 2.21 (s, 3H), 1.89 (m, 2H), 1.70 (m, 2H). | 538.3 |
| 148 | | J | 19 | 8.6 (s, 1H), 8.04 (s, 1H), 7.23 (d, J = 8.3 Hz, 1H), 6.9 (t, J = 6.8 Hz, 1H), 6.72 (dd, J = 2.4 and 8.6 Hz, 1H), 6.42 (d, J = 2.4 Hz, 1H), 3.26 (brs, 2H), 3.14 (m, 4H), 3.06 (m, 4H), 2.43 (m, 4H), 2.21 (s, 3H), 1.93 (m, 1H), 1.81 (t, J = 6.2 Hz, 2H), 1.65 (m, 2H), 1.25 (s, 6H), 0.81 (m, 2H), 0.58 (m, 2H). | 562.3 |

TABLE I-continued
Exemplary compounds.
| Example Number | Product | Method | Yield (%) | $^1$H NMR (400 MHz, DMSO-$d_6$): δ | LC-MS (m/z: (M + H$^+$) |
|---|---|---|---|---|---|
| 149 | 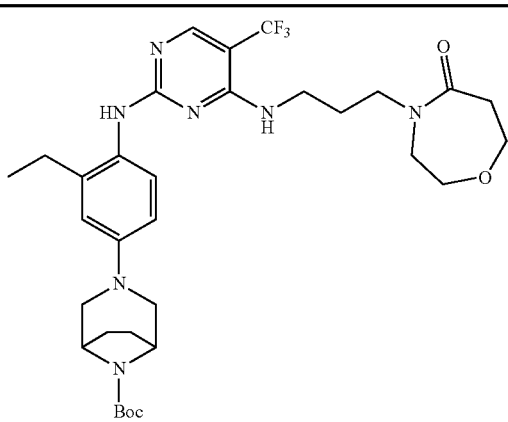 | J | 30 | 8.57 (s, 1H), 8.01 (s, 1H), 7.07 (brm, 1H), 6.89 (t, J = 5.8 Hz, 1H), 6.70 (s, 1H), 6.66 (d, J = 8.8 Hz, 1H), 4.24 (brm, 2H), 3.48-3.58 (brm, 6H), 3.21 (brm, 4H), 3.03-3.24 (brm, 6H), 2.54-2.63 (m, 2H), 1.89 (brm, 2H), 1.62 (m, 2H), 1.51 (brm, 2H), 1.38 (s, 9H), 1.05 (t, J = 7.5 Hz, 3H). | 648.4 |
| 150 | 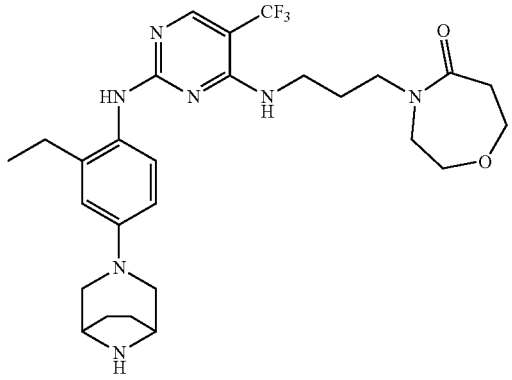 | K | 42 | 10.13 (br s, 1H), 9.75 (brs, 1H), 9.22 (br s, 1H), 8.48 (brs, 1H), 7.32 (brs, 1H), 6.83 (m, 2H), 4.44 (s, 2H), 3.19-3.70 (brm, 8H), 2.93-3.11 (m, 4H), 2.59 (brs, 4H), 2.15 (m, 2H), 2.08 (m, 4H), 1.56-1.75 (brm, 2H), 1.13 (t, J = 7.5 Hz, 3H). | 548.3 |
| 151 | 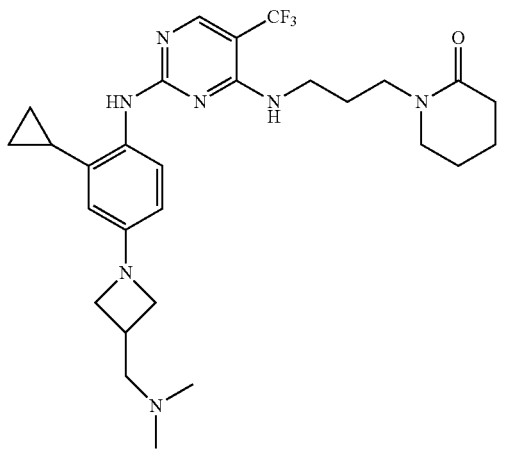 | J | 20 | 8.60 (s, 1H), 8.06 (s, 1H), 7.17 (brm, 1H), 7.00 (t, J = 6.0 Hz, 1H), 6.23 (m, 1H), 5.95 (d, J = 2.5 Hz, 1H), 3.94 (m, 2H), 3.47 (m 2H), 3.0-3.32 (m, 7H), 2.79 (brs, 2H), 2.37 (s, 6H), 2.25 (m, 2H), 1.94 (m, 1H), 1.72 (s, 4H), 1.64 (brs, 2H), 0.84 (m, 2H), 0.58 (m, 2H). | 546.4 |

TABLE I-continued

Exemplary compounds.

| Example Number | Product | Method | Yield (%) | $^1$H NMR (400 MHz, DMSO-$d_6$): δ | LC-MS (m/z: (M + H$^+$)) |
|---|---|---|---|---|---|
| 152 | (structure: pyrimidine with CF$_3$, HN-linked ethyl-phenyl bearing azetidinyl-CH$_2$-N(CH$_3$)$_2$, and NH-propyl-oxazepanone) | J | 40 | 8.57 (s, 1H), 7.98 (m, 1H), 7.04 (d, J = 8.0 Hz, 1H), 6.88 (t, J = 8.0 Hz, 1H), 6.24 (m, 2H), 3.96 (q, J = 7.5 Hz, 2H), 3.61 (m, 4H), 3.53 (m, 2H), 3.36 (m, 2H), 3.20 (m, 4H), 3.10 (m, 2H), 2.61 (s, 7H), 2.49 (m, 4H), 1.54 (brs, 2H), 1.04 (m, 3H). | 550.2 |
| 153 | (structure: pyrimidine with CF$_3$, HN-linked phenyl bearing N-methylpiperazinyl, and NH-propyl-oxazepanone) | J | 34 | 9.36 (s, 1H), 8.11 (s, 1H), 7.54 (d, J = 8.7 Hz, 2H), 7.06 (brs, 1H), 6.87 (d, J = 8.8 Hz, 2H), 3.61 (m, 4H), 3.33-3.42 (m, 6 H), 3.04 (t, J = 4.8 Hz, 4H), 2.61-2.63 (m, 2H), 2.43 (t, J = 4.8 Hz, 4H), 2.20 (s, 3H), 1.69 (m, 2H). | 508.4 |

Example 130. Biochemical Assay for ULK1.2 (SEQ. ID NO: 1)

Activity of ULK1 kinase was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942). Assays were conducted in 384-well plates (100 uL final volume) using 19 nM ULK1 (Eurofins CAT #14-959), 0.25 mg/mL myelin basic protein, 1.5 units pyruvate kinase, 2.1 units lactate dehydrogenase, 1 mM phosphoenol pyruvate, 0.28 mM NADH and 1 mM ATP in assay buffer (100 mM Tris, pH 7.5, 15 mM MgCl$_2$, 0.5 mM DTT, 0.1% octyl-glucoside, 0.002% (w/v) BSA, and 0.002% Triton X-100). Inhibition of ULK1 was measured by adding serial diluted test compound (final assay concentration of 1% DMSO). A decrease in absorption at 340 nm was monitored continuously for 6 hours at 30° C. on a multi-mode microplate reader (BioTek). The reaction rate was calculated using the 2-3 h time frame. The reaction rate at each concentration of compound was converted to percent inhibition using controls (i.e. reaction with no test compound and reaction with a known inhibitor) and IC$_{50}$ values were calculated by fitting a four-parameter sigmoidal curve to the data using Prism (GraphPad software).

```
ULK1 protein sequence (residues 1-314 with
N-terminal His tag; SEQ. ID NO: 1)
MSYYHHHHHHDYDIPTTENLYFQGAMDPFFMEPGRGGTET

VGKFEFSRKDLIGHGAFAVVFKGRHREKHDLEVAVKCINKKN

LAKSQTLLGKEIKILKELKHENIVALYDFQEMANSVYLVMEY

CNGGDLADYLHAMRTLSEDTIRLFLQQIAGAMRLLHSKGIIH

RDLKPQNILLSNPAGRRANPNSIRVKIADFGFARYLQSNMMA

ATLCGSPMYMAPEVIMSQHYDGKADLWSIGTIVYQCLTGKAP

FQASSPQDLRLFYEKNKTLVPTIPRETSAPLRQLLLALLQRN

HKDRMDFDEFFHHPFLDASPSVRKSPPVPVPSYPSSGSGSSS

SSSSTSHLAS
```

Example 131. Biochemical Assay for ULK1.3 (SEQ. ID NO: 2)

Activity of ULK1 kinase was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942). Assays were conducted in 384-well plates (100 uL final volume) using 0.1 nM ULK1 (from Beryllium), 0.075 mM peptide substrate (YANW-LAASIYLDGKKK (SEQ ID NO: 5)), 1.5 units pyruvate kinase, 2.1 units lactate dehydrogenase, 1 mM phosphoenol pyruvate, 0.28 mM NADH and 1 mM ATP in assay buffer (100 mM Tris, pH 7.5, 15 mM $MgCl_2$, 0.5 mM DTT, 0.004% (w/v) BSA, and 0.004% Triton X-100). Inhibition of ULK1 was measured by adding serial diluted test compound (final assay concentration of 1% DMSO). A decrease in absorption at 340 nm was monitored continuously for 6 hours at 30° C. on a multi-mode microplate reader (BioTek). The reaction rate was calculated using the 2-3 h time frame. The reaction rate at each concentration of compound was converted to percent inhibition using controls (i.e. reaction with no test compound and reaction with a known inhibitor) and $IC_{50}$ values were calculated using software routines in Prism (GraphPad software).

```
ULK1 protein sequence (residues 1-283;
SEQ. ID NO: 2)
MEPGRGGTETVGKFEFSRKDLIGHGAFAVVFKGRHRAAH

DLEVAVKCINKKNLAKSQTLLGKEIKILKELKHENIVAL

YDFQEMANSVYLVMEYCNGGDLADYLHAMRTLSEDTIRL

FLQQIAGAMRLLHSKGIIHRDLKPQNILLSNPAGRRANP

NSIRVKIADFGFARYLQSNMMAATLCGSPMYMAPEVIMS

QHYDGKADLWSIGTIVYQCLTGKAPFQASSPQDLRLFYE

KNKTLVPTIPRETSAPLRQLLLALLQRNHKDRMDFDEFF

HHPFLDASPS
```

Example 132. Biochemical Assay for ULK2 (SEQ. ID NO: 3)

Activity of ULK2 kinase was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942). Assays were conducted in 384-well plates (100 uL final volume) using 9.7 nM ULK2 (Eurofins CAT #14-772), 0.25 mg/mL myelin basic protein, 1.5 units pyruvate kinase, 2.1 units lactate dehydrogenase, 1 mM phosphoenol pyruvate, 0.28 mM NADH and 1 mM ATP in assay buffer (100 mM Tris, pH 7.5, 15 mM $MgCl_2$, 0.5 mM DTT, 0.1% octyl-glucoside, 0.002% (w/v) BSA, and 0.002% Triton X-100). Inhibition of ULK2 was measured by adding serial diluted test compound (final assay concentration of 1% DMSO). A decrease in absorption at 340 nm was monitored continuously for 6 hours at 30° C. on a multi-mode microplate reader (BioTek). The reaction rate was calculated using the 2-3 h time frame. The reaction rate at each concentration of compound was converted to percent inhibition using controls (i.e. reaction with no test compound and reaction with a known inhibitor) and $IC_{50}$ values were calculated by fitting a four-parameter sigmoidal curve to the data using Prism (GraphPad software).

```
ULK2 protein sequence (residues 1-306 with
N-terminal GST and His tag; SEQ. ID NO: 3)
MSPILGYWKIKGLVQPTRLLLEYLEEKYEEHLYERDEGDKWR

NKKFELGLEFPNLPYYIDGDVKLTQSMAIIRYIADKHNMLGG

CPKERAEISMLEGAVLDIRYGVSRIAYSKDFETLKVDFLSKL

PEMLKMFEDRLCHKTYLNGDHVTHPDFMLYDALDVVLYMDPM

CLDAFPKLVCFKKRIEAIPQIDKYLKSSKYIAWPLQGWQATF

GGGDHPPKSDLEVLFQGPEFMEVVGDFEYSKRDLVGHGAFAV

VFRGRHRQKTDWEVAIKSINKKNLSKSQILLGKEIKILKELQ

HENIVALYDVQELPNSVFLVMEYCNGGDLADYLQAKGTLSED

TIRVFLHQIAAAMRILHSKGIIHRDLKPQNILLSYANRRKSS

VSGIRIKIADFGFARYLHSNMMAATLCGSPMYMAPEVIMSQ

HYDAKADLWSIGTVIYQCLVGKPPFQANSPQDLRMFYEKNRS

LMPSIPRETSPYLANLLLGLLQRNQKDRMDFEAFFSHPFLEQ

GPVKKSCPVPVPMYSGSVSGSSCGSSPSCRFASHHHHHH
```

TABLE 1

Inhibition of biochemical activity of ULK1 and ULK2 kinases by exemplary compounds shown in Table I.

| Example (Compound) Number | ULK1.2 | ULK1.3 | ULK2.2 |
|---|---|---|---|
| 1 | + + + + | | |
| 2 | + + + | | |
| 3 | + + + | | |
| 4 | + + | | + + + |
| 5 | + + + + | | |
| 6 | + + + + | | |
| 7 | + + | | + + + |
| 8 | + + | | + + + |
| 9 | + | | + |
| 10 | + | | + |
| 11 | + | | + |
| 12 | + | | + |
| 13 | + | | + |
| 14 | + | + | + |
| 15 | | + + | |
| 16 | + | | |
| 17 | + | | |
| 18 | + + + | | + + |
| 19 | + | | + + |
| 20 | + | | + + |
| 21 | + | | + |
| 22 | + | | + + + |
| 23 | + + | | + + + |
| 24 | | + | |
| 26 | | + | |
| 27 | | + + | |
| 28 | | + | |
| 29 | | + + + | |
| 30 | | + + | |
| 31 | | + | |
| 32 | | + + | |
| 33 | | + | |
| 34 | | + | |
| 35 | | + + | |
| 36 | | + + | |
| 37 | | + | |
| 38 | | + | |
| 39 | + | + | + + |
| 40 | | + | |
| 41 | | + | + + |
| 42 | | + | |
| 43 | | + + | |

TABLE 1-continued

Inhibition of biochemical activity of ULK1 and ULK2 kinases by exemplary compounds shown in Table I.

| Example (Compound) Number | ULK1.2 | ULK1.3 | ULK2.2 |
|---|---|---|---|
| 44 |  | + |  |
| 45 |  | + + + |  |
| 46 |  | + | + + |
| 47 |  | + + |  |
| 48 |  | + + + |  |
| 49 |  | + + + |  |
| 50 | + + + |  | + + + + |
| 51 | + + + |  | + + + + |
| 52 | + | + | + + |
| 53 |  | + + |  |
| 54 | + |  | + + |
| 55 | + + + |  | + + + |
| 56 |  | + + |  |
| 57 | + + + + |  | + + + + |
| 58 | + + + |  | + + + + |
| 59 | + + + + |  | + + + + |
| 60 | + |  |  |
| 61 |  | + + + + |  |
| 62 |  | + |  |
| 63 |  | + + |  |
| 64 |  | + + + |  |
| 65 | + |  | + + |
| 66 | + | + | + + |
| 67 |  | + |  |
| 68 |  | + |  |
| 69 |  | + |  |
| 70 | + | + | + + |
| 71 | + |  | + + + + |
| 72 | + + |  | + + + + |
| 73 | + |  | + + + |
| 74 |  | + | + |
| 75 |  | + |  |
| 76 | + | + |  |
| 77 |  | + + |  |
| 78 |  | + + + |  |
| 79 |  | + |  |
| 80 |  | + + |  |
| 81 |  | + |  |
| 82 |  | + + |  |
| 83 |  | + + + + |  |
| 84 |  | + | + + |
| 85 |  | + |  |
| 86 |  | + + |  |
| 87 |  | + + |  |
| 88 |  | + + |  |
| 89 |  | + + + |  |
| 90 | + + + + |  | + + + + |
| 91 | + + | + + | + + + |
| 92 |  | + |  |
| 93 |  | + + + |  |
| 94 |  | + + |  |
| 95 | + + + |  | + + + + |
| 96 | + + + + |  | + + + + |
| 97 |  | + + + |  |
| 98 |  | + + |  |
| 99 |  | + | + + |
| 100 |  | + + |  |
| 101 |  | + |  |
| 102 |  | + |  |
| 103 |  | + |  |
| 104 |  | + + + |  |
| 105 |  | + |  |
| 106 |  | + |  |
| 107 |  | + |  |
| 108 | + + + + |  | + + + + |
| 109 | + + + + |  | + + + + |
| 110 |  | + |  |
| 111 |  | + |  |
| 112 |  | + |  |
| 113 |  | + |  |
| 114 |  | + + |  |
| 115 |  | + + + |  |
| 116 |  | + + |  |
| 117 |  | + + |  |
| 118 |  | + + |  |
| 119 |  | + |  |
| 120 |  | + |  |
| 121 |  | + |  |
| 122 |  | + |  |
| 123 |  | + |  |
| 124 |  | + |  |
| 125 |  | + |  |
| 126 |  | + |  |
| 127 |  | + |  |
| 128 |  | + |  |
| 129 |  | + + |  |
| 130 |  | + + |  |
| 131 |  | + |  |
| 132 |  | + |  |
| 133 |  | + + + |  |
| 134 |  | + + + + |  |
| 135 |  | + + + |  |
| 136 |  | + |  |
| 137 |  | + |  |
| 138 |  | + + + |  |
| 139 |  | + + + + |  |
| 140 |  | + + + |  |
| 141 |  | + + |  |
| 142 |  | + |  |
| 143 |  | + |  |
| 144 |  | + |  |
| 145 |  | + |  |
| 146 |  | + + |  |
| 147 |  | + |  |
| 148 |  | + |  |
| 150 |  | + |  |
| 151 |  | + |  |
| 152 |  | + |  |

For Table 1, "+" refers to an $IC_{50}$ greater than 1 nM and less than or equal to 25 nM; "+ +" refers to an $IC_{50}$ greater than 25 nM and less than or equal to 100 nM; "+ + +" refers to an $IC_{50}$ greater than 100 nM and less than or equal to 500 nM; and "+ + + +" refers to an $IC_{50}$ greater than 500 nM.

Example 133. Cellular Inhibition of ULK Kinase Substrate ATG13 Protein pATG13 Levels of Mutant KRas A549 Cells after Treatment with ULK Inhibitors in Combination with Trametinib A549 (KRAS mutant) human lung cancer cells (6,000 cells/well) were added to a 384-well tissue-culture treated plate in 50 μL of pre-warmed DMEM medium supplemented with 10% characterized fetal bovine serum (Invitrogen, Carlsbad, Calif.), 100 units/mL penicillin G, and 100 μg/mL streptomycin and allowed to grow overnight at 37° C., 5% CO2, and 95% humidity. The following day, 10 μL of media containing trametinib or DMSO as a control was added to wells. The final concentration of trametinib in wells was 250 nM. A dose response of a test compound (0.6 μL per well) was added. DMSO (0.6 μL) was added to control wells. The plate was briefly shaken to mix wells and then incubated at 37° C. overnight. The next day, the media was aspirated and cells were washed with Dulbecco's Phosphate Buffered Saline (Gibco). Cells were lysed using MPER lysis buffer (Pierce, Rockford, Ill.) containing Halt Phosphatase and Protease Inhibitors (Pierce, Rockford, Ill.) and Phosphatase inhibitor cocktail 2 (Sigma, St. Louis, Mo.) at 4° C. for 10 minutes with shaking.

Cellular levels of phospho-Serine 318 ATG13 (pATG13) were measured via an ELISA method. Total ATG13 Antibody (Cell Signaling Cat #13273) was used to coat the wells. The plate was incubated at 4° C. overnight and washed with ELISA wash buffer (Biolegend Cat #421601). The wells were then blocked with assay diluent (Biolegend Cat #421203) for 1 hour at room temperature. Plate wells were washed with ELISA wash buffer. Cell lysate was added to wells and incubated at room temperature for 2 hours. Plate wells were washed with ELISA wash buffer. Biotinylated pS318-ATG13 antibody (Rockland Immunochemicals Cat #600-401-C49) was diluted in assay diluent and added to each well and incubated at room temperature for 1 hour. Plate wells were washed with ELISA wash buffer. Streptavidin linked to horseradish peroxidase (Thermo Fisher Cat #21140) was diluted in assay diluent and added to each well and incubated at room temperature for 1 hour. Plate wells were washed with ELISA wash buffer. High sensitivity TMB substrate (Biolegend Cat #421101) was added to each well and incubated at room temperature for 20 minutes. The reaction was stopped with 2N Sulfuric Acid. The plate was analyzed at on a plate reader measuring absorbance at 450 nm and 540 nm (background). Signal was calculated by first subtracting the background absorbance at 540 nm from the absorbance at 450 nm for each well. Next, the background corrected absorbance at 450 nm from blank wells was subtracted from test wells. Data was compared to control wells to determine % ATG13 phosphorylation. GraphPad Prism was used to calculate $IC_{50}$ values.

Example 134. pATG13 Levels of Mutant KRas MiaPaCa-2 Cells after Treatment with ULK Inhibitors in Combination with Trametinib MiaPaCa-2 human pancreatic cancer cells (10000 cells/well) were added to a 384-well tissue-culture treated plate in 50 μL of pre-warmed DMEM medium supplemented with 10% characterized fetal bovine serum (Invitrogen, Carlsbad, Calif.), 100 units/mL penicillin G, 100 pg/mL streptomycin, and 2.5% Horse Serum and allowed to grow overnight at 37° C., 5% CO2, and 95% humidity. The following day, 10 μL of media containing trametinib or DMSO as a control was added to wells. The final concentration of trametinib in wells was 250 nM. A dose response of a test compound (0.6 μL per well) was added. DMSO (0.6 μL) was added to control wells. The plate was briefly shaken to mix wells and then incubated at 37° C. overnight. The next day, the media was aspirated and cells were washed with Dulbecco's Phosphate Buffered Saline (Gibco). Cells were lysed using MPER lysis buffer (Pierce, Rockford, Ill.) containing Halt Phosphatase and Protease Inhibitors (Pierce, Rockford, Ill.) and Phosphatase inhibitor cocktail 2 (Sigma, St. Louis, Mo.) at 4° C. for 10 minutes with shaking.

Cellular levels of phospho-Serine 318 ATG13 (pATG13) were measured via an ELISA method. Total ATG13 Antibody (Cell Signaling Cat #13273) was used to coat the wells. The plate was incubated at 4° C. overnight and washed with ELISA wash buffer (Biolegend Cat #421601). The wells were then blocked with assay diluent (Biolegend Cat #421203) for 1 hour at room temperature. Plate wells were washed with ELISA wash buffer. Cell lysate was added to wells and incubated at room temperature for 2 hours. Plate wells were washed with ELISA wash buffer. Biotinylated pS318-ATG13 antibody (Rockland Immunochemicals Cat #600-401-C49) was diluted in assay diluent and added to each well and incubated at room temperature for 1 hour. Plate wells were washed with ELISA wash buffer. Streptavidin linked to horseradish peroxidase (Thermo Fisher Cat #21140) was diluted in assay diluent and added to each well and incubated at room temperature for 1 hour. Plate wells were washed with ELISA wash buffer. High sensitivity TMB substrate (Biolegend Cat #421101) was added to each well and incubated at room temperature for 20 minutes. The reaction was stopped with 2N Sulfuric Acid. The plate was analyzed at on a plate reader measuring absorbance at 450 nm and 540 nm (background). Signal was calculated by first subtracting the background absorbance at 540 nm from the absorbance at 450 nm for each well. Next, the background corrected absorbance at 450 nm from blank wells was subtracted from test wells. Data was compared to control wells to determine % ATG13 phosphorylation. GraphPad Prism was used to calculate $IC_{50}$ values.

Example 135. pATG13 Levels of Mutant KRas HCT-116 Cells after Treatment with ULK Inhibitors in Combination with Trametinib HCT-116 human colon cancer cells (10000 cells/well) were added to a 384-well tissue-culture treated plate in 50 μL of pre-warmed DMEM medium supplemented with 10% characterized fetal bovine serum (Invitrogen, Carlsbad, Calif.), 100 units/mL penicillin G, and 100 pg/mL streptomycin and allowed to grow overnight at 37° C., 5% CO2, and 95% humidity. The following day, 10 μL of media containing trametinib or DMSO as a control was added to wells. The final concentration of trametinib in wells was 250 nM. A dose response of a test compound (0.6 μL per well) was added. DMSO (0.6 μL) was added to control wells. The plate was briefly shaken to mix wells and then incubated at 37° C. overnight. The next day, the media was aspirated and cells were washed with Dulbecco's Phosphate Buffered Saline (Gibco). Cells were lysed using MPER lysis buffer (Pierce, Rockford, Ill.) containing Halt Phosphatase and Protease Inhibitors (Pierce, Rockford, Ill.) and Phosphatase inhibitor cocktail 2 (Sigma, St. Louis, Mo.) at 4° C. for 10 minutes with shaking.

Cellular levels of phospho-Serine 318 ATG13 (pATG13) were measured via an ELISA method. Total ATG13 Antibody (Cell Signaling Cat #13273) was used to coat the wells. The plate was incubated at 4° C. overnight and washed with ELISA wash buffer (Biolegend Cat #421601). The wells were then blocked with assay diluent (Biolegend Cat #421203) for 1 hour at room temperature. Plate wells were washed with ELISA wash buffer. Cell lysate was added to wells and incubated at room temperature for 2 hours. Plate wells were washed with ELISA wash buffer. Biotinylated pS318-ATG13 antibody (Rockland Immunochemicals Cat #600-401-C49) was diluted in assay diluent and added to each well and incubated at room temperature for 1 hour. Plate wells were washed with ELISA wash buffer. Streptavidin linked to horseradish peroxidase (Thermo Fisher Cat #21140) was diluted in assay diluent and added to each well and incubated at room temperature for 1 hour. Plate wells were washed with ELISA wash buffer. High sensitivity TMB substrate (Biolegend Cat #421101) was added to each well and incubated at room temperature for 20 minutes. The reaction was stopped with 2N Sulfuric Acid. The plate was analyzed at on a plate reader measuring absorbance at 450 nm and 540 nm (background). Signal was calculated by first subtracting the background absorbance at 540 nm from the absorbance at 450 nm for each well. Next, the background corrected absorbance at 450 nm from blank wells was subtracted from test wells. Data was compared to control wells to determine % ATG13 phosphorylation. GraphPad Prism was used to calculate IC$_{50}$ values.

Example 136. pATG13 Levels of Mutant BRAF A375 Cells after Treatment with ULK Inhibitors in Combination with Trametinib A375 human malignant melanoma cancer cells (20000 cells/well) were added to a 96-well tissue-culture treated plate in 100 μL of pre-warmed DMEM medium supplemented with 10% characterized fetal bovine serum (Invitrogen, Carlsbad, Calif.), 100 units/mL penicillin G, and 100 μg/mL streptomycin and allowed to grow overnight at 37° C., 5% CO$_2$, and 95% humidity. The following day, 100 μL of media containing trametinib or DMSO as a control was added to wells. The final concentration of trametinib in wells was 250 nM. A dose response of a test compound (0.5 μL per well) was added. DMSO (0.5 μL) was added to control wells. The plate was briefly shaken to mix wells and then incubated at 37° C. overnight. The next day, the media was aspirated and cells were washed with Dulbecco's Phosphate Buffered Saline (Gibco). Cells were lysed using MPER lysis buffer (Pierce, Rockford, Ill.) containing Halt Phosphatase and Protease Inhibitors (Pierce, Rockford, Ill.) and Phosphatase inhibitor cocktail 2 (Sigma, St. Louis, Mo.) at 4° C. for 10 minutes with shaking.

Cellular levels of phospho-Serine 318 ATG13 (pATG13) were measured via an ELISA method. Total ATG13 Antibody (Cell Signaling Cat #13273) was used to coat the wells. The plate was incubated at 4° C. overnight and washed with ELISA wash buffer (Biolegend Cat #421601). The wells were then blocked with assay diluent (Biolegend Cat #421203) for 1 hour at room temperature. Plate wells were washed with ELISA wash buffer. Cell lysate was added to wells and incubated at room temperature for 2 hours. Plate wells were washed with ELISA wash buffer. Biotinylated pS318-ATG13 antibody (Rockland Immunochemicals Cat #600-401-C49) was diluted in assay diluent and added to each well and incubated at room temperature for 1 hour. Plate wells were washed with ELISA wash buffer. Streptavidin linked to horseradish peroxidase (Thermo Fisher Cat #21140) was diluted in assay diluent and added to each well and incubated at room temperature for 1 hour. Plate wells were washed with ELISA wash buffer. High sensitivity TMB substrate (Biolegend Cat #421101) was added to each well and incubated at room temperature for 20 minutes. The reaction was stopped with 2N Sulfuric Acid. The plate was analyzed at on a plate reader measuring absorbance at 450 nm and 540 nm (background). Signal was calculated by first subtracting the background absorbance at 540 nm from the absorbance at 450 nm for each well. Next, the background corrected absorbance at 450 nm from blank wells was subtracted from test wells. Data was compared to control wells to determine % ATG13 phosphorylation. GraphPad Prism was used to calculate IC$_{50}$ values.

Example 137. pATG13 Levels of Mutant HRas T24 Cells after Treatment with ULK Inhibitors in Combination with Trametinib T24 human urinary bladder cancer cells (25000 cells/well) were added to a 96-well tissue-culture treated plate in 100 μL of pre-warmed DMEM medium supplemented with 10% characterized fetal bovine serum (Invitrogen, Carlsbad, Calif.), 100 units/mL penicillin G, and 100 μg/mL streptomycin and allowed to grow overnight at 37° C., 5% CO2, and 95% humidity. The following day, 100 μL of media containing trametinib or DMSO as a control was added to wells. The final concentration of trametinib in wells was 250 nM. A dose response of a test compound (0.5 μL per well) was added. DMSO (0.5 μL) was added to control wells. The plate was briefly shaken to mix wells and then incubated at 37° C. overnight. The next day, the media was aspirated and cells were washed with Dulbecco's Phosphate Buffered Saline (Gibco). Cells were lysed using MPER lysis buffer (Pierce, Rockford, Ill.) containing Halt Phosphatase and Protease Inhibitors (Pierce, Rockford, Ill.) and Phosphatase inhibitor cocktail 2 (Sigma, St. Louis, Mo.) at 4° C. for 10 minutes with shaking.

Cellular levels of phospho-Serine 318 ATG13 (pATG13) were measured via an ELISA method. Total ATG13 Antibody (Cell Signaling Cat #13273) was used to coat the wells. The plate was incubated at 4° C. overnight and washed with ELISA wash buffer (Biolegend Cat #421601). The wells were then blocked with assay diluent (Biolegend Cat #421203) for 1 hour at room temperature. Plate wells were washed with ELISA wash buffer. Cell lysate was added to wells and incubated at room temperature for 2 hours. Plate wells were washed with ELISA wash buffer. Biotinylated pS318-ATG13 antibody (Rockland Immunochemicals Cat #600-401-C49) was diluted in assay diluent and added to each well and incubated at room temperature for 1 hour. Plate wells were washed with ELISA wash buffer. Streptavidin linked to horseradish peroxidase (Thermo Fisher Cat #21140) was diluted in assay diluent and added to each well and incubated at room temperature for 1 hour. Plate wells were washed with ELISA wash buffer. High sensitivity TMB substrate (Biolegend Cat #421101) was added to each well and incubated at room temperature for 20 minutes. The reaction was stopped with 2N Sulfuric Acid. The plate was analyzed at on a plate reader measuring absorbance at 450 nm and 540 nm (background). Signal was calculated by first subtracting the background absorbance at 540 nm from the absorbance at 450 nm for each well. Next, the background corrected absorbance at 450 nm from blank wells was subtracted from test wells. Data was compared to control wells to determine % ATG13 phosphorylation. GraphPad Prism was used to calculate IC$_{50}$ values.

TABLE 2

Inhibition of ULK kinase in mutant Ras or mutant BRAF cell lines by exemplary compounds shown in Table I.

| Example (Compound) No. | A549 pATG13 ELISA | MiaPaca-2 pATG13 ELISA | HCT-116 pATG13 ELISA | T24 pATG13 ELISA | A375 pATG13 ELISA |
|---|---|---|---|---|---|
| 4 | +++ | +++ | | | |
| 7 | ++++ | | | | |
| 8 | ++ | | | | |
| 10 | ++ | ++ | | | |
| 11 | ++ | + | + | | + |
| 12 | + | + | | | |
| 13 | + | + | | | |
| 14 | + | + | + | + | + |
| 16 | + | + | | | |
| 19 | ++ | ++ | | | |
| 20 | +++ | ++ | ++ | | |
| 21 | +++ | ++ | | | |
| 23 | + | + | + | | + |
| 26 | ++ | + | | | |
| 27 | ++ | ++ | | | |
| 28 | ++ | ++ | | | |
| 30 | +++ | ++ | | | |
| 31 | +++ | ++ | | | |
| 33 | ++ | + | | | |
| 34 | + | + | + | ++ | |

TABLE 2-continued

Inhibition of ULK kinase in mutant Ras or mutant BRAF cell lines by exemplary compounds shown in Table I.

| Example (Compound) No. | A549 pATG13 ELISA | MiaPaca-2 pATG13 ELISA | HCT-116 pATG13 ELISA | T24 pATG13 ELISA | A375 pATG13 ELISA |
|---|---|---|---|---|---|
| 35 | + + | + + | | | |
| 36 | + + + + | + + + + | | | |
| 37 | + + | + | | | + + + |
| 39 | + | + | + | + | + |
| 40 | + | + | | | |
| 41 | + | + | + | + | + |
| 42 | + | + | | | |
| 44 | + | + | | | |
| 46 | + | + | + + | + + | + + |
| 47 | + + | + + + | + + | | + + + |
| 50 | + + + + | + + + + | | | |
| 52 | + | + | + | | + + |
| 54 | + | + | + | | |
| 55 | + + | + | + | | + + |
| 57 | + + + + | | | | |
| 58 | + + | + | + | | |
| 60 | + + | + + | + | | + + + |
| 62 | + + | + | | | |
| 65 | + | + + | | | |
| 66 | + | + | + | + | + |
| 67 | + + | + + | | | |
| 68 | + | + | | | |
| 69 | + | + | + | | |
| 70 | + | + | + | + | + |
| 71 | | + + + + | | | |
| 72 | | + + + | | | |
| 73 | + + | + + | + | | + |
| 74 | + | + | + | + | |
| 75 | + + | + | + + | | + + |
| 76 | + | + | + | + | |
| 79 | + + | + | | | |
| 80 | + + + + | + + | | | |
| 81 | + + | + | | | |
| 82 | + + | + + | | | |
| 84 | + | + | + | + + | + + |
| 85 | + | + | + + | | + + |
| 86 | + | + | + + | + + | + |
| 87 | + + + | + + + | | | |
| 88 | + + + | + + | | | |
| 91 | + + | + + + + | | | |
| 92 | + + + | + + | | | |
| 99 | + | + + | | + + | + + |
| 100 | + + | + + | | | |
| 101 | + + + | + + + + | | | |
| 102 | + + | + + | | | |
| 103 | + | + | | | |
| 105 | + | + | + | | |
| 106 | + | + | + | | |
| 107 | + | + | | | |
| 109 | + + + + | | | | |
| 110 | + + | + | | | |
| 112 | + + | + + | | | |
| 116 | + + | + | | | |
| 117 | + + | + | | | |
| 119 | + + | + | | | |
| 120 | + + | + + | | | |
| 122 | + + + | + + | | | |
| 123 | + | | | | |
| 124 | + | + | | | |
| 125 | + | + | | | |
| 126 | + + | + | | | |
| 127 | + + | + + | | | |
| 129 | + + + | + + | | | |
| 130 | + + + | + + + | | | |
| 131 | + + | + + + | | | |
| 132 | + + | + | | | |
| 137 | + + | + | | | |
| 147 | + + | + + | | | |
| 148 | + | + | | | |
| 150 | + + | + | | | |

For Table 2, "+" refers to an IC$_{50}$ greater than 10 nM and less than or equal to 100 nM; "+ +" refers to an IC$_{50}$ greater than 100 nM and less than or equal to 300 nM; "+ + +" refers to an IC$_{50}$ greater than 300 nM and less than or equal to 600 nM; and "+ + + +" refers to an IC$_{50}$ greater than 600 nM.

Example 138. Biochemical Assay for LRRK2 (SEQ. ID NO: 4)

Activity of LRRK2 kinase was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942). Assays were conducted in 384-well plates (100 µL final volume) using 26.4 nM LRRK2 (Thermo Fisher), 0.1 mM peptide substrate (RL-GRDKYKTLRQIRQ (SEQ ID NO: 6)), 1.5 units pyruvate kinase, 2.1 units lactate dehydrogenase, 1 mM phosphoenol pyruvate, 0.28 mM NADH and 1 mM ATP in assay buffer (100 mM Tris, pH 7.5, 15 mM MgCl$_2$, 0.5 mM DTT, 0.004% (w/v) BSA, and 0.004% Triton X-100). Inhibition of LRRK2 was measured by adding serial diluted test compound (final assay concentration of 1% DMSO). A decrease in absorption at 340 nm was monitored continuously for 6 hours at 30° C. on a multi-mode microplate reader (BioTek). The reaction rate was calculated using the 2-3 h time frame. The reaction rate at each concentration of compound was converted to percent inhibition using controls (i.e. reaction with no test compound and reaction with a known inhibitor) and IC$_{50}$ values were calculated using software routines in Prism (GraphPad software).

```
LRRK2 protein sequence (residues 970-2528;
SEQ. ID NO: 4)
MAPILGYWKIKGLVQPTRLLLEYLEEKYEEHLYERDEGDKWR

NKKFELGLEFPNLPYYIDGDVKLTQSMAIIRYIADKHNMLGG

CPKERAEISMLEGAVLDIRYGVSRIAYSKDFETLKVDFLSKL

PEMLKMFEDRLCHKTYLNGDHVTHPDFMLYDALDVVLYMDPM

CLDAFPKLVCFKKRIEAIPQIDKYLKSSKYIAWPLQGWQATF

GGGDHPPKSDLVPRHNQTSLYKKAGTMHSDSISSLASEREYI

TSLDLSANELRDIDALSQKCCISVHLEHLEKLELHQNALTSF

PQQLCETLKSLTHLDLHSNKFTSFPSYLLKMSCIANLDVSRN

DIGPSVVLDPTVKCPTLKQFNLSYNQLSFVPENLTDVVEKLE

QLILEGNKISGICSPLRLKELKILNLSKNHISSLSENFLEAC

PKVESFSARMNFLAAMPFLPPSMTILKLSQNKFSCIPEAILN

LPHLRSLDMSSNDIQYLPGPAHWKSLNLRELLFSHNQISILD

LSEKAYLWSRVEKLHLSHNKLKEIPPEIGCLENLTSLDVSYN

LELRSFPNEMGKLSKIWDLPLDELHLNFDFKHIGCKAKDIIR

FLQQRLKKAVPYNRMKLMIVGNTGSGKTTLLQQLMKTKKSDL

GMQSATVGIDVKDWPIQIRDKRKRDLVLNVWDFAGREEFYST
```

-continued

HPHFMTQRALYLAVYDLSKGQAEVDAMKPWLFNIKARASSSP

VILVGTHLDVSDEKQRKACMSKITKELLNKRGFPAIRDYHFV

NATEESDALAKLRKTIINESLNFKIRDQLVVGQLIPDCYVEL

EKIILSERKNVPIEFPVIDRKRLLQLVRENQLQLDENELPHA

VHFLNESGVLLHFQDPALQLSDLYFVEPKWLCKIMAQILT

VKVEGCPKHPKGIISRRDVEKFLSKKRKFPKNYMSQYFKLLE

KFQIALPIGEEYLLVPSSLSDHRPVIELPHCENSEIIIRLYE

MPYFPMGFWSRLINRLLEISPYMLSGRERALRPNRMYWRQG

IYLNWSPEAYCLVGSEVLDNHPESFLKITVPSCRKGCILLGQ

VVDHIDSLMEEWFPGLLEIDICGEGETLLKKWALYSFNDGEE

HQKILLDDLMKKAEEGDLLVNPDQPRLTIPISQIAPDLILAD

LPRNIMLNNDELEFEQAPEFLLGDGSFGSVYRAAYEGEEVAV

KIFNKHTSLRLLRQELVVLCHLHHPSLISLLAAGIRPRMLVM

ELASKGSLDRLLQQDKASLTRTLQHRIALHVADGLRYLHSAM

IIYRDLKPHNVLLFTLYPNAAIIAKIADYGIAQYCCRMGIKT

SEGTPGFRAPEVARGNVIYNQQADVYSFGLLLYDILTTGGRI

VEGLKFPNEFDELEIQGKLPDPVKEYGCAPWPMVEKLIKQCL

KENPQERPTSAQVFDILNSAELVCLTRRILLPKNVIVECMVA

THHNSRNASIWLGCGHTDRGQLSFLDLNTEGYTSEEVADSRI

LCLALVHLPVEKESWIVSGTQSGTLLVINTEDGKKRHTLEKM

TDSVTCLYCNSFSKQSKQKNFLLVGTADGKLAIFEDKTVKLK

GAAPLKILNIGNVSTPLMCLSESTNSTERNVMWGGCGTKIFS

FSNDFTIQKLIETRTSQLFSYAAFSDSNIITVVVDTALYIAK

QNSPVVEVWDKKTEKLCGLIDCVHFLREVMVKENKESKHKMS

YSGRVKTLCLQKNTALWIGTGGGHILLLDLSTRRLIRVIYNF

CNSVRVMMTAQLGSLKNVMLVLGYNRKNTEGTQKQKEIQSCL

TVWDINLPHEVQNLEKHIEVRKELAEKMRRTSVE

TABLE 3

Inhibition of LRRK2 kinase activity by exemplary compounds shown in Table I.

| Example (Compound) No. | LRRK2 |
|---|---|
| 1 | + + + + |
| 2 | + |
| 5 | + + |
| 14 | + |
| 18 | + |
| 33 | + + + |
| 35 | + |
| 37 | + + |
| 39 | + |
| 41 | + |
| 46 | + + |
| 47 | + + |
| 48 | + + |
| 49 | + + |
| 50 | + |
| 51 | + |

TABLE 3-continued

Inhibition of LRRK2 kinase activity by exemplary compounds shown in Table I.

| Example (Compound) No. | LRRK2 |
|---|---|
| 52 | + |
| 55 | + + |
| 56 | + + |
| 58 | + + |
| 61 | + + + + |
| 64 | + |
| 66 | + + |
| 68 | + + |
| 69 | + + + |
| 70 | + |
| 74 | + + + |
| 76 | + + |
| 78 | + + |
| 79 | + + |
| 84 | + + |
| 86 | + |
| 87 | + + + |
| 90 | + + + |
| 92 | + + + + |
| 93 | + + |
| 99 | + |
| 105 | + |
| 106 | + + |
| 107 | + + |
| 108 | + |
| 109 | + |
| 111 | + + |
| 112 | + + |
| 113 | + + |
| 114 | + |
| 115 | + + |
| 116 | + |
| 117 | + |
| 118 | + |
| 119 | + + |
| 120 | + + |
| 122 | + |
| 123 | + + |
| 124 | + + |
| 125 | + |
| 126 | + |
| 127 | + + + |
| 129 | + + + + |
| 131 | + + |
| 132 | + |
| 147 | + + + |
| 148 | + + |

For Table 3, "+" refers to an $IC_{50}$ greater than 1 nM and less than or equal to 100 nM; "+ +" refers to an $IC_{50}$ greater than 100 nM and less than or equal to 300 nM; "+ + +" refers to an $IC_{50}$ greater than 300 nM and less than or equal to 600 nM; and "+ + + +" refers to an $IC_{50}$ greater than 600 nM.

Example 139. Evaluation of ULK Inhibitors in Pancreatic Ductal Adenocarcinoma (PDAC) In Vitro and In Vivo ULK inhibitors will be evaluated in PDAC flux assays, and the $IC_{50}$ of the compounds in a panel of multiple PDAC cell lines, including cells derived from primary tumors of a Trp53$^{lox/+}$, LSL-Kras$^{G12D}$, Rosa-rtTA$^{LSL}$, p48Cre$^+$) will be determined using a clonogenicity 2D assay and a 3D organoid assay, in the absence or the presence of trametinib.

The inhibition of autophagic flux using flux reporters in PDAC tumors in vivo using syngeneic orthotopic models after single and multiple doses will be evaluated.

The therapeutic efficacy of ULK inhibitors in PDAC models will be evaluated by (i) assessing the tumor kinetics of PDAC subcutaneously; (ii) assessing the tumor kinetics of PDAC (KPC implanted C57 black mice) orthotopically in the pancreas in syngeneic models; (iii) assessing tumor growth kinetics in syngeneic models with ULK inhibitors and MEK inhibitors; (iv) assessing the compounds in the PDAC autochthonous model; (v) assessing histological changes in the tumor microenvironment; (vi) assessing the changes in the immune cell infiltrates in the tumors upon inhibition by ULK inhibitors; (vii) assessing the efficacy of ULK inhibitors in combination with immune checkpoint blockade.

EQUIVALENTS

While specific embodiments have been discussed, the above specification is illustrative and not restrictive. Many variations of the embodiments will become apparent to those skilled in the art upon review of this specification. The full scope of what is disclosed should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained.

What is claimed is:

1. A compound represented by:

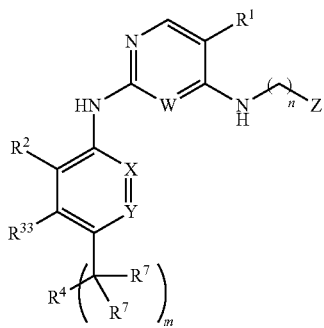

Formula I or a pharmaceutically acceptable salt, enantiomer, stereoisomer, or tautomer thereof, wherein:

W is CH or N;

X is CH or N;

Y is $C(R^3)$ or N;

$R^1$ is selected from the group consisting of halogen, cyano, $C_1$-$C_5$alkyl, and $C_3$-$C_5$cycloalkyl, wherein each $C_1$-$C_5$alkyl and $C_3$-$C_5$cycloalkyl may be optionally substituted by one, two or three independent occurrences of fluorine;

$R^2$ is selected from the group consisting of H, halogen, cyano, $C_1$-$C_5$alkyl, $C_3$-$C_6$cycloalkyl, $C_2$-$C_5$alkenyl, $C_2$-$C_5$alkynyl, $C_1$-$C_5$alkoxy, and $C_1$-$C_5$alkoxy-$C_2$-$C_5$alkyl, wherein each $C_1$-$C_5$alkyl, $C_3$-$C_6$cycloalkyl, $C_2$-$C_5$alkenyl, $C_2$-$C_5$alkynyl, and $C_1$-$C_5$alkoxy may be optionally substituted by one, two, or three independent occurrences of fluorine or cyano;

each occurrence of $R^3$ and $R^{33}$ is independently selected from the group consisting of H, halogen, $C_1$-$C_6$alkyl, and $C_1$-$C_6$alkoxy, wherein each $C_1$-$C_6$alkyl and $C_1$-$C_6$alkoxy may be optionally substituted by one or more independent occurrences of fluorine;

$R^4$ is selected from the group consisting of B, D, $NR^6R^9$, NR—$(C(R^{10})_2)_p$—$NR^6R^6$, C(O)—$NR^6R^9$, C(O)—B, C(O)-D, and CN;

B is selected from an N-linked heterocyclyl having at least one nitrogen and optionally having an additional ring nitrogen or oxygen and heteroaryl, wherein B may be optionally substituted on one or more available carbons by $R^7$ and may be optionally substituted on an available nitrogen by $R^9$;

D is selected from a C-linked heterocyclyl having at least one nitrogen and optionally having an additional ring nitrogen or oxygen and heteroaryl, wherein D may be optionally substituted on one or more available carbons by $R^7$ and may be optionally substituted on an available nitrogen by $R^9$;

each occurrence of $R^5$ is independently selected from the group consisting of H, $C_1$-$C_6$alkyl, $C_3$-$C_6$cycloalkyl, and heterocyclyl, wherein each $C_1$-$C_6$alkyl and $C_3$-$C_6$cycloalkyl may be optionally substituted by one or more independent occurrences of fluorine;

each occurrence of $R^7$ is independently selected from the group consisting of H, $C_1$-$C_6$alkyl, $C_3$-$C_6$cycloalkyl, cyano, and $(C(R^{10})_2)_n$—$NR^9R^9$, wherein each $C_1$-$C_6$alkyl and $C_3$-$C_6$cycloalkyl may be optionally substituted by one or more independent occurrences of fluorine, or two $R^7$ are joined together with the atom to which they are attached to form oxo;

each occurrence of $R^6$ and $R^9$ is independently selected from the group consisting of H, $C_1$-$C_6$alkyl, $C_3$-$C_6$cycloalkyl, $C_1$-$C_5$alkoxy-$C_2$-$C_5$alkyl, $C(=O)R^5$, $SO_2R^5$, C-linked heterocyclyl having at least one nitrogen and optionally having an additional ring nitrogen or oxygen, and heteroaryl, wherein each $C_1$-$C_6$alkyl and $C_3$-$C_6$cycloalkyl may be optionally substituted by one or more independent occurrences of fluorine;

each occurrence of $R^{10}$ is independently selected from the group consisting of H, $C_1$-$C_3$alkyl, and $C_3$-$C_5$cycloalkyl, wherein each $C_1$-$C_3$alkyl and $C_3$-$C_5$cycloalkyl may be optionally substituted by one or more independent occurrences of fluorine, or two $R^{10}$ are joined together with the carbon to which they are attached to form a $C_3$-$C_5$cycloalkyl;

Z is selected from the group consisting of a 4 membered lactam ring bound through the nitrogen atom and a 6-10 membered lactam ring bound through the nitrogen atom, wherein a lactam ring atom may optionally be oxygen or $NR^6$ when the lactam ring is a 6-10 membered ring and an available carbon atom on 4 membered lactam ring or a 6-10 membered lactam is optionally substituted by $R^{36}$;

each occurrence of $R^{36}$ is independently selected from $C_1$-$C_6$alkyl and $C_3$-$C_6$cycloalkyl, wherein each $C_1$-$C_6$alkyl and $C_3$-$C_6$cycloalkyl may be optionally substituted by one or more independent occurrences of fluorine, or two $R^{36}$ are joined together with the carbon to which they are attached to form a $C_3$-$C_6$cycloalkyl;

h is 1, 2, or 3;
m is 0, 1, 2, or 3;
n is 2, 3, or 4; and
p is 2 or 3;
provided that both X and Y are not N.

2. The compound of claim 1, wherein Z is selected from:

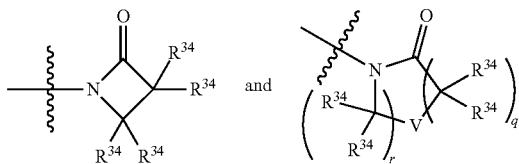

wherein
V is selected from the group consisting of oxygen, $C(R^{34})_2$, and $NR^6$;
each occurrence of $R^{34}$ is independently selected from H and $R^{36}$, wherein each occurrence of $R^{36}$ is independently selected from $C_1$-$C_6$alkyl and $C_3$-$C_6$cycloalkyl, or two $R^{36}$ are joined together with the carbon to which they are attached to form a $C_3$-$C_6$cycloalkyl;
q is 0, 1, 2, or 3; and
r is 2 or 4;
provided that, if q is 0, then r is not 2.

3. The compound of claim 1, wherein Z is selected from:

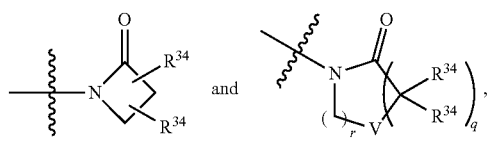

wherein
V is selected from the group consisting of oxygen, $C(R^{34})_2$, and $NR^6$;
each occurrence of $R^{34}$ is independently selected from H and $R^{36}$, wherein each occurrence of $R^{36}$ is independently selected from $C_1$-$C_6$alkyl and $C_3$-$C_6$cycloalkyl, or two $R^{36}$ are joined together with the carbon to which they are attached to form a $C_3$-$C_6$cycloalkyl;
q is 0, 1, 2, or 3; and
r is 2 or 3;
provided that, if q is 0, then r is not 2.

4. The compound of claim 2, wherein Z is selected from the group consisting of:

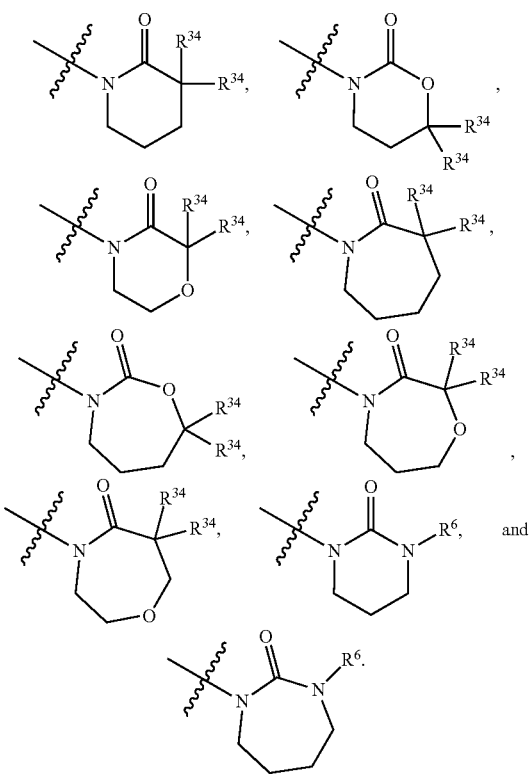

5. The compound of claim 1, wherein $R^4$ is selected from the group consisting of:

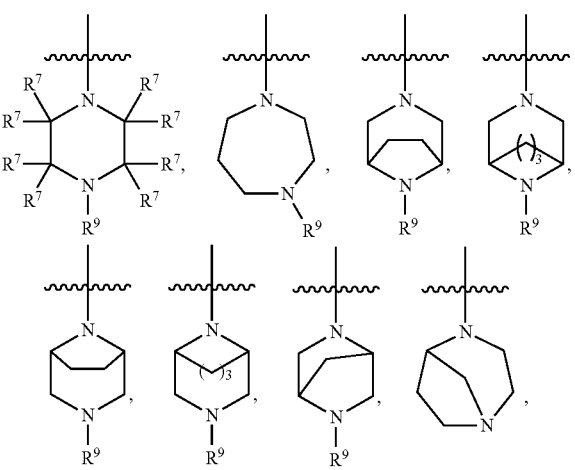

-continued

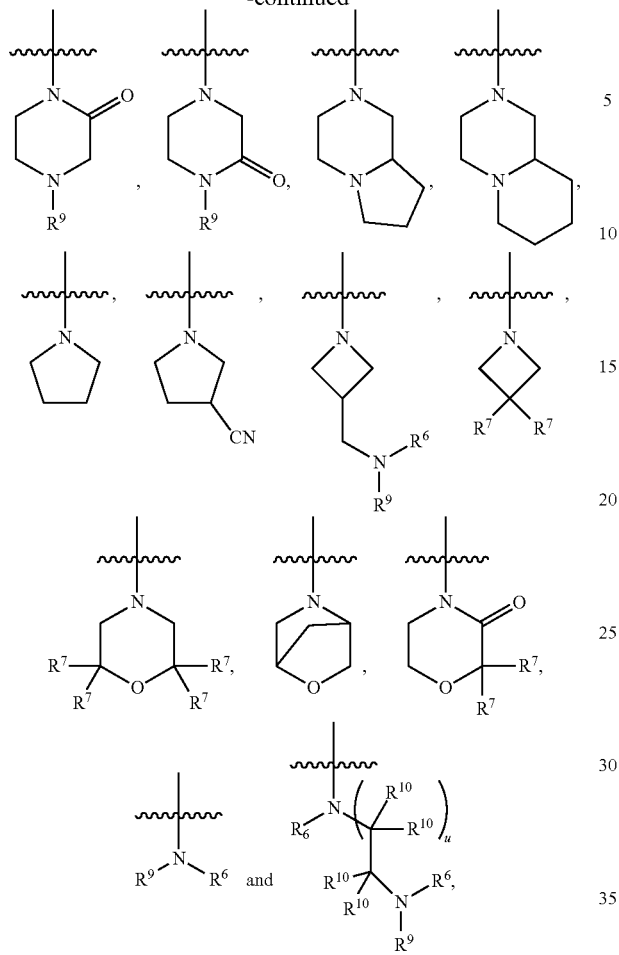

wherein u is 1 or 2.

6. The compound of claim 1, wherein $R^1$ is selected from the group consisting of halogen, $C_1$-$C_5$alkyl, and $C_3$-$C_5$cycloalkyl, wherein $C_1$-$C_5$alkyl may be optionally substituted with one, two, or three occurrences of fluorine.

7. The compound of claim 1, wherein $R^2$ is selected from the group consisting of $C_{1-2}$alkyl and $C_{3-4}$cycloalkyl.

8. The compound of claim 1, wherein $R^2$ is selected from the group consisting of chloro and bromo.

9. The compound of claim 1, wherein n is 3.

10. The compound of claim 1 represented by:

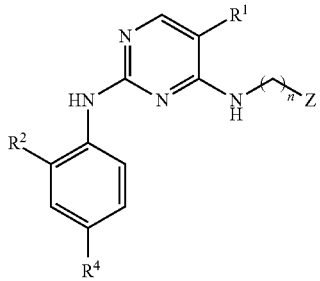

Formula II or a pharmaceutically acceptable salt thereof, wherein:
n is 2, 3, or 4;
Z is selected from the group consisting of:

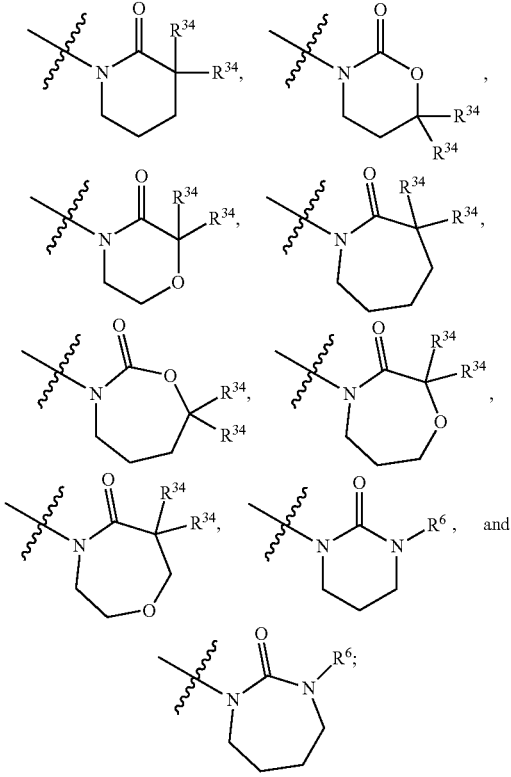

$R^1$ is selected from the group consisting of halogen, cyano, $C_1$-$C_5$alkyl, and $C_3$-$C_5$cycloalkyl, wherein each $C_1$-$C_5$alkyl and $C_3$-$C_5$cycloalkyl may be optionally substituted by one, two or three independent occurrences of fluorine;

$R^2$ is selected from the group consisting of halogen, $C_1$-$C_2$alkyl and $C_3$-$C_4$cycloalkyl;

$R^4$ is selected from the group consisting of:

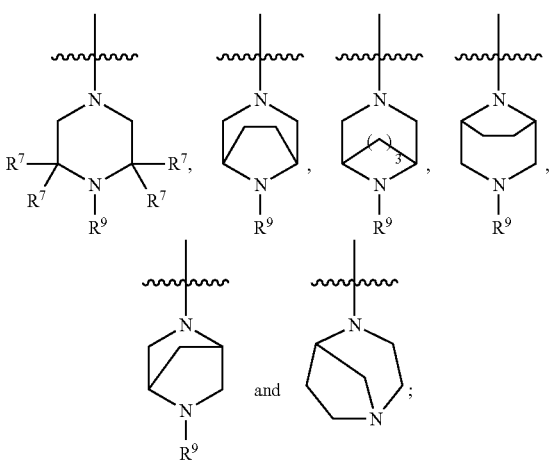

each occurrence of $R^6$ and $R^9$ is independently selected from the group consisting of H, $C_1$-$C_6$alkyl, $C_3$-$C_6$cycloalkyl, C(=O)$R^5$, SO$_2$$R^5$, , wherein each $C_1$-$C_6$alkyl and $C_3$-$C_6$cycloalkyl may be optionally substituted by one or more independent occurrences of fluorine;

each occurrence of $R^5$ is independently selected from the group consisting of H, $C_1$-$C_6$alkyl, $C_3$-$C_6$cycloalkyl, and heterocyclyl, wherein each $C_1$-$C_6$alkyl and $C_3$-$C_6$cycloalkyl may be optionally substituted by one or more independent occurrences of fluorine;

each occurrence of $R^7$ is independently selected from the group consisting of H, $C_1$-$C_6$ alkyl, and $C_3$-$C_6$cycloalkyl, wherein each $C_1$-$C_6$alkyl and $C_3$-$C_6$cycloalkyl may be optionally substituted by one or more independent occurrences of fluorine, or two $R^7$ are joined together with the atom to which they are attached to form oxo;

D is selected from a C-linked heterocyclyl having at least one nitrogen and optionally having an additional ring nitrogen or oxygen and heteroaryl, wherein D may be optionally substituted on one or more available carbons by $R^7$ and may be optionally substituted on an available nitrogen by $R^9$; and each occurrence of $R^{34}$ is independently selected from H and $R^{36}$, wherein each occurrence of $R^{36}$ is independently selected from $C_1$-$C_6$alkyl and $C_3$-$C_6$cycloalkyl, wherein each $C_1$-$C_6$alkyl and $C_3$-$C_6$cycloalkyl may be optionally substituted by one or more independent occurrences of fluorine, or two $R^{36}$ are joined together with the carbon to which they are attached to form a $C_3$-$C_6$cycloalkyl.

11. The compound of claim 10, wherein $R^1$ is selected from the group consisting of halogen, $C_1$-$C_5$alkyl, and $C_3$-$C_5$cycloalkyl, wherein $C_1$-$C_5$alkyl may be optionally substituted with one, two, or three occurrences of fluorine.

12. The compound of claim 11, wherein $R^1$ is $CF_3$.

13. The compound of claim 1, wherein $R^2$ is selected from the group consisting of H, $C_3$-$C_4$cycloalkyl, $C_1$-$C_5$alkyl, and halogen.

14. The compound of claim 10, wherein $R^4$ is selected from the group consisting of:

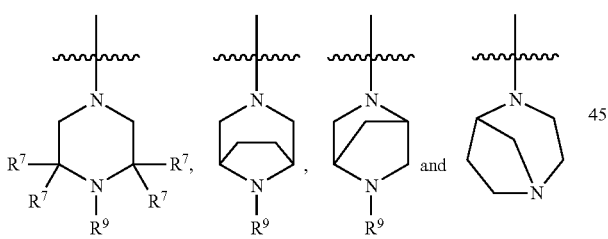

15. The compound of claim 10, wherein Z is selected from the group consisting of:

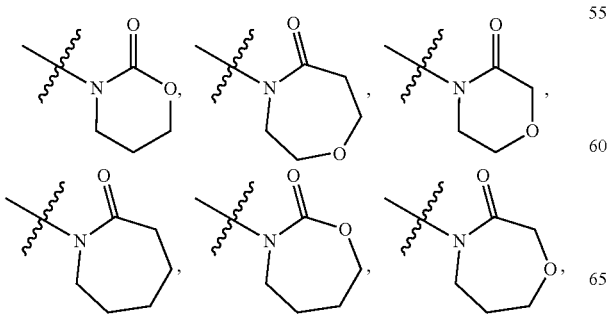

-continued

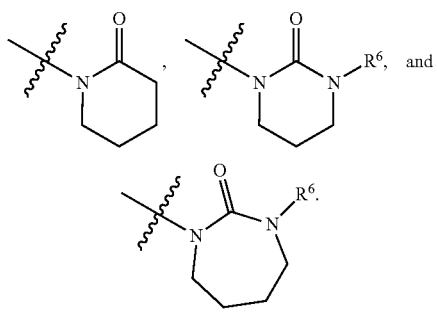

16. The compound of claim 1 represented by:

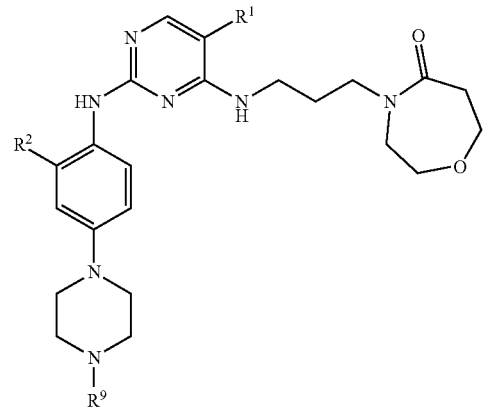

Forula IIA.2-A wherein $R^1$ is selected from the group consisting of $CF_3$, $CF_2H$, bromo, chloro, and cyclopropyl;

$R^2$ is selected from the group consisting of $C_1$-$C_2$alkyl, $C_3$-$C_4$cycloalkyl, and halogen; and $R^9$ is selected from the group consisting of $C_1$-$C_3$alkyl, H, and $C_3$-$C_5$cycloalkyl.

17. The compound of claim 1 represented by:

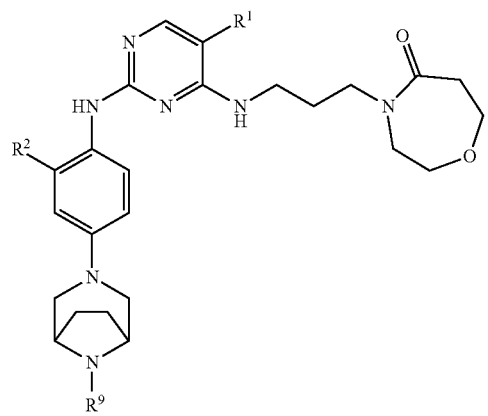

Formula IIA.11-A wherein
R¹ is selected from the group consisting of bromo, chloro, CF₃, CF₂H, and cyclopropyl;
R² is selected from the group consisting of C₁-C₂alkyl, C₃-C₄cycloalkyl, and halogen; and
R⁹ is selected from the group consisting of C₁-C₃alkyl, H, and C₃-C₅cycloalkyl.

18. The compound of claim 17, wherein R¹ is CF₃; R² is selected from the group consisting of C₁-C₂alkyl, C₃-C₄cycloalkyl, bromo, and chloro; and R⁹ is selected from C₁-C₃alkyl and H.

19. The compound of claim 1 selected from the group consisting of: 1-(3-((5-bromo-2-((2-cyclopropyl-4-(4-methylpiperazin-1-yl)phenyl)amino)pyrimidin-4-yl)amino)propyl)piperidin-2-one, 1-(3-((2-((4-(4-ethylpiperazin-1-yl)-2-methylphenyl)amino)-5-(trifluoromethyl)pyrimidin-4-yl)amino)propyl)piperidin-2-one, 1-(3-((5-chloro-2-((2-cyclopropyl-4-(4-methylpiperazin-1-yl)phenyl)amino)pyrimidin-4-yl)amino)propyl)piperidin-2-one, 1-(3-((2-(2-cyclopropyl-4-(4-methyl-1,4-diazepan-1-yl)phenyl)amino)-5-(trifluoromethyl)pyrimidin-4-yl)amino)propyl)piperidin-2-one, 1-(3-((5-chloro-2-((2-methyl-4-(1-methylpiperidin-4-yl)phenyl)amino)pyrimidin-4-yl)amino)propyl)piperidin-2-one, (R)-1-(3-ethyl-4-((4-((3-(2-oxopiperidin-1-yl)propyl)amino)-5-(trifluoromethyl)pyrimidin-2-yl)amino)phenyl)pyrrolidine-3-carbonitrile, 1-(3-((2-((4-(4-cyclopropylpiperazin-1-yl)-2-methylphenyl)amino)-5-(trifluoromethyl)pyrimidin-4-yl)amino)propyl)piperidin-2-one, 1-(3-((5-bromo-2-((2-isopropyl-4-(4-methylpiperazin-1-yl)phenyl)amino)pyrimidin-4-yl)amino)propyl)piperidin-2-one, 1-(3-((2-((2-ethyl-4-(4-ethylpiperazin-1-yl)phenyl)amino)-5-(trifluoromethyl)pyrimidin-4-yl)amino)propyl)piperidin-2-one, 1-(3-((2-((2-cyclopropyl-4-(4-methylpiperazin-1-yl)phenyl)amino)-5-(trifluoromethyl)pyrimidin-4-yl)amino)propyl)piperidin-2-one, 4-(3-cyclopropyl-4-((4-((3-(2-oxopiperidin-1-yl)propyl)amino)-5-(trifluoromethyl)pyrimidin-2-yl)amino)phenyl)-1-methylpiperazin-2-one, 1-(3-((5-bromo-2-((4-(4-ethylpiperazin-1-yl)-2-isopropylphenyl)amino)pyrimidin-4-yl)amino)propyl)piperidin-2-one, 1-(3-((2-((2-ethyl-4-(4-methylpiperazin-1-yl)phenyl)amino)-5-(trifluoromethyl)pyrimidin-4-yl)amino)propyl)piperidin-2-one, 1-(3-((2-(2-methyl-4-(1-methylpiperidin-4-yl)phenyl)amino)-5-(trifluoromethyl)pyrimidin-4-yl)amino)propyl)piperidin-2-one, 1-(3-((5-chloro-2-((4-(4-ethylpiperazin-1-yl)-2-isopropylphenyl)amino)pyrimidin-4-yl)amino)propyl)piperidin-2-one, 1-(3-((2-((2-cyclopropyl-4-(piperazin-1-yl)phenyl)amino)-5-(trifluoromethyl)pyrimidin-4-yl)amino)propyl)piperidin-2-one, 1-(3-((2-((2-cyclopropyl-5-fluoro-4-(4-methylpiperazin-1-yl)phenyl)amino)-5-(trifluoromethyl)pyrimidin-4-yl)amino)propyl)piperidin-2-one, 1-(3-((2-((2-methyl-4-(piperazin-1-yl)phenyl)amino)-5-(trifluoromethyl)pyrimidin-4-yl)amino)propyl)piperidin-2-one, 1-(3-((2-((2-methyl-4-(4-methylpiperazin-1-yl)phenyl)amino)-5-(trifluoromethyl)pyrimidin-4-yl)amino)propyl)piperidin-2-one, 1-(3-((2-((4-(4-(2-fluoroethyl)piperazin-1-yl)-2-methylphenyl)amino)-5-(trifluoromethyl)pyrimidin-4-yl)amino)propyl)piperidin-2-one, 1-(3-((5-chloro-2-((2-methyl-4-(piperidin-4-yl)phenyl)amino)pyrimidin-4-yl)amino)propyl)piperidin-2-one, 1-(3-((2-((4-(4-acetylpiperazin-1-yl)-2-cyclopropylphenyl)amino)-5-(trifluoromethyl)pyrimidin-4-yl)amino)propyl)piperidin-2-one, 1-(3-((5-chloro-2-((2-ethyl-4-(4-methylpiperazin-1-yl)phenyl)amino)pyrimidin-4-yl)amino)propyl)piperidin-2-one, (S)-1-(3-ethyl-4-((4-((3-(2-oxopiperidin-1-yl)propyl)amino)-5-(trifluoromethyl)pyrimidin-2-yl)amino)phenyl)pyrrolidine-3-carbonitrile, 1-(3-((5-bromo-2-((2-ethyl-4-(4-methylpiperazin-1-yl)phenyl)amino)pyrimidin-4-yl)amino)propyl)piperidin-2-one, 1-(3-((2-((4-(4-isopropylpiperazin-1-yl)-2-methylphenyl)amino)-5-(trifluoromethyl)pyrimidin-4-yl)amino)propyl)piperidin-2-one, 1-(3-((2-((2-isopropyl-4-(4-methylpiperazin-1-yl)phenyl)amino)-5-(trifluoromethyl)pyrimidin-4-yl)amino)propyl)piperidin-2-one, 1-(3-((2-((4-(4-cyclobutylpiperazin-1-yl)-2-methylphenyl)amino)-5-(trifluoromethyl)pyrimidin-4-yl)amino)propyl)piperidin-2-one, 1-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)piperidin-2-one, 1-(3-((2-((2-cyclopropyl-4-(4-ethylpiperazin-1-yl)phenyl)amino)-5-(trifluoromethyl)pyrimidin-4-yl)amino)propyl)piperidin-2-one, 1-(3-((2-((2-methyl-4-(piperidin-4-yl)phenyl)amino)-5-(trifluoromethyl)pyrimidin-4-yl)amino)propyl)piperidin-2-one, 1-(3-((2-((4-(1,4-diazepan-1-yl)phenyl)amino)-5-(trifluoromethyl)pyrimidin-4-yl)amino)propyl)piperidin-2-one, 1-(3-((2-((2-ethyl-4-(4-methyl-1,4-diazepan-1-yl)phenyl)amino)-5-(trifluoromethyl)pyrimidin-4-yl)amino)propyl)piperidin-2-one, 1-(3-((2-((4-(4-ethylpiperazin-1-yl)-2-isopropylphenyl)amino)-5-(trifluoromethyl)pyrimidin-4-yl)amino)propyl)piperidin-2-one, 1-(3-((2-((4-(4-ethyl-1,4-diazepan-1-yl)phenyl)amino)-5-(trifluoromethyl)pyrimidin-4-yl)amino)propyl)piperidin-2-one, 1-(3-((2-((4-methyl-6-morpholinopyridin-3-yl)amino)-5-(trifluoromethyl)pyrimidin-4-yl)amino)propyl)piperidin-2-one, 3-(3-((2-((2-ethyl-4-(4-methylpiperazin-1-yl)phenyl)amino)-5-(trifluoromethyl)pyrimidin-4-yl)amino)propyl)-1,3-oxazinan-2-one, 3-(3-((2-((2-cyclopropyl-4-(4-methylpiperazin-1-yl)phenyl)amino)-5-(trifluoromethyl)pyrimidin-4-yl)amino)propyl)-1,3-oxazinan-2-one, 3-(3-((5-chloro-2-((2-ethyl-4-(4-methylpiperazin-1-yl)phenyl)amino)pyrimidin-4-yl)amino)propyl)-1,3-oxazinan-2-one, 3-(3-((5-bromo-2-((2-ethyl-4-(4-methylpiperazin-1-yl)phenyl)amino)pyrimidin-4-yl)amino)propyl)-1,3-oxazinan-2-one, 3-(3-((5-cyclopropyl-2-((2-ethyl-4-(4-methylpiperazin-1-yl)phenyl)amino)pyrimidin-4-yl)amino)propyl)-1,3-oxazinan-2-one, 3-(3-((2-((2-ethyl-4-(piperazin-1-yl)phenyl)amino)-5-(trifluoromethyl)pyrimidin-4-yl)amino)propyl)-1,3-oxazinan-2-one, 3-(3-((2-((2-cyclopropyl-4-(piperazin-1-yl)phenyl)amino)-5-(trifluoromethyl)pyrimidin-4-yl)amino)propyl)-1,3-oxazinan-2-one, 3-(3-((5-bromo-2-((2-cyclopropyl-4-(4-methylpiperazin-1-yl)phenyl)amino)pyrimidin-4-yl)amino)propyl)-1,3-oxazinan-2-one, 3-(3-((2-((2-methyl-4-(piperazin-1-yl)phenyl)amino)-5-(trifluoromethyl)pyrimidin-4-yl)amino)propyl)-1,3-oxazinan-2-one, 3-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-1,3-oxazinan-2-one, rac-(R)-3-(3-((2-((2-ethyl-4-(hexahydropyrrolo[1,2-a]pyrazin-2(1H)-yl)phenyl)amino)-5-(trifluoromethyl)pyrimidin-4-yl)amino)propyl)-1,3-oxazinan-2-one, rac-(R)-3-(3-((2-((2-cyclopropyl-4-(hexahydropyrrolo[1,2-a]pyrazin-2(1H)-yl)phenyl)amino)-5-(trifluoromethyl)pyrimidin-4-yl)amino)propyl)-1,3-oxazinan-2-one, 3-(3-((2-((2-ethyl-4-(4-methyl-2-oxopiperazin-1-yl)phenyl)amino)-5-(trifluoromethyl)pyrimidin-4-yl)amino)propyl)-1,3-oxazinan-2-one, 3-(3-((2-((2-methyl-4-(4-methylpiperazin-1-yl)phenyl)amino)-5-(trifluoromethyl)pyrimidin-4-yl)amino)propyl)-1,3-oxazinan-2-one, 4-(3-((2-((2-cyclopropyl-4-(4-methylpiperazin-1-yl)phenyl)amino)-5-(trifluoromethyl)pyrimidin-4-yl)amino)propyl)morpholin-3-one, 1-(3-((2-((2-cyclopropyl-4-(4-methylpiperazin-1-yl)phenyl)amino)-5-(trifluoromethyl)pyrimidin-4-yl)amino)propyl)azepan-2-one, 4-(3-((2-((2-ethyl-4-morpholinophenyl)amino)-5-

(trifluoromethyl)pyrimidin-4-yl)amino)propyl)-1,4-oxazepan-3-one, 4-(3-((2-((2-cyclopropyl-4-morpholinophenyl)amino)-5-(trifluoromethyl)pyrimidin-4-yl)amino)propyl)-1,4-oxazepan-3-one, 4-(3-((2-((2-cyclopropyl-4-(4-methylpiperazin-1-yl)phenyl)amino)-5-(trifluoromethyl)pyrimidin-4-yl)amino)propyl)-1,4-oxazepan-3-one, 4-(3-((2-((2-ethyl-4-(4-methylpiperazin-1-yl)phenyl)amino)-5-(trifluoromethyl)pyrimidin-4-yl)amino)propyl)-1,4-oxazepan-3-one, 4-(3-((5-chloro-2-((2-cyclopropyl-4-(4-methylpiperazin-1-yl)phenyl)amino)pyrimidin-4-yl)amino)propyl)-1,4-oxazepan-3-one, 4-(3-((5-chloro-2-((2-ethyl-4-morpholinophenyl)amino)pyrimidin-4-yl)amino)propyl)-1,4-oxazepan-3-one, 4-(3-((5-chloro-2-((2-ethyl-4-(4-methylpiperazin-1-yl)phenyl)amino)pyrimidin-4-yl)amino)propyl)-1,4-oxazepan-3-one, 4-(3-((5-chloro-2-((2-cyclopropyl-4-morpholinophenyl)amino)pyrimidin-4-yl)amino)propyl)-1,4-oxazepan-3-one, 4-(3-((2-((4-(4-ethylpiperazin-1-yl)-2-isopropylphenyl)amino)-5-(trifluoromethyl)pyrimidin-4-yl)amino)propyl)-1,4-oxazepan-3-one, 4-(3-((5-cyclopropyl-2-((2-ethyl-4-(4-methylpiperazin-1-yl)phenyl)amino)pyrimidin-4-yl)amino)propyl)-1,4-oxazepan-3-one, 4-(3-((2-((2-cyclopropyl-4-(piperazin-1-yl)phenyl)amino)-5-(trifluoromethyl)pyrimidin-4-yl)amino)propyl)-1,4-oxazepan-3-one, 4-(3-((2-((2-ethyl-4-(4-methyl-1,4-diazepan-1-yl)phenyl)amino)-5-(trifluoromethyl)pyrimidin-4-yl)amino)propyl)-1,4-oxazepan-3-one, 4-(3-((2-((2-ethyl-5-fluoro-4-(4-methylpiperazin-1-yl)phenyl)amino)-5-(trifluoromethyl)pyrimidin-4-yl)amino)propyl)-1,4-oxazepan-3-one, 4-(3-((5-bromo-2-((2-cyclopropyl-4-(4-methylpiperazin-1-yl)phenyl)amino)pyrimidin-4-yl)amino)propyl)-1,4-oxazepan-3-one, 4-(3-((5-bromo-2-((2-ethyl-4-(4-methyl-1,4-diazepan-1-yl)phenyl)amino)pyrimidin-4-yl)amino)propyl)-1,4-oxazepan-3-one, 4-(3-((5-bromo-2-((2-isopropyl-4-(4-methylpiperazin-1-yl)phenyl)amino)pyrimidin-4-yl)amino)propyl)-1,4-oxazepan-3-one, 4-(3-((2-((2-methyl-4-(4-methylpiperazin-1-yl)phenyl)amino)-5-(trifluoromethyl)pyrimidin-4-yl)amino)propyl)-1,4-oxazepan-5-one, 4-(3-((2-((2-ethyl-4-(4-methylpiperazin-1-yl)phenyl)amino)-5-(trifluoromethyl)pyrimidin-4-yl)amino)propyl)-1,4-oxazepan-5-one, 4-(3-((2-((2-cyclopropyl-4-(4-methylpiperazin-1-yl)phenyl)amino)-5-(trifluoromethyl)pyrimidin-4-yl)amino)propyl)-1,4-oxazepan-5-one, 4-(3-((2-((2-cyclopropyl-4-morpholinophenyl)amino)-5-(trifluoromethyl)pyrimidin-4-yl)amino)propyl)-1,4-oxazepan-5-one, 4-(3-((2-((2-ethyl-4-morpholinophenyl)amino)-5-(trifluoromethyl)pyrimidin-4-yl)amino)propyl)-1,4-oxazepan-5-one, 4-(3-((2-((4-(4-ethylpiperazin-1-yl)-2-isopropylphenyl)amino)-5-(trifluoromethyl)pyrimidin-4-yl)amino)propyl)-1,4-oxazepan-5-one, 4-(3-((2-((2-methyl-4-(piperazin-1-yl)phenyl)amino)-5-(trifluoromethyl)pyrimidin-4-yl)amino)propyl)-1,4-oxazepan-5-one, 4-(3-((5-bromo-2-((2-ethyl-4-(4-methylpiperazin-1-yl)phenyl)amino)pyrimidin-4-yl)amino)propyl)-1,4-oxazepan-5-one, rac-4-(3-((2-((4-((1R,4R)-2-oxa-5-azabicyclo[2.2.1]heptan-5-yl)-2-methylphenyl)amino)-5-(trifluoromethyl)pyrimidin-4-yl)amino)propyl)-1,4-oxazepan-5-one, 4-(3-((2-((2-ethyl-4-(4-methyl-1,4-diazepan-1-yl)phenyl)amino)-5-(trifluoromethyl)pyrimidin-4-yl)amino)propyl)-1,4-oxazepan-5-one, 4-(3-((5-chloro-2-((2-ethyl-4-(4-methylpiperazin-1-yl)phenyl)amino)pyrimidin-4-yl)amino)propyl)-1,4-oxazepan-5-one, 4-(3-((5-bromo-2-((2-cyclopropyl-4-(4-methylpiperazin-1-yl)phenyl)amino)pyrimidin-4-yl)amino)propyl)-1,4-oxazepan-5-one, 4-(3-((5-chloro-2-((2-cyclopropyl-4-(4-methylpiperazin-1-yl)phenyl)amino)pyrimidin-4-yl)amino)propyl)-1,4-oxazepan-5-one, 4-(3-((5-cyclopropyl-2-((2-ethyl-4-(4-methylpiperazin-1-yl)phenyl)amino)pyrimidin-4-yl)amino)propyl)-1,4-oxazepan-5-one, 4-(3-((2-((2-ethyl-4-(piperazin-1-yl)phenyl)amino)-5-(trifluoromethyl)pyrimidin-4-yl)amino)propyl)-1,4-oxazepan-5-one, 4-(3-((2-((2-cyclopropyl-4-(piperazin-1-yl)phenyl)amino)-5-(trifluoromethyl)pyrimidin-4-yl)amino)propyl)-1,4-oxazepan-5-one, 4-(3-((2-((2-ethyl-5-fluoro-4-(4-methylpiperazin-1-yl)phenyl)amino)-5-(trifluoromethyl)pyrimidin-4-yl)amino)propyl)-1,4-oxazepan-5-one, 4-(3-((5-bromo-2-((2-isopropyl-4-(4-methylpiperazin-1-yl)phenyl)amino)pyrimidin-4-yl)amino)propyl)-1,4-oxazepan-5-one, 4-(3-((5-chloro-2-((2-isopropyl-4-(4-methylpiperazin-1-yl)phenyl)amino)pyrimidin-4-yl)amino)propyl)-1,4-oxazepan-5-one, 4-(3-((5-chloro-2-((2-cyclopropyl-4-(piperazin-1-yl)phenyl)amino)pyrimidin-4-yl)amino)propyl)-1,4-oxazepan-5-one, 4-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-5-one, rac-(R)-4-(3-((2-((2-ethyl-4-(hexahydropyrrolo[1,2-a]pyrazin-2(1H)-yl)phenyl)amino)-5-(trifluoromethyl)pyrimidin-4-yl)amino)propyl)-1,4-oxazepan-5-one, 1-(3-((2-((2-cyclopropyl-4-(4-methylpiperazin-1-yl)phenyl)amino)-5-(trifluoromethyl)pyridin-4-yl)amino)propyl)piperidin-2-one, 4-(3-((2-((2-ethyl-4-(4-methylpiperazin-1-yl)phenyl)amino)-5-(trifluoromethyl)pyridin-4-yl)amino)propyl)-1,4-oxazepan-5-one, 4-(3-((2-((2-cyclopropyl-4-(4-methylpiperazin-1-yl)phenyl)amino)-5-(trifluoromethyl)pyridin-4-yl)amino)propyl)-1,4-oxazepan-5-one, 3-(3-((2-((4-(4-methylpiperazin-1-yl)phenyl)amino)-5-(trifluoromethyl)pyridin-4-yl)amino)propyl)-1,3-oxazinan-2-one, 1-(3-((2-((4-(4-methylpiperazin-1-yl)phenyl)amino)-5-(trifluoromethyl)pyridin-4-yl)amino)propyl)piperidin-2-one, 1-(3-((2-((4-methyl-6-(4-methylpiperazin-1-yl)pyridin-3-yl)amino)-5-(trifluoromethyl)pyridin-4-yl)amino)propyl)piperidin-2-one, 1-(3-((2-((4-methyl-6-morpholinopyridin-3-yl)amino)-5-(trifluoromethyl)pyridin-4-yl)amino)propyl)piperidin-2-one, 4-(3-((5-chloro-2-((2-cyclopropyl-4-(4-methylpiperazin-1-yl)phenyl)amino)pyridin-4-yl)amino)propyl)-1,4-oxazepan-5-one, 4-(3-((2-((4-ethyl-6-(4-methylpiperazin-1-yl)pyridin-3-yl)amino)-5-(trifluoromethyl)pyrimidin-4-yl)amino)propyl)-1,4-oxazepan-3-one, 4-(3-((2-((4-ethyl-6-(4-methylpiperazin-1-yl)pyridin-3-yl)amino)-5-(trifluoromethyl)pyrimidin-4-yl)amino)propyl)-1,4-oxazepan-5-one, (R)-4-(3-((2-(2-cyclopropyl-4-(hexahydropyrrolo[1,2-a]pyrazin-2(1H)-yl)phenyl)amino)-5-(trifluoromethyl)pyrimidin-4-yl)amino)propyl)-1,4-oxazepan-5-one, 4-(3-((2-((2-ethyl-4-((1S,4S)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 3-(3-((2-((2-ethyl-4-((1S,4S)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 4-(3-((2-((2-cyclopropyl-4-((1S,4S)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 3-(3-((2-((2-cyclopropyl-4-((1S,4S)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 4-(3-((2-((2-ethyl-4-((1R,4R)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 4-(3-((2-((2-cyclopropyl-4-((1R,4R)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 3-(3-((2-((2-ethyl-4-((1R,4R)-5-methyl-2,5-diazabicyclo[2.2.1]heptan-2-yl)phenyl)amino)-5-

(trifluoromethyl)pyrimidin-4-yl)amino)propyl)-1,3-oxazinan-2-one, 4-(3-((2-((2-(methoxymethyl)-4-(4-methylpiperazin-1-yl)phenyl)amino)-5-(trifluoromethyl)pyrimidin-4-yl)amino)propyl)-1,4-oxazepan-5-one, 3-(3-((2-((4-ethyl-6-(4-methylpiperazin-1-yl)pyridin-3-yl)amino)-5-(trifluoromethyl)pyrimidin-4-yl)amino)propyl)-1,3-oxazinan-2-one, 2-((2-ethyl-4-(4-methylpiperazin-1-yl)phenyl)amino)-4-((3-(5-oxo-1,4-oxazepan-4-yl)propyl)amino)pyrimidine-5-carbonitrile, 3-(3-((2-((2-cyclopropyl-4-((1R,4R)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, (S)-2-(4-(3-ethyl-4-((4-((3-(2-oxo-1,3-oxazinan-3-yl)propyl)amino)-5-(trifluoromethyl)pyrimidin-2-yl)amino)phenyl)-1-methylpiperazin-2-yl)acetonitrile, (R)-2-(4-(3-ethyl-4-((4-((3-(2-oxo-1,3-oxazinan-3-yl)propyl)amino)-5-(trifluoromethyl)pyrimidin-2-yl)amino)phenyl)-1-methylpiperazin-2-yl)acetonitrile, (S)-2-(1-methyl-4-(3-methyl-4-((4-((3-(5-oxo-1,4-oxazepan-4-yl)propyl)amino)-5-(trifluoromethyl)pyrimidin-2-yl)amino)phenyl)piperazin-2-yl)acetonitrile, (R)-2-(1-methyl-4-(3-methyl-4-((4-((3-(5-oxo-1,4-oxazepan-4-yl)propyl)amino)-5-(trifluoromethyl)pyrimidin-2-yl)amino)phenyl)piperazin-2-yl)acetonitrile, 4-(3-((5-(difluoromethyl)-2-((2-ethyl-4-(4-methylpiperazin-1-yl)phenyl)amino)pyrimidin-4-yl)amino)propyl)-1,4-oxazepan-5-one, 3-(3-((5-(difluoromethyl)-2-((2-ethyl-4-(4-methylpiperazin-1-yl)phenyl)amino)pyrimidin-4-yl)amino)propyl)-1,3-oxazinan-2-one, 2-((2-ethyl-4-(4-methylpiperazin-1-yl)phenyl)amino)-4-((3-(2-oxo-1,3-oxazinan-3-yl)propyl)amino)pyrimidine-5-carbonitrile, 4-(3-((2-((2-ethyl-4-(1-methylpiperidin-4-yl)phenyl)amino)-5-(trifluoromethyl)pyrimidin-4-yl)amino)propyl)-1,4-oxazepan-5-one, 4-(3-((2-((2-ethyl-4-((1R,5S)-3-methyl-3,8-diazabicyclo[3.2.1]octan-8-yl)phenyl)amino)-5-(trifluoromethyl)pyrimidin-4-yl)amino)propyl)-1,4-oxazepan-5-one, 4-(3-((2-((2-ethyl-4-(9-methyl-3,9-diazabicyclo[3.3.1]nonan-3-yl)phenyl)amino)-5-(trifluoromethyl)pyrimidin-4-yl)amino)propyl)-1,4-oxazepan-5-one, 4-(3-((2-((2-ethyl-4-(3-methyl-3,9-diazabicyclo[3.3.1]nonan-9-yl)phenyl)amino)-5-(trifluoromethyl)pyrimidin-4-yl)amino)propyl)-1,4-oxazepan-5-one, 4-(3-((2-((2-ethyl-4-(1-methylpyrrolidin-3-yl)phenyl)amino)-5-(trifluoromethyl)pyrimidin-4-yl)amino)propyl)-1,4-oxazepan-5-one, 4-(3-((2-((2-ethynyl-4-(4-methylpiperazin-1-yl)phenyl)amino)-5-(trifluoromethyl)pyrimidin-4-yl)amino)propyl)-1,4-oxazepan-5-one, 4-(3-((2-((2-(ethynyl-d)-4-(4-methylpiperazin-1-yl)phenyl)amino)-5-(trifluoromethyl)pyrimidin-4-yl)amino)propyl)-1,4-oxazepan-5-one, 4-(3-((2-((2-(ethyl-d5)-4-(4-methylpiperazin-1-yl)phenyl)amino)-5-(trifluoromethyl)pyrimidin-4-yl)amino)propyl)-1,4-oxazepan-5-one, 4-(3-((2-((4-(4-methylpiperazin-1-yl)-2-(2,2,2-trifluoroethyl)phenyl)amino)-5-(trifluoromethyl)pyrimidin-4-yl)amino)propyl)-1,4-oxazepan-5-one, 4-(3-((2-((2-(1,1-difluoroethyl)-4-(4-methylpiperazin-1-yl)phenyl)amino)-5-(trifluoromethyl)pyrimidin-4-yl)amino)propyl)-1,4-oxazepan-5-one, 5-(4-methylpiperazin-1-yl)-2-((4-((3-(5-oxo-1,4-oxazepan-4-yl)propyl)amino)-5-(trifluoromethyl)pyrimidin-2-yl)amino)benzonitrile, 2-methyl-2-(5-(4-methylpiperazin-1-yl)-2-((4-((3-(5-oxo-1,4-oxazepan-4-yl)propyl)amino)-5-(trifluoromethyl)pyrimidin-2-yl)amino)phenyl)propanenitrile, 2-(5-(4-methylpiperazin-1-yl)-2-((4-((3-(5-oxo-1,4-oxazepan-4-yl)propyl)amino)-5-(trifluoromethyl)pyrimidin-2-yl)amino)phenyl)acetonitrile, 4-(3-((2-((4-(4-methylpiperazin-1-yl)-2-(trifluoromethyl)phenyl)amino)-5-(trifluoromethyl)pyrimidin-4-yl)amino)propyl)-1,4-oxazepan-5-one, 4-(3-((2-((2-(difluoromethyl)-4-(4-methylpiperazin-1-yl)phenyl)amino)-5-(trifluoromethyl)pyrimidin-4-yl)amino)propyl)-1,4-oxazepan-5-one, 4-(3-((2-((2-bromo-4-(4-methylpiperazin-1-yl)phenyl)amino)-5-(trifluoromethyl)pyrimidin-4-yl)amino)propyl)-1,4-oxazepan-5-one, 4-(3-((2-((2-chloro-4-(4-methylpiperazin-1-yl)phenyl)amino)-5-(trifluoromethyl)pyrimidin-4-yl)amino)propyl)-1,4-oxazepan-5-one, 4-(3-((2-((2-cyclopropyl-4-(3-((dimethylamino)methyl)azetidin-1-yl)phenyl)amino)-5-(trifluoromethyl)pyrimidin-4-yl)amino)propyl)-1,4-oxazepan-5-one, 1-(3-((2-((2-ethyl-4-(4-methylpiperazin-1-yl)phenyl)amino)-5-(trifluoromethyl)pyrimidin-4-yl)amino)propyl)-3-methyltetrahydropyrimidin-2(1H)-one, 1-(3-((2-((2-cyclopropyl-4-(4-methylpiperazin-1-yl)phenyl)amino)-5-(trifluoromethyl)pyrimidin-4-yl)amino)propyl)-3-methyltetrahydropyrimidin-2(1H)-one, 3-(3-((2-((2-ethyl-4-(4-methylpiperazin-1-yl)phenyl)amino)-5-(trifluoromethyl)pyrimidin-4-yl)amino)propyl)-1,3-oxazepan-2-one, 3-(3-((2-((2-cyclopropyl-4-(4-methylpiperazin-1-yl)phenyl)amino)-5-(trifluoromethyl)pyrimidin-4-yl)amino)propyl)-1,3-oxazepan-2-one, 1-(3-((2-((2-ethyl-4-(4-methylpiperazin-1-yl)phenyl)amino)-5-(trifluoromethyl)pyrimidin-4-yl)amino)propyl)-4-methyl-1,4-diazepan-2-one, 1-(3-((2-((2-cyclopropyl-4-(4-methylpiperazin-1-yl)phenyl)amino)-5-(trifluoromethyl)pyrimidin-4-yl)amino)propyl)-4-methyl-1,4-diazepan-2-one, 4-(3-((2-((2-ethyl-4-(4-methylpiperazin-1-yl)phenyl)amino)-5-(trifluoromethyl)pyrimidin-4-yl)amino)propyl)-1-methyl-1,4-diazepan-5-one, 4-(3-((2-((2-cyclopropyl-4-(4-methylpiperazin-1-yl)phenyl)amino)-5-(trifluoromethyl)pyrimidin-4-yl)amino)propyl)-1-methyl-1,4-diazepan-5-one, 1-(3-((2-((2-ethyl-4-(4-methylpiperazin-1-yl)phenyl)amino)-5-(trifluoromethyl)pyrimidin-4-yl)amino)propyl)-3-methyl-1,3-diazepan-2-one, 1-(3-((2-((2-cyclopropyl-4-(4-methylpiperazin-1-yl)phenyl)amino)-5-(trifluoromethyl)pyrimidin-4-yl)amino)propyl)-3-methyl-1,3-diazepan-2-one, 3-(3-((2-((2-cyclopropyl-4-(4-methylpiperazin-1-yl)phenyl)amino)-5-(difluoromethyl)pyrimidin-4-yl)amino)propyl)-1,3-oxazinan-2-one, 3-(3-((5-(difluoromethyl)-2-((2-ethyl-4-((1R,5S)-8-methyl-3,8-diazabicyclo[3.2.1]octan-3-yl)phenyl)amino)pyrimidin-4-yl)amino)propyl)-1,3-oxazinan-2-one, 3-(3-((2-((2-cyclopropyl-4-((1R,5S)-8-methyl-3,8-diazabicyclo[3.2.1]octan-3-yl)phenyl)amino)-5-(difluoromethyl)pyrimidin-4-yl)amino)propyl)-1,3-oxazinan-2-one, 3-(3-((5-(difluoromethyl)-2-((2-ethyl-4-((1S,4S)-5-methyl-2,5-diazabicyclo[2.2.1]heptan-2-yl)phenyl)amino)pyrimidin-4-yl)amino)propyl)-1,3-oxazinan-2-one, 3-(3-((5-(difluoromethyl)-2-((2-ethyl-4-((1R,4R)-5-methyl-2,5-diazabicyclo[2.2.1]heptan-2-yl)phenyl)amino)pyrimidin-4-yl)amino)propyl)-1,3-oxazinan-2-one, (R)-3-(3-((5-(difluoromethyl)-2-((2-ethyl-4-(hexahydropyrrolo[1,2-a]pyrazin-2(1H)-yl)phenyl)amino)pyrimidin-4-yl)amino)propyl)-1,3-oxazinan-2-one, (S)-3-(3-((5-(difluoromethyl)-2-((2-ethyl-4-(hexahydropyrrolo[1,2-a]pyrazin-2(1H)-yl)phenyl)amino)pyrimidin-4-yl)amino)propyl)-1,3-oxazinan-2-one, 3-(3-((5-(difluoromethyl)-2-((2-ethyl-4-(piperazin-1-yl)phenyl)amino)pyrimidin-4-yl)amino)propyl)-1,3-oxazinan-2-one, 3-(3-((2-((2-cyclopropyl-4-(piperazin-1-yl)phenyl)amino)-5-(difluoromethyl)pyrimidin-4-yl)amino)propyl)-1,3-oxazinan-2-one, 1-(3-((5-(difluoromethyl)-2-((2-ethyl-4-(4-methylpiperazin-1-yl)phenyl)amino)pyrimidin-4-yl)amino)propyl)-3-methyltetrahydropyrimidin-2(1H)-one, 1-(3-((2-((2-cyclopropyl-4-(4-methylpiperazin-1-yl)phenyl)amino)-5-(difluoromethyl)pyrimidin-4-yl)amino)propyl)-3-methyltetrahydropyrimidin-2(1H)-one, 4-(3-((5-(difluoromethyl)-2-((2-ethyl-4-(4-methylpiperazin-1-yl)phenyl)amino)pyrimidin-4-yl)amino)propyl)-1,4-oxazepan- 3-one, 4-(3-((2-((2-cyclopropyl-4-(4-methylpiperazin-1-yl)phenyl)amino)-5-(difluoromethyl)pyrimidin-4-yl)amino)propyl)-1,4-oxazepan-3-one, 4-(3-((2-((2-cyclopropyl-4-(4-methylpiperazin-1-yl)phenyl)amino)-5-(difluoromethyl)pyrimidin-4-yl)amino)propyl)-1,4-oxazepan-5-one, 3-(3-((5-(difluoromethyl)-2-((2-ethyl-4-(4-methylpiperazin-1-yl)phenyl)amino)pyrimidin-4-yl)amino)propyl)-1,3-oxazepan-2-one, 3-(3-((2-((2-cyclopropyl-4-(4-methylpiperazin-1-yl)phenyl)amino)-5-(difluoromethyl)pyrimidin-4-yl)amino)propyl)-1,3-oxazepan-2-one, 1-(3-((5-(difluoromethyl)-2-((2-ethyl-4-(4-methylpiperazin-1-yl)phenyl)amino)pyrimidin-4-yl)amino)propyl)-4-methyl-1,4-diazepan-2-one, 1-(3-((2-((2-cyclopropyl-4-(4-methylpiperazin-1-yl)phenyl)amino)-5-(difluoromethyl)pyrimidin-4-yl)amino)propyl)-4-methyl-1,4-diazepan-2-one, 4-(3-((5-(difluoromethyl)-2-((2-ethyl-4-(4-methylpiperazin-1-yl)phenyl)amino)pyrimidin-4-yl)amino)propyl)-1-methyl-1,4-diazepan-5-one, 4-(3-((2-((2-cyclopropyl-4-(4-methylpiperazin-1-yl)phenyl)amino)-5-(difluoromethyl)pyrimidin-4-yl)amino)propyl)-1-methyl-1,4-diazepan-5-one, 1-(3-((5-(difluoromethyl)-2-((2-ethyl-4-(4-methylpiperazin-1-yl)phenyl)amino)pyrimidin-4-yl)amino)propyl)-3-methyl-1,3-diazepan-2-one, 1-(3-((2-((2-cyclopropyl-4-(4-methylpiperazin-1-yl)phenyl)amino)-5-(difluoromethyl)pyrimidin-4-yl)amino)propyl)-3-methyl-1,3-diazepan-2-one, 2-((2-cyclopropyl-4-(4-methylpiperazin-1-yl)phenyl)amino)-4-((3-(2-oxo-1,3-oxazinan-3-yl)propyl)amino)pyrimidine-5-carbonitrile, 2-((2-cyclopropyl-4-((1R,5S)-8-methyl-3,8-diazabicyclo[3.2.1]octan-3-yl)phenyl)amino)-4-((3-(2-oxo-1,3-oxazinan-3-yl)propyl)amino)pyrimidine-5-carbonitrile, 2-((2-ethyl-4-((1R,5S)-8-methyl-3,8-diazabicyclo[3.2.1]octan-3-yl)phenyl)amino)-4-((3-(2-oxo-1,3-oxazinan-3-yl)propyl)amino)pyrimidine-5-carbonitrile, 2-((2-ethyl-4-((1S,4S)-5-methyl-2,5-diazabicyclo[2.2.1]heptan-2-yl)phenyl)amino)-4-((3-(2-oxo-1,3-oxazinan-3-yl)propyl)amino)pyrimidine-5-carbonitrile, 2-((2-ethyl-4-((1R,4R)-5-methyl-2,5-diazabicyclo[2.2.1]heptan-2-yl)phenyl)amino)-4-((3-(2-oxo-1,3-oxazinan-3-yl)propyl)amino)pyrimidine-5-carbonitrile, (R)-2-((2-ethyl-4-(hexahydropyrrolo[1,2-a]pyrazin-2(1H)-yl)phenyl)amino)-4-((3-(2-oxo-1,3-oxazinan-3-yl)propyl)amino)pyrimidine-5-carbonitrile, (S)-2-((2-ethyl-4-(hexahydropyrrolo[1,2-a]pyrazin-2(1H)-yl)phenyl)amino)-4-((3-(2-oxo-1,3-oxazinan-3-yl)propyl)amino)pyrimidine-5-carbonitrile, 2-((2-ethyl-4-(piperazin-1-yl)phenyl)amino)-4-((3-(2-oxo-1,3-oxazinan-3-yl)propyl)amino)pyrimidine-5-carbonitrile, 2-((2-cyclopropyl-4-(piperazin-1-yl)phenyl)amino)-4-((3-(2-oxo-1,3-oxazinan-3-yl)propyl)amino)pyrimidine-5-carbonitrile, 2-((2-ethyl-4-(4-methylpiperazin-1-yl)phenyl)amino)-4-((3-(3-methyl-2-oxotetrahydropyrimidin-1(2H)-yl)propyl)amino)pyrimidine-5-carbonitrile, 2-((2-cyclopropyl-4-(4-methylpiperazin-1-yl)phenyl)amino)-4-((3-(3-methyl-2-oxotetrahydropyrimidin-1(2H)-yl)propyl)amino)pyrimidine-5-carbonitrile, 2-((2-ethyl-4-(4-methylpiperazin-1-yl)phenyl)amino)-4-((3-(3-oxo-1,4-oxazepan-4-yl)propyl)amino)pyrimidine-5-carbonitrile, 2-((2-cyclopropyl-4-(4-methylpiperazin-1-yl)phenyl)amino)-4-((3-(3-oxo-1,4-oxazepan-4-yl)propyl)amino)pyrimidine-5-carbonitrile, 2-((2-cyclopropyl-4-(4-methylpiperazin-1-yl)phenyl)amino)-4-((3-(5-oxo-1,4-oxazepan-4-yl)propyl)amino)pyrimidine-5-carbonitrile, 2-((2-ethyl-4-(4-methylpiperazin-1-yl)phenyl)amino)-4-((3-(2-oxo-1,3-oxazinan-3-yl)propyl)amino)pyrimidine-5-carbonitrile, 2-((2-cyclopropyl-4-(4-methylpiperazin-1-yl)phenyl)amino)-4-((3-(2-oxo-1,3-oxazepan-3-yl)propyl)amino)pyrimidine-5-carbonitrile, 2-((2-cyclopropyl-4-(4-methylpiperazin-1-yl)phenyl)amino)-4-((3-(4-methyl-2-oxo-1,4-diazepan-1-yl)propyl)amino)pyrimidine-5-carbonitrile, 2-((2-ethyl-4-(4-methylpiperazin-1-yl)phenyl)amino)-4-((3-(4-methyl-7-oxo-1,4-diazepan-1-yl)propyl)amino)pyrimidine-5-carbonitrile, 2-((2-cyclopropyl-4-(4-methylpiperazin-1-yl)phenyl)amino)-4-((3-(4-methyl-7-oxo-1,4-diazepan-1-yl)propyl)amino)pyrimidine-5-carbonitrile, 2-((2-ethyl-4-(4-methylpiperazin-1-yl)phenyl)amino)-4-((3-(3-methyl-2-oxo-1,3-diazepan-1-yl)propyl)amino)pyrimidine-5-carbonitrile, 2-((2-cyclopropyl-4-(4-methylpiperazin-1-yl)phenyl)amino)-4-((3-(3-methyl-2-oxo-1,3-diazepan-1-yl)propyl)amino)pyrimidine-5-carbonitrile, 1-(3-((2-((2-cyclopropyl-4-((1R,5S)-8-methyl-3,8-diazabicyclo[3.2.1]octan-3-yl)phenyl)amino)-5-(trifluoromethyl)pyrimidin-4-yl)amino)propyl)piperidin-2-one, 1-(3-((2-((2-cyclopropyl-4-((1R,5S)-8-methyl-3,8-diazabicyclo[3.2.1]octan-3-yl)phenyl)amino)-5-(difluoromethyl)pyrimidin-4-yl)amino)propyl)piperidin-2-one, 3-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-6,6-dimethyl-1,3-oxazinan-2-one, 4-(3-((2-((2-cyclopropyl-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-5-one, 4-(3-((2-((2-cyclopropyl-4-(5-methyl-2,5-diazabicyclo[2.2.1]heptan-2-yl)phenyl)amino)-5-(difluoromethyl)pyrimidin-4-yl)amino)propyl)-1,4-oxazepan-5-one, 4-(3-((5-(difluoromethyl)-2-((2-ethyl-4-(5-methyl-2,5-diazabicyclo[2.2.1]heptan-2-yl)phenyl)amino)pyrimidin-4-yl)amino)propyl)-1,4-oxazepan-5-one, 4-(3-((5-(difluoromethyl)-2-((2-ethyl-4-((1R,5S)-8-methyl-3,8-diazabicyclo[3.2.1]octan-3-yl)phenyl)amino)pyrimidin-4-yl)amino)propyl)-1,4-oxazepan-3-one, 4-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-3-one, 4-(3-((5-(difluoromethyl)-2-((2-ethyl-4-(5-methyl-2,5-diazabicyclo[2.2.1]heptan-2-yl)phenyl)amino)pyrimidin-4-yl)amino)propyl)-1,4-oxazepan-3-one, 4-(3-((2-((2-ethyl-4-(5-methyl-2,5-diazabicyclo[2.2.1]heptan-2-yl)phenyl)amino)-5-(trifluoromethyl)pyrimidin-4-yl)amino)propyl)-1,4-oxazepan-3-one, 3-(3-((5-(difluoromethyl)-2-((2-ethyl-4-((1R,5S)-8-methyl-3,8-diazabicyclo[3.2.1]octan-3-yl)phenyl)amino)pyrimidin-4-yl)amino)propyl)-1,3-oxazepan-2-one, 3-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-1,3-oxazepan-2-one, 4-(3-((2-((2-ethyl-4-methylpiperazin-1-yl)phenyl)amino)-5-(trifluoromethyl)pyrimidin-4-yl)amino)propyl)-6,6-dimethyl-1,4-oxazepan-5-one, 3-(3-((2-((2-ethyl-4-(4-methylpiperazin-1-yl)phenyl)amino)-5-(trifluoromethyl)pyrimidin-4-yl)amino)propyl)-6,6-dimethyl-1,3-oxazinan-2-one, 4-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-2,2-dimethyl-1,4-oxazepan-3-one, 4-(3-((2-((2-ethyl-4-(4-methylpiperazin-1-yl)phenyl)amino)-5-(trifluoromethyl)pyrimidin-4-yl)amino)propyl)-2,2-dimethyl-1,4-oxazepan-3-one, 4-(3-((5-(difluoromethyl)-2-((2-ethyl-4-(4-methylpiperazin-1-yl)phenyl)amino)pyrimidin-4-yl)amino)propyl)-6,6-dimethyl-1,4-oxazepan-5-one, 8-(3-((2-((2-ethyl-4-(4-methylpiperazin-1-yl)phenyl)amino)-5-(trifluoromethyl)pyrimidin-4-yl)amino)propyl)-5-oxa-8-azaspiro[2.6]nonan-9-one, 4-(3-((2-((4-(1,4-diazabicyclo[3.2.1]octan-4-yl)-2-ethylphenyl)amino)-5-(trifluoromethyl)pyrimidin-4-yl)amino)propyl)-1,4-oxazepan-5-one, 4-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-6,6- dimethyl-1,4-oxazepan-5-one, 4-(3-((5-(difluoromethyl)-2-((2-ethyl-4-((1R,5S)-8-methyl-3,8-diazabicyclo[3.2.1]octan-3-yl)phenyl)amino)pyrimidin-4-yl)amino)propyl)-6,6-dimethyl-1,4-oxazepan-5-one, 4-(3-((2-((4-(1,4-diazabicyclo[3.2.1]octan-4-yl)-2-ethylphenyl)amino)-5-(trifluoromethyl)pyrimidin-4-yl)amino)propyl)-6,6-dimethyl-1,4-oxazepan-5-one, 4-(3-((2-((4-(1,4-diazabicyclo[3.2.1]octan-4-yl)-2-ethylphenyl)amino)-5-(difluoromethyl)pyrimidin-4-yl)amino)propyl)-6,6-dimethyl-1,4-oxazepan-5-one, 1-(3-((2-((2-ethyl-4-(4-methylpiperazin-1-yl)phenyl)amino)-5-(trifluoromethyl)pyrimidin-4-yl)amino)propyl)azetidin-2-one, 1-(3-((2-((2-ethyl-4-(4-methylpiperazin-1-yl)phenyl)amino)-5-(trifluoromethyl)pyrimidin-4-yl)amino)propyl)-3,3-dimethylazetidin-2-one, 1-(3-((2-((4-(1,4-diazabicyclo[3.2.1]octan-4-yl)-2-ethylphenyl)amino)-5-(trifluoromethyl)pyrimidin-4-yl)amino)propyl)azetidin-2-one, 1-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)azetidin-2-one, 1-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)-3,3-dimethylazetidin-2-one, 1-(3-((2-((4-(1,4-diazabicyclo[3.2.1]octan-4-yl)-2-ethylphenyl)amino)-5-(trifluoromethyl)pyrimidin-4-yl)amino)propyl)-3,3-dimethylazetidin-2-one, 1-(3-((2-((2-ethyl-4-(hexahydropyrrolo[1,2-a]pyrazin-2(1H)-yl)phenyl)amino)-5-(trifluoromethyl)pyrimidin-4-yl)amino)propyl)azetidin-2-one, 1-(3-((2-((2-ethyl-4-(hexahydropyrrolo[1,2-a]pyrazin-2(1H)-yl)phenyl)amino)-5-(trifluoromethyl)pyrimidin-4-yl)amino)propyl)-3,3-dimethylazetidin-2-one, 1-(3-((2-((2-ethyl-4-(5-methyl-2,5-diazabicyclo[2.2.1]heptan-2-yl)phenyl)amino)-5-(trifluoromethyl)pyrimidin-4-yl)amino)propyl)azetidin-2-one, 1-(3-((2-((2-ethyl-4-(5-methyl-2,5-diazabicyclo[2.2.1]heptan-2-yl)phenyl)amino)-5-(trifluoromethyl)pyrimidin-4-yl)amino)propyl)-3,3-dimethylazetidin-2-one, 1-(3-((2-((2-ethyl-4-(5-methyl-2,5-diazabicyclo[2.2.1]heptan-2-yl)phenyl)amino)-5-(trifluoromethyl)pyrimidin-4-yl)amino)propyl)pyrrolidin-2-one, 1-(3-((5-(difluoromethyl)-2-((2-ethyl-4-(5-methyl-2,5-diazabicyclo[2.2.1]heptan-2-yl)phenyl)amino)pyrimidin-4-yl)amino)propyl)pyrrolidin-2-one, 1-(3-((2-((2-ethyl-4-(5-methyl-2,5-diazabicyclo[2.2.1]heptan-2-yl)phenyl)amino)-5-(trifluoromethyl)pyrimidin-4-yl)amino)propyl)-3,3-dimethylpyrrolidin-2-one, 1-(3-((2-((2-ethyl-4-((1R,5S)-8-methyl-3,8-diazabicyclo[3.2.1]octan-3-yl)phenyl)amino)-5-(trifluoromethyl)pyrimidin-4-yl)amino)propyl)pyrrolidin-2-one, 1-(3-((5-bromo-2-((2-ethyl-4-((1R,5S)-8-methyl-3,8-diazabicyclo[3.2.1]octan-3-yl)phenyl)amino)pyrimidin-4-yl)amino)propyl)pyrrolidin-2-one, 1-(3-((2-((4-(1,4-diazabicyclo[3.2.1]octan-4-yl)-2-ethylphenyl)amino)-5-bromopyrimidin-4-yl)amino)propyl)pyrrolidin-2-one, 1-(3-((5-bromo-2-((2-ethyl-4-(hexahydropyrrolo[1,2-a]pyrazin-2(1H)-yl)phenyl)amino)pyrimidin-4-yl)amino)propyl)pyrrolidin-2-one, 4-(3-((2-((4-(3-(diethylamino)propyl)-2-ethylphenyl)amino)-5-(trifluoromethyl)pyrimidin-4-yl)amino)propyl)-1,4-oxazepan-5-one, 4-(3-((2-(2-cyclopropyl-4-(3-morpholinopropyl)phenyl)amino)-5-(trifluoromethyl)pyrimidin-4-yl)amino)propyl)-1,4-oxazepan-3-one, 3-(3-((2-((2-ethyl-4-(2-(pyrrolidin-1-yl)ethyl)phenyl)amino)-5-(trifluoromethyl)pyrimidin-4-yl)amino)propyl)-1,3-oxazinan-2-one, 3-(3-((2-(2-cyclopropyl-4-((dimethylamino)methyl)phenyl)amino)-5-(trifluoromethyl)pyrimidin-4-yl)amino)propyl)-1,3-oxazinan-2-one, 3-(3-((2-((2-cyclopropyl-4-(4-methylpiperazine-1-carbonyl)phenyl)amino)-5-(trifluoromethyl)pyrimidin-4-yl)amino)propyl)-1,3-oxazinan-2-one, 3-methoxy-N-(1-methylpiperidin-4-yl)-4-((4-((3-(5-oxo-1,4-oxazepan-4-yl)propyl)amino)-5-(trifluoromethyl)pyrimidin-2-yl)amino)benzamide, 1-(3-((2-((2-cyclopropyl-4-(morpholinomethyl)phenyl)amino)-5-(trifluoromethyl)pyrimidin-4-yl)amino)propyl)piperidin-2-one, 1-(3-((2-((2-ethyl-4-(2-(pyrrolidin-1-yl)propan-2-yl)phenyl)amino)-5-(trifluoromethyl)pyrimidin-4-yl)amino)propyl)piperidin-2-one, 4-(3-((2-((2-ethyl-4-(2-(4-methylpiperazin-1-yl)-2-oxoethyl)phenyl)amino)-5-(trifluoromethyl)pyrimidin-4-yl)amino)propyl)-1,4-oxazepan-5-one, 4-(3-((2-((4-(4-((dimethylamino)methyl)piperidin-1-yl)-2-ethylphenyl)amino)-5-(trifluoromethyl)pyrimidin-4-yl)amino)propyl)-1,4-oxazepan-5-one, 44-(3-((2-((4-(3,3-dimethylpiperazin-1-yl)-2-ethylphenyl)amino)-5-(trifluoromethyl)pyrimidin-4-yl)amino)propyl)-1,4-oxazepan-3-one, 4-(3-((2-((2-ethyl-4-(3,3,5,5-tetramethylpiperazin-1-yl)phenyl)amino)-5-(trifluoromethyl)pyrimidin-4-yl)amino)propyl)-1,4-oxazepan-3-one, 4-(3-((2-((2-cyclopropyl-4-(3,4,5-trimethylpiperazin-1-yl)phenyl)amino)-5-(trifluoromethyl)pyrimidin-4-yl)amino)propyl)-1,4-oxazepan-5-one, 4-(3-((2-((2-ethyl-4-(3,3,4-trimethylpiperazin-1-yl)phenyl)amino)-5-(trifluoromethyl)pyrimidin-4-yl)amino)propyl)-1,4-oxazepan-3-one, 4-(3-((2-((2-ethyl-4-(3,3,4,5,5-pentamethylpiperazin-1-yl)phenyl)amino)-5-(trifluoromethyl)pyrimidin-4-yl)amino)propyl)-1,4-oxazepan-3-one, 1-(3-((2-((2-chloro-4-(3,4-dimethylpiperazin-1-yl)phenyl)amino)-5-(trifluoromethyl)pyrimidin-4-yl)amino)propyl)azepan-2-one, 3-(3-((2-((4-(hexahydropyrrolo[1,2-a]pyrazin-2(1H)-yl)phenyl)amino)-5-(trifluoromethyl)pyridin-4-yl)amino)propyl)-1,3-oxazepan-2-one, 4-(3-((2-((4-(hexahydropyrrolo[1,2-a]pyrazin-2(1H)-yl)phenyl)amino)-5-(trifluoromethyl)pyridin-4-yl)amino)propyl)-1,4-oxazepan-3-one, 4-(3-((2-((4-(octahydro-2H-pyrido[1,2-a]pyrazin-2-yl)phenyl)amino)-5-(trifluoromethyl)pyridin-4-yl)amino)propyl)-1,4-oxazepan-3-one, 3-(3-((2-((4-(4-methylpiperazin-1-yl)phenyl)amino)-5-(trifluoromethyl)pyridin-4-yl)amino)propyl)-1,3-oxazepan-2-one, 4-(3-((2-((4-(4-methylpiperazin-1-yl)phenyl)amino)-5-(trifluoromethyl)pyridin-4-yl)amino)propyl)-1,4-oxazepan-3-one, 4-(3-((2-((4-(5-methyl-2,5-diazabicyclo[2.2.1]heptan-2-yl)phenyl)amino)-5-(trifluoromethyl)pyridin-4-yl)amino)propyl)-1,4-oxazepan-5-one, 3-(3-((2-((2-bromo-4-(4-methylpiperazin-1-yl)phenyl)amino)-5-(trifluoromethyl)pyridin-4-yl)amino)propyl)-1,3-oxazepan-2-one, 4-(3-((2-((2-methyl-4-(4-methylpiperazin-1-yl)phenyl)amino)-5-(trifluoromethyl)pyridin-4-yl)amino)propyl)-1,4-oxazepan-3-one, 4-(3-((2-((6-(5-methyl-2,5-diazabicyclo[2.2.1]heptan-2-yl)pyridin-3-yl)amino)-5-(trifluoromethyl)pyridin-4-yl)amino)propyl)-1,4-oxazepan-5-one, 1-(3-((2-((4-((1R,5S)-8-methyl-3,8-diazabicyclo[3.2.1]octan-3-yl)phenyl)amino)-5-(trifluoromethyl)pyridin-4-yl)amino)propyl)azepan-2-one, 4-(3-((2-((4-(4-methylpiperazin-1-yl)-2-(trifluoromethyl)phenyl)amino)-5-(trifluoromethyl)pyridin-4-yl)amino)propyl)-1,4-oxazepan-5-one, 4-(3-((2-((2-methyl-4-(4-(methylsulfonyl)piperazin-1-yl)phenyl)amino)-5-(trifluoromethyl)pyridin-4-yl)amino)propyl)-1,4-oxazepan-5-one, 4-(3-((2-((4-(43-(3-((2-((2-ethyl-4-(4-methylpiperazine-1-carbonyl)phenyl)amino)-5-(trifluoromethyl)pyrimidin-4-yl)amino)propyl)-1,3-oxazinan-2-one, 1-(3-((2-((2-cyclopropyl-4-(morpholinomethyl)phenyl)amino)-5-(trifluoromethyl)pyridin-4-yl)amino)propyl)piperidin-2-one, 3-(3-((2-((2-ethyl-4-(2-(pyrrolidin-1-yl)ethyl)phenyl)amino)-5-(trifluoromethyl)pyridin-4-yl)amino)propyl)-1,3-oxazinan-2-one, 3-(3-((2-((2-fluoro-4-(3-morpholinopropyl)phenyl)

amino)-5-(trifluoromethyl)pyridin-4-yl)amino)propyl)-1,3-oxazinan-2-one, 3-(3-((2-((4-(3-(diethylamino)propyl)-2-(trifluoromethyl)phenyl)amino)-5-(trifluoromethyl)pyridin-4-yl)amino)propyl)-1,3-oxazinan-2-one, 4-(3-((2-((2-chloro-4-(3,4-dimethylpiperazin-1-yl)phenyl)amino)-5-(trifluoromethyl)pyridin-4-yl)amino)propyl)-1,4-oxazepan-5-one, 4-(3-((2-((2-methyl-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-5-one, 4-(3-((2-((2-chloro-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-5-one, -(trifluoromethyl)pyrimidin-4-yl)amino)propyl)-1,4-oxazepan-5-one, 4-(3-((2-((2-methyl-4-((1S,4S)-5-methyl-2,5-diazabicyclo[2.2.1]heptan-2-yl)phenyl)amino)-5-((1S,4S)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 4-(3-((2-((2-(14-(3-((2-((2-methyl-4-((1R,4R)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 4-(3-((2-((2-chloro-4-((1R,4R)-5-methyl-2,5-diazabicyclo[2.2.1]heptan-2-yl)phenyl)amino)-5-(trifluoromethyl)pyrimidin-4-yl)amino)propyl)-1,4-oxazepan-5-one, 3-(3-((2-((2-chloro-4-(4-methylpiperazin-1-yl)phenyl)amino)-5-(trifluoromethyl)pyrimidin-4-yl)amino)propyl)-1,3-oxazinan-2-one, 3-(3-((2-((2-(1-hydroxyethyl)-4-(4-methylpiperazin-1-yl)phenyl)amino)-5-(trifluoromethyl)pyrimidin-4-yl)amino)propyl)-1,3-oxazinan-2-one, 3-(3-((2-((2-chloro-4-((1R,5S)-8-methyl-3,8-diazabicyclo[3.2.1]octan-3-yl)phenyl)amino)-5-(trifluoromethyl)pyrimidin-4-yl)amino)propyl)-1,3-oxazinan-2-one, 3-(3-((2-((2-(13-(3-((2-((2-methyl-4-((1S,4S)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 3-(3-((2-((2-chloro-4-((1S,4S)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 3-(3-((2-((2-methyl-4-((1R,4R)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 3-(3-((2-((2-chloro-4-((1R,4R)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 3-(3-((2-((2-(1-hydroxyethyl)-4-((1R,4R)-5-methyl-2,5-diazabicyclo[2.2.1]heptan-2-yl)phenyl)amino)-5-(trifluoromethyl)pyrimidin-4-yl)amino)propyl)-1,3-oxazinan-2-one, 4-(3-((2-((2-methyl-4-(4-methylpiperazin-1-yl)phenyl)amino)-5-(trifluoromethyl)pyrimidin-4-yl)amino)propyl)-1,4-oxazepan-3-one, 4-(3-((2-((2-chloro-4-(4-methylpiperazin-1-yl)phenyl)amino)-5-(trifluoromethyl)pyrimidin-4-yl)amino)propyl)-1,4-oxazepan-3-one, 4-(3-((2-((2-methyl-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-3-one, 4-(3-((2-((2-chloro-4-((1R,5S)-8-methyl-3,8-diazabicyclo[3.2.1]octan-3-yl)phenyl)amino)-5-(trifluoromethyl)pyrimidin-4-yl)amino)propyl)-1,4-oxazepan-3-one, 4-(3-((2-((4-(4-methylpiperazin-1-yl)-2-(trifluoromethoxy)phenyl)amino)-5-(trifluoromethyl)pyrimidin-4-yl)amino)propyl)-1,4-oxazepan-5-one, 4-(3-((2-((2-(difluoromethoxy)-4-(4-methylpiperazin-1-yl)phenyl)amino)-5-(trifluoromethyl)pyrimidin-4-yl)amino)propyl)-1,4-oxazepan-5-one, 3-(3-((2-((2-cyclopropyl-4-(4-methylpiperazin-1-yl)phenyl)amino)-5-(trifluoromethyl)pyrimidin-4-yl)amino)propyl)-6,6-dimethyl-1,3-oxazinan-2-one, 4-(3-((2-((4-((1R,5S)-3,8-diazabicyclo[3.2.1]octan-3-yl)-2-ethylphenyl)amino)-5-(trifluoromethyl)pyrimidin-4-yl)amino)propyl)-1,4-oxazepan-5-one, 1-(3-((2-((2-cyclopropyl-4-(3-((dimethylamino)methyl)azetidin-1-yl)phenyl)amino)-5-(trifluoromethyl)pyridin-4-yl)amino)propyl)piperidin-2-one, 4-(3-((2-((4-(3-((dimethylamino)methyl)azetidin-1-yl)-2-ethylphenyl)amino)-5-(trifluoromethyl)pyrimidin-4-yl)amino)propyl)-1,4-oxazepan-5-one, 4-(3-((2-((4-(4-methylpiperazin-1-yl)phenyl)amino)-5-(trifluoromethyl)pyrimidin-4-yl)amino)propyl)-1,4-oxazepan-5-one, and pharmaceutically acceptable salts, enantiomers, stereoisomers, and tautomers thereof.

20. A pharmaceutical composition comprising a compound of claim 1 and a pharmaceutically acceptable excipient.

21. A pharmaceutical composition comprising a compound of claim 1, one or more additional therapeutic agents, and a pharmaceutically acceptable excipient.

22. The pharmaceutical composition of claim 21, wherein the additional therapeutic agent is a MAPKAP pathway inhibitor.

23. The pharmaceutical composition of claim 22, wherein the MAPKAP pathway inhibitor is selected from the group consisting of a MEK inhibitor, an ERK inhibitor, a RAF inhibitor, and a Ras inhibitor.

24. The pharmaceutical composition of claim 23, wherein the MEK inhibitor is selected from the group consisting of trametinib, selumetinib, cobimetinib, binimetinib, and pharmaceutically acceptable salts thereof, the ERK inhibitor is selected from the group consisting of ulixertinib, SCH772984, LY3214996, ravoxertinib, VX-11e, and pharmaceutically acceptable salts thereof, the RAF inhibitor is selected from the group consisting of LY3009120, LXH254, RAF709, dabrafenib, vemurafenib, and pharmaceutically acceptable salts thereof; or the Ras inhibitor is selected from the group consisting of AMG-510, MRTX849, and pharmaceutically acceptable salts thereof.

25. The pharmaceutical composition of claim 21, wherein the additional therapeutic agent is a chemotherapeutic agent.

26. A method of treating a cancer in a patient in need thereof, comprising administering to the patient a therapeutically effective amount of a compound of claim 1.

27. The method of claim 26, wherein the cancer is selected from the group consisting of gastrointestinal stromal tumors, esophageal cancer, gastric cancer, melanomas, gliomas, glioblastomas, ovarian cancer, bladder cancer, pancreatic cancer, prostate cancer, lung cancers, breast cancers, renal cancers, hepatic cancers, osteosarcomas, multiple myelomas, cervical carcinomas, cancers that are metastatic to bone, papillary thyroid carcinoma, non-small cell lung cancer, and colorectal cancers.

28. The method of claim 26, further comprising administering to the patient one or more additional therapeutic agents.

29. The method of claim 28, wherein the additional therapeutic agent is a MAPKAP pathway inhibitor.

30. The method of claim 29, wherein the MAPKAP pathway inhibitor is selected from the group consisting of a MEK inhibitor, an ERK inhibitor, a RAF inhibitor, and a Ras inhibitor.

31. The method of claim 30, wherein the MEK inhibitor is selected from the group consisting of trametinib, selumetinib, cobimetinib, binimetinib, and pharmaceutically acceptable salts thereof, the ERK inhibitor is selected from the group consisting of ulixertinib, SCH772984, LY3214996, ravoxertinib, VX-11e, and pharmaceutically acceptable salts thereof; the RAF inhibitor is selected from the group consisting of LY3009120, LXH254, RAF709, dabrafenib, vemurafenib, and pharmaceutically acceptable salts thereof; or the Ras inhibitor is selected from the group consisting of AMG-510, MRTX849, and pharmaceutically acceptable salts thereof.

32. The method of claim 28, wherein the additional therapeutic agent is a chemotherapeutic agent.

33. The method of claim 32, wherein the chemotherapeutic agent is a selected from the group consisting of anti-tubulin agents, vinorelbine, DNA-alkylating agents, DNA intercalating agents, 5-fluorouracil, capecitabine, cytarabine, decitabine, 5-aza cytadine, gemcitabine, and methotrexate.

34. The compound of claim 1, wherein the compound is selected from the group consisting of:

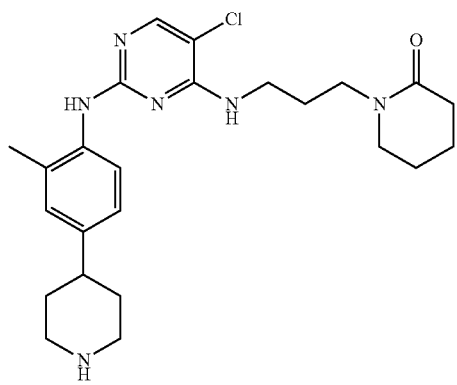

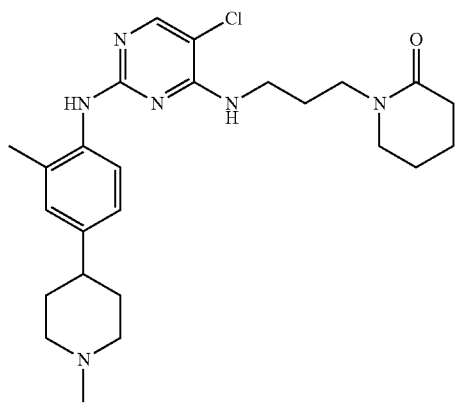

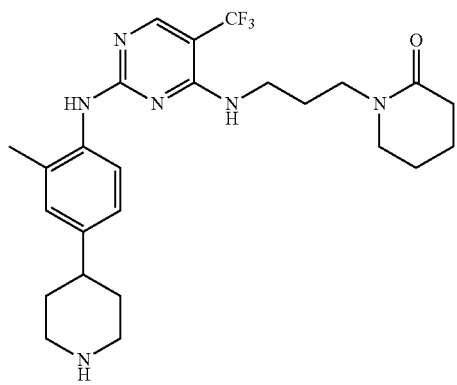 [SMILES: Cc1cc(N2CCNCC2)ccc1Nc1ncc(C(F)(F)F)c(NCCCN2CCCCC2=O)n1]

-continued

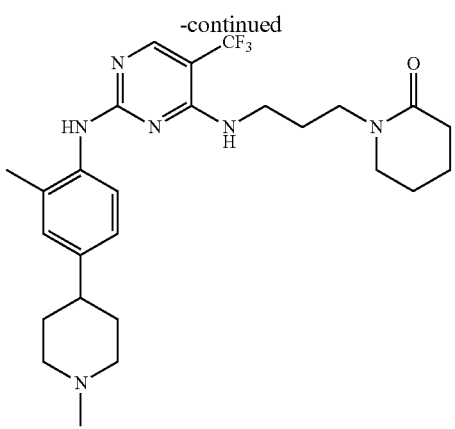

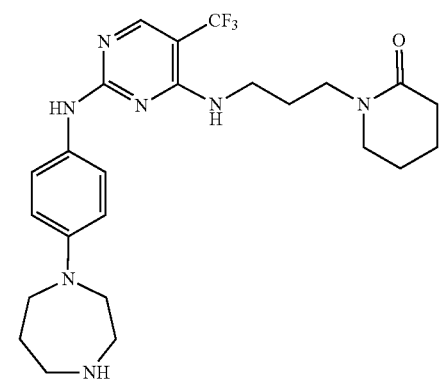

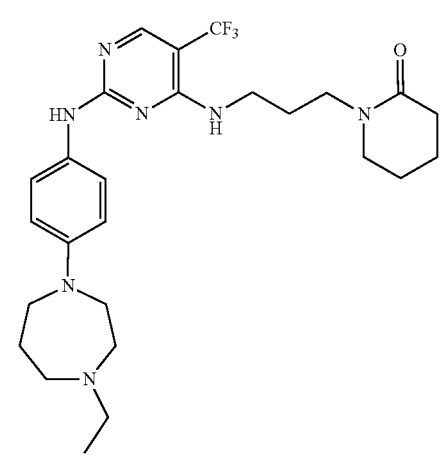

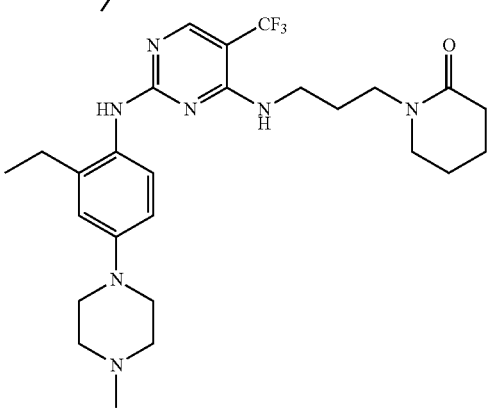

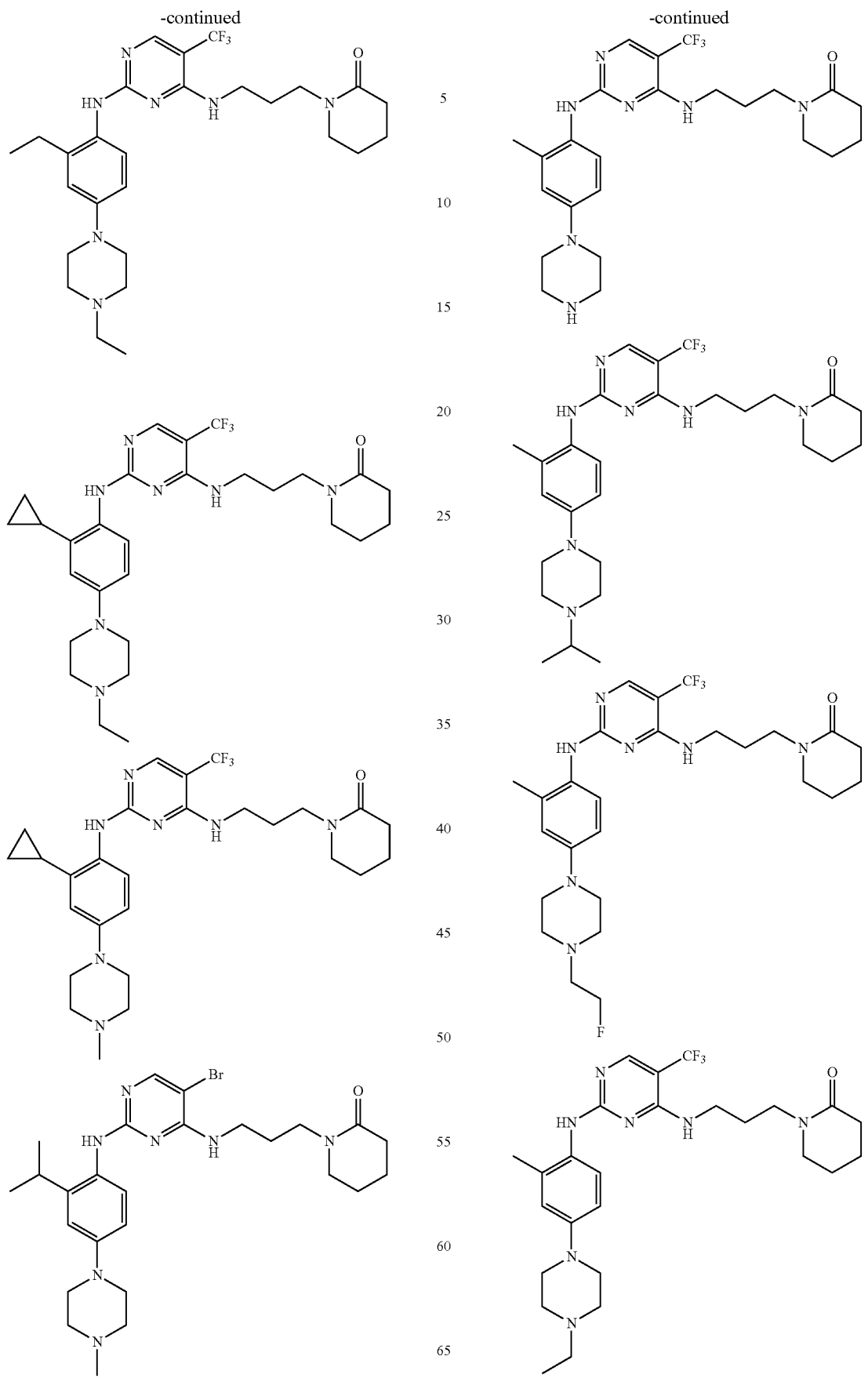

347
-continued
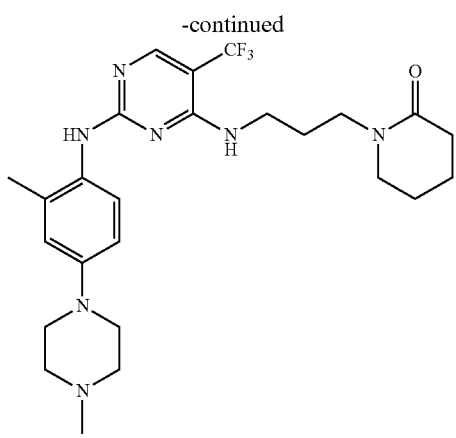
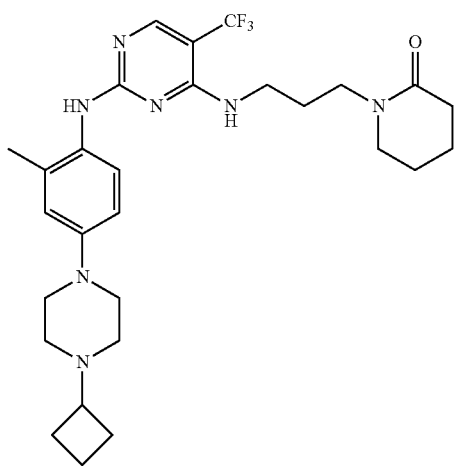 [SMILES: Cc1cc(N2CCN(C3CCC3)CC2)ccc1Nc1ncc(C(F)(F)F)c(NCCCN2CCCCC2=O)n1]
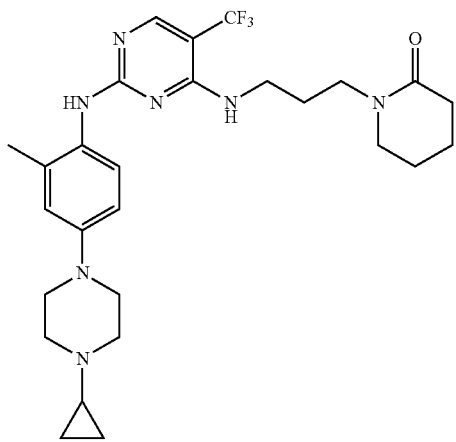 [SMILES: Cc1cc(N2CCN(C3CC3)CC2)ccc1Nc1ncc(C(F)(F)F)c(NCCCN2CCCCC2=O)n1]
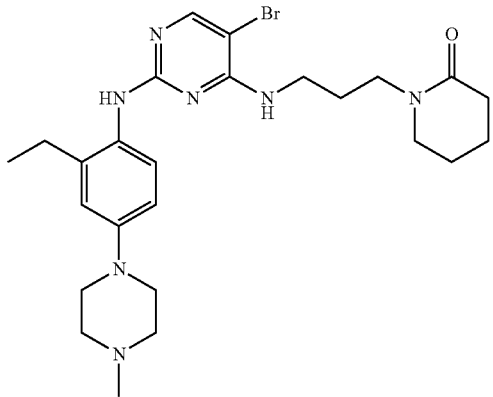
348
-continued
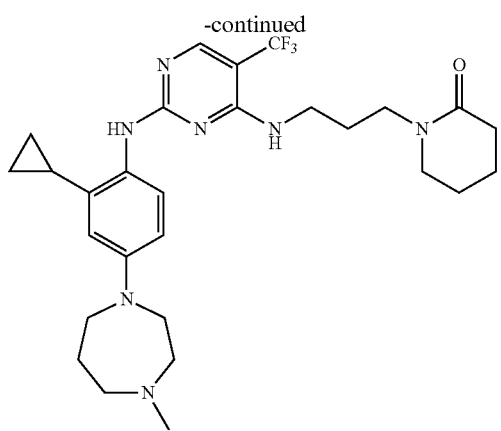
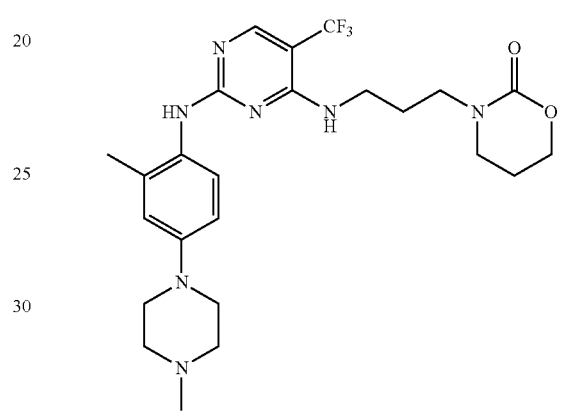
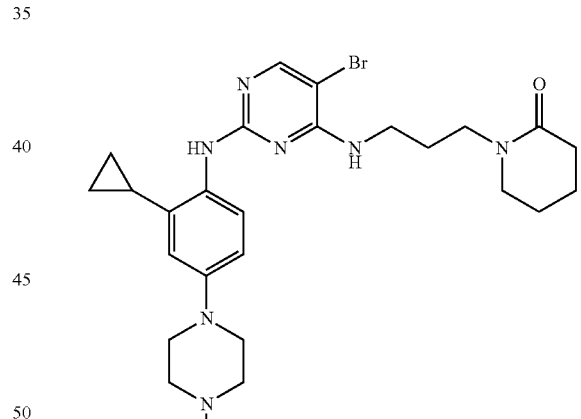
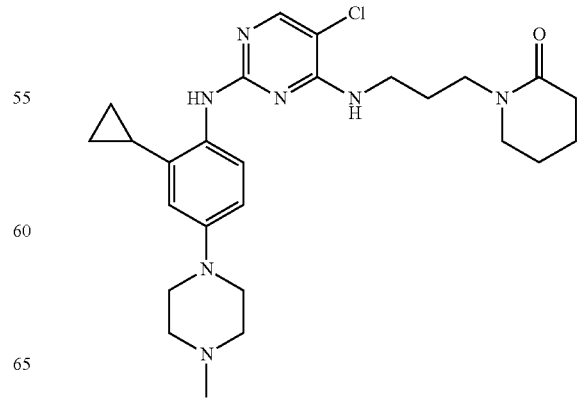

349
-continued
350
-continued
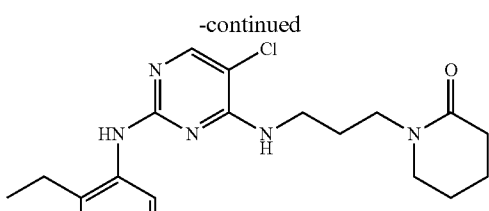
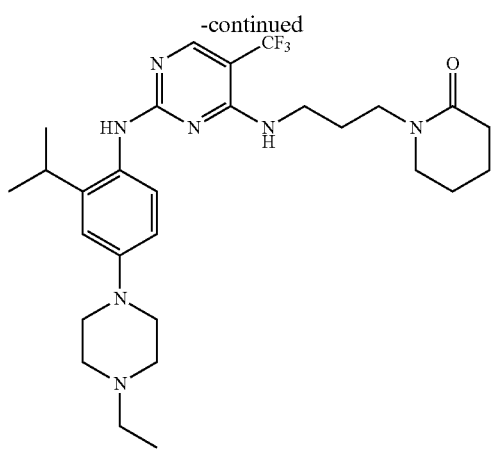
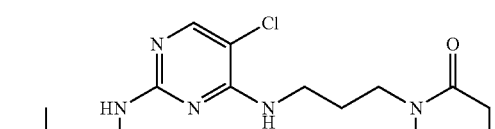
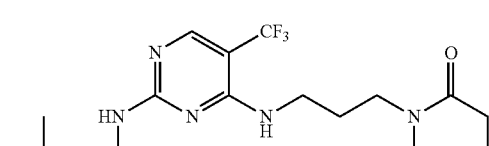
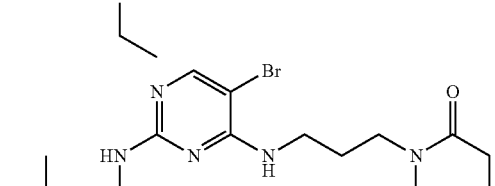
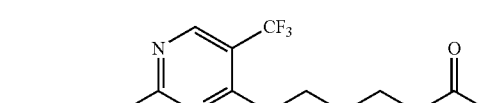
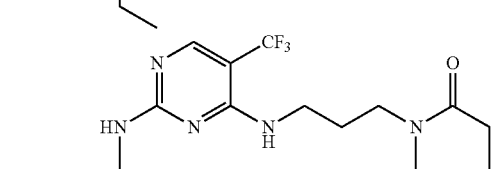
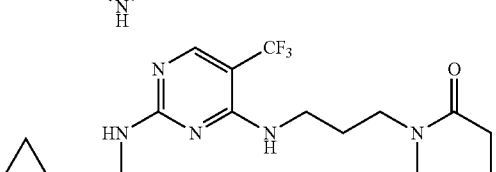
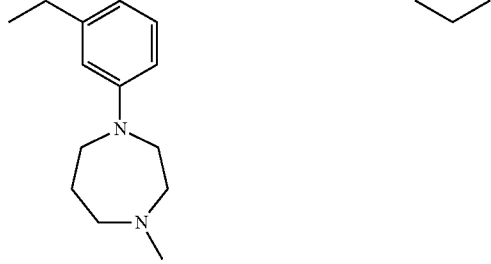

351 -continued
352 -continued
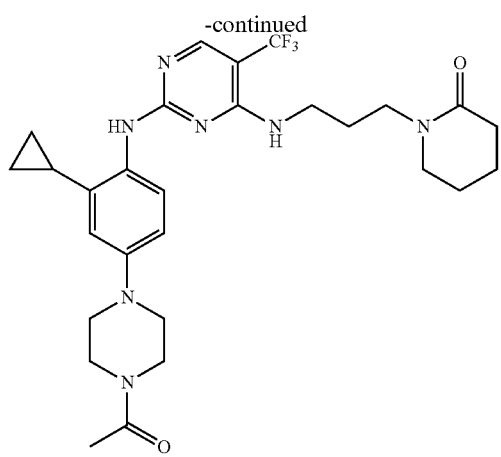
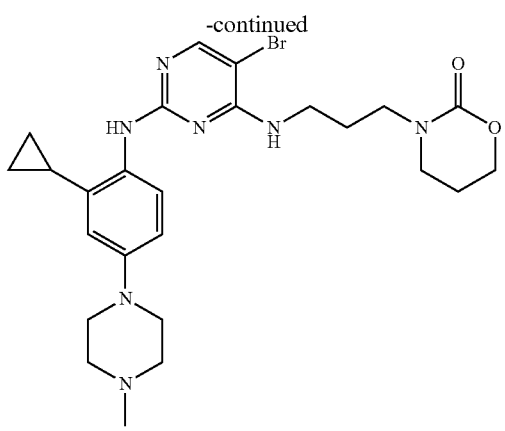
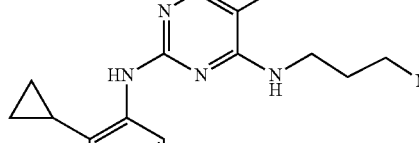

353
-continued
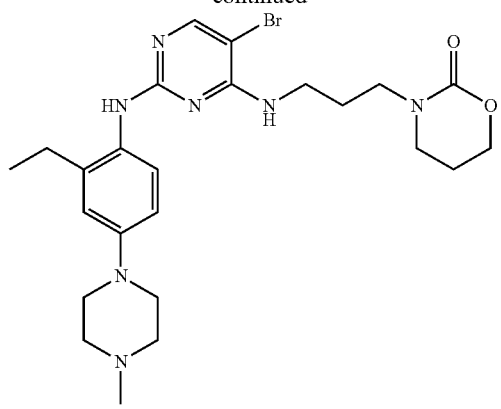
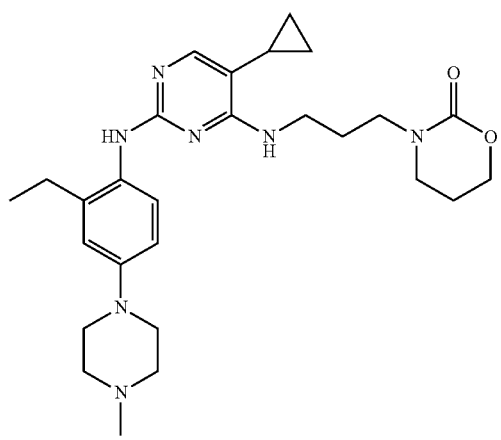 [SMILES: CCc1cc(N2CCN(C)CC2)ccc1Nc1ncc(C2CC2)c(NCCCN2CCCOC2=O)n1]
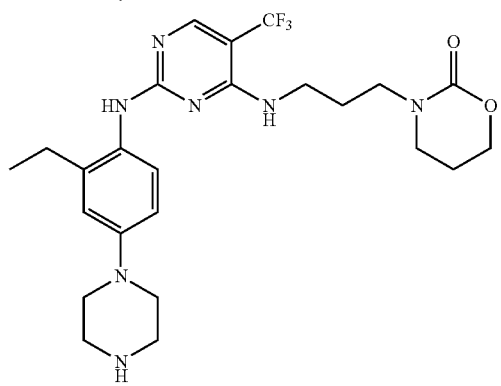
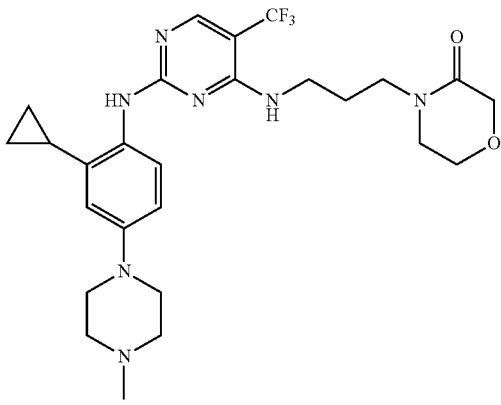 [SMILES: CN1CCN(c2ccc(Nc3ncc(C(F)(F)F)c(NCCCN4CCOCC4=O)n3)c(C3CC3)c2)CC1]
354
-continued
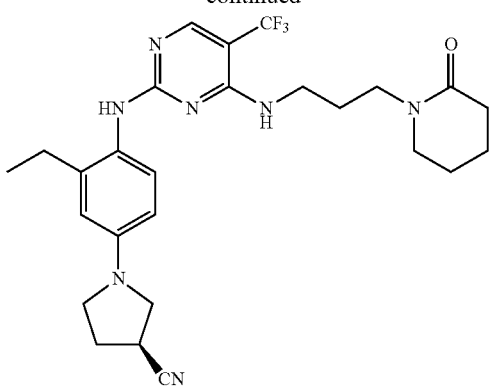
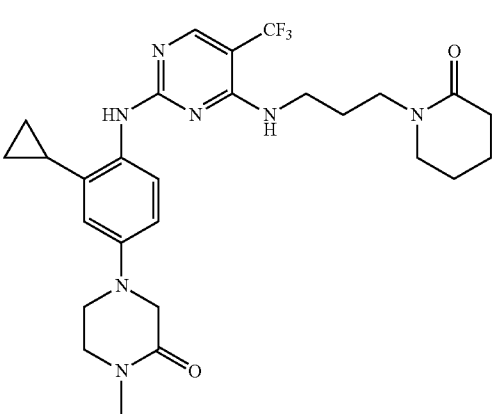 [SMILES: CN1CCN(c2ccc(Nc3ncc(C(F)(F)F)c(NCCCN4CCCCC4=O)n3)c(C3CC3)c2)CC1=O]
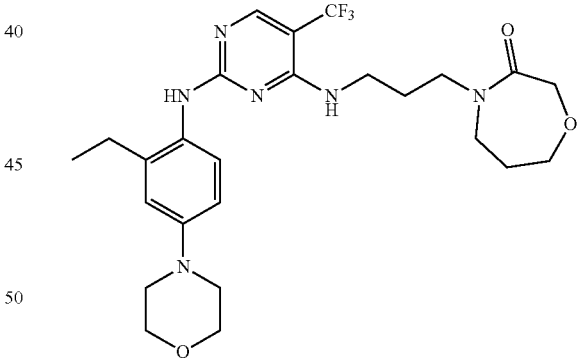
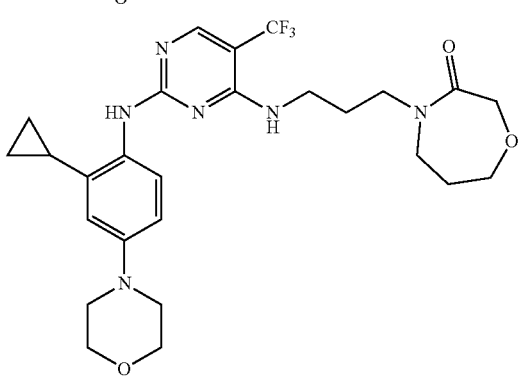

355
-continued
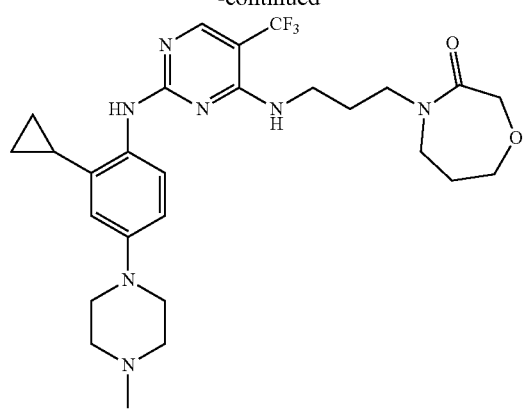
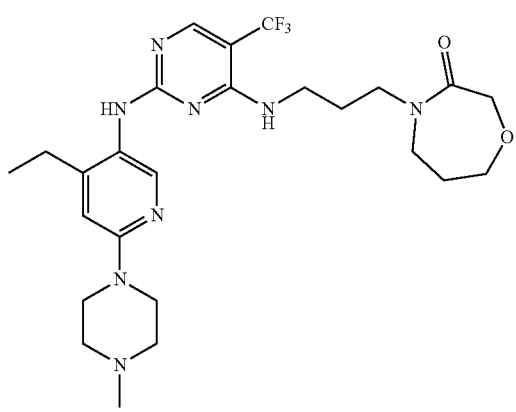 [SMILES: CCc1cc(N2CCN(C)CC2)ncc1Nc1ncc(C(F)(F)F)c(NCCCN2CCCOCC2=O)n1]
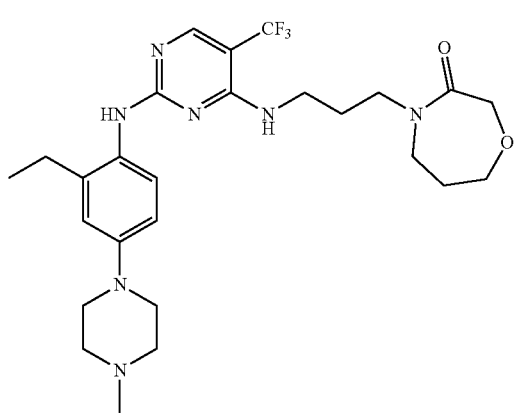
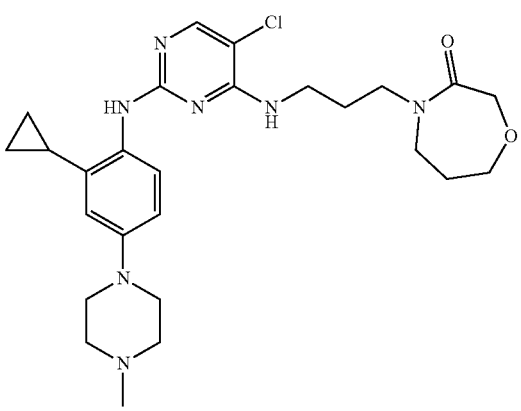 [SMILES: CN1CCN(c2ccc(Nc3ncc(Cl)c(NCCCN4CCCOCC4=O)n3)c(C3CC3)c2)CC1]
356
-continued
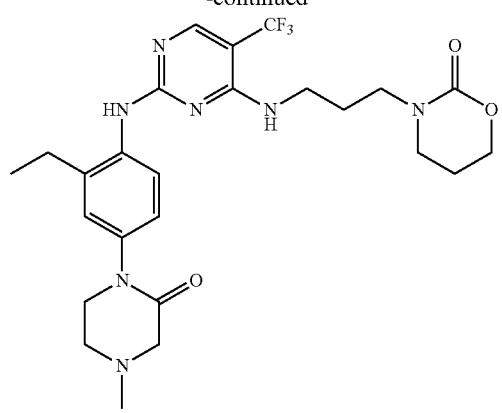
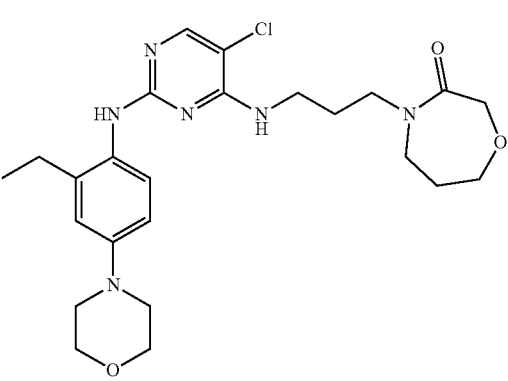
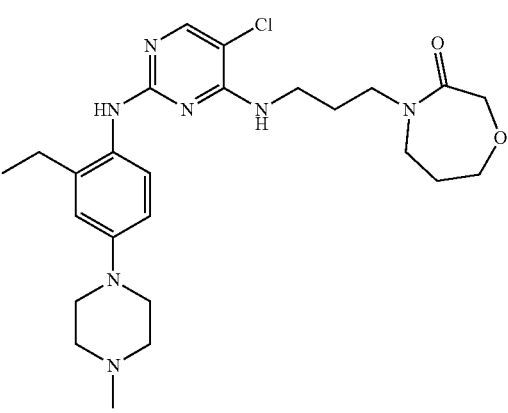

357
-continued
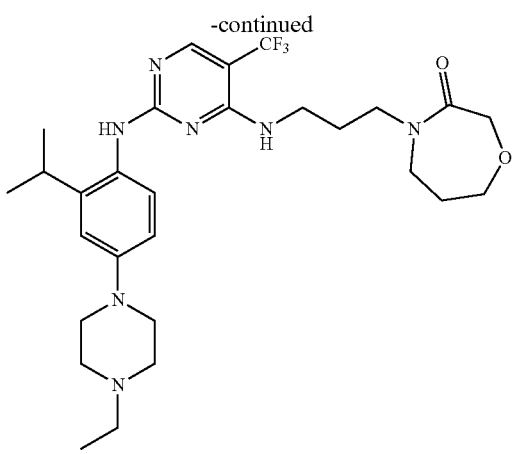
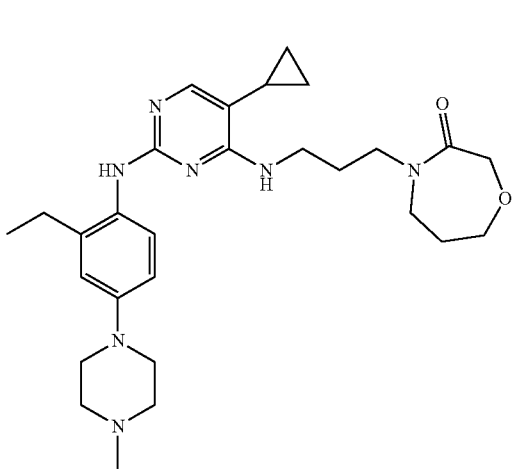 [SMILES: CCc1cc(N2CCN(C)CC2)ccc1Nc1ncc(C2CC2)c(NCCCN2CCCOCC2=O)n1]
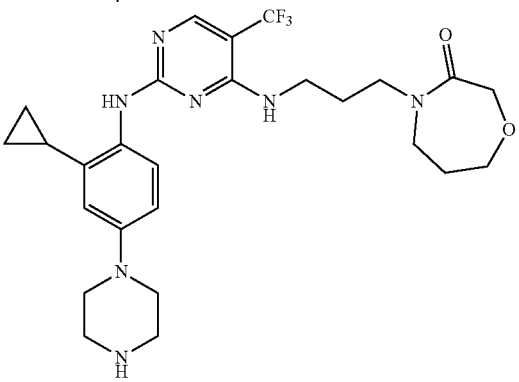
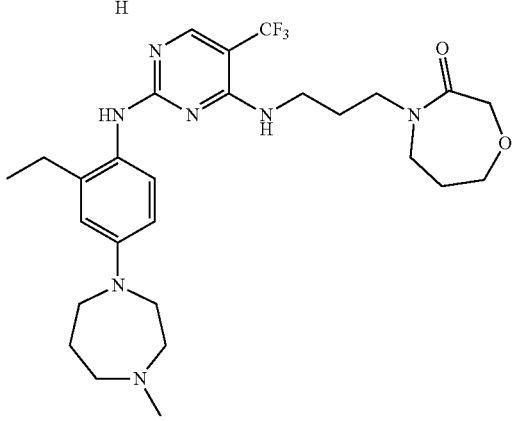
358
-continued
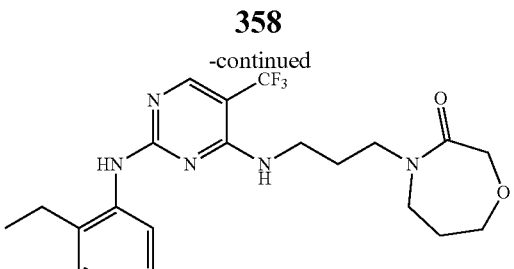
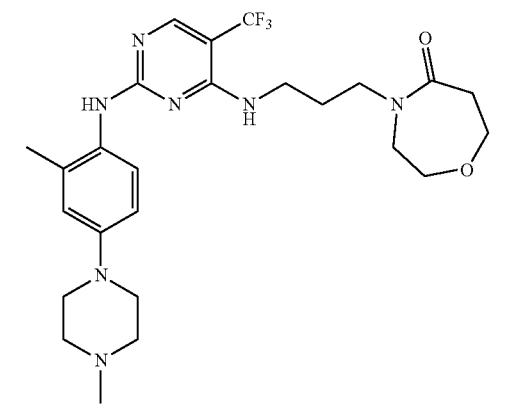 [SMILES: Cc1cc(N2CCN(C)CC2)ccc1Nc1ncc(C(F)(F)F)c(NCCCN2CCOCCC2=O)n1]
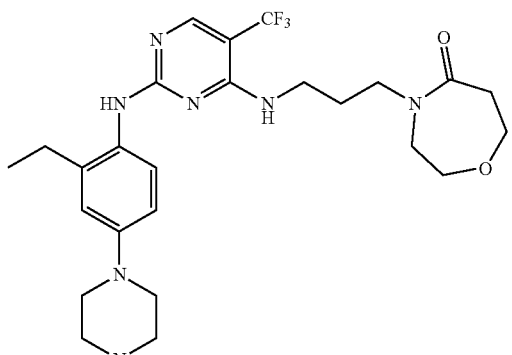
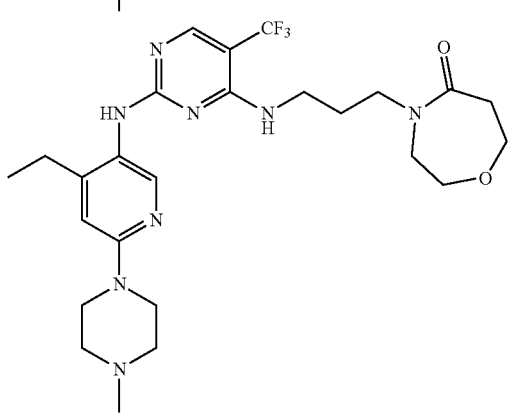

359
-continued
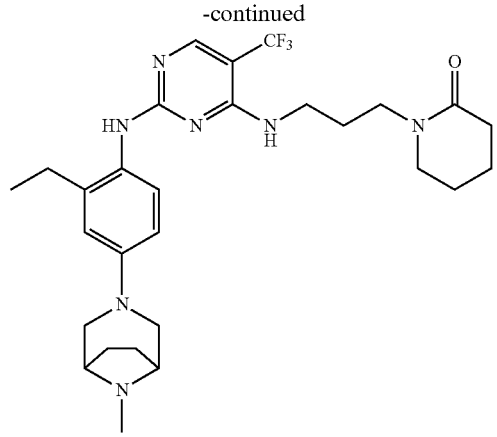
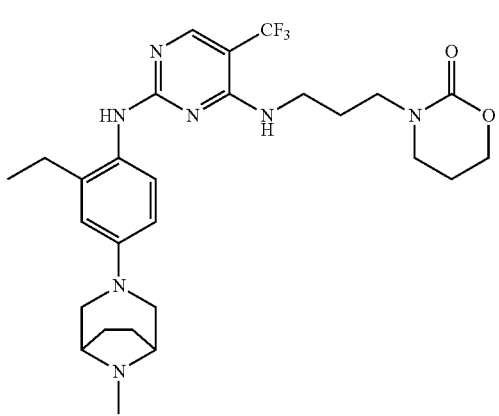
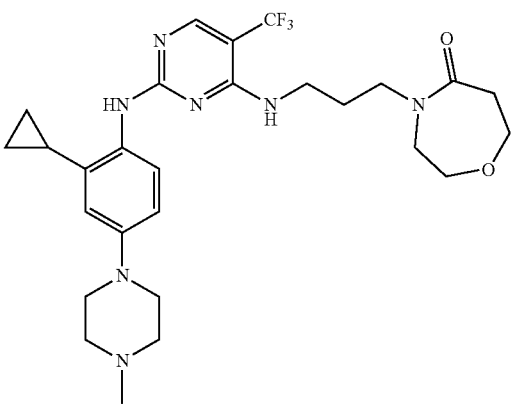
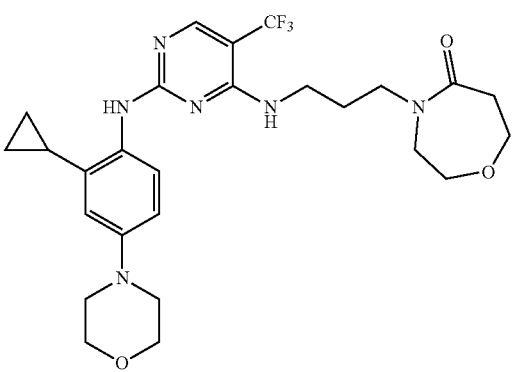 [SMILES: O=C1CCOCCN1CCCNc1nc(Nc2ccc(N3CCOCC3)cc2C2CC2)ncc1C(F)(F)F]
360
-continued
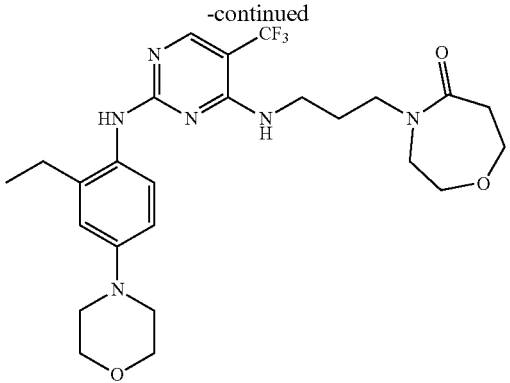
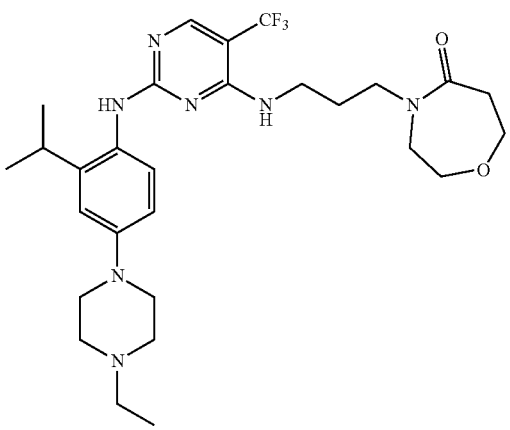 [SMILES: CCN1CCN(c2ccc(Nc3ncc(C(F)(F)F)c(NCCCN4CCOCCC4=O)n3)c(C(C)C)c2)CC1]
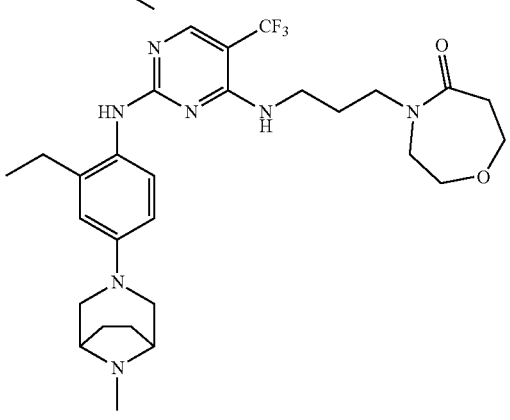
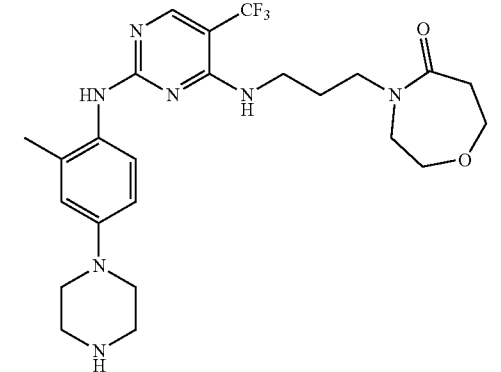 [SMILES: Cc1cc(N2CCNCC2)ccc1Nc1ncc(C(F)(F)F)c(NCCCN2CCOCCC2=O)n1]

361
-continued
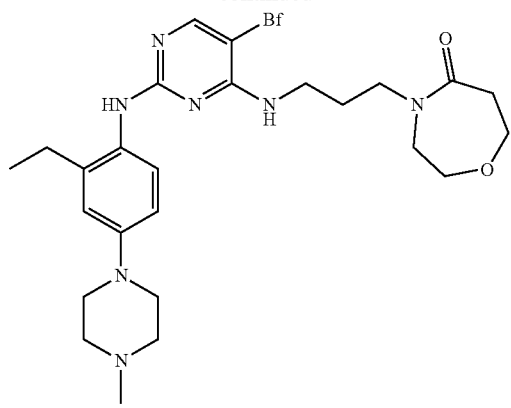 [SMILES: CCc1cc(N2CCN(C)CC2)ccc1Nc1ncc(Br)c(NCCCN2CCOCCC2=O)n1]
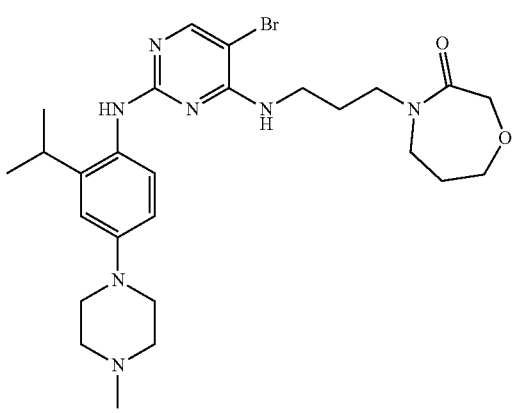 [SMILES: CC(C)c1cc(N2CCN(C)CC2)ccc1Nc1ncc(Br)c(NCCCN2CCCOCC2=O)n1]
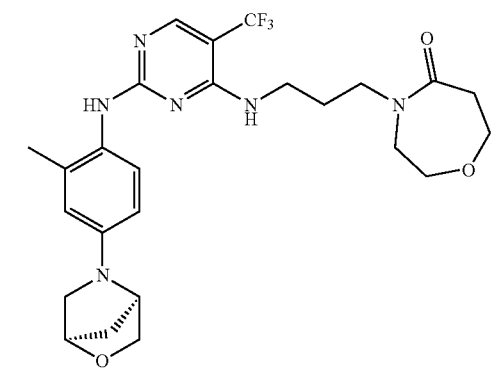 [SMILES: Cc1cc(N2C[C@H]3C[C@@H]2CO3)ccc1Nc1ncc(C(F)(F)F)c(NCCCN2CCOCCC2=O)n1]
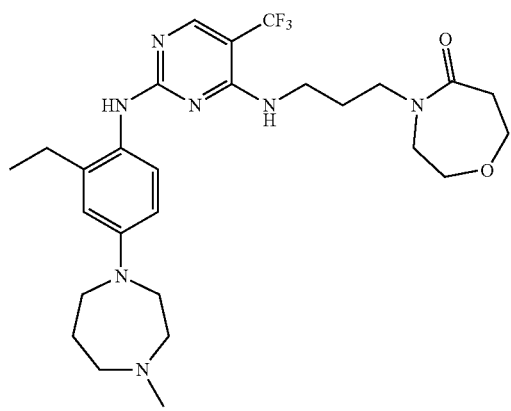 [SMILES: CCc1cc(N2CCCN(C)CC2)ccc1Nc1ncc(C(F)(F)F)c(NCCCN2CCOCCC2=O)n1]
362
-continued
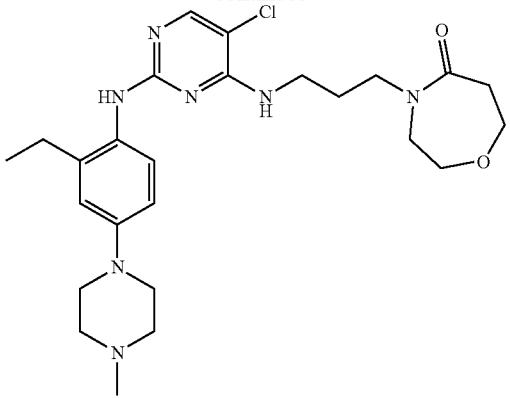 [SMILES: CCc1cc(N2CCN(C)CC2)ccc1Nc1ncc(Cl)c(NCCCN2CCOCCC2=O)n1]
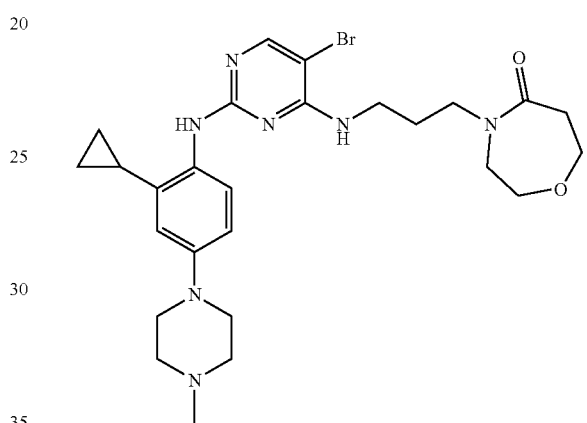
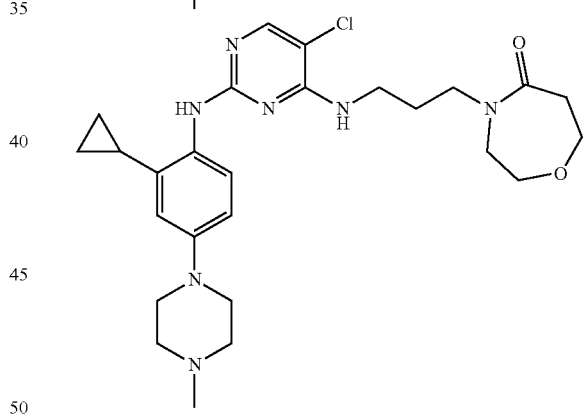
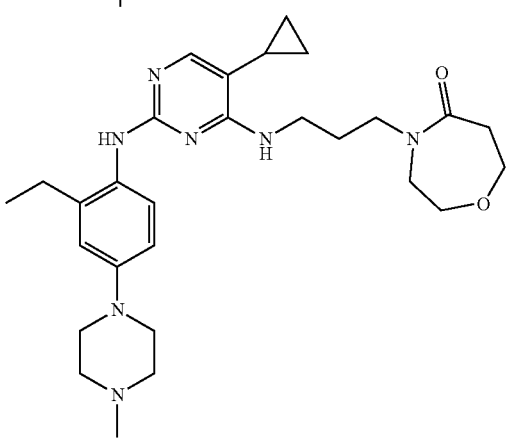

363
-continued
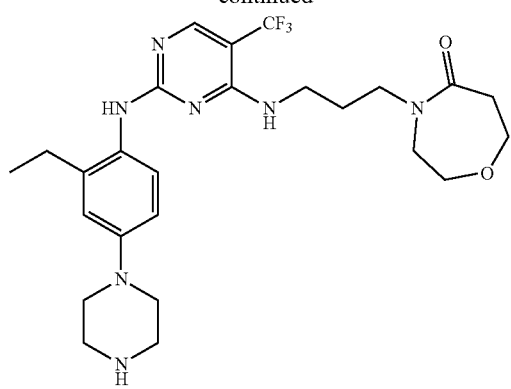
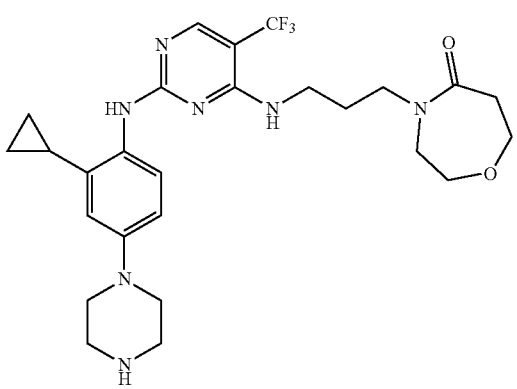 [SMILES: O=C1CCOCCN1CCCNc1nc(Nc2ccc(N3CCNCC3)cc2C2CC2)ncc1C(F)(F)F]
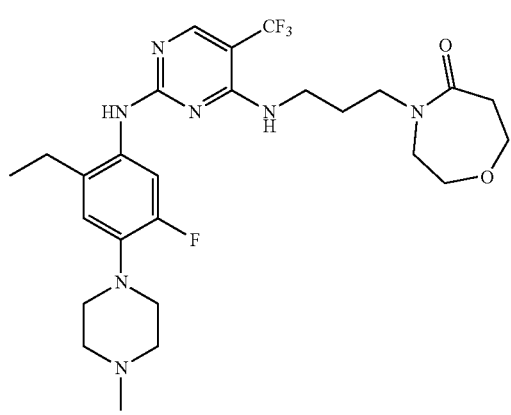 [SMILES: CCc1cc(N2CCN(C)CC2)c(F)cc1Nc1ncc(C(F)(F)F)c(NCCCN2CCOCCC2=O)n1]
364
-continued
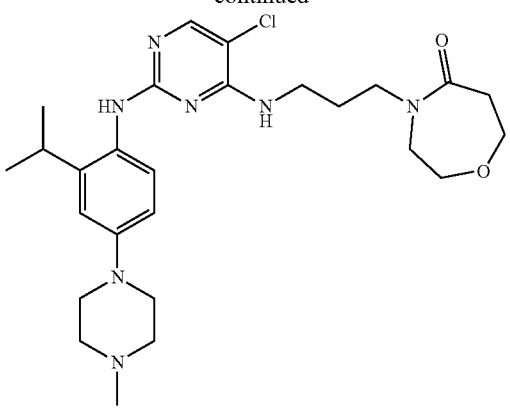
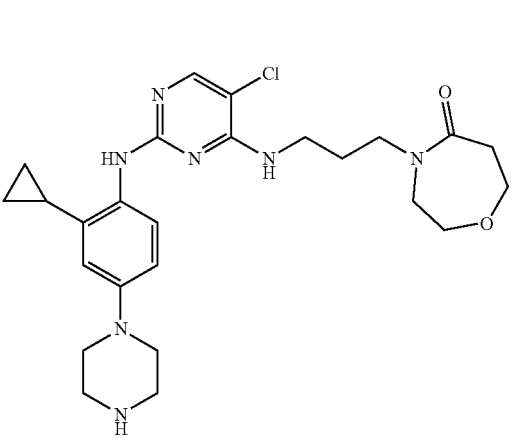 [SMILES: O=C1CCOCCN1CCCNc1nc(Nc2ccc(N3CCNCC3)cc2C2CC2)ncc1Cl]
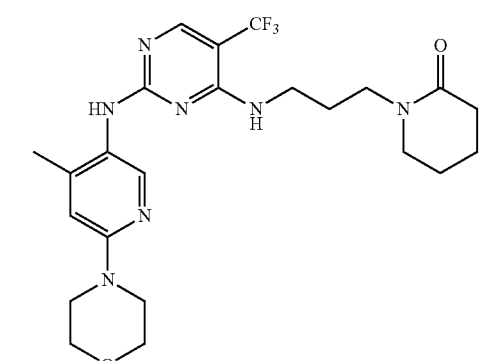
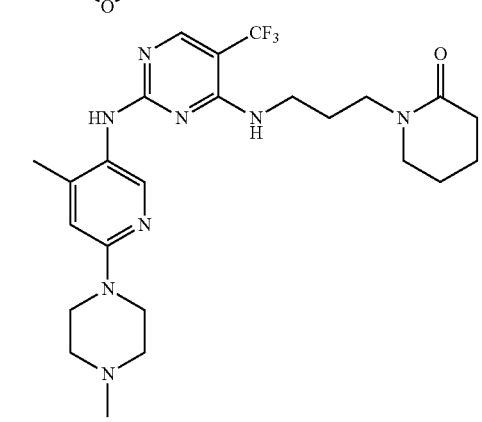

365
-continued
366
-continued
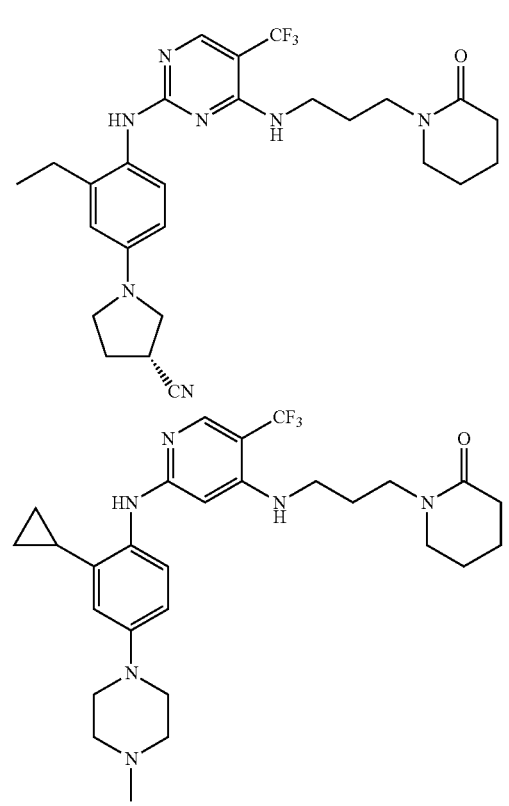
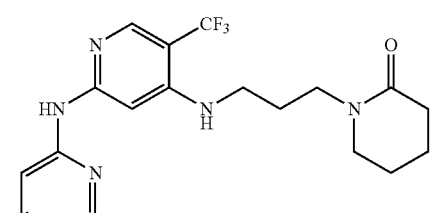
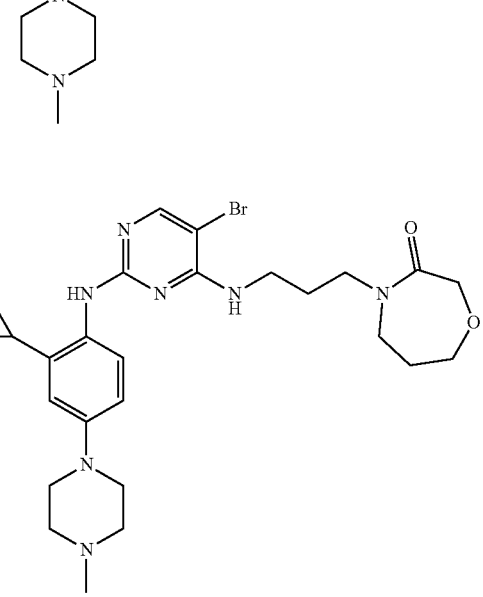
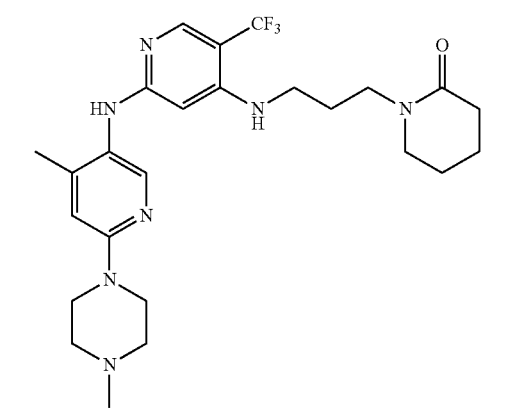 [SMILES: Cc1cc(N2CCN(C)CC2)ncc1Nc1cc(NCCCN2CCCCC2=O)c(C(F)(F)F)cn1]
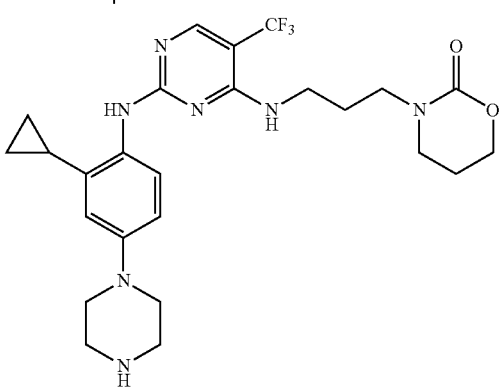

367
-continued
368
-continued
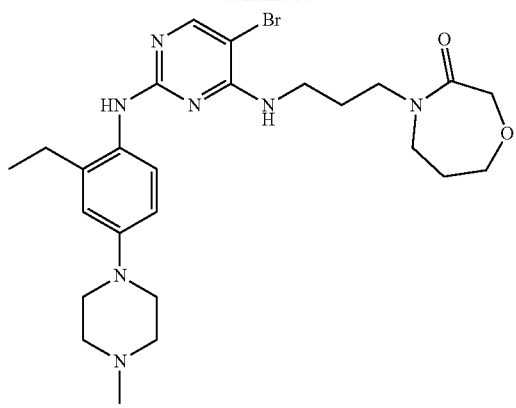 [SMILES: CCc1cc(N2CCN(C)CC2)ccc1Nc1ncc(Br)c(NCCCN2CCCOCC2=O)n1]
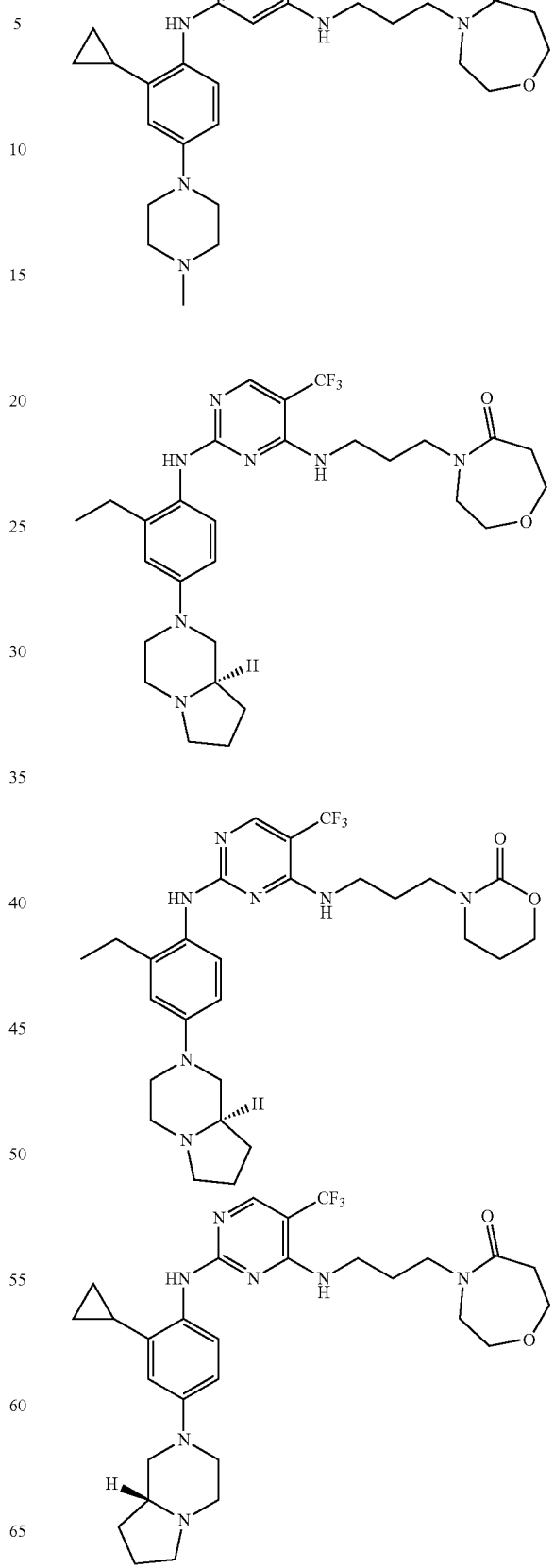

369
-continued
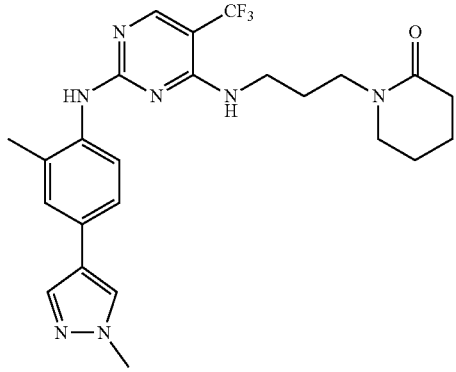 [SMILES: Cc1cc(-c2cnn(C)c2)ccc1Nc1ncc(C(F)(F)F)c(NCCCN2CCCCC2=O)n1]
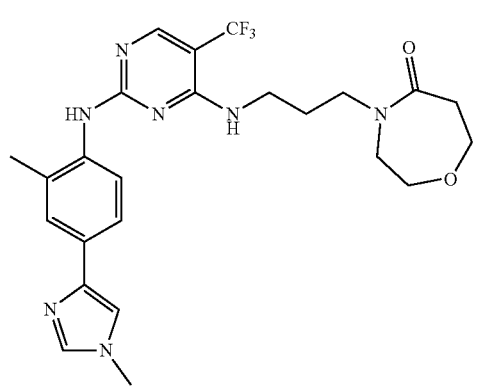 [SMILES: Cc1cc(-c2cn(C)cn2)ccc1Nc1ncc(C(F)(F)F)c(NCCCN2CCOCCC2=O)n1]
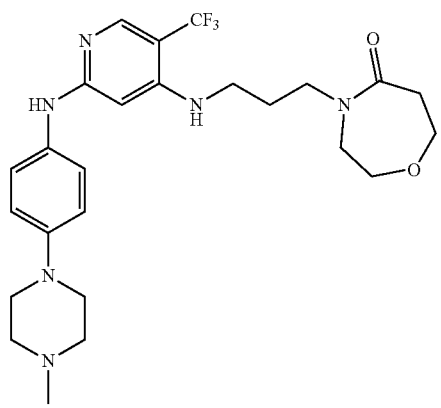
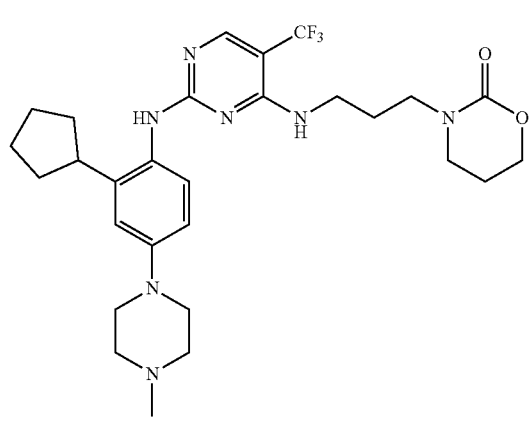 [SMILES: CN1CCN(c2ccc(Nc3ncc(C(F)(F)F)c(NCCCN4CCCOC4=O)n3)c(C3CCCC3)c2)CC1]
370
-continued
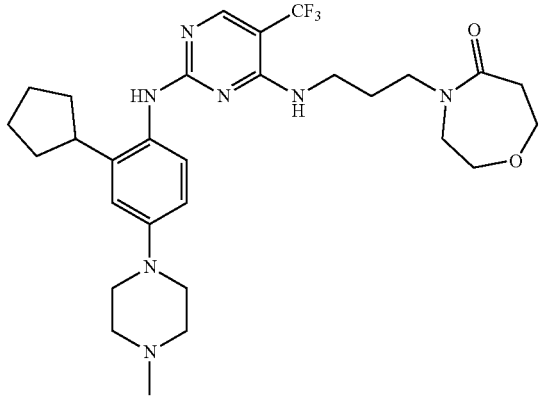 [SMILES: CN1CCN(c2ccc(Nc3ncc(C(F)(F)F)c(NCCCN4CCOCCC4=O)n3)c(C3CCCC3)c2)CC1]
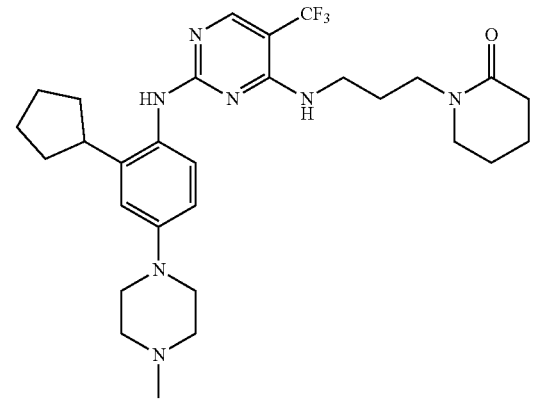 [SMILES: CN1CCN(c2ccc(Nc3ncc(C(F)(F)F)c(NCCCN4CCCCC4=O)n3)c(C3CCCC3)c2)CC1]
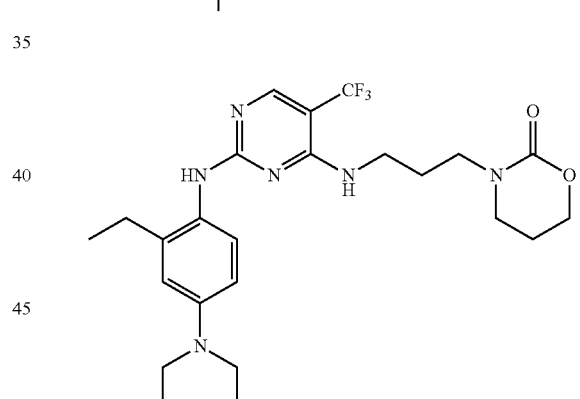
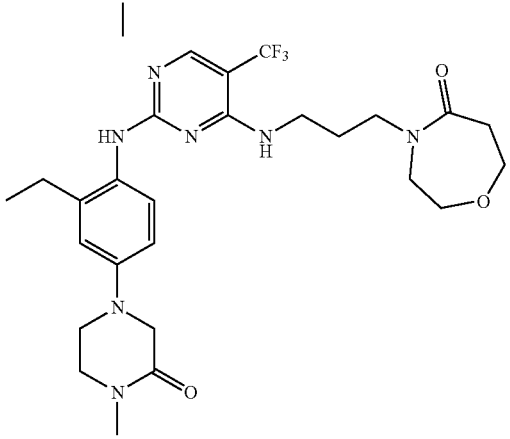

371
-continued
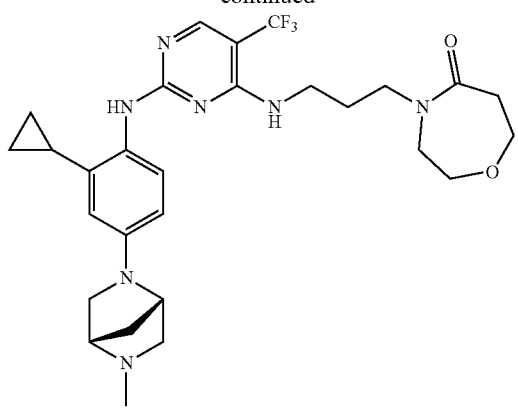
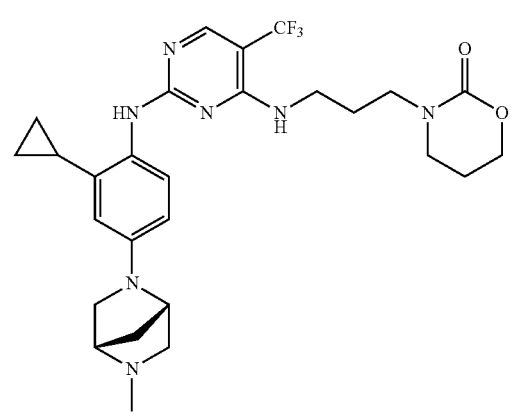 [SMILES: CN1C[C@@H]2C[C@H]1CN2c1ccc(Nc2ncc(C(F)(F)F)c(NCCCN3CCCOC3=O)n2)c(C2CC2)c1]
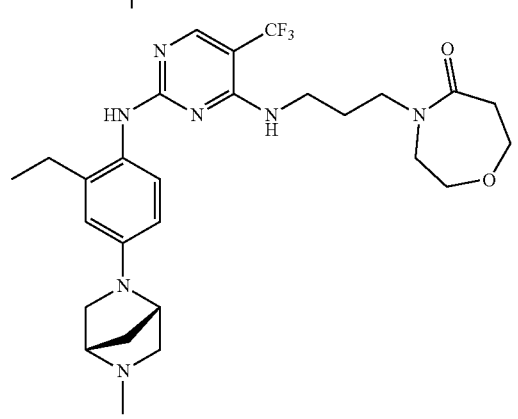
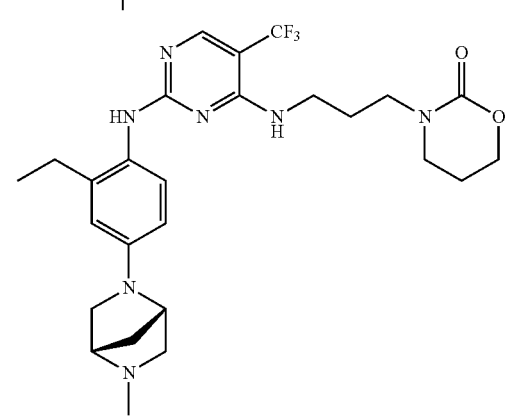
372
-continued
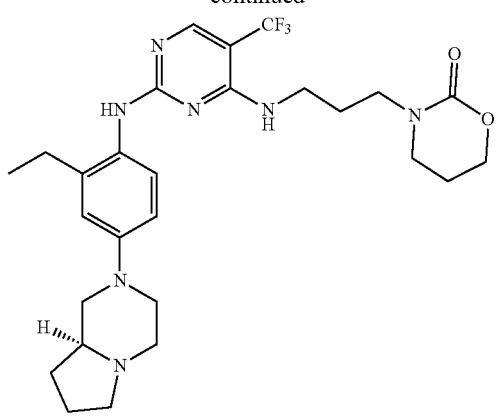
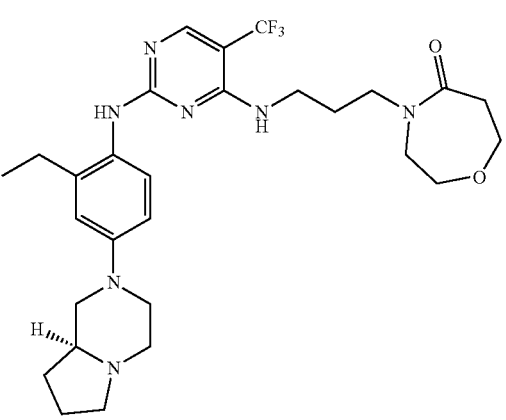 [SMILES: CCc1cc(N2CCN3CCC[C@H]3C2)ccc1Nc1ncc(C(F)(F)F)c(NCCCN2CCOCCC2=O)n1]
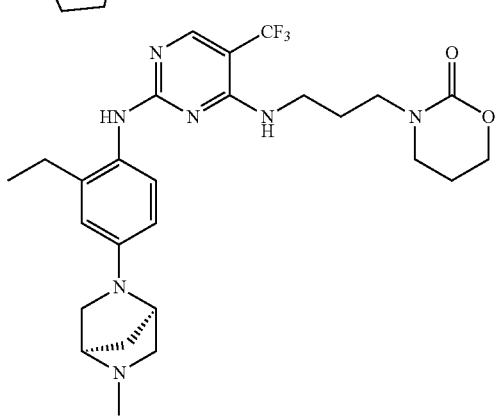
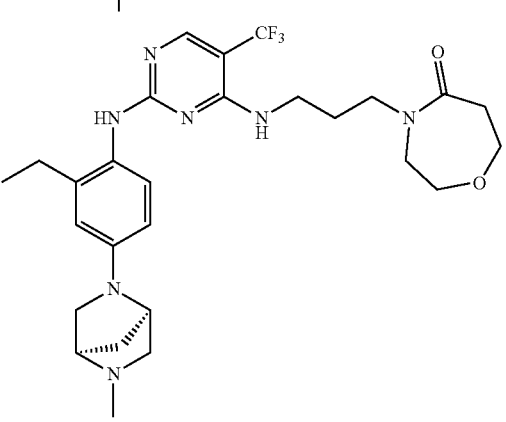

| 373 | 374 |
|---|---|
| 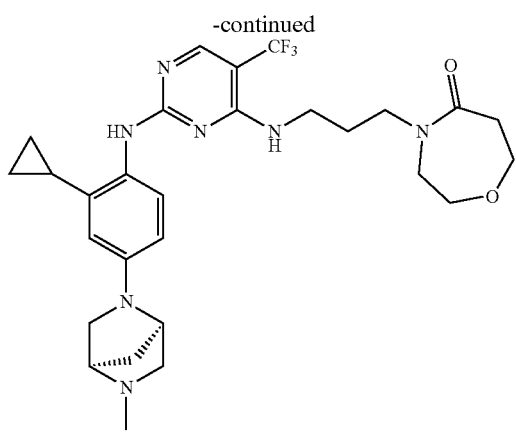 | 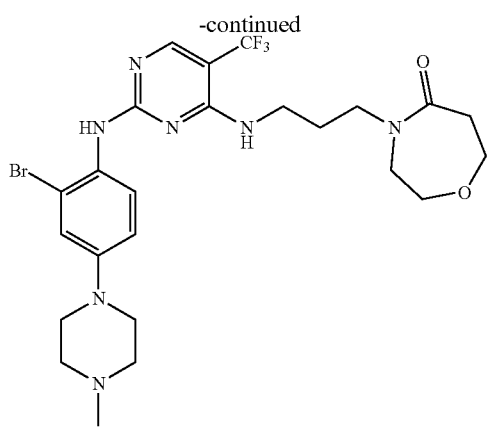 |
| 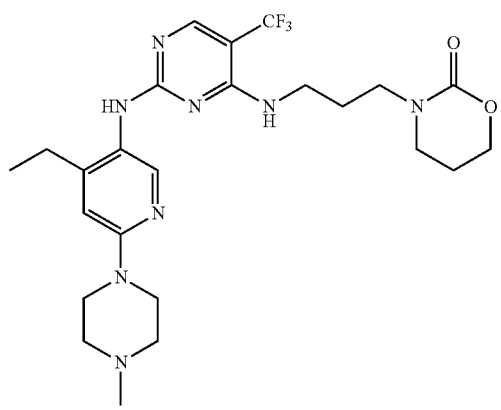 [SMILES: CCc1cc(N2CCN(C)CC2)ncc1Nc1ncc(C(F)(F)F)c(NCCCN2CCCOC2=O)n1] | 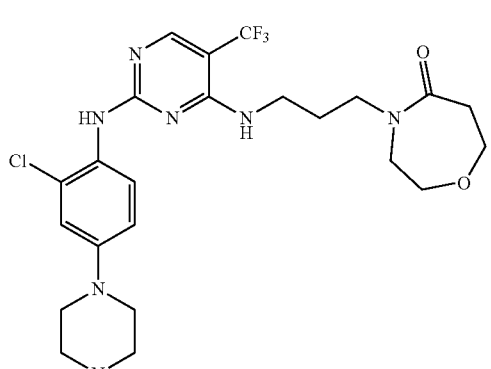 |
| 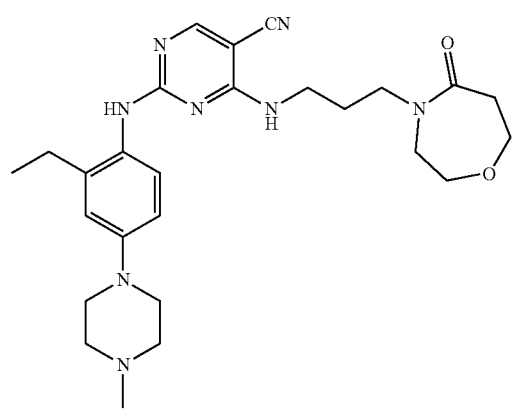 [SMILES: CCc1cc(N2CCN(C)CC2)ccc1Nc1ncc(C#N)c(NCCCN2CCOCCC2=O)n1] | 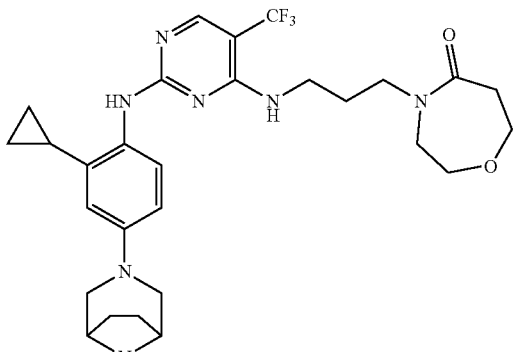 |
| 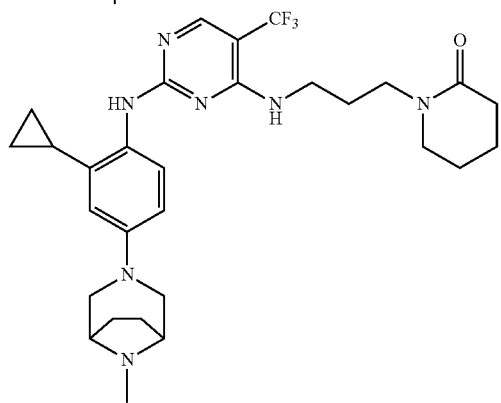 | 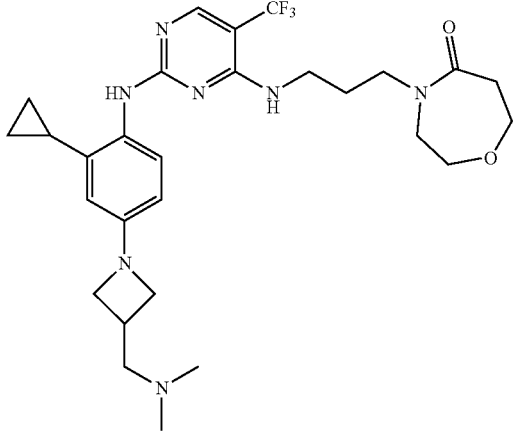 [SMILES: CN(C)CC1CN(c2ccc(Nc3ncc(C(F)(F)F)c(NCCCN4CCOCCC4=O)n3)c(C3CC3)c2)C1] |

375
-continued
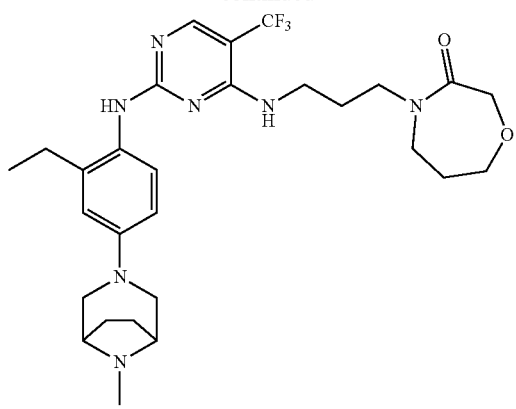 [SMILES: CCc1cc(N2CC3CCC(C2)N3C)ccc1Nc1ncc(C(F)(F)F)c(NCCCN2CCCOCC2=O)n1]
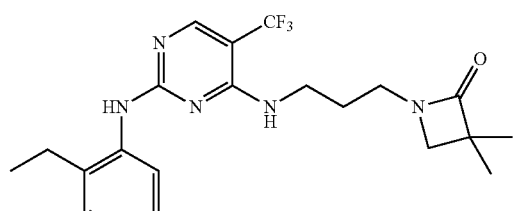
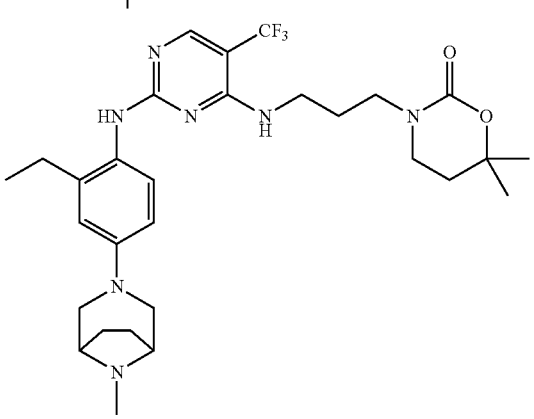
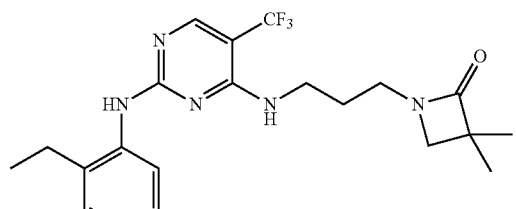
376
-continued
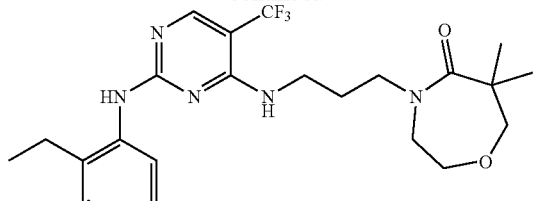
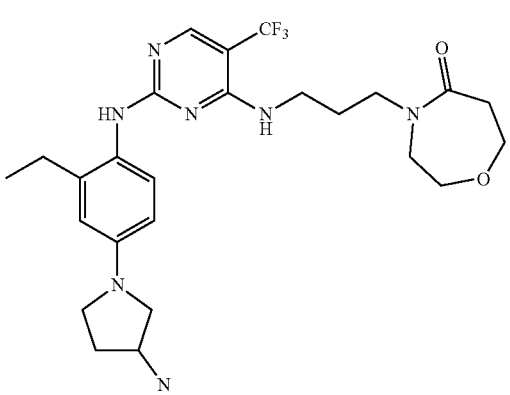 [SMILES: CCc1cc(C2CCN(C)C2)ccc1Nc1ncc(C(F)(F)F)c(NCCCN2CCOCCC2=O)n1]
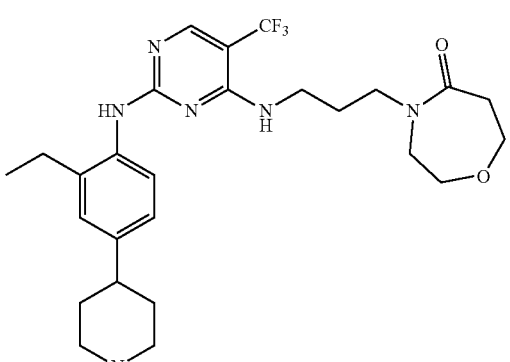
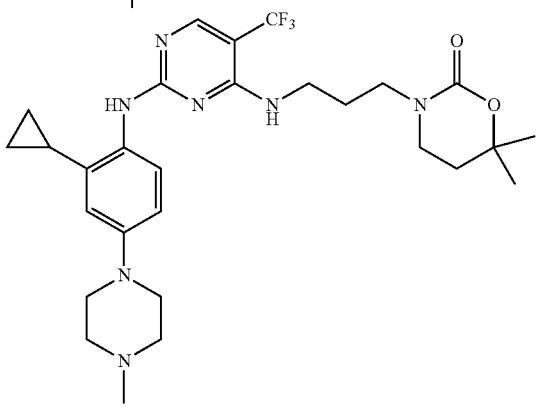

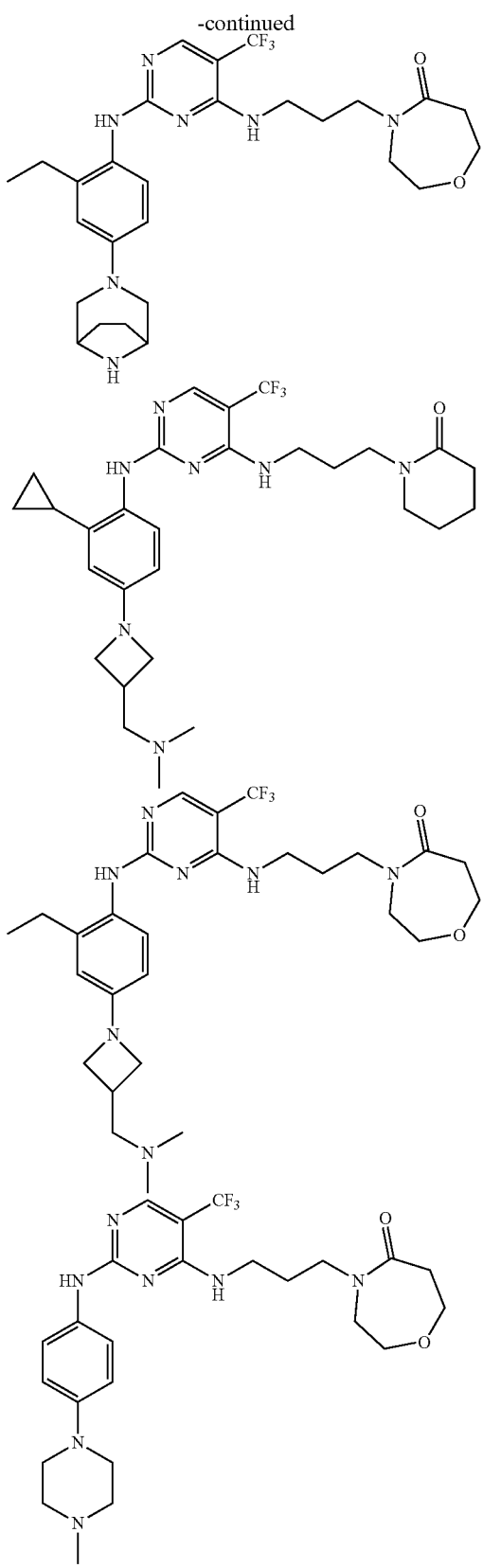
35. A compound represented by:
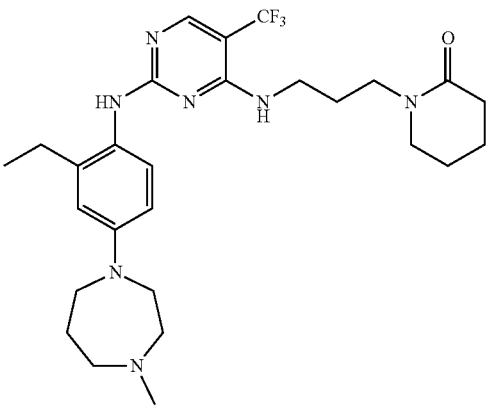 [SMILES: CCc1cc(N2CCCN(C)CC2)ccc1Nc1ncc(C(F)(F)F)c(NCCCN2CCCCC2=O)n1]
or a pharmaceutically acceptable salt thereof.
36. A compound represented by:
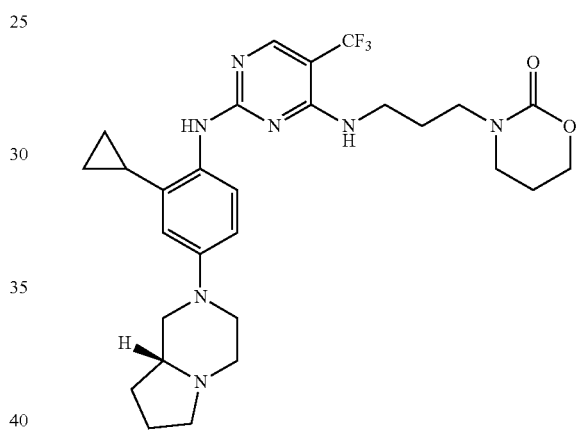
or a pharmaceutically acceptable salt thereof.
37. A compound represented by:
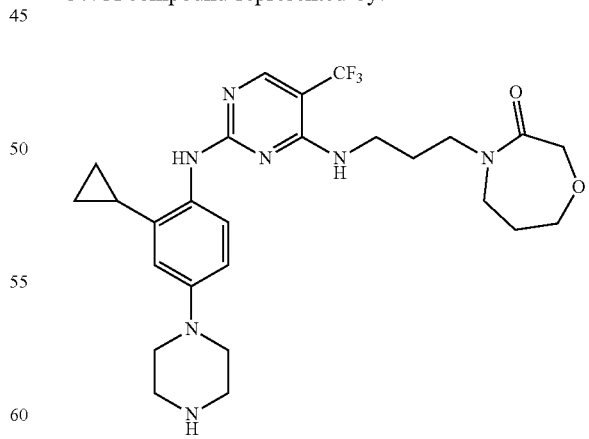
or a pharmaceutically acceptable salt thereof.
and pharmaceutically acceptable salts thereof.
\* \* \* \* \*

```
                        SEQUENCE LISTING

<160> NUMBER OF SEQ ID NOS: 6

<210> SEQ ID NO 1
<211> LENGTH: 344
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Ser Tyr Tyr His His His His His His Asp Tyr Asp Ile Pro Thr
1               5                   10                  15

Thr Glu Asn Leu Tyr Phe Gln Gly Ala Met Asp Pro Phe Phe Met Glu
            20                  25                  30

Pro Gly Arg Gly Gly Thr Glu Thr Val Gly Lys Phe Glu Phe Ser Arg
        35                  40                  45

Lys Asp Leu Ile Gly His Gly Ala Phe Ala Val Val Phe Lys Gly Arg
    50                  55                  60

His Arg Glu Lys His Asp Leu Glu Val Ala Val Lys Cys Ile Asn Lys
65                  70                  75                  80

Lys Asn Leu Ala Lys Ser Gln Thr Leu Leu Gly Lys Glu Ile Lys Ile
                85                  90                  95

Leu Lys Glu Leu Lys His Glu Asn Ile Val Ala Leu Tyr Asp Phe Gln
            100                 105                 110

Glu Met Ala Asn Ser Val Tyr Leu Val Met Glu Tyr Cys Asn Gly Gly
        115                 120                 125

Asp Leu Ala Asp Tyr Leu His Ala Met Arg Thr Leu Ser Glu Asp Thr
    130                 135                 140

Ile Arg Leu Phe Leu Gln Gln Ile Ala Gly Ala Met Arg Leu Leu His
145                 150                 155                 160

Ser Lys Gly Ile Ile His Arg Asp Leu Lys Pro Gln Asn Ile Leu Leu
                165                 170                 175

Ser Asn Pro Ala Gly Arg Arg Ala Asn Pro Asn Ser Ile Arg Val Lys
            180                 185                 190

Ile Ala Asp Phe Gly Phe Ala Arg Tyr Leu Gln Ser Asn Met Met Ala
        195                 200                 205

Ala Thr Leu Cys Gly Ser Pro Met Tyr Met Ala Pro Glu Val Ile Met
    210                 215                 220

Ser Gln His Tyr Asp Gly Lys Ala Asp Leu Trp Ser Ile Gly Thr Ile
225                 230                 235                 240

Val Tyr Gln Cys Leu Thr Gly Lys Ala Pro Phe Gln Ala Ser Ser Pro
                245                 250                 255
```

```
Gln Asp Leu Arg Leu Phe Tyr Glu Lys Asn Lys Thr Leu Val Pro Thr
        260                 265                 270

Ile Pro Arg Glu Thr Ser Ala Pro Leu Arg Gln Leu Leu Leu Ala Leu
    275                 280                 285

Leu Gln Arg Asn His Lys Asp Arg Met Asp Phe Asp Glu Phe Phe His
290                 295                 300

His Pro Phe Leu Asp Ala Ser Pro Ser Val Arg Lys Ser Pro Pro Val
305                 310                 315                 320

Pro Val Pro Ser Tyr Pro Ser Ser Gly Ser Gly Ser Ser Ser Ser Ser
                325                 330                 335

Ser Ser Thr Ser His Leu Ala Ser
        340

<210> SEQ ID NO 2
<211> LENGTH: 283
<212> TYPE: PRT
<213> ORGANISM: Unknown
<220> FEATURE:
<221> NAME/KEY: source
<223> OTHER INFORMATION: /note="Description of Unknown:
      ULK1 sequence"

<400> SEQUENCE: 2

Met Glu Pro Gly Arg Gly Gly Thr Glu Thr Val Gly Lys Phe Glu Phe
1               5                   10                  15

Ser Arg Lys Asp Leu Ile Gly His Gly Ala Phe Ala Val Val Phe Lys
                20                  25                  30

Gly Arg His Arg Ala Ala His Asp Leu Glu Val Ala Val Lys Cys Ile
            35                  40                  45

Asn Lys Lys Asn Leu Ala Lys Ser Gln Thr Leu Leu Gly Lys Glu Ile
    50                  55                  60

Lys Ile Leu Lys Glu Leu Lys His Glu Asn Ile Val Ala Leu Tyr Asp
65                  70                  75                  80

Phe Gln Glu Met Ala Asn Ser Val Tyr Leu Val Met Glu Tyr Cys Asn
                85                  90                  95

Gly Gly Asp Leu Ala Asp Tyr Leu His Ala Met Arg Thr Leu Ser Glu
            100                 105                 110

Asp Thr Ile Arg Leu Phe Leu Gln Gln Ile Ala Gly Ala Met Arg Leu
        115                 120                 125

Leu His Ser Lys Gly Ile Ile His Arg Asp Leu Lys Pro Gln Asn Ile
    130                 135                 140

Leu Leu Ser Asn Pro Ala Gly Arg Arg Ala Asn Pro Asn Ser Ile Arg
145                 150                 155                 160

Val Lys Ile Ala Asp Phe Gly Phe Ala Arg Tyr Leu Gln Ser Asn Met
                165                 170                 175

Met Ala Ala Thr Leu Cys Gly Ser Pro Met Tyr Met Ala Pro Glu Val
            180                 185                 190

Ile Met Ser Gln His Tyr Asp Gly Lys Ala Asp Leu Trp Ser Ile Gly
        195                 200                 205

Thr Ile Val Tyr Gln Cys Leu Thr Gly Lys Ala Pro Phe Gln Ala Ser
    210                 215                 220

Ser Pro Gln Asp Leu Arg Leu Phe Tyr Glu Lys Asn Lys Thr Leu Val
225                 230                 235                 240

Pro Thr Ile Pro Arg Glu Thr Ser Ala Pro Leu Arg Gln Leu Leu Leu
                245                 250                 255
```

```
Ala Leu Leu Gln Arg Asn His Lys Asp Arg Met Asp Phe Asp Glu Phe
                260                 265                 270

Phe His His Pro Phe Leu Asp Ala Ser Pro Ser
            275                 280

<210> SEQ ID NO 3
<211> LENGTH: 542
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65              70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Glu Val Leu
    210                 215                 220

Phe Gln Gly Pro Glu Phe Met Glu Val Val Gly Asp Phe Glu Tyr Ser
225                 230                 235                 240

Lys Arg Asp Leu Val Gly His Gly Ala Phe Ala Val Phe Arg Gly
                245                 250                 255

Arg His Arg Gln Lys Thr Asp Trp Glu Val Ala Ile Lys Ser Ile Asn
            260                 265                 270

Lys Lys Asn Leu Ser Lys Ser Gln Ile Leu Leu Gly Lys Glu Ile Lys
        275                 280                 285

Ile Leu Lys Glu Leu Gln His Glu Asn Ile Val Ala Leu Tyr Asp Val
    290                 295                 300

Gln Glu Leu Pro Asn Ser Val Phe Leu Val Met Glu Tyr Cys Asn Gly
305                 310                 315                 320

Gly Asp Leu Ala Asp Tyr Leu Gln Ala Lys Gly Thr Leu Ser Glu Asp
```

```
                    325                 330                 335

Thr Ile Arg Val Phe Leu His Gln Ile Ala Ala Met Arg Ile Leu
                340                 345                 350

His Ser Lys Gly Ile Ile His Arg Asp Leu Lys Pro Gln Asn Ile Leu
            355                 360                 365

Leu Ser Tyr Ala Asn Arg Arg Lys Ser Ser Val Ser Gly Ile Arg Ile
        370                 375                 380

Lys Ile Ala Asp Phe Gly Phe Ala Arg Tyr Leu His Ser Asn Met Met
385                 390                 395                 400

Ala Ala Thr Leu Cys Gly Ser Pro Met Tyr Met Ala Pro Glu Val Ile
                405                 410                 415

Met Ser Gln His Tyr Asp Ala Lys Ala Asp Leu Trp Ser Ile Gly Thr
            420                 425                 430

Val Ile Tyr Gln Cys Leu Val Gly Lys Pro Pro Phe Gln Ala Asn Ser
        435                 440                 445

Pro Gln Asp Leu Arg Met Phe Tyr Glu Lys Asn Arg Ser Leu Met Pro
    450                 455                 460

Ser Ile Pro Arg Glu Thr Ser Pro Tyr Leu Ala Asn Leu Leu Leu Gly
465                 470                 475                 480

Leu Leu Gln Arg Asn Gln Lys Asp Arg Met Asp Phe Glu Ala Phe Phe
                485                 490                 495

Ser His Pro Phe Leu Glu Gln Gly Pro Val Lys Lys Ser Cys Pro Val
            500                 505                 510

Pro Val Pro Met Tyr Ser Gly Ser Val Ser Gly Ser Ser Cys Gly Ser
        515                 520                 525

Ser Pro Ser Cys Arg Phe Ala Ser His His His His His His
    530                 535                 540

<210> SEQ ID NO 4
<211> LENGTH: 1795
<212> TYPE: PRT
<213> ORGANISM: Unknown
<220> FEATURE:
<221> NAME/KEY: source
<223> OTHER INFORMATION: /note="Description of Unknown:
      LRRK2 sequence"

<400> SEQUENCE: 4

Met Ala Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140
```

```
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

His Asn Gln Thr Ser Leu Tyr Lys Lys Ala Gly Thr Met His Ser Asp
225                 230                 235                 240

Ser Ile Ser Ser Leu Ala Ser Glu Arg Glu Tyr Ile Thr Ser Leu Asp
                245                 250                 255

Leu Ser Ala Asn Glu Leu Arg Asp Ile Asp Ala Leu Ser Gln Lys Cys
            260                 265                 270

Cys Ile Ser Val His Leu Glu His Leu Glu Lys Leu Glu Leu His Gln
        275                 280                 285

Asn Ala Leu Thr Ser Phe Pro Gln Gln Leu Cys Glu Thr Leu Lys Ser
290                 295                 300

Leu Thr His Leu Asp Leu His Ser Asn Lys Phe Thr Ser Phe Pro Ser
305                 310                 315                 320

Tyr Leu Leu Lys Met Ser Cys Ile Ala Asn Leu Asp Val Ser Arg Asn
                325                 330                 335

Asp Ile Gly Pro Ser Val Val Leu Asp Pro Thr Val Lys Cys Pro Thr
            340                 345                 350

Leu Lys Gln Phe Asn Leu Ser Tyr Asn Gln Leu Ser Phe Val Pro Glu
        355                 360                 365

Asn Leu Thr Asp Val Val Glu Lys Leu Glu Gln Leu Ile Leu Glu Gly
    370                 375                 380

Asn Lys Ile Ser Gly Ile Cys Ser Pro Leu Arg Leu Lys Glu Leu Lys
385                 390                 395                 400

Ile Leu Asn Leu Ser Lys Asn His Ile Ser Ser Leu Ser Glu Asn Phe
                405                 410                 415

Leu Glu Ala Cys Pro Lys Val Glu Ser Phe Ser Ala Arg Met Asn Phe
            420                 425                 430

Leu Ala Ala Met Pro Phe Leu Pro Pro Ser Met Thr Ile Leu Lys Leu
        435                 440                 445

Ser Gln Asn Lys Phe Ser Cys Ile Pro Glu Ala Ile Leu Asn Leu Pro
    450                 455                 460

His Leu Arg Ser Leu Asp Met Ser Ser Asn Asp Ile Gln Tyr Leu Pro
465                 470                 475                 480

Gly Pro Ala His Trp Lys Ser Leu Asn Leu Arg Glu Leu Leu Phe Ser
                485                 490                 495

His Asn Gln Ile Ser Ile Leu Asp Leu Ser Glu Lys Ala Tyr Leu Trp
            500                 505                 510

Ser Arg Val Glu Lys Leu His Leu Ser His Asn Lys Leu Lys Glu Ile
        515                 520                 525

Pro Pro Glu Ile Gly Cys Leu Glu Asn Leu Thr Ser Leu Asp Val Ser
    530                 535                 540

Tyr Asn Leu Glu Leu Arg Ser Phe Pro Asn Glu Met Gly Lys Leu Ser
545                 550                 555                 560
```

-continued

```
Lys Ile Trp Asp Leu Pro Leu Asp Glu Leu His Leu Asn Phe Asp Phe
                565                 570                 575

Lys His Ile Gly Cys Lys Ala Lys Asp Ile Ile Arg Phe Leu Gln Gln
            580                 585                 590

Arg Leu Lys Lys Ala Val Pro Tyr Asn Arg Met Lys Leu Met Ile Val
        595                 600                 605

Gly Asn Thr Gly Ser Gly Lys Thr Thr Leu Leu Gln Gln Leu Met Lys
    610                 615                 620

Thr Lys Lys Ser Asp Leu Gly Met Gln Ser Thr Val Gly Ile Asp
625                 630                 635                 640

Val Lys Asp Trp Pro Ile Gln Ile Arg Asp Lys Arg Lys Arg Asp Leu
                645                 650                 655

Val Leu Asn Val Trp Asp Phe Ala Gly Arg Glu Glu Phe Tyr Ser Thr
            660                 665                 670

His Pro His Phe Met Thr Gln Arg Ala Leu Tyr Leu Ala Val Tyr Asp
        675                 680                 685

Leu Ser Lys Gly Gln Ala Glu Val Asp Ala Met Lys Pro Trp Leu Phe
    690                 695                 700

Asn Ile Lys Ala Arg Ala Ser Ser Pro Val Ile Leu Val Gly Thr
705                 710                 715                 720

His Leu Asp Val Ser Asp Glu Lys Gln Arg Lys Ala Cys Met Ser Lys
                725                 730                 735

Ile Thr Lys Glu Leu Leu Asn Lys Arg Gly Phe Pro Ala Ile Arg Asp
            740                 745                 750

Tyr His Phe Val Asn Ala Thr Glu Glu Ser Asp Ala Leu Ala Lys Leu
        755                 760                 765

Arg Lys Thr Ile Ile Asn Glu Ser Leu Asn Phe Lys Ile Arg Asp Gln
    770                 775                 780

Leu Val Val Gly Gln Leu Ile Pro Asp Cys Tyr Val Glu Leu Glu Lys
785                 790                 795                 800

Ile Ile Leu Ser Glu Arg Lys Asn Val Pro Ile Glu Phe Pro Val Ile
                805                 810                 815

Asp Arg Lys Arg Leu Leu Gln Leu Val Arg Glu Asn Gln Leu Gln Leu
            820                 825                 830

Asp Glu Asn Glu Leu Pro His Ala Val His Phe Leu Asn Glu Ser Gly
        835                 840                 845

Val Leu Leu His Phe Gln Asp Pro Ala Leu Gln Leu Ser Asp Leu Tyr
    850                 855                 860

Phe Val Glu Pro Lys Trp Leu Cys Lys Ile Met Ala Gln Ile Leu Thr
865                 870                 875                 880

Val Lys Val Glu Gly Cys Pro Lys His Pro Lys Gly Ile Ile Ser Arg
                885                 890                 895

Arg Asp Val Glu Lys Phe Leu Ser Lys Arg Lys Phe Pro Lys Asn
            900                 905                 910

Tyr Met Ser Gln Tyr Phe Lys Leu Leu Glu Lys Phe Gln Ile Ala Leu
        915                 920                 925

Pro Ile Gly Glu Glu Tyr Leu Leu Val Pro Ser Ser Leu Ser Asp His
    930                 935                 940

Arg Pro Val Ile Glu Leu Pro His Cys Glu Asn Ser Glu Ile Ile Ile
945                 950                 955                 960

Arg Leu Tyr Glu Met Pro Tyr Phe Pro Met Gly Phe Trp Ser Arg Leu
                965                 970                 975

Ile Asn Arg Leu Leu Glu Ile Ser Pro Tyr Met Leu Ser Gly Arg Glu
```

```
              980              985              990
Arg Ala Leu Arg Pro Asn Arg Met  Tyr Trp Arg Gln Gly  Ile Tyr Leu
            995                  1000             1005

Asn Trp Ser Pro Glu Ala Tyr  Cys Leu Val Gly Ser  Glu Val Leu
    1010            1015             1020

Asp Asn His Pro Glu Ser Phe  Leu Lys Ile Thr Val  Pro Ser Cys
    1025            1030             1035

Arg Lys Gly Cys Ile Leu Leu  Gly Gln Val Val Asp  His Ile Asp
    1040            1045             1050

Ser Leu Met Glu Glu Trp Phe  Pro Gly Leu Leu Glu  Ile Asp Ile
    1055            1060             1065

Cys Gly Glu Gly Glu Thr Leu  Leu Lys Lys Trp Ala  Leu Tyr Ser
    1070            1075             1080

Phe Asn Asp Gly Glu Glu His  Gln Lys Ile Leu Leu  Asp Asp Leu
    1085            1090             1095

Met Lys Lys Ala Glu Glu Gly  Asp Leu Leu Val Asn  Pro Asp Gln
    1100            1105             1110

Pro Arg Leu Thr Ile Pro Ile  Ser Gln Ile Ala Pro  Asp Leu Ile
    1115            1120             1125

Leu Ala Asp Leu Pro Arg Asn  Ile Met Leu Asn Asn  Asp Glu Leu
    1130            1135             1140

Glu Phe Glu Gln Ala Pro Glu  Phe Leu Leu Gly Asp  Gly Ser Phe
    1145            1150             1155

Gly Ser Val Tyr Arg Ala Ala  Tyr Glu Gly Glu Glu  Val Ala Val
    1160            1165             1170

Lys Ile Phe Asn Lys His Thr  Ser Leu Arg Leu Leu  Arg Gln Glu
    1175            1180             1185

Leu Val Val Leu Cys His Leu  His His Pro Ser Leu  Ile Ser Leu
    1190            1195             1200

Leu Ala Ala Gly Ile Arg Pro  Arg Met Leu Val Met  Glu Leu Ala
    1205            1210             1215

Ser Lys Gly Ser Leu Asp Arg  Leu Leu Gln Gln Asp  Lys Ala Ser
    1220            1225             1230

Leu Thr Arg Thr Leu Gln His  Arg Ile Ala Leu His  Val Ala Asp
    1235            1240             1245

Gly Leu Arg Tyr Leu His Ser  Ala Met Ile Ile Tyr  Arg Asp Leu
    1250            1255             1260

Lys Pro His Asn Val Leu Leu  Phe Thr Leu Tyr Pro  Asn Ala Ala
    1265            1270             1275

Ile Ile Ala Lys Ile Ala Asp  Tyr Gly Ile Ala Gln  Tyr Cys Cys
    1280            1285             1290

Arg Met Gly Ile Lys Thr Ser  Glu Gly Thr Pro Gly  Phe Arg Ala
    1295            1300             1305

Pro Glu Val Ala Arg Gly Asn  Val Ile Tyr Asn Gln  Gln Ala Asp
    1310            1315             1320

Val Tyr Ser Phe Gly Leu Leu  Leu Tyr Asp Ile Leu  Thr Thr Gly
    1325            1330             1335

Gly Arg Ile Val Glu Gly Leu  Lys Phe Pro Asn Glu  Phe Asp Glu
    1340            1345             1350

Leu Glu Ile Gln Gly Lys Leu  Pro Asp Pro Val Lys  Glu Tyr Gly
    1355            1360             1365

Cys Ala Pro Trp Pro Met Val  Glu Lys Leu Ile Lys  Gln Cys Leu
    1370            1375             1380
```

-continued

```
Lys Glu Asn Pro Gln Glu Arg Pro Thr Ser Ala Gln Val Phe Asp
1385                1390                1395

Ile Leu Asn Ser Ala Glu Leu Val Cys Leu Thr Arg Arg Ile Leu
1400                1405                1410

Leu Pro Lys Asn Val Ile Val Glu Cys Met Val Ala Thr His His
1415                1420                1425

Asn Ser Arg Asn Ala Ser Ile Trp Leu Gly Cys Gly His Thr Asp
1430                1435                1440

Arg Gly Gln Leu Ser Phe Leu Asp Leu Asn Thr Glu Gly Tyr Thr
1445                1450                1455

Ser Glu Glu Val Ala Asp Ser Arg Ile Leu Cys Leu Ala Leu Val
1460                1465                1470

His Leu Pro Val Glu Lys Glu Ser Trp Ile Val Ser Gly Thr Gln
1475                1480                1485

Ser Gly Thr Leu Leu Val Ile Asn Thr Glu Asp Gly Lys Lys Arg
1490                1495                1500

His Thr Leu Glu Lys Met Thr Asp Ser Val Thr Cys Leu Tyr Cys
1505                1510                1515

Asn Ser Phe Ser Lys Gln Ser Lys Gln Lys Asn Phe Leu Leu Val
1520                1525                1530

Gly Thr Ala Asp Gly Lys Leu Ala Ile Phe Glu Asp Lys Thr Val
1535                1540                1545

Lys Leu Lys Gly Ala Ala Pro Leu Lys Ile Leu Asn Ile Gly Asn
1550                1555                1560

Val Ser Thr Pro Leu Met Cys Leu Ser Glu Ser Thr Asn Ser Thr
1565                1570                1575

Glu Arg Asn Val Met Trp Gly Gly Cys Gly Thr Lys Ile Phe Ser
1580                1585                1590

Phe Ser Asn Asp Phe Thr Ile Gln Lys Leu Ile Glu Thr Arg Thr
1595                1600                1605

Ser Gln Leu Phe Ser Tyr Ala Ala Phe Ser Asp Ser Asn Ile Ile
1610                1615                1620

Thr Val Val Val Asp Thr Ala Leu Tyr Ile Ala Lys Gln Asn Ser
1625                1630                1635

Pro Val Val Glu Val Trp Asp Lys Lys Thr Glu Lys Leu Cys Gly
1640                1645                1650

Leu Ile Asp Cys Val His Phe Leu Arg Glu Val Met Val Lys Glu
1655                1660                1665

Asn Lys Glu Ser Lys His Lys Met Ser Tyr Ser Gly Arg Val Lys
1670                1675                1680

Thr Leu Cys Leu Gln Lys Asn Thr Ala Leu Trp Ile Gly Thr Gly
1685                1690                1695

Gly Gly His Ile Leu Leu Leu Asp Leu Ser Thr Arg Arg Leu Ile
1700                1705                1710

Arg Val Ile Tyr Asn Phe Cys Asn Ser Val Arg Val Met Met Thr
1715                1720                1725

Ala Gln Leu Gly Ser Leu Lys Asn Val Met Leu Val Leu Gly Tyr
1730                1735                1740

Asn Arg Lys Asn Thr Glu Gly Thr Gln Lys Gln Lys Glu Ile Gln
1745                1750                1755

Ser Cys Leu Thr Val Trp Asp Ile Asn Leu Pro His Glu Val Gln
1760                1765                1770
```

```
Asn Leu Glu Lys His Ile Glu  Val Arg Lys Glu  Leu  Ala Glu Lys
    1775                1780              1785

Met Arg  Arg Thr Ser Val Glu
    1790             1795

<210> SEQ ID NO 5
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Tyr Ala Asn Trp Leu Ala Ala Ser Ile Tyr Leu Asp Gly Lys Lys Lys
1               5                   10                  15

<210> SEQ ID NO 6
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Arg Leu Gly Arg Asp Lys Tyr Lys Thr Leu Arg Gln Ile Arg Gln
1               5                   10                  15
```